United States Patent
Byrne et al.

(10) Patent No.: US 12,006,356 B2
(45) Date of Patent: Jun. 11, 2024

(54) ANTI-CCT5 BINDING MOLECULES AND CHIMERIC ANTIGEN RECEPTORS COMPRISING THE SAME

(71) Applicant: Juno Therapeutics, Inc., Seattle, WA (US)

(72) Inventors: Susan Byrne, Seattle, WA (US);
Richard Sullivan, Seattle, WA (US);
Francois Vigneault, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 811 days.

(21) Appl. No.: 16/771,954

(22) PCT Filed: Dec. 14, 2018

(86) PCT No.: PCT/US2018/065866
§ 371 (c)(1),
(2) Date: Jun. 11, 2020

(87) PCT Pub. No.: WO2019/118937
PCT Pub. Date: Jun. 20, 2019

(65) Prior Publication Data
US 2021/0070845 A1    Mar. 11, 2021

Related U.S. Application Data

(60) Provisional application No. 62/599,682, filed on Dec. 15, 2017.

(51) Int. Cl.
| | | |
|---|---|---|
| *C07K 16/18* | (2006.01) | |
| *A61K 47/68* | (2017.01) | |
| *C07K 14/705* | (2006.01) | |
| *C07K 16/28* | (2006.01) | |
| *C07K 16/30* | (2006.01) | |
| *C07K 19/00* | (2006.01) | |
| *C12N 5/0783* | (2010.01) | |

(52) U.S. Cl.
CPC .......... *C07K 16/18* (2013.01); *A61K 47/6803* (2017.08); *A61K 47/6843* (2017.08); *C07K 14/70521* (2013.01); *C07K 14/70578* (2013.01); *C07K 16/2806* (2013.01); *C07K 16/2809* (2013.01); *C07K 16/2863* (2013.01); *C07K 16/30* (2013.01); *C12N 5/0636* (2013.01); *C07K 2317/21* (2013.01); *C07K 2317/31* (2013.01); *C07K 2317/34* (2013.01); *C07K 2317/622* (2013.01); *C07K 2319/02* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| | | |
|---|---|---|
| 4,235,871 A | 11/1980 | Papahadjopoulos et al. |
| 4,256,746 A | 3/1981 | Miyashita et al. |
| 4,294,757 A | 10/1981 | Asai |
| 4,307,016 A | 12/1981 | Asai et al. |
| 4,313,946 A | 2/1982 | Powell et al. |
| 4,315,929 A | 2/1982 | Freedman et al. |
| 4,322,348 A | 3/1982 | Asai et al. |
| 4,331,498 A | 5/1982 | Pagay et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,234 A | 5/1984 | Hasegawa et al. |
| 4,452,773 A | 6/1984 | Molday |
| 4,501,728 A | 2/1985 | Geho et al. |
| 4,690,915 A | 9/1987 | Rosenberg |
| 4,795,698 A | 1/1989 | Owen et al. |
| 4,837,028 A | 6/1989 | Allen |
| 4,920,143 A | 4/1990 | Levy et al. |
| 4,968,715 A | 11/1990 | Dougherty et al. |
| 5,019,369 A | 5/1991 | Presant et al. |
| 5,028,594 A | 7/1991 | Carson |

(Continued)

FOREIGN PATENT DOCUMENTS

| | | |
|---|---|---|
| EP | 0452342 | 10/1991 |
| EP | 1866339 | 12/2007 |

(Continued)

OTHER PUBLICATIONS

US 8,252,592 B2, 08/2012, Sadelain (withdrawn)
MacCallum et al. (1996). J. Mol. Biol. 262:732-745.*
De Pascalis et al. (2002). Journal of Immunology. 169:3076-3084.*
Casset et al. (2003). Biochemical and Biophysical Research Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*

(Continued)

*Primary Examiner* — Christine J Saoud
*Assistant Examiner* — Jon M Lockard
(74) *Attorney, Agent, or Firm* — MORRISON & FOERSTER LLP

(57) ABSTRACT

Provided are CCT5-binding molecules, including anti-CCT5 antibodies and antigen-binding fragments thereof such as heavy chain variable (VH) regions and single-chain antibody fragments, and conjugates comprising the anti-CCT5 binding molecules such as immunoconjugates and antibody-drug conjugates, and chimeric receptors comprising the anti-CCT5 binding molecules such as chimeric antigen receptors (CARs). In some embodiments, the anti-CCT5 antibodies or antigen-binding fragments thereof specifically bind to CCT5. Also provided are genetically engineered cells expressing the CARs or CCT5-binding molecules and uses thereof such as in adoptive cell therapy.

28 Claims, 5 Drawing Sheets

Specification includes a Sequence Listing.

(56) References Cited

U.S. PATENT DOCUMENTS

| | | |
|---|---|---|
| 5,053,423 A | 10/1991 | Liu |
| 5,082,927 A | 1/1992 | Pastan et al. |
| 5,087,616 A | 2/1992 | Myers et al. |
| 5,087,617 A | 2/1992 | Smith et al. |
| 5,087,636 A | 2/1992 | Jamieson et al. |
| 5,093,246 A | 3/1992 | Cech et al. |
| 5,093,349 A | 3/1992 | Pandey et al. |
| 5,109,016 A | 4/1992 | Dixon et al. |
| 5,109,124 A | 4/1992 | Kuzhalmannam et al. |
| 5,116,742 A | 5/1992 | Cech et al. |
| 5,135,917 A | 8/1992 | Burch |
| 5,144,019 A | 9/1992 | Rossi et al. |
| 5,149,708 A | 9/1992 | Dolphin et al. |
| 5,168,053 A | 12/1992 | Altman et al. |
| 5,171,749 A | 12/1992 | Levy et al. |
| 5,175,269 A | 12/1992 | Stavrianopoulos |
| 5,176,996 A | 1/1993 | Hogan et al. |
| 5,180,818 A | 1/1993 | Cech et al. |
| 5,190,931 A | 3/1993 | Inouye |
| 5,192,788 A | 3/1993 | Dixon et al. |
| 5,200,084 A | 4/1993 | Liberti et al. |
| 5,202,317 A | 4/1993 | Bruice |
| 5,208,020 A | 5/1993 | Chari et al. |
| 5,217,966 A | 6/1993 | Bruice |
| 5,218,088 A | 6/1993 | Gorenstein et al. |
| 5,219,740 A | 6/1993 | Miller et al. |
| 5,225,539 A | 7/1993 | Winter |
| 5,238,940 A | 8/1993 | Liu et al. |
| 5,252,720 A | 10/1993 | Sessler et al. |
| 5,257,970 A | 11/1993 | Dougherty et al. |
| 5,272,262 A | 12/1993 | Rossi et al. |
| 5,283,173 A | 2/1994 | Fields et al. |
| 5,424,297 A | 6/1995 | Rubio et al. |
| 5,468,614 A | 11/1995 | Fields et al. |
| 5,504,090 A | 4/1996 | Neely et al. |
| 5,545,627 A | 8/1996 | Jacobson et al. |
| 5,565,566 A | 10/1996 | Olsson |
| 5,585,089 A | 12/1996 | Queen et al. |
| 5,635,517 A | 6/1997 | Muller et al. |
| 5,663,149 A | 9/1997 | Pettit et al. |
| 5,670,501 A | 9/1997 | Peck et al. |
| 5,712,291 A | 1/1998 | D'Amato |
| 5,786,360 A | 7/1998 | Neely |
| 5,798,368 A | 8/1998 | Muller et al. |
| 5,861,405 A | 1/1999 | Jacobson et al. |
| 5,981,524 A | 11/1999 | Peck et al. |
| 6,040,177 A | 3/2000 | Riddell et al. |
| 6,060,273 A | 5/2000 | Dirks et al. |
| 6,066,642 A | 5/2000 | Jacobson et al. |
| 6,111,090 A | 8/2000 | Gorman et al. |
| 6,117,998 A | 9/2000 | Neely |
| 6,207,453 B1 | 3/2001 | Maass et al. |
| 6,214,345 B1 | 4/2001 | Firestone et al. |
| 6,232,297 B1 | 5/2001 | Linden et al. |
| 6,281,230 B1 | 8/2001 | Muller et al. |
| 6,313,131 B1 | 11/2001 | Lawyer |
| 6,316,471 B1 | 11/2001 | Muller et al. |
| 6,322,771 B1 | 11/2001 | Linden et al. |
| 6,326,390 B1 | 12/2001 | Leung et al. |
| 6,335,349 B1 | 1/2002 | Muller et al. |
| 6,380,239 B1 | 4/2002 | Muller et al. |
| 6,395,754 B1 | 5/2002 | Muller et al. |
| 6,403,613 B1 | 6/2002 | Man et al. |
| 6,410,319 B1 | 6/2002 | Raubitschek et al. |
| 6,451,995 B1 | 9/2002 | Cheung et al. |
| 6,458,810 B1 | 10/2002 | Muller et al. |
| 6,476,052 B1 | 11/2002 | Muller et al. |
| 6,562,806 B1 | 5/2003 | Thurston et al. |
| 6,602,684 B1 | 8/2003 | Umana et al. |
| 6,608,192 B1 | 8/2003 | Thurston et al. |
| 6,747,144 B1 | 6/2004 | Thurston et al. |
| 7,025,962 B1 | 4/2006 | Gorman et al. |
| 7,049,311 B1 | 5/2006 | Thurston et al. |
| 7,070,995 B2 | 7/2006 | Jensen |
| 7,091,353 B2 | 8/2006 | Robarge et al. |
| 7,132,255 B2 | 11/2006 | Blumberg |
| 7,141,575 B2 | 11/2006 | Gillespie et al. |
| 7,244,759 B2 | 7/2007 | Muller et al. |
| 7,265,209 B2 | 9/2007 | Jensen |
| 7,320,991 B2 | 1/2008 | Figg et al. |
| 7,354,762 B2 | 4/2008 | Jensen |
| 7,405,219 B2 | 7/2008 | Gillespie et al. |
| 7,446,179 B2 | 11/2008 | Jensen et al. |
| 7,446,190 B2 | 11/2008 | Sadelain et al. |
| 7,446,191 B2 | 11/2008 | Jensen |
| 7,521,541 B2 | 4/2009 | Eigenbrot et al. |
| 7,528,126 B2 | 5/2009 | Howard et al. |
| 7,618,632 B2 | 11/2009 | Collins et al. |
| 7,741,319 B2 | 6/2010 | Howard et al. |
| 7,812,135 B2 | 10/2010 | Smith et al. |
| 7,855,275 B2 | 12/2010 | Eigenbrot et al. |
| 7,943,743 B2 | 5/2011 | Korman et al. |
| 8,008,449 B2 | 8/2011 | Korman et al. |
| 8,080,554 B2 | 12/2011 | Sitkovsky et al. |
| 8,124,084 B2 | 2/2012 | Lefrancois et al. |
| 8,142,784 B2 | 3/2012 | Ebens et al. |
| 8,324,353 B2 | 12/2012 | Jensen |
| 8,339,645 B2 | 12/2012 | Jun |
| 8,354,509 B2 | 1/2013 | Carven et al. |
| 8,388,967 B2 | 3/2013 | Smith et al. |
| 8,389,282 B2 | 3/2013 | Sadelain et al. |
| 8,497,118 B2 | 7/2013 | Jensen |
| 8,586,023 B2 | 11/2013 | Shiku et al. |
| 8,591,886 B2 | 11/2013 | Ponath et al. |
| 8,592,576 B2 | 11/2013 | Howard et al. |
| 8,609,089 B2 | 12/2013 | Langermann et al. |
| 8,716,301 B2 | 5/2014 | Sitkovsky et al. |
| 8,716,315 B2 | 5/2014 | Figg et al. |
| 8,802,374 B2 | 8/2014 | Jensen |
| 8,883,500 B2 | 11/2014 | Sitkovsky et al. |
| 8,911,993 B2 | 12/2014 | June et al. |
| 8,987,279 B2 | 3/2015 | Bamford et al. |
| 2002/0045643 A1 | 4/2002 | Muller et al. |
| 2002/0131960 A1 | 9/2002 | Sadelain et al. |
| 2002/0164328 A1 | 11/2002 | Shinkawa et al. |
| 2003/0045552 A1 | 3/2003 | Robarge et al. |
| 2003/0096743 A1 | 5/2003 | Senter et al. |
| 2003/0115614 A1 | 6/2003 | Kanda et al. |
| 2003/0130189 A1 | 7/2003 | Senter et al. |
| 2003/0157108 A1 | 8/2003 | Presta |
| 2003/0170238 A1 | 9/2003 | Gruenberg et al. |
| 2004/0047858 A1 | 3/2004 | Blumberg et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2005/0123546 A1 | 6/2005 | Umana et al. |
| 2005/0276812 A1 | 12/2005 | Ebens et al. |
| 2006/0270045 A1 | 11/2006 | Cregg et al. |
| 2007/0116690 A1 | 5/2007 | Yang et al. |
| 2009/0082299 A1 | 3/2009 | Felber et al. |
| 2010/0028330 A1 | 2/2010 | Collins et al. |
| 2010/0247521 A1 | 9/2010 | Jones et al. |
| 2011/0003380 A1 | 1/2011 | Miltenyi et al. |
| 2011/0020343 A1 | 1/2011 | Senter et al. |
| 2011/0081311 A1 | 4/2011 | Pavlakis et al. |
| 2011/0217321 A1 | 9/2011 | Torgov et al. |
| 2012/0039906 A1 | 2/2012 | Olive |
| 2012/0114649 A1 | 5/2012 | Langermann et al. |
| 2012/0141413 A1 | 6/2012 | Pavlakis et al. |
| 2012/0177598 A1 | 7/2012 | Lefrancois et al. |
| 2013/0149337 A1 | 6/2013 | Cooper et al. |
| 2013/0156774 A1 | 6/2013 | Kuchroo et al. |
| 2013/0287748 A1 | 10/2013 | June et al. |
| 2014/0056922 A1 | 2/2014 | Sitkovsky et al. |
| 2014/0271618 A1 | 9/2014 | Markel et al. |
| 2014/0377240 A1 | 12/2014 | Sitkovsky et al. |
| 2015/0210769 A1 | 7/2015 | Freeman et al. |
| 2015/0218274 A1 | 8/2015 | Sabatos-Peyton et al. |

(56) References Cited

U.S. PATENT DOCUMENTS

| | | |
|---|---|---|
| 2015/0259420 A1 | 9/2015 | Triebel et al. |
| 2016/0313300 A1 | 10/2016 | Trotter et al. |

FOREIGN PATENT DOCUMENTS

| | | |
|---|---|---|
| EP | 1947183 | 7/2008 |
| EP | 2537416 | 12/2012 |
| WO | WO 1992/008796 | 5/1992 |
| WO | WO 1993/01286 | 1/1993 |
| WO | WO 1993/02192 | 2/1993 |
| WO | WO 1994/028143 | 12/1994 |
| WO | WO 1996/06641 | 3/1996 |
| WO | WO 1997/030087 | 8/1997 |
| WO | WO 1998/003502 | 1/1998 |
| WO | WO 1998/054170 | 12/1998 |
| WO | WO 1998/058964 | 12/1998 |
| WO | WO 1999/020758 | 4/1999 |
| WO | WO 1999/022764 | 5/1999 |
| WO | WO 1999/40196 | 8/1999 |
| WO | WO 1999/052552 | 10/1999 |
| WO | WO 2000/014257 | 3/2000 |
| WO | WO 2000/061739 | 10/2000 |
| WO | WO 2001/03720 | 1/2001 |
| WO | WO 2001/029246 | 4/2001 |
| WO | WO 2002/031140 | 4/2002 |
| WO | WO 2002/055083 | 7/2002 |
| WO | WO 2002/059106 | 8/2002 |
| WO | WO 2002/068414 | 9/2002 |
| WO | WO 2002/088172 | 11/2002 |
| WO | WO 2003/011878 | 2/2003 |
| WO | WO 2003/026577 | 4/2003 |
| WO | WO 2003/043583 | 5/2003 |
| WO | WO 2003/084570 | 10/2003 |
| WO | WO 2003/085107 | 10/2003 |
| WO | WO 2003/085119 | 10/2003 |
| WO | WO 2004/032828 | 4/2004 |
| WO | WO 2004/056312 | 7/2004 |
| WO | WO 2004/079368 | 9/2004 |
| WO | WO 2005/007190 | 1/2005 |
| WO | WO 2005/035586 | 4/2005 |
| WO | WO 2005/035778 | 4/2005 |
| WO | WO 2005/053742 | 6/2005 |
| WO | WO 2005/055808 | 6/2005 |
| WO | WO 2005/115451 | 12/2005 |
| WO | WO 2006/083289 | 8/2006 |
| WO | WO 2006/121168 | 11/2006 |
| WO | WO 2007/005874 | 1/2007 |
| WO | WO 2007/133822 | 11/2007 |
| WO | WO 2008/147482 | 12/2008 |
| WO | WO 2008/154252 | 12/2008 |
| WO | WO 2009/072003 | 6/2009 |
| WO | WO 2009/101611 | 8/2009 |
| WO | WO 2009/114335 | 9/2009 |
| WO | WO 2010/003118 | 1/2010 |
| WO | WO 2010/019570 | 2/2010 |
| WO | WO 2010/027827 | 3/2010 |
| WO | WO 2010/033140 | 3/2010 |
| WO | WO 2010/077634 | 7/2010 |
| WO | WO 2010/125571 | 11/2010 |
| WO | WO 2011/028683 | 3/2011 |
| WO | WO 2011/051726 | 5/2011 |
| WO | WO 2011/066342 | 6/2011 |
| WO | WO 2011/090754 | 7/2011 |
| WO | WO 2012/129514 | 9/2012 |
| WO | WO 2013/006490 | 1/2013 |
| WO | WO 2013/039954 | 3/2013 |
| WO | WO 2013/071154 | 5/2013 |
| WO | WO 2013/082366 | 6/2013 |
| WO | WO 2013/123061 | 8/2013 |
| WO | WO 2013/126726 | 8/2013 |
| WO | WO 2013/166321 | 11/2013 |
| WO | WO 2014/022332 | 2/2014 |
| WO | WO 2014/031687 | 2/2014 |
| WO | WO 2014/055668 | 4/2014 |
| WO | WO 2014/059251 | 4/2014 |
| WO | WO 2015/079417 | 6/2015 |
| WO | WO 2019/020758 | 1/2019 |

OTHER PUBLICATIONS

Allard et al., "Targeting CD73 Enhances the Antitumor Activity of Anti-PD-1 and Anti-CTLA-4 mAbs," Clin Cancer Res (2013) 19(20):5626-5635.

Al-Lazikani et al., "Standard conformations for the canonical structures of immunoglobulins," JMB (1997) 273:927-948.

Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93.

Arima et al., "Studies on Tomaymycin, a New Antibiotic. I Isolation and Properties of Tomaymyin," J Antibiotics (1972) 25:437-444.

Axworthy et al., "Cure of human carcinoma xenografts by a single dose of pretargeted yttrium-90 with negligible toxicity," Proc Natl Acad Sci USA (2000) 97(4):1802-1807.

Beavis et al., "Blockade of A2A receptors potently suppresses the metastasis of CD73+ tumors," PNAS (2013) 110(36):14711-14716.

Berger et al., "Phase I safety and pharmacokinetic study of CT-011, a humanized antibody interacting with PD-1, in patients with advanced hematologic malignancies," Clin Cancer Res (2008) 14(10):3044-3051.

Bertilaccio et al., "Low-Dose Lenalidomide Improves CAR-Based Immunotherapy in CLL by Reverting T-Cell Defects In Vivo," Blood (2013) 122:4171.

Blank et al., "Contribution of the PD-L1/PD-1 pathway to T-cell exhaustion: an update on implications for chronic infections and tumor evasion," Cancer Immunol Immunother (2007) 56(5):739-745.

Boris-Lawrie et al., "Recent advances in retrovirus vector technology," Cur. Opin. Genet. Develop. (1993) 3:102-109.

Brahmer et al., "Safety and Activity of Anti-PD-L1 Antibody in Patients with Advanced Cancer," N Engl J Med (2012) 366:2455-2465.

Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.

Brummelkamp et al., "A system for stable expression of short interfering RNAs in mammalian cells," Science (2002) 296(5567):550-553.

Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.

Carlens et al., "Ex vivo T lymphocyte expansion for retroviral transduction: influence of serum-free media on variations in cell expansion rates and lymphocyte subset distribution," Exp Hematol (2000) 28(10): 1137-46.

Carroll et al., "Targeting the molecular basis for tumour hypoxia," Expert Rev Mol Med (2005) 7(6):1-16.

Cavalieri et al., "Human T lymphocytes transduced by lentiviral vectors in the absence of TCR activation maintain an intact immune competence," Blood (2003) 102(2): 497-505.

Chicaybam et al., "An efficient low cost method for gene transfer to T lymphocytes," PLoS ONE (2013) 8(3): e60298.

Cho et al., "Human mammalian cell sorting using a highly integrated micro-fabricated fluorescence-activated cell sorter (microFACS)," Lab Chip (2010) 10: 1567-1573.

Clackson et al., "Making antibody fragments using phage display libraries," Nature (1991) 352:624-628.

Clusel et al., "Ex vivo regulation of specific gene expression by nanomolar concentration of double-stranded dumbbell oligonucleotides," Nucleic Acids Research (1993) 21(15):3405-3411.

Collins et al., "Chemical approaches to targeted protein degradation through modulation of the ubiquitin-proteasome pathway," Biochem J (2017) 474(7):1127-1147.

(56) References Cited

OTHER PUBLICATIONS

Cooper et al., "T-cell clones can be rendered specific for CD19: toward the selective augmentation of the graft-versus-B-lineage leukemia effect," Blood. (2003) 101:1637-1644.
Cronstein et al., "Adenosine modulates the generation of superoxide anion by stimulated human neutrophils via interaction with a specific cell surface receptor," Ann NY Acad Sci (1985) 451:291-301.
Cronstein et al., "Engagement of adenosine receptors inhibits hydrogen peroxide (H2O2–) release by activated human neutrophils," Clin Immunol Immunopathol (1987) 42(1):76-85.
Dang et al., "Nuclear and nucleolar targeting sequences of c-erb-A, c-myb, N-myc, p53, HSP70, and HIV tat proteins," JBC (1989) 264:18019-18023.
Davila et al., "CD19 CAR-targeted T cells induce long-term remission and B Cell Aplasia in an immunocompetent mouse model of B cell acute lymphoblastic leukemia," PLoS ONE (2013) 8(4): e61338.
De Felipe et al., "Skipping the co-expression problem: the new 2A "CHYSEL" technology," Genetics Vaccines and Therapy (2004) 2:13.
Dosio et al., "Immunotoxins and Anticancer Drug Conjugate Assemblies: The Role of the Linkage between Components," Toxins (2011) 3(7):848-883.
Endo et al., "High-throughput, genome-scale protein production method based on the wheat germ cell-free expression system," Biotechnol. Adv. (2003) 21: 695-713.
Fecteau et al., "Lenalidomide inhibits the proliferation of CLL cells via a cereblon/p21WAF1/Cip1-dependent mechanism independent of functional p53," Blood (2014) 124:1637-1644.
Fedorov et al., "PD-1- and CTLA-4-based inhibitory chimeric antigen receptors (iCARs) divert off-target immunotherapy responses," Sci. Transl. Medicine (2013) 5(215).
Finger et al., "The human PD-1 gene: complete cDNA, genomic organization, and developmentally regulated expression in B cell progenitors," Gene (1997) 197(1-2):177-187.
Flatman et al., "Process analytics for purification of monoclonal antibodies," J. Chromatogr. (2007) B 848:79-87.
Forsstrom et al., "Proteome-wide epitope mapping of antibodies using ultra-dense peptide arrays," Mol Cell Proteomics (2014) 13(6):1585-1597.
Gerngross et al, "Advances in the production of human therapeutic proteins in yeasts and filamentous fungi," Nat. Biotech. (2004) 22:1409-1414.
Gildener-Leapman et al., "Promising systemic immunotherapies in head and neck squamous cell carcinoma," Oral Oncol (2013) 49(12):1089-1096.
Godin et al., "Microfluidics and photonics for Bio-System-on-a-Chip: a review of advancements in technology towards a microfluidic flow cytometry chip," J Biophoton. (2008) 1(5):355-376.
Hara et al., "DC 102, A New Glycosidic PYRROLO(1, 4)Benzodiazepine Antibiotic Produced by *Streptomyces* SP," J Antibiotics (1988) 41(5):702-704.
Hartley et al., "SG2285, a Novel C2-Aryl-Substituted Pyrrolobenzodiazepine Dimer Prodrug That Cross-links DNA and Exerts Highly Potent Antitumor Activity," Cancer Research (2010) 70(17):6849-6858.
Hausler et al., "Anti-CD39 and anti-CD73 antibodies A1 and 7G2 improve targeted therapy in ovarian cancer by blocking adenosine-dependent immune evasion," Am J transl Res (2014) 6(2):129-139.
Helissey et al., "DNA minor groove cleaving agents: synthesis, binding and strand cleaving properties of anthraquinone-oligopyrrolecarboxamide hybrids," Anti-Cancer Drug Design (1996) 11(7):527-551.
Hermans et al., "The VITAL assay: a versatile fluorometric technique for assessing CTL- and NKT-mediated cytotoxicity against multiple targets in vitro and in vivo," J. Immunological Methods (2004) 285(1): 25-40.
Hershfield, "PEG-ADA: an alternative to haploidentical bone marrow transplantation and an adjunct to gene therapy for adenosine deaminase deficiency," Hum Mutat (1995) 5(2):107-112.

Hob et al., "Sibanomicin, a New Pyrrolo[1, 4]—Benzodiazepine Antitumor Antibiotic Produced by a *Micromonospora* SP," J Antibiotics (1988) 41(9):1281-1284.
Hochlowski et al., "Abbeymycin, a New Anthramycin-Type Antibiotic Produced by a Streptomycete," J Antibiotics (1987) 40(2):145-148.
Honegger A and Plückthun A, "Yet another numbering scheme for immunoglobulin variable domains: an automatic modeling and analysis tool," J Mol Biol, (2001) 8;309(3):657-70.
Hoogenboom et al., "Overview of antibody phage-display technology and its applications," Methods in Molecular Biology (2002) 178:1-37.
Huang et al., "DNA transposons for modification of human primary T lymphocytes," Methods Mol Biol (2009) 506: 115-126.
Hudecek et al., "Receptor affinity and extracellular domain modifications affect tumor recognition by ROR1-specific chimeric antigen receptor T cells," Clin. Cancer Res. (2013) 19:3153.
Ito et al., "Identification of a primary target of thalidomide teratogenicity," Science (2010) 327:1345-1350.
Jin et al., "CD73 on tumor cells impairs antitumor T-cell responses: a novel mechanism of tumor-induced immune suppression," Cancer Res (2010) 70(6):2245-2255.
Johnston, et al., "Biolistic transformation: microbes to mice," Nature (1990) 346: 776-777.
Kanda, Y. et al., "Comparison of cell lines for stable production of fucose-negative antibodies with enhanced ADCC," Biotechnol. Bioeng. (2006) 94(4):680-688.
Kim et al., "Cloning and Sequence Analysis of Another Shiga-Like Toxin IIe Variant Gene (slt-IIera) from an *Escherichia coli* R107 Strain Isolated from Rabbit," Microbiology and Immunology (1997) 41(1):805-808.
Klebanoff et al., "Sorting through subsets: which T-cell populations mediate highly effective adoptive immunotherapy?," J Immunother. (2012) 35(9): 651-660.
Kochenderfer et al., "Construction and preclinical evaluation of an anti-CD19 chimeric antigen receptor," J. Immunotherapy (2009) 32(7): 689-702.
Koste et al., "T-cell receptor transfer into human T cells with ecotropic retroviral vectors," Gene Therapy (2014) 21: 533-538.
Kunimoto et al., "Mazethramycin, a New Member of Anthramycin Group Antibiotics," J Antibiotics (1980) 33(6):665-667.
Kuramitsu et al., "Lenalidomide enhances the function of chimeric antigen receptor T cells against the epidermal growth factor receptor variant III by enhancing immune synapses," Cancer Gene Therapy (2015) 22(10):487-495.
Lefranc et al., "IMGT unique numbering for immunoglobulin and T cell receptor variable domains and Ig superfamily V-like domains," Dev Comp Immunol (2003) 27(1):55-77.
Leone et al., "A2aR antagonists: Next generation checkpoint blockade for cancer immunotherapy," Comput Struct Biotechnol J. (2015) 13:265-272.
Li et al., "Optimization of humanized IgGs in glycoengineered Pichia pastoris," Nat. Biotech. (2006) 24:210-215.
Lim et al., "Anti-CD20 monoclonal antibodies: historical and future perspectives," Haematologica (2010) 95(1):135-143.
Lipson et al., "Durable cancer regression off-treatment and effective reinduction therapy with an anti-PD-1 antibody," Clin Cancer Res (2013) 19(2):462-468.
Liu et al., "Inclusion of Strep-tag II in design of antigen receptors for T-cell immunotherapy," Nat Biotechnol (2016) 34(4):430-434.
Lopez-Girona et al., "Cereblon is a direct protein target for immunomodulatory and antiproliferative activities of lenalidomide and pomalidomide," Leukemia (2012) 26:2326-2335.
Lupton S. D. et al., "Dominant positive and negative selection using a hygromycin phosphotransferase-thymidine kinase fusion gene," Mol. and Cell Biol. (1991) 11:6.
MacCallum et al., "Antibody-antigen interactions: Contact analysis and binding site topography," J. Mol. Biol. (1996) 262, 732-745.
Manuri et al., "piggyBac transposon/transposase system to generate CD19-specific T cells for the treatment of B-lineage malignancies," Hum Gene Ther (2010) 21(4): 427-437.
Martin et al., "Modeling antibody hypervariable loops: a combined algorithm," Proc Natl Acad Sci U S A. (1989) Dec;86(23):9268-72.

(56) References Cited

OTHER PUBLICATIONS

Menzies et al., "New combinations and immunotherapies for melanoma: latest evidence and clinical utility," Ther Adv Med Oncol (2013) 5(5):278-285.
Miller et al., "Improved retroviral vectors for gene transfer and expression," BioTechniques (1989) 7:980-990.
Miller et al., "Retrovirus packaging cells," Human Gene Therapy (1990) 1:5-14.
Millon et al., "Synthesis of a New Reagent, Ethyl 4-azidobenzoylaminoacetimidate, and Its Use for RNA-Protein Cross-linking within Escherichia coli Ribosomal 30-S Subunits," Eur J Biochetn (1980) 110:485-492.
Millrine et al., "A brighter side to thalidomide: It's potential use in immunological Disorders," Trends in Mol Medicine (2017) 23(4):348-364.
Miyagishi et al., "U6 promoter-driven siRNAs with four uridine 3' overhangs efficiently suppress targeted gene expression in mammalian cells" Nat Biotechnol (2002) 20(5):497-500.
Monney et al., "Th1-specific cell surface protein Tim-3 regulates macrophage activation and severity of an autoimmune disease," Nature (2002) 415(6871):536-541.
Moody et al., "Regiospecific inhibition of DNA duplication by antisense phosphate-methylated oligodeoxynucleotides," Nucl Acids Res (1989) 17:4769-4782.
Mullen et al., "Transfer of the bacterial gene for cytosine deaminase to mammalian cells confers lethal sensitivity to 5-fluorocytosine: a negative selection system," Proc. Natl. Acad. Sci. USA (1992) 89:33.
Nelson., "CD20+ B cells: the other tumor-infiltrating lymphocytes," J Immunol. (2010) 185(9):4977-4982.
Ngiow et al., "Anti-TIM3 Antibody Promotes T Cell IFN-γ-Mediated Antitumor Immunity and Suppresses Established Tumors," Cancer Res (2011) 71(10):3540-3551.
Ogawa et al., "A cytotoxic Ribonuclease targeting specific transfer RNA anticodons," Science (1999) 283:2097-2100.
Ohta et al., "A2A adenosine receptor protects tumors from antitumor T cells," PNAS U.S.A. (2006) 103(35):13132-13137.
Okazaki et al., "Fucose depletion from human IgG1 oligosaccharide enhances binding enthalpy and association rate between IgG1 and FcgammaRIIIa," J. Mol. Biol. (2004) 336:1239-1249.
Oshima et al., "Immunomodulatory Drugs (IMiDs)," Nihon Rinsho (2014) 72(6):1130-1135.
Otahal et al., "Lenalidomide enhances antitumor functions of chimeric antigen receptor modified T cells," Oncoimmunology (2015) 5(4):e1115940.
Ott et al., "CTLA-4 and PD-1/PD-L1 Blockade: New Immunotherapeutic Modalities with Durable Clinical Benefit in Melanoma Patients," Clin Cancer Res (2013) 19(19):5300.
Pardoll, "The blockade of immune checkpoints in cancer immunotherapy," Nature (2012) 12:252-264.
Park et al., "Treating cancer with genetically engineered T cells," Trends Biotechnol. (2011) 29(11): 550-557.
Pettit et al., "Specific Activities of Dolastatin 10 and Peptide Derivatives against Cryptococcus neoformans," Antimicrobial agents and chemo (1998) 42:2961-2965.
Pinna et al., "Novel investigational adenosine A2A receptor antagonists for Parkinson's disease," Expert Opin Investig Drugs (2009) 18:1619-1631.
Portolano et al., "Lack of promiscuity in autoantigen-specific H and L chain combinations as revealed by human H and L chain "roulette"," J. Immunol. (1993) 150:880-887.
Radvanyi et al., "Antagonist antibodies to PD-1 and B7-H1 (PD-L1) in the treatment of advanced human cancer—letter," Clin Cancer Res (2013) 19(19):5541.
Rahman et al., "Effect of base sequence on the DNA cross-linking properties of pyrrolobenzodiazepine (PBD) dimers," Nucleic Acids Resarch (2011) 39(13):5800-5812.
Riddell et al., "Phase I study of cellular adoptive immunotherapy using genetically modified CD8+ HIV-specific T cells for HIV seropositive patients undergoing allogeneic bone marrow transplant," Human Gene Therapy (1992) 3:319-338.
Ripka et al., "Two Chinese hamster ovary glycosylation mutants affected in the conversion of GDP-mannose to GDP-fucose," Arch. Biochem. Biophys. (1986) 249:533-545.
Robert et al., "What is the role of cytotoxic T lymphocyte-associated antigen 4 blockade in patients with metastatic melanoma?," Oncologist (2009) 14(8):848-861.
Roberts et al., "Inhibition by adenosine of reactive oxygen metabolite production by human polymorphonuclear leucocytes," Biochem J (1985) 227(2):669-674.
Rosenberg, et al., "Cell transfer immunotherapy for metastatic solid cancer—what clinicians need to know," Nat Rev Clin Oncol. (2011) 8(10):577-85).
Sadelain et al., "The basic principles of chimeric antigen receptor design," Cancer Discov. (2013) 3(4): 388-398.
Sanderson et al., "In vivo Drug-Linker Stability of an Anti-CD30 Dipeptide-Linked Auristatin Immunoconjugate," Clin Can Res (2005) 11(2):843-852.
Scarpa et al., "Characterization of recombinant helper retroviruses from Moloney-based vectors in ecotropic and amphotropic packaging cell lines," Virology (1991) 180:849-852.
Scatchard, "The attractions of proteins for small molecules and ions," Annals of the New York Academy of Sciences (1949) 51(4):660-672.
Schrier et al., "The effects of adenosine agonists on human neutrophil function," J Immunol (1986) 137(10):3284-3289.
Seetharam et al., "Increased cytotoxic activity of Pseudomonas exotoxin and two chimeric toxins ending in KDEL," JBC (1991) 266(26):17376-17381.
Sharma et al., "Efficient sleeping beauty DNA transposition from DNA minicircles," Molec Ther Nucl Acids (2013) 2, e74.
Shinohara et al., "Structure and chromosomal localization of the human PD-1 gene (PDCD1)," Genomics (1994) 23:704-706.
Sitaraman et al., "High-throughput protein expression using cell-free system," Methods Mol. Biol. (2009) 498: 229-44.
Sitkovsky et al., "Hostile, hypoxia-A2-adenosinergic tumor biology as the next barrier to overcome for tumor immunologists," Cancer Immunol Re (2014) 2(7):598-605.
Spirin, et al., "High-throughput cell-free systems for synthesis of functionally active proteins," Trends Biotechnol. (2004) 22: 538-45.
Stirpe et al., Bio/Technology 10:405-12, 1992.
Sun et al. (2002) Bioorganic & Medicinal Chemistry Letters 12:2213-2215.
Sun et al. (2003) Bioorganic & Medicinal Chemistry 11:1761-1768.
Szoka et al., "Comparative properties and methods of preparation of lipid vesicles (liposomes)," Ann. Rev. Biophys. Bioeng. (1980) 9: 467.
Takeuchi et al., J. Antibiotics, 29, 93-96 (1976).
Terakura et al., "Generation of CD19-chimeric antigen receptor modified CD8+ T cells derived from virus-specific central memory T cells," Blood (2012) 1:72-82.
Themeli et al., "Generation of tumor-targeted human T lymphocytes from induced pluripotent stem cells for cancer therapy," Nat Biotechnol. (2013) 31(10): 928-933.
Toki et al. J Org Chem (2002) 67:1866-1872.
Topalian et al., "Safety, Activity, and Immune Correlates of Anti-PD-1 Antibody in Cancer," N Engl J Med (2012) 366:2443-2454.
Tsukahara et al., "CD19 target-engineered T-cells accumulate at tumor lesions in human B-cell lymphoma xenograft mouse models," Biochem Biophys Res Commun (2013) 438(1): 84-9.
Tsunakawa, et al., J. Antibiotics, 41, 1366-1373 (1988)).
Turtle et al., "Engineered T cells for anti-cancer therapy," Curr. Opin. Immunol. (2012) 24(5): 633-39.
Unno et al., Chem. Pharm. Bull. 45:125-133, 1997.
Van Tendeloo et al., "High-level transgene expression in primary human T lymphocytes and adult bone marrow CD34+ cells via electroporation-mediated gene delivery," Gene Therapy (2000) 7(16): 1431-1437).
Verhoeyen et al., "Lentiviral vector gene transfer into human T cells," Methods Mol Biol. (2009) 506: 97-114.
Wada et al., "Sequencing CTLA-4 blockade with cell-based immunotherapy for prostate cancer," J Transl Med (2013) 11:89.

(56) References Cited

OTHER PUBLICATIONS

Wadhwa et al., "Receptor mediated glycotargeting," J. Drug Targeting (1995) 3: 111.
Wang et al., "Phenotypic and functional attributes of lentivirus-modified CD19-specific human CD8+ central memory T cells manufactured at clinical scale," J Immunother. (2012) 35(9):689-701.
Weber, "Review: anti-CTLA-4 antibody ipilimumab: case studies of clinical response and immune-related adverse events," Oncologist (2007) 12(7):864-872.
Wigler et al., Cell 2:223, 1977.
Wilson, "Tech.Sight. Analyzing biomolecular interactions," Science (2002) 295(5562):2103-2105.
Wolff et al., "Monoclonal Antibody Homodimers: Enhanced Antitumor Activity in Nude Mice," Can Res (1993) 53:2560-2565.
Woyke et al. (2001) Antimicrob. Agents and Chemother. 45(12):3580-3584.
Wu et al., "Adoptive T-cell therapy using autologous tumor-infiltrating lymphocytes for metastatic melanoma: current status and future outlook," Cancer (2012) 18(2): 160-75.
Yamane-Ohnuki et al., "Establishment of FUT8 knockout Chinese hamster ovary cells: an ideal host cell line for producing completely defucosylated antibodies with enhanced antibody-dependent cellular cytotoxicity," Biotech. Bioeng. (2004) 87: 614.
Yu et al. (2002) PNAS 99:7968-7973.
Zhang et al., "CD73: a novel target for cancer immunotherapy," Cancer Res (2010) 70(16):6407-6411.
Zheng et al., "A novel anti-CEACAM5 monoclonal antibody, CC4, suppresses colorectal tumor growth and enhances NK cells-mediated tumor immunity," PLoS One (2011) 6(6):e21146.
Agrawal et al., "Oligodeoxynucleoside methylphosphonates: synthesis and enzymic degradation," Tetrahedron Letters (1987) 28(31): 3539-3542.
Armstrong et al., "A Phase I Study of Chemically Synthesized Verotoxin (Shiga-like Toxin) Pk-Trisaccharide Receptors Attached to Chromosorb for Preventing Hemolytic-Uremic Syndrome," J Infect Diseases (1995) 171(4):1042-1045.
Bassiouni et al., "Chaperonin Containing TCP-1 Protein Level in Breast Cancer Cells Predicts Therapeutic Application of a Cytotoxic Peptide," Clin Cancer Res (2016) 22(17):4366-79.
Baumert et al., "RNA-Protein Neighbourhoods of the Ribosome Obtained by Crosslinking," Eur J Biochem (1978) 89:353-359.
Behroozi et al., "1,2-Dithiolan-3-one 1-Oxides: A Class of Thiol-Activated DNA-Cleaving Agents That Are Structurally Related to the Natural Product Leinamycin," Biochemistry (1996) 35:1768-1774.
Bose et al., "Effect of linker length on DNA-binding affinity, cross-linking efficiency and cytotoxicity of C8-linked pyrrolobenzodiazepine dimers," J Chem Soc Chem Commun (1992) 14:1518-1520.
Bose et al., "Rational design of a highly efficient irreversible DNA interstrand cross-linking agent based on the pyrrolobenzodiazepine ring system," J Am Chem Soc (1992) 114:4939-4941.
Bose et al., "New approaches to pyrrolo[2,1-c][1,4]benzodiazepines: synthesis, DNA-binding and cytotoxicity of DC-81," Tetrahedron (1992) 48(4):751-758.
Brinkmann et al., "Immunotoxins against cancer," Biochim Biophys Acta (1994) 1198(1):27-45.
Buchner et al., "A method for increasing the yield of properly folded recombinant fusion proteins: single-chain immunotoxins from renaturation of bacterial inclusion bodies," Anal Biochem. (1992) 205(2): 263-270.
Doronina et al., "Development of potent monoclonal antibody auristatin conjugates for cancer therapy," Nature Biotechnology (2003) 21:778-784.
Doronina et al., "Enhanced Activity of Monomethylauristatin F through Monoclonal Antibody Delivery: Effects of Linker Technology on Efficacy and Toxicity," Bioconjugate Chem (2006) 17:114-124.

Ducry et al., "Antibody-drug conjugates: linking cytotoxic payloads to monoclonal antibodies," Bioconjug Chem (2010) 21(1):5-13.
Eckstein et al., "Nucleoside Phosphorothioates," Ann Rev Biochem. (1985) 54:367-402.
Eckstein et al., "Phosphorothioates in molecular biology," Trends Biochem Sci (1989) 14(3):97-100.
Fields et al., "Solid phase peptide synthesis utilizing 9-fluorenylmethoxycarbonyl amino acids," Int J Peptode Protein Res (1990) 35:161-214.
Fiser et al., "Photoaffinity reaction between polyuridylic acid and protein S1 on the *Escherichia coli* ribosome," FEBS Lett. (1975) 52(2): 281-283.
Gao et al., "Chaperonin containing TCP1 subunit 5 is a tumor associated antigen of non-small cell lung cancer," Oncotarget (2017) 8(38):64170-64179.
Geiser et al., "Automation of solid-phase peptide synthesis," Macromolecular Sequencing and Synthesis (1988) p. 199-218.
Gregson et al., "Design, Synthesis, and Evaluation of a Novel Pyrrolobenzodiazepine DNA-Interactive Agent with Highly Efficient Cross-Linking Ability and Potent Cytotoxicity," J Med Chem (2001) 44:737-748.
Gregson et al., "Linker Length Modulates DNA Cross-Linking Reactivity and Cytotoxic Potency of C8/C8' Ether-Linked C2-exo-Unsaturated Pyrrolo[2,1-c][1,4]benzodiazepine (PBD) Dimers," J Med Chem (2004) 47:1161-1174.
Hermanson et al., Bioconjugate Techniques; Academic Press: New York, p. 234-242.
Hurley et al., "Covalent binding of antitumor antibiotics in the minor groove of DNA. Mechanism of action of CC-1065 and the pyrrolo(1,4)benzodiazepines," Acc. Chem. Res. (1986) 19(8): 230-237.
Hynes et al., "Analysis of chaperonin-containing TCP-1 subunits in the human keratinocyte two-dimensional protein database: Further characterisation of antibodies to individual subunits," Electrophoresis (1996) 17(11):1720-1727.
Hynes et al., "Individual subunits of the eukaryotic cytosolic chaperonin mediate interactions with binding sites located on subdomains of beta-actin," Journal of Biological Chemistry (2000) 275(25):18985-18994.
Islam et at., "Structure-activity studies of antitumor agents based on pyrrolo[1,2-a]benzimidazoles: new reductive alkylating DNA cleaving agents," J. Med. Chem. (1991) 34(10) 2954-2961.
Issell et al., "Maytansine," Cancer Treat Rev (1978) 5(4):199-207.
Jager et al., "Oligonucleotide N-alkylphosphoramidates: synthesis and binding to polynucleotides," Biochemistry (1988) 27:7237-7246.
King et al., "Facile synthesis of maleimide bifunctional linkers," Tetrahedron Letters (2002) 43(11):1987-1990.
Kohn, "Anthramycin," In Antibiotics III. Springer-Verlag, New York, (1975) pp. 3-11.
Konishi et al., "Chicamycin, a new antitumor antibiotic. II. Structure determination of chicamycins A and B," J Antibiotics (1984) 37(3):200-206.
Langley et al., "A versatile and efficient synthesis of carbinolamine-containing pyrrolo[1,4]benzodiazepines via the cyclization of N-(2-aminobenzoyl)pyrrolidine-2-carboxaldehyde diethyl thioacetals: total synthesis of prothracarcin," J Org Chem (1987) 52:91-97.
Leber et al., "A revised structure of sibiromycin," J Am Chem Soc (1988) 110: 2992-2993.
Lee et al., "T cells expressing CD19 chimeric antigen receptors for acute lymphoblastic leukaemia in children and yound adults: a phase 1 dose escalation trial," The Lancet (2015) 385(9967): 517-528.
Leimgruber et al., "Isolation and Characterization of Anthramycin, a New Antitumor Antibiotic," J Am Chem Soc (1965) 87: 5791-5793.
Letsinger et al., "Some developments in the phosphitetriester method for synthesis of oligonucleotides," Tetrahedron (1984) 40:137-143.
Lewis et al., "Maleimidocysteineamido-DOTA derivatives: new reagents for radiometal chelate conjugation to antibody sulfhydryl groups undergo pH-dependent cleavage reactions," Bioconjug Chem (1998) 9(1):72-86.

(56) References Cited

OTHER PUBLICATIONS

Mesri et al., "Heparin-binding transforming growth factor alpha-Pseudomonas exotoxin A. A heparan sulfate-modulated recombinant toxin cytotoxic to cancer cells and proliferating smooth muscle cells.," J. Biol. Chem. (1993) 268(7): 4853-4862.
Miller et al., "Conformation and interaction of dinucleoside mono- and diphosphates. V. Syntheses and properties of adenine and thymine nucleoside alkyl phosphotriesters, the neutral analogs of dinucleoside monophosphates," J Am Chem Soc (1971) 93: 6657-6665.
Oste et al., "The use of sym-triazine trichloride in RNA-protein cross-linking studies with *Escherichia coli* ribosomal subunits," Mol General Genetics MGG (1979) 168:81-86.
Pastan et al., "Recombinant toxins as novel therapeutic agents," Annu Rev Biochem (1992) 61:331-354.
Remillard et al., "Antimitotic activity of the potent tumor inhibitor maytansine," Science (1975) 189(4207):1002-1005.
Rinke et al., "The use of azidoarylimidoesters in RNA-protein cross-linking studies with *Escherichia coli* ribosomes," J Mol Biol. (1980) 137:301-304.
Roh et al., "Contribution of the Type II Chaperonin, TRIC/CCT, to Oncogenesis," Int J Mol Sci (2015) 16(11): 26706-20.
Routier et al., "Synthesis, DNA binding, and cleaving properties of an ellipticine-salen.copper conjugate," Bioconjug Chem (1997) 8(6):789-792.
Sandvig et al., "Endocytosis, intracellular transport, and cytotoxic action of Shiga toxin and ricin," Physiologocial Reviews (1996) 76: 949-966.
Schroder et al., "Formation of the Peptide Bond", The Peptides (1965) vol. 1; 76-136.
Senter et al., "Immunoconjugates comprised of drugs with impaired cellular permeability: A new approach to targeted therapy," Proc Amer Assoc Cancer Res (2004) vol. 45 Abstract 623.
Senter et al., "Potent antibody drug conjugates for cancer therapy," Curr Opin Chem Biol (2009) 13(3): 235-244.
Shimizu, et al., J. Antibiotics, (1982) 35(8):972-978.
Skibo et al., "Structure-activity studies of benzimidazole-based DNA-cleaving agents. Comparison of benzimidazole, pyrrolobenzimidazole, and tetrahydropyridobenzimidazole analogs," J Med Chem (1994) 37: 78-92.

Skinner et al., "Inhibition of prokaryotic translation by the Shiga toxin enzymatic subunit," Microbial Pathogenesis (1998) 24(2): 117-122.
Smarda et al., "Colicins—Exocellular lethal proteins of *Escherichia coli*," Folia Microbiologica (1998) 43: 563-582.
Sperling et al., "Photochemical cross-linking of histones to DNA in nucleosomes," Nucleic Acids Research (1978) 5(8): 2755-2774.
Stec et al., "Synthesis and absolute configuration of P-chiral—isopropyl oligonucleotide triesters," Tetrahedron Letters (1985) 25(18): 2191-2194.
Stein et al., "Phosphorothioate Oligodeoxynucleotide Analogues," In: Oligodeoxynucleotides. Antisense Inhibitors of Gene Expression, Cohen, ed, Macmillan Press, London, (1989) pp. 97-117.
Sullenger et al., "Tethering ribozymes to a retroviral packaging signal for destruction of viral RNA," Science (1993) 262:1566-1569.
Thurston et al., "Synthesis of Sequence-Selective C8-Linked Pyrrolo[2,1-c][1,4]benzodiazepine DNA Interstrand Cross-Linking Agents," J Org Chem (1996) 61: 8141-8147.
Thurston et al., "The molecular recognition of DNA" Chem. Brit. (1990) 26; 767-772.
Unno et al., "Structure-activity relationships of cyclic enediynes related to dynemicin A—I. Synthesis and antitumor activity of 9-acetoxy enediynes equipped with aryl carbamate moieties," Bioorg. Med. Chem. (1997) 5(5): 883-901.
Unno et al., "Structure-activity relationships of cyclic enediynes related to dynemicin A. II. Synthesis and antitumor activity of 9- and 12-substituted enediynes equipped with aryl carbamate moieties," Bioorg. Med. Chem. (1997) 5(5): 903-919.
Vanin et al., "p-Azidophenylglyoxal: A Heterobifunctional Photosensitive Reagent," FEBS Lett (1981) 124(1): 89-92.
Wool et al., "Ribotoxin recognition of ribosomal RNA and a proposal for the mechanism of translocation," Trends Biochem. Sci., (1992) 17(7): 266-269.
Xu et al., "DNA Damage Produced by Enediynes in the Human Phosphoglycerate Kinase Gene in Vivo: Esperamicin A1 as a Nucleosome Footprinting Agent," Biochemistry (1998) 37(7):1890-1897.
Hynes et al., "Antibody characterisation of two distinct conformations of the chaperonin-containing TCP-1 from mouse testis," FEBS Letters (1995) 358(2):129-132.

* cited by examiner

US 12,006,356 B2

ANTI-CCT5 BINDING MOLECULES AND CHIMERIC ANTIGEN RECEPTORS COMPRISING THE SAME

CROSS-REFERENCE TO RELATED APPLICATIONS

This application is a national stage application under 35 U.S.C. § 371 of International Application No. PCT/US2018/065866, filed internationally on Dec. 14, 2018 which claims priority to U.S. provisional application 62/599,682, filed Dec. 15, 2017, entitled "ANTI-CCT5 BINDING MOLECULES AND METHODS OF USE THEREOF," the contents of which are incorporated by reference in their entirety for all purposes.

INCORPORATION BY REFERENCE OF SEQUENCE LISTING

The present application is being filed along with a Sequence Listing in electronic format. The Sequence Listing is provided as a file entitled 735042014600SubSeqList.txt, created Apr. 5, 2021, which is 98,304 bytes in size. The information in the electronic format of the Sequence Listing is incorporated by reference in its entirety.

FIELD

The present disclosure relates in some aspects to binding molecules that bind to Chaperonin Containing TCP1 Subunit 5 (CCT5), in particular, to anti-CCT5 antibodies, including antibody fragments. The present disclosure further relates to antibody conjugates, including antibody-drug conjugates; bispecific antibodies; and recombinant receptors, such as chimeric antigen receptors (CARs) containing such antibodies. The disclosure further relates to genetically engineered cells expressing such receptors and antibodies, and use thereof in adoptive cell therapy.

BACKGROUND

Various binding molecules against tumor antigens, including antibodies or antigen-binding fragments, are available. In some cases, such binding molecules, in particular antigen-binding fragments of antibodies (e.g. scFv) have been employed as antigen-binding domains in chimeric antigen receptors (CARs) and expressed on the surface of engineered cells, e.g. CAR-T cells. Improved binding molecules and engineered tumor-targeting cells, such as CAR-T cells, are needed. For example, there is a need for molecules and cells, including antibody fragments that specifically bind to a solid tumor target antigen, and chimeric receptors expressing such human antibodies for use in adoptive cell therapy. Provided herein are embodiments that meet such needs.

SUMMARY

Provided herein is an antibody or antigen-binding fragment thereof, wherein the antibody or antigen-binding fragment specifically binds to a peptide sequence set forth in SEQ ID NO:68 ($X_1SVEX_5X_6KX_8$), wherein X is any amino acid and/or a peptide comprising an amino acid sequence set forth in SEQ ID NO:68 ($X_1SVEX_5X_6KX_8$), wherein X is any amino acid. Also provided herein is an antibody or antigen-binding fragment thereof, wherein the antibody or antigen-binding fragment specifically binds to an epitope that is or is contained within the peptide sequence set forth in SEQ ID NO:68 ($X_1SVEX_5X_6KX_8$), wherein X is any amino acid.

In certain embodiments of any of the provided antibodies or antigen-binding fragments, $X_1$ is threonine, serine or aspartic acid, $X_5$ is aspartic acid or alanine, $X_6$ is tyrosine, phenylalanine, or isoleucine and $X_8$ is alanine or arginine. In particular embodiments of any of the provided antibodies or antigen-binding fragments, wherein the peptide sequence consists of the sequence TSVEDYKA (SEQ ID NO:70), SSVEAFKR (SEQ ID NO:71) OR DSVEAIKA (SEQ ID NO:72).

In some embodiments of any of the provided antibodies or antigen-binding fragments, the antibody or antigen-binding fragment comprises: a heavy chain variable ($V_H$) region having at least 90%, 91%, 92%, 93%, 94%, 95%, 96%, 97%, 98% or 99% sequence identity to the $V_H$ region amino acid sequence set forth in SEQ ID NO:1; and a light chain variable ($V_L$) region having at least 90%, 91%, 92%, 93%, 94%, 95%, 96%, 97%, 98% or 99% sequence identity to the $V_L$ region amino acid sequence set forth in SEQ ID NO:2.

In certain embodiments of any of the provided antibodies or antigen-binding fragments, the antibody or antigen-binding fragment comprises: a heavy chain variable ($V_H$) region having at least 90%, 91%, 92%, 93%, 94%, 95%, 96%, 97%, 98% or 99% sequence identity to the $V_H$ region amino acid sequence set forth in SEQ ID NO:1; and a light chain variable ($V_L$) region having at least 90%, 91%, 92%, 93%, 94%, 95%, 96%, 97%, 98% or 99% sequence identity to the $V_L$ region amino acid sequence set forth in SEQ ID NO:2.

In particular embodiments of any of the provided antibodies or antigen-binding fragments: the $V_H$ region comprises a CDR-H3 comprising the amino acid sequence set forth in SEQ ID NO:13 or a CDR-H3 contained within the $V_H$ region amino acid sequence set forth in SEQ ID NO:1; and/or the $V_L$ region comprises a CDR-L3 comprising the amino acid sequence set forth in SEQ ID NO: 23, or a CDR-L3 contained within the $V_L$ region amino acid sequence set forth in SEQ ID NO:2. In some embodiments of any of the provided antibodies or antigen-binding fragments: the $V_H$ region comprises a CDR-H1 and a CDR-H2 contained within the $V_H$ region amino acid sequence set forth in SEQ ID NO:1.; and/or the $V_L$ region comprises a CDR-L1 and a CDR-L2 contained within the $V_L$ region amino acid sequence set forth in SEQ ID NO:2.

Provided herein is an antibody or antigen-binding fragment thereof comprising: a heavy chain variable ($V_H$) region comprising a heavy chain complementarity determining region 1 (CDR-H1) 1, a CDR-H2, and a CDR-H3, respectively, comprising the amino acid sequences of CDR-H1, CDR-H2, and CDR-H3 sequences contained within the $V_H$ region amino acid sequence set forth in SEQ ID NO: 1; and/or a light chain variable ($V_L$) region comprising a light chain complementarity determining region 1 (CDR-L1), a CDR-L2, and a CDR-L3, respectively, comprising the amino acid sequences of CDR-L1, CDR-L2, and CDR-L3 sequences contained within the light chain variable ($V_L$) region amino acid sequence set forth in SEQ ID NO: 2.

In certain embodiments of any of the provided antibodies or antigen-binding fragments: the $V_H$ region comprises a CDR-H1 comprising the amino acid sequence set forth in SEQ ID NO:11; a CDR-H2 comprising the amino acid sequence set forth in SEQ ID NO: 12; and a CDR-H3 comprising the amino acid sequence set forth in SEQ ID NO: 13; and/or the $V_L$ region comprises a CDR-L1 comprising the amino acid sequence set forth in SEQ ID NO:21; a CDR-L 2 comprises the amino acid sequence set forth in SEQ ID NO: 22; and a CDR-L3 comprising the amino acid sequence set forth in SEQ ID NO: 23.

Provided herein is an antibody or antigen-binding fragment thereof, wherein the antibody or antigen-binding fragment comprises: a heavy chain variable ($V_H$) region comprising a CDR-H1 comprising the amino acid sequence set forth in SEQ ID NO:11; a CDR-H2 comprising the amino acid sequence set forth in SEQ ID NO: 12; and a CDR-H3 comprising the amino acid sequence set forth in SEQ ID NO: 13; and/or a light chain variable ($V_L$) region comprising a CDR-L1 comprising the amino acid sequence set forth in SEQ ID NO:21; a CDR-L 2 comprises the amino acid sequence set forth in SEQ ID NO: 22; and a CDR-L3 comprising the amino acid sequence set forth in SEQ ID NO: 23.

In particular embodiments of any of the provided antibodies or antigen-binding fragments, the antibody or antigen binding fragment comprises a $V_H$ region comprising a CDR-H1, CDR-H2, and CDR-H3 comprising the amino acid sequence of SEQ ID NOs: 11, 12, and 13, respectively and a $V_L$ region comprising a CDR-L1, CDR-L2, and CDR-L3 comprising the amino acid sequence of SEQ ID NOs: 21, 22, and 23, respectively.

In some embodiments of any of the provided antibodies or antigen-binding fragments, the $V_H$ region comprises the amino acid sequence set forth in SEQ ID NO: 1. In certain embodiments of any of the provided antibodies or antigen-binding fragments, the $V_L$ region comprises the amino acid sequence set forth in SEQ ID NO: 2. In particular embodiments of any of the provided antibodies or antigen-binding fragments, the $V_H$ and $V_L$ regions of the antibody or antigen-binding fragment thereof comprise the amino acid sequences of SEQ ID NOs:1 and 2, respectively.

In some embodiments, any of the provided antibodies or antigen-binding fragments are anti-CCT5 antibodies or antigen-binding fragments.

In some embodiments of any of the provided antibodies or antigen-binding fragments, the antibody or antigen-binding fragment specifically binds to the same or an overlapping epitope as specifically bound by any of the provided antibody or antigen-binding fragment. In certain embodiments of any of the provided antibodies or antigen-binding fragments, the antibody or antigen-binding fragment competes with any of the provided antibodies or antigen-binding fragment for binding to CCT5, to a peptide set forth in SEQ ID NO:68 ($X_1SVEX_5X_6KX_8$), wherein X is any amino acid, or to a peptide set forth in SEQ ID NO:69.

In particular embodiments of any of the provided antibodies or antigen-binding fragments, said antibody or antigen-binding fragment specifically binds to a chaperonin containing TCP1 subunit 5 (CCT5) protein. In some embodiments of any of the provided antibodies or antigen-binding fragments, the CCT5 protein is a human CCT5 protein, a mouse CCT5 protein, or a non-human primate CCT5 protein. In certain embodiments of any of the provided antibodies or antigen-binding fragments, the CCT5 protein is a human CCT5 protein.

In particular embodiments of any of the provided antibodies or antigen-binding fragments, the CCT5 comprises the sequence set forth in SEQ ID NO:45 or 46 or a sequence of amino acids that exhibits at least or about at least 90%, 91%, 92%, 93%, 94%, 95%, 96%, 97%, 98%, 99% or more sequence identity to SEQ ID NO:45 or 46. In some embodiments of any of the provided antibodies or antigen-binding fragments, the CCT5 protein comprises the amino acid sequence set forth in SEQ ID NO:45 or 46. In some embodiments of any of the provided antibodies or antigen-binding fragments, the CCT5 protein is expressed on the surface of a cell, optionally a tumor or a cancer cell.

In certain embodiments of any of the provided antibodies or antigen-binding fragments, the antibody or antigen-binding fragment specifically binds to a peptide sequence set forth in SEQ ID NO:68 ($X_1SVEX_5X_6KX_8$), wherein X is any amino acid. In particular embodiments of any of the provided antibodies or antigen-binding fragments, $X_1$ is threonine, serine or aspartic acid, $X_5$ is aspartic acid or alanine, $X_6$ is tyrosine, phenylalanine, or isoleucine and $X_8$ is alanine or arginine. In some embodiments of any of the provided antibodies or antigen-binding fragments, the peptide sequence consists of the sequence TSVEDYKA (SEQ ID NO:70), SSVEAFKR (SEQ ID NO:71) OR DSVEAIKA (SEQ ID NO:72). In certain embodiments of any of the provided antibodies or antigen-binding fragments, the antibody or antigen-binding fragment is human. In particular embodiments of any of the provided antibodies or antigen-binding fragments, the antibody is a human antibody.

In some embodiments of any of the provided antibodies or antigen-binding fragments: the antibody or antigen-binding fragment comprises a heavy chain variable ($V_H$) region, said $V_H$ region comprises a portion having at least 95%, 96%, 97%, 98%, 99%, or 100% sequence identity to an amino acid sequence encoded by a germline nucleotide human heavy chain V segment, a portion with at least 95%, 96%, 97%, 98%, 99%, or 100% sequence identity to an amino acid sequence encoded by a germline nucleotide human heavy chain D segment, and/or a portion having at least 95%, 96%, 97%, 98%, 99%, or 100% sequence identity to an amino acid sequence encoded by a germline nucleotide human heavy chain J segment; and/or the antibody or antigen-binding fragment comprises a light chain variable ($V_L$) region, said $V_L$ region comprises a portion with at least 95%, 96%, 97%, 98%, 99%, or 100% sequence identity to an amino acid sequence encoded by a germline nucleotide human kappa or lambda chain V segment, and/or a portion with at least 95%, 96%, 97%, 98%, 99%, or 100% sequence identity to an amino acid sequence encoded by a germline nucleotide human kappa or lambda chain J segment.

In certain embodiments of any of the provided antibodies or antigen-binding fragments: the CDR-H1 and/or CDR-H2 comprises a sequence 100% identical or with no more than one amino acid difference as compared to an amino acid sequence of a CDR-H1 and/or CDR-H2, respectively, within a sequence encoded by a germline nucleotide human heavy chain V segment; and/or the CDR-L1 and/or CDR-L2 comprises a sequence 100% identical or with no more than one amino acid difference as compared to an amino acid sequence of a CDR-L1 and/or CDR-L2, respectively, within a sequence encoded by a germline nucleotide human kappa or lambda v segment.

In particular embodiments of any of the provided antibodies or antigen-binding fragments, the antibody or antigen-binding fragment is recombinant. In some embodiments of any of the provided antibodies or antigen-binding fragments, the antibody or antigen-binding fragment is monoclonal. In certain embodiments of any of the provided antibodies or antigen-binding fragments, the antibody or antigen-binding fragment thereof is an antigen-binding fragment. In particular embodiments of any of the provided antibodies or antigen-binding fragments, the antibody or antigen-binding fragment thereof is a single chain fragment. In some embodiments of any of the provided antibodies or antigen-binding fragments, the antigen-binding fragment comprises an scFv. In certain embodiments of any of the provided antibodies or antigen-binding fragments, the $V_H$ region is amino-terminal to the $V_L$ region. In particular embodiments of any of the provided antibodies or antigen-binding fragments, the $V_H$ region is carboxy-terminal to the $V_L$ region.

In some embodiments of any of the provided antibodies or antigen-binding fragments, the antibody or antigen binding fragment is a fragment comprising antibody $V_H$ and $V_L$ regions joined by a flexible linker. In certain embodiments of any of the provided antibodies or antigen-binding fragments, the scFv comprises a linker comprising the amino acid sequence GGGGSGGGGSGGGGS (SEQ ID NO:49).

In particular embodiments of any of the provided antibodies or antigen-binding fragments, the scFv comprises the amino acid sequence set forth in SEQ ID NO:52, or an amino acid sequence having at least 90%, 91%, 92%, 93%, 94%, 95%, 96%, 97%, 98%, or 99% sequence identity to the amino acid sequence set forth in SEQ ID NO:52. In some embodiments of any of the provided antibodies or antigen-binding fragments, the antibody or antigen-binding fragment thereof further comprises at least a portion of an immunoglobulin constant region.

In certain embodiments of any of the provided antibodies or antigen-binding fragments, the antibody or antigen-binding fragment thereof is a whole or intact antibody. In particular embodiments of any of the provided antibodies or antigen-binding fragments, the antibody or antigen-binding fragment thereof is a bispecific antibody. In some embodiments of any of the provided antibodies or antigen-binding fragments, the antibody or antigen-binding fragment thereof further specifically binds to a second antigen. In some embodiments of any of the provided antibodies or antigen-binding fragments, the second antigen is expressed on a tumor cell or a T cell.

In certain embodiments of any of the provided antibodies or antigen-binding fragments, the antibody or antigen-binding fragment thereof the second antigen is expressed on a tumor cell, optionally a tumor cell that expresses or aberrantly expresses CCT5, or a T cell. In particular embodiments of any of the provided antibodies or antigen-binding fragments, the antibody or antigen-binding fragment thereof the second antigen is expressed on a tumor cell and the tumor cell is of an epithelial cell cancer. In some embodiments of any of the provided antibodies or antigen-binding fragments, the second antigen is expressed on a T cell and the T cell antigen is CD2 or CD3.

Provided herein is a single chain cell-surface protein, comprising any of the provided antibody or antigen-binding fragment, and optionally a transmembrane domain. Provided herein is a single chain cell-surface protein, comprising an antibody or antigen-binding fragment that specifically binds to CCT5, and optionally a transmembrane domain. In certain embodiments of any of the provided single chain cell surface proteins, the single chain cell surface protein is an antigen-binding fragment, optionally an scFv. In particular embodiments of any of the provided single chain cell surface proteins, the antigen-binding fragment is an scFv and the scFv comprises the amino acid sequence set forth in SEQ ID NO: 52 or a sequence of amino acids that exhibits at least 85%, 90%, 91%, 92%, 93%, 94%, 95%, 96%, 97%, 98% or 99% sequence identity to SEQ ID NO:52 and that binds CCT5 or a peptide comprising the sequence set forth in SEQ ID NO:68, optionally a peptide set forth in any of SEQ ID NOS: 70-72.

Provided herein is a conjugate, comprising any of the provided antibody or antigen-binding fragments and a heterologous molecule or moiety. Provided herein is a conjugate, comprising an antibody or antigen-binding fragment that specifically binds to CCT5 and a heterologous molecule or moiety. In some embodiments of any of the provided conjugates, the heterologous molecule or moiety is a protein, peptide, nucleic acid or small molecule. In certain embodiments of any of the provided conjugates, the heterologous molecule or moiety is a cytotoxic agent, a toxin, a radioisotope, a chemotherapeutic agent, a lytic peptide or a cytokine. In particular embodiments of any of the provided conjugates, the antibody or antigen-binding fragment and moiety are linked directly or indirectly via a linker. In some embodiments of any of the provided conjugates, the antibody or antigen-binding fragment and the moiety are covalently or chemically linked. In certain embodiments of any of the provided conjugates, the moiety is a protein or peptide and the conjugate is a fusion protein.

Provided herein is a chimeric antigen receptor (CAR) comprising an extracellular portion comprising any of the provided antibody or antigen-binding fragments and an intracellular signaling region. Provided herein is a chimeric antigen receptor (CAR) comprising an extracellular portion comprising an antibody or antigen-binding fragment that specifically binds CCT5 and an intracellular signaling region. In particular embodiments of any of the provided chimeric antigen receptors, the extracellular portion comprises an antigen-binding fragment and the antigen-binding fragment is an scFv. In some embodiments of any of the provided chimeric antigen receptors, the scFv comprises the amino acid sequence set forth in SEQ ID NO: 52 or a sequence of amino acids that exhibits at least 85%, 90%, 91%, 92%, 93%, 94%, 95%, 96%, 97%, 98% or 99% sequence identity to SEQ ID NO:52 and that binds CCT5 or a peptide comprising the sequence set forth in SEQ ID NO:68, optionally a peptide set forth in any of SEQ ID NOS: 70-72.

In certain embodiments of any of the provided chimeric antigen receptors, wherein the intracellular signaling region is or comprises a primary signaling domain, an signaling domain that is capable of inducing a primary activation signal in a T cell, a signaling domain of a T cell receptor (TCR) component, and/or a signaling domain comprising an immunoreceptor tyrosine-based activation motif (ITAM). In particular embodiments of any of the provided chimeric antigen receptors, the intracellular signaling region is or comprises an intracellular signaling domain of a CD3 chain, optionally a CD3-zeta (CD3ζ) chain, or a signaling portion thereof.

In some embodiments of any of the provided chimeric antigen receptors, the CAR further comprises a transmembrane domain disposed between the extracellular domain and the intracellular signaling region. In certain embodiments of any of the provided chimeric antigen receptors, the transmembrane domain comprises a transmembrane portion of CD28. In particular embodiments of any of the provided chimeric antigen receptors, the intracellular signaling region further comprises a costimulatory signaling domain. In some embodiments of any of the provided chimeric antigen receptors, the costimulatory signaling domain comprises an intracellular signaling domain of a T cell costimulatory molecule or a signaling portion thereof. In certain embodiments of any of the provided chimeric antigen receptors, the costimulatory signaling domain comprises an intracellular signaling domain of a CD28, a 4-1BB or an ICOS or a signaling portion thereof. In particular embodiments of any of the provided chimeric antigen receptors, the costimulatory signaling domain comprises an intracellular signaling domain of a 4-1BB or a signaling portion thereof. In some embodiments of any of the provided chimeric antigen receptors, the costimulatory signaling domain is between the transmembrane domain and the intracellular signaling domain.

Provided herein is a polynucleotide encoding any of the provided antibody or antigen-binding fragment thereof, any of the provided single chain cell surface protein, any of the provided conjugates or any of the provided chimeric antigen receptors. In certain embodiments, the provided polynucleotide further encodes a signal sequence, optionally wherein the signal sequence is a GM-CSF signal sequence, a CD8 signal sequence, an Ig kappa signal sequence or a CD33 signal sequence.

Provided herein is a vector, comprising any of the provided polynucleotides. In particular embodiments of any of the provided vectors, the vector is an expression vector. In some embodiments of any of the provided vectors, the vector is a viral vector. In certain embodiments of any of the provided vectors, the viral vector is a retroviral vector. In particular embodiments of any of the provided vectors, the viral vector is a lentiviral vector. In some embodiments of any of the provided vectors, the lentiviral vector is derived from HIV-1.

Provided herein is an engineered cell comprising any of the provided vectors. Provided herein is an engineered cell expressing a receptor comprising any of the provided antibody or antigen-binding fragment, any of the provided single chain cell surface proteins, any of the provided conjugates or any of the provided chimeric antigen receptor. In certain embodiments of any of the provided engineered cells, the cell is an immune cell. In particular embodiments of any of the provided engineered cells, the immune cell is a T cell. In some embodiments of any of the provided engineered cells, the T cell is a CD4+ or CD8+ T cell. In certain embodiments of any of the provided engineered cells, the cell is an induced pluripotent stem cell (iPS cell). Particular embodiments of any of the provided engineered cells further comprise another genetically engineered antigen receptor that is a chimeric costimulatory receptor that specifically binds to another antigen and is capable of inducing a costimulatory signal to the cell, optionally wherein the another antigen is expressed on the same cell as CCT5 or is a tumor antigen.

Some embodiments of any of the provided engineered cells further comprise another generally engineered antigen receptor that is a inhibitory chimeric antigen receptor that specifically binds to another antigen and is capable of inducing an inhibitory or immunosuppressive or repressive signal to the cell upon recognition of the second antigen, optionally wherein the second antigen is expressed on a normal cell or is expressed on a prostate or mammary epithelial cell.

Provided herein is a composition comprising any of the provided antibody or antigen-binding fragment thereof, any of the provided single chain cell surface proteins, any of the provided conjugates, any of the provided chimeric antigen receptor or any of the provided engineered cells.

Certain embodiments of any of the provided compositions further comprise a pharmaceutically acceptable excipient. Provided herein is a method of treatment, comprising administering any of the provided antibody or antigen-binding fragment thereof, any of the provided single chain cell surface protein, any of the provided conjugate, any of the provided chimeric antigen receptor, any of the provided engineered cell or any of the provided compositions to a subject having a disease or disorder.

Provided herein is a method of treatment, the method comprising administering to a subject a binding molecule comprising an antibody or antigen-binding fragment that specifically binds CCT5 for treating a disease or disorder. In particular embodiments of any of the provided methods, the binding molecule is a conjugate, optionally an antibody-drug conjugate (ADC). In some embodiments of any of the provided methods, binding molecule is a chimeric antigen receptor and engineered cells expressing the chimeric antigen receptor are administered to the subject.

In certain embodiments of any of the provided methods, the disease or disorder is associated with CCT5, optionally aberrantly expressed CCT5, optionally surface CCT5 or membrane localized CCT5.

In particular embodiments of any of the provided methods, the disease or disorder is a tumor or a cancer. In some embodiments of any of the provided methods, the disease or disorder is a leukemia, a lymphoma, or a solid tumor, optionally a sarcoma or a carcinoma. In certain embodiments of any of the provided methods, the disease or condition is a pancreatic cancer, bladder cancer, colorectal cancer, breast cancer, prostate cancer, renal cancer, hepatocellular cancer, lung cancer, ovarian cancer, cervical cancer, pancreatic cancer, rectal cancer, thyroid cancer, uterine cancer, gastric cancer, esophageal cancer, head and neck cancer, melanoma, neuroendocrine cancers, CNS cancers, brain tumors, bone cancer, or soft tissue sarcoma. In particular embodiments of any of the provided methods, the disease or disorder is a carcinoma or epithelial cell cancer. In some embodiments of any of the provided methods, the carcinoma or epithelial cell cancer is selected from a squamous cell carcinoma (skin), basal cell carcinoma, gastric carcinoma, an adenocarcinoma, adenosquamous carcinoma, anaplastic carcinoma, transitional cell carcinoma, large cell carcinoma, small cell carcinoma, hepatocellular carcinoma, renal cell carcinoma, endometrial carcinoma, invasive carcinoma of the breast, or a carcinoma metastasis. In certain embodiments of any of the provided methods, the disease or condition is a colon cancer, breast cancer, ovarian cancer, prostate cancer, pancreatic cancer, bladder cancer, or a lung cancer.

DETAILED DESCRIPTION

Figure 1A:
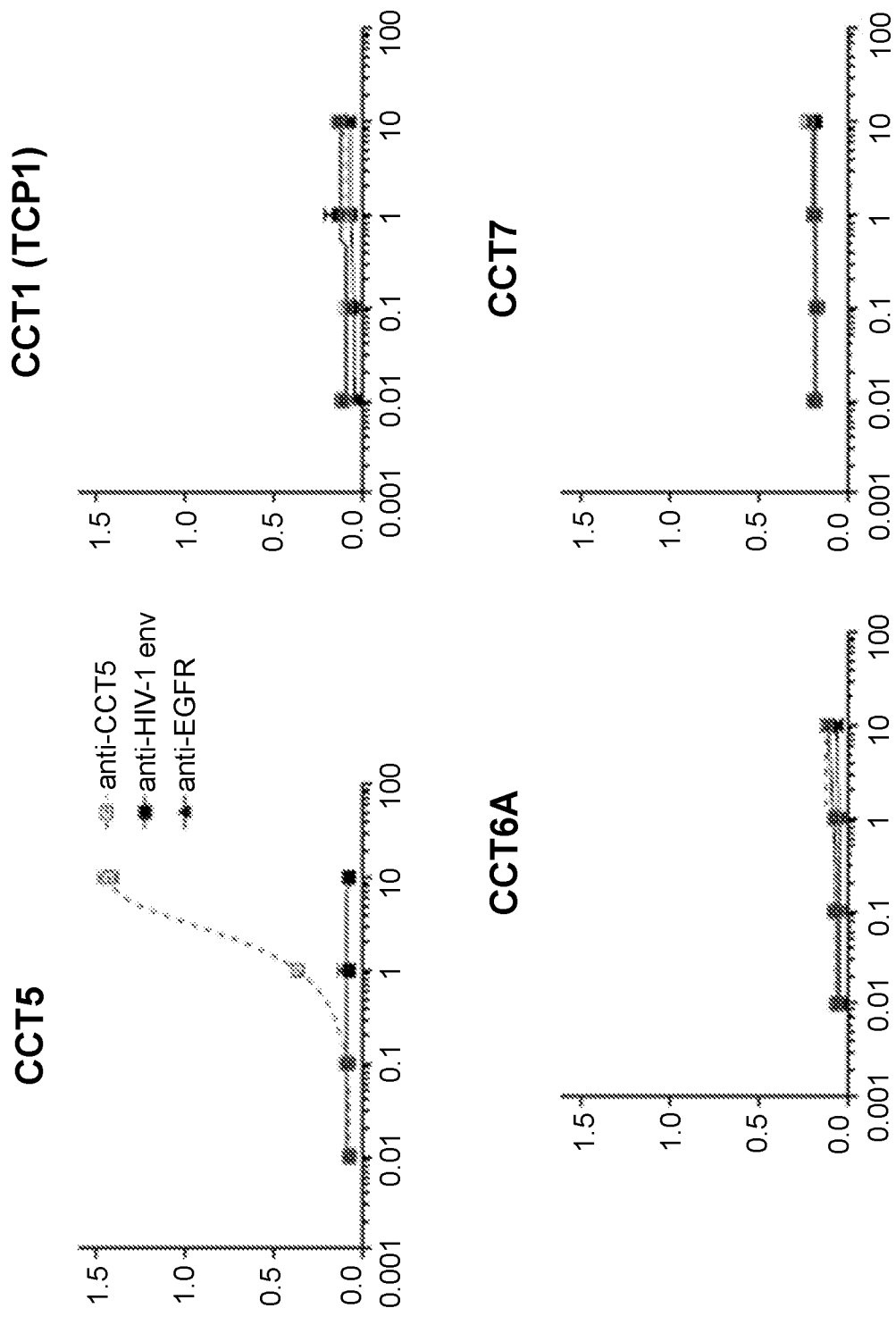
FIGS. 1A and 1B depict binding of the anti-CCT5 antibody to recombinant proteins from the TRiC ring complex

Provided are binding molecules to Chaperonin Containing TCP1 Subunit 5 (CCT5), including antibodies or antigen-binding antibody fragments, such as single chain fragments, including scFvs. In some aspects, CCT5 is also referred to as T-complex protein 1 (TCP1) subunit epsilon or TCP1 subunit 5. Also provided are nucleic acid molecules encoding such antibodies and antigen-binding fragments, and cells, such as recombinant cells for expressing and production of these antibodies or antigen-binding fragments thereof. Also provided are antibody conjugates containing such antibodies and antigen-binding fragments, and recombinant receptors, including chimeric antigen receptors (CARs), containing such antibodies and antigen-binding fragments. Also provided are methods of making and using the antibodies and antigen-binding fragments as well as cells (e.g., engineered cells) expressing or containing the antibodies, antigen-binding fragments, and/or recombinant receptors. In some embodiments, such molecules and engineered cells can be used in methods for treating cancers, particularly solid tumors.

In some aspects, therapeutic strategies to treat cancers, including solid tumors, are not completely satisfactory due to the lack of a suitable target antigen. In many cases, target antigens are expressed to some degree on the surface of non-target tissues, which, in some aspects, can lead to off-target activity, including off-target toxicity. Also, many tumor antigens are expressed in only one or a few tumor types, thereby rendering many patients resistant to and/or not responsive to treatments targeting many tumor antigens. Strategies that include targeting an antigen expressed on, or differentially expressed in, tumor cells or tissues but not on non-tumor cells or tissues are desirable, such as to avoid or minimize off-target toxicity. Also, target antigens that are abundant and/or relatively widely expressed on a variety of tumor types or tissues are desired.

The provided embodiments are based on the identification of CCT5 as a tumor target antigen in a wide variety of tumors, including solid tumors. In particular, CCT5 is identified herein as a target antigen from patient-derived tumor infiltrating lymphocytes (TILs), specifically B cell infiltrating lymphocytes, which indicates it is a relevant tumor antigen. The presence of TILs are implicated in killing tumor cells, and their presence in tumors is often associated with better clinical outcomes, including with survival of the patient for many cancers (Nelson (2010) J. Immunol. 185 (9):4977-82). In some cases, B cells can make up 40% or more of TILS, where they are often enriched for autoreactive and tumor reactive antibodies. The finding that CCT5 is a target of such TILs validates it as a suitable tumor antigen for targeting as a therapeutic intervention for treating cancers.

CCT5 is part of the tailless complex polypeptide 1 (TCP1) ring complex (TRiC) (also called chaperonin containing TCP1 [CCT]), which is a hetero-oligomeric complex that, in some aspects, facilitates the proper folding of many cellular proteins such as actin and tubulin. There are at least eight (8) subunits that assemble to form the TRiC which share approximately 30% identity. Each subunit is thought to have common and specific functions. Mutations in CCT5 have in some respects been associated with hereditary sensory and autonomic neuropathy with spastic paraplegia (HSNSP).

The observations herein indicate CCT5 exhibits desirable features for use as a target antigen. CCT5 expression, as a part of the TRiC, is localized to the cytosol and nucleoli. In normal cells, CCT5 is not generally expressed or is expressed at low levels on the cell surface, and hence would not normally be recognized as a target antigen. However, CCT5 is upregulated or overexpressed at the surface of, or is aberrantly expressed in, a number of tumor cells, including in multiple aggressive cancer indications, such as breast cancer, including p53 mutant tumors, non-small cell lung cancer, cervical cancer, urethral cancer, Non-Hodgkin lymphoma (NHL), head and neck cancer, ovarian cancer, testicular cancer and others. In some aspects, it is contemplated that its wide surface and/or aberrant expression in a variety of cancers, but not in normal tissues and cells, reduces or minimizes off-target activity and/or toxicity.

In some embodiments, the provided binding molecules (including antibodies or antigen-binding fragments thereof), conjugates containing such binding molecules (e.g. ADCs) or engineered cells expressing such binding molecules (e.g. CAR-expressing T cells) specifically bind to human CCT5 (e.g. set forth in SEQ ID NO:45 or SEQ ID NO: 46; UniProt No. P4883). In some aspects, the provided binding molecules exhibit cross-species reactivity, such that they specifically bind to human CCT5 and to one or more other CCT5 species, such as one or more primate or rodent species of CCT5. CCT5 exhibits high sequence homology between and among different mammalian species with approximately 96% homology between human and mouse or rat CCT5 and even greater identity between human and primate species. In some aspects, the high sequence homology between and among species is favored because it allows for the use of the antibody in in vivo animal models to assess efficacy, including anti-tumor activity, and/or impacts on toxicity.

Among provided embodiments are engineered cells expressing a recombinant receptor, e.g. CAR, for use in connection with adoptive cell therapy. Cell therapies, such as T cell-based therapies, for example, adoptive T cell therapies (including those involving the administration of cells expressing chimeric receptors specific for a disease or disorder of interest, such as chimeric antigen receptors (CARs) and/or other recombinant antigen receptors, as well as other adoptive immune cell and adoptive T cell therapies) can be effective in the treatment of cancer and other diseases and disorders. The engineered expression of recombinant receptors, such as chimeric antigen receptors (CARs), on the surface of T cells enables the redirection of T-cell specificity. In certain contexts, however, available approaches to adoptive cell therapy may not always be entirely satisfactory. In some contexts, optimal efficacy can depend on the ability of the administered cells to recognize and bind to a target, e.g., target antigen, which, often, is not adequately achieved. In some aspects, the provided embodiments are based on findings that reformatting the provided anti-CCT5 antibody, such as an antigen-binding fragment (e.g. scFv), as a CAR for expression on the surface of an engineered cell is particularly effective, resulting in target-specific activity of CAR+ T cells. Such activity is observed against a wide variety of cancer cell lines.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. CCT5-BINDING MOLECULES

Provided in some aspects are binding molecules, including antibodies and antigen-binding fragments thereof that specifically bind to a CCT5 protein or that specifically bind to a sequence set forth in SEQ ID NO:68 ($X_1SVEX_5X_6KX_8$), wherein X is any amino acid, such as a peptide sequence set forth in any of SEQ ID NOs:69-72. In some embodiments, the CCT5 is a human CCT5 protein. Also among the binding molecules are polypeptides containing such antibodies or antigen-binding fragments thereof, including antibody conjugates, such as antibody-drug conjugates, multispecific (e.g. bispecific) antibodies, and single chain cell surface proteins, e.g., recombinant receptors such as chimeric antigen receptors (CARs). In some aspects, the recombinant receptors, such as CARs, are expressed on a cell, such as engineered cells used in connection with adoptive cell therapy.

A. Anti-CCT5 Antibodies

Provided are anti-CCT5 antibodies, including functional antigen-binding fragments. In some embodiments, the antibodies include a heavy chain variable region and/or a light chain variable region. In some embodiments, the antibodies include a heavy chain variable region and a light chain variable region. The antibodies include antibodies that specifically bind to CCT5, e.g., human CCT5. Among the provided anti-CCT5 antibodies are human antibodies. The CCT5-binding molecules include isolated or recombinant molecules.

The term "antibody" herein is used in the broadest sense and includes polyclonal and monoclonal antibodies, including intact antibodies and functional (antigen-binding) antibody fragments, including fragment antigen binding (Fab) fragments, F(ab')2 fragments, Fab' fragments, Fv fragments, recombinant IgG (rIgG) fragments, heavy chain variable ($V_H$) regions capable of specifically binding the antigen, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific or trispecific, antibodies, diabodies, triabodies, and tetrabodies, tandem di-scFv, tandem tri-scFv. Unless otherwise stated, the term "antibody" should be understood to encompass functional antibody fragments thereof also referred to herein as "antigen-binding fragments." The term also encompasses intact or full-length antibodies, including antibodies of any class or sub-class, including IgG and sub-classes thereof, IgM, IgE, IgA, and IgD.

The terms "complementarity determining region," and "CDR," synonymous with "hypervariable region" or "HVR," are known to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4).

The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme); Al-Lazikani et al., (1997) JMB 273,927-948 ("Chothia" numbering scheme); MacCallum et al., J. Mol. Biol. 262: 732-745 (1996), "Antibody-antigen interactions: Contact analysis and binding site topography," J. Mol. Biol. 262, 732-745." ("Contact" numbering scheme); Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme); Honegger A and Pluckthun A, "Yet another numbering scheme for immunoglobulin variable domains: an automatic modeling and analysis tool," J Mol Biol, 2001 Jun. 8; 309(3):657-70, ("Aho" numbering scheme); and Martin et al., "Modeling antibody hypervariable loops: a combined algorithm," PNAS, 1989, 86(23): 9268-9272, ("AbM" numbering scheme).

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. The AbM scheme is a compromise between Kabat and Chothia definitions based on that used by Oxford Molecular's AbM antibody modeling software.

Table 1, below, lists exemplary position boundaries of CDR-L1, CDR-L2, CDR-L3 and CDR-H1, CDR-H2, CDR-H3 as identified by Kabat, Chothia, AbM, and Contact schemes, respectively. For CDR-H1, residue numbering is listed using both the Kabat and Chothia numbering schemes. FRs are located between CDRs, for example, with FR-L1 located before CDR-L1, FR-L2 located between CDR-L1 and CDR-L2, FR-L3 located between CDR-L2 and CDR-L3 and so forth. It is noted that because the shown Kabat numbering scheme places insertions at H35A and H35B, the end of the Chothia CDR-H1 loop when numbered using the shown Kabat numbering convention varies between H32 and H34, depending on the length of the loop.

TABLE 1

Boundaries of CDRs according to various numbering schemes.

| CDR | Kabat | Chothia | AbM | Contact |
|---|---|---|---|---|
| CDR-L1 | L24 - - - L34 | L24 - - - L34 | L24 - - - L34 | L30 - - - L36 |
| CDR-L2 | L50 - - - L56 | L50 - - - L56 | L50 - - - L56 | L46 - - - L55 |
| CDR-L3 | L89 - - - L97 | L89 - - - L97 | L89 - - - L97 | L89 - - - L96 |
| CDR-H1 (Kabat Numbering[1]) | H31 - - - H35B | H26 - - - H32 . . . 34 | H26 - - - H35B | H30 - - - H35B |
| CDR-H1 (Chothia Numbering[2]) | H31 - - - H35 | H26 - - - H32 | H26 - - - H35 | H30 - - - H35 |
| CDR-H2 | H50 - - - H65 | H52 - - - H56 | H50 - - - H58 | H47 - - - H58 |
| CDR-H3 | H95 - - - H102 | H95 - - - H102 | H95 - - - H102 | H93 - - - H101 |

[1]Kabat et al. (1991), "Sequences of Proteins of Immunological Interest," 5th Ed. Public Health Service, National Institutes of Health, Bethesda, MD
[2]Al-Lazikani et al., (1997) JMB 273,927-948

Thus, unless otherwise specified, a "CDR" or "complementary determining region," or individual specified CDRs (e.g., CDR-H1, CDR-H2, CDR-H3), of a given antibody or region thereof, such as a variable region thereof, should be understood to encompass a (or the specific) complementary determining region as defined by any of the aforementioned schemes. For example, where it is stated that a particular CDR (e.g., a CDR-H3) contains the amino acid sequence of a corresponding CDR in a given $V_H$ or $V_L$ region amino acid sequence, it is understood that such a CDR has a sequence of the corresponding CDR (e.g., CDR-H3) within the variable region, as defined by any of the aforementioned schemes. In some embodiments, specific CDR sequences are specified. Exemplary CDR sequences of provided antibodies are described using various numbering schemes, although it is understood that a provided antibody can include CDRs as described according to any of the other aforementioned numbering schemes or other numbering schemes known.

Likewise, unless otherwise specified, a FR or individual specified FR(s) (e.g., FR-H1, FR-H2, FR-H3, FR-H4), of a given antibody or region thereof, such as a variable region thereof, should be understood to encompass a (or the specific) framework region as defined by any of the known schemes. In some instances, the scheme for identification of a particular CDR, FR, or FRs or CDRs is specified, such as the CDR as defined by the Kabat, Chothia, AbM or Contact method. In other cases, the particular amino acid sequence of a CDR or FR is given.

The term "variable region" or "variable domain" refers to the domain of an antibody heavy or light chain that is involved in binding the antibody to antigen. The variable regions of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W. H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352:624-628 (1991).

Among the provided antibodies are antibody fragments. An "antibody fragment" or "antigen-binding fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; heavy chain variable ($V_H$) regions, single-chain antibody molecules such as scFvs and single-domain antibodies comprising only the $V_H$ region; and multispecific antibodies formed from antibody fragments. In particular embodiments, the antibodies are single-chain antibody fragments comprising a heavy chain variable ($V_H$) region and/or a light chain variable ($V_L$) region, such as scFvs.

Single-domain antibodies (sdAbs) are antibody fragments comprising all or a portion of the heavy chain variable region or all or a portion of the light chain variable region of an antibody. In certain embodiments, a single-domain antibody is a human single-domain antibody. In some embodiments, the provided antibodies include those that are single domain antibodies, containing a heavy chain variable ($V_H$) region that, without pairing with a light chain antigen-binding site (e.g., light chain variable ($V_L$) region) and/or without any additional antibody domain or binding site, are capable of specifically binding to CCT5.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some aspects, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity. (See, e.g., Queen, U.S. Pat. No. 5,585,089 and Winter, U.S. Pat. No. 5,225, 539.) Such chimeric and humanized monoclonal antibodies can be produced by recombinant DNA techniques.

Among the provided antibodies or antigen-binding fragments, including anti-CCT5 antibodies or fragments, are human antibodies. A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human. The term includes antigen-binding fragments of human antibodies.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. Human antibodies also may be derived from human antibody libraries, including phage display and cell-free libraries, containing antibody-encoding sequences derived from a human repertoire.

Among the provided antibodies are monoclonal antibodies, including monoclonal antibody fragments. The term "monoclonal antibody" as used herein refers to an antibody obtained from or within a population of substantially homogeneous antibodies, i.e., the individual antibodies comprising the population are identical, except for possible variants containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. The term is not to be construed as requiring production of the antibody by any particular method. A monoclonal antibody may be made by a variety of techniques, including but not limited to generation from a hybridoma, recombinant DNA methods, phage-display and other antibody display methods.

In some embodiments, the antibody, e.g., the anti-CCT5 antibody or antigen-binding fragment thereof, contains a heavy chain variable ($V_H$) and/or light chain variable ($V_L$) region sequence as described, or a sufficient antigen-binding portion thereof. In some embodiments, the antibody, e.g., the anti-CCT5 antibody or antigen-binding fragment thereof, contains a heavy chain variable ($V_H$) and light chain variable ($V_L$) region sequence as described, or a sufficient antigen-binding portion thereof. In some embodiments, the anti-CCT5 antibody or antigen-binding fragment thereof, contains a $V_H$ region sequence or sufficient antigen-binding portion thereof that contains a CDR-H1, CDR-H2 and/or CDR-H3 as described. In some embodiments, the anti-CCT5 antibody or antigen-binding fragment thereof, contains a $V_L$ region sequence or sufficient antigen-binding portion that contains a CDR-L1, CDR-L2 and/or CDR-L3 as described. In some embodiments, the anti-CCT5 antibody or antigen-binding fragment thereof, contains a $V_H$ region sequence that contains a CDR-H1, CDR-H2 and/or CDR-H3 as described and contains a $V_L$ region sequence that contains a CDR-L1, CDR-L2 and/or CDR-L3 as described. In some embodiments, the anti-CCT5 antibody or antigen-binding fragment thereof, contains a $V_H$ region sequence that contains a CDR-H1, CDR-H2 and CDR-H3 as described and contains a $V_L$ region sequence that contains a CDR-L1, CDR-L2 and CDR-L3 as described. Also among the provided antibodies are those having sequences at least at or about 90%, about 91%, about 92%, about 93%, about 94%, about 95%, about 96%, about 97%, about 98%, or about 99% identical to such a sequence.

In some embodiments, the antibody, e.g., antigen-binding fragment thereof, has a heavy chain variable ($V_H$) region having the amino acid sequence set forth in SEQ ID NO:1, or an amino acid sequence that has at least 90%, 91%, 92%, 93%, 94%, 95%, 96%, 97%, 98%, or 99% sequence identity to the $V_H$ region amino acid set forth in SEQ ID NO:1. In some embodiments, the antibody e.g., antigen-binding fragment thereof, has the $V_H$ region amino acid set forth in SEQ ID NO:1.

In some embodiments, the $V_H$ region of a provided antibody or antigen-binding fragment thereof comprises a CDR-H1, CDR-H2, and/or CDR-H3 according to Kabat numbering as shown in Table 1. In some embodiments, the $V_H$ region of a provided antibody or antigen-binding fragment thereof comprises a CDR-H1, CDR-H2, and/or CDR-H3 according to Chothia numbering as shown in Table 1. In some embodiments, the $V_H$ region of a provided antibody or antigen-binding fragment thereof comprises a CDR-H1, CDR-H2, and/or CDR-H3 according to AbM numbering as shown in Table 1. In some embodiments, the $V_H$ region of a provided antibody or antigen-binding fragment thereof comprises a CDR-H1, CDR-H2, and/or CDR-H3 according to Contact numbering as shown in Table 1.

Provided are antibodies or antigen-binding fragments thereof that include a heavy chain variable ($V_H$) region comprising a heavy chain complementarity determining region 1 (CDR-H1), CDR-H2, and CDR-H3, wherein the CDR-H1 comprises the amino acid sequence set forth in SEQ ID NO: 11, 14, 16 or 18; the CDR-H2 comprises the amino acid sequence set forth in SEQ ID NO: 12, 15, 17 or 19; and/or the CDR-H3 comprises the amino acid sequence set forth in SEQ ID NO: 13 or 20. In some embodiments, provided are antibodies or antigen-binding fragments thereof that include a CDR-H1 having the amino acid sequence set forth in SEQ ID NO: 11, 14, 16 or 18; a CDR-H2 having the amino acid sequence set forth in SEQ ID NO: 12, 15, 17 or 19; and a CDR-H3 having the amino acid sequence set forth in SEQ ID NO: 13 or 20.

In some embodiments, the $V_H$ region of a provided antibody or antigen-binding fragment thereof comprises a CDR-H3 contained within the $V_H$ region amino acid sequence set forth in SEQ ID NO:1. In some embodiments, the provided antibody or antigen-binding fragment thereof comprises a CDR-H3 comprising the amino acid sequence set forth in SEQ ID NO:13. In some embodiments, the provided antibody or antigen-binding fragment thereof comprises a CDR-H3 comprising the amino acid sequence set forth in SEQ ID NO:20.

In some embodiments, the VH region of a provided antibody or antigen-binding fragment thereof contains a CDR-H1 contained within the $V_H$ region amino acid sequence set forth in SEQ ID NO: 1. In some embodiments, the $V_H$ region of a provided antibody or antigen-binding fragment thereof contains a CDR-H1 having the amino acid sequence set forth in SEQ ID NO:11. In some embodiments, the $V_H$ region of a provided antibody or antigen-binding fragment thereof contains a CDR-H1 having the amino acid sequence comprising the amino acid sequence set forth in SEQ ID NO:14. In some embodiments, the $V_H$ region of a provided antibody or antigen-binding fragment thereof contains a CDR-H1 having the amino acid sequence comprising the amino acid sequence set forth in SEQ ID NO:16. In some embodiments, the $V_H$ region of a provided antibody or antigen-binding fragment thereof contains a CDR-H1 having the amino acid sequence comprising the amino acid sequence set forth in SEQ ID NO:18.

In some embodiments, the $V_H$ region of a provided antibody or antigen-binding fragment thereof contains a CDR-H2 contained within the $V_H$ region amino acid sequence set forth in SEQ ID NO:1. In some embodiments, the $V_H$ region of a provided antibody or antigen-binding fragment thereof contains a CDR-H2 having the amino acid sequence set forth in SEQ ID NO:12. In some embodiments, the $V_H$ region of a provided antibody or antigen-binding fragment thereof contains a CDR-H2 having the amino acid sequence comprising the amino acid sequence set forth in SEQ ID NO:15. In some embodiments, the $V_H$ region of a provided antibody or antigen-binding fragment thereof contains a CDR-H2 having the amino acid sequence comprising the amino acid sequence set forth in SEQ ID NO:17. In some embodiments, the $V_H$ region of a provided antibody or antigen-binding fragment thereof contains a CDR-H2 having the amino acid sequence comprising the amino acid sequence set forth in SEQ ID NO:19.

In some embodiments, the provided antibody or antigen-binding fragment thereof comprises a CDR-H1, CDR-H2 and CDR-H3, respectively, comprising the amino acid sequence of a CDR-H1, a CDR-H2, and a CDR-H3 contained within the $V_H$ region amino acid sequence set forth in SEQ ID NO:1. In some embodiments, the provided antibody or antigen-binding fragment thereof contains a CDR-H1 that is or comprises the amino acid sequence set forth in SEQ ID NO:11; a CDR-H2 that is or comprises the amino acid sequence set forth in SEQ ID NO:12; and a CDR-H3 that is or comprises the amino acid sequence set forth in SEQ ID NO:13. In some embodiments, the provided antibody or antigen-binding fragment thereof contains a CDR-H1 that is or comprises the amino acid sequence set forth in SEQ ID NO:14; a CDR-H2 that is or comprises the amino acid sequence set forth in SEQ ID NO: 15; and a CDR-H3 that is or comprises the amino acid sequence set forth in SEQ ID NO: 13. In some embodiments, the provided antibody or antigen-binding fragment thereof contains a CDR-H1 that is or comprises the amino acid sequence set forth in SEQ ID NO:16; a CDR-H2 that is or comprises the amino acid sequence set forth in SEQ ID NO: 17; and a CDR-H3 that is or comprises the amino acid sequence set forth in SEQ ID NO: 13. In some embodiments, the provided antibody or antigen-binding fragment thereof contains a CDR-H1 that is or comprises the amino acid sequence set forth in SEQ ID NO: 18; a CDR-H2 that is or comprises the amino acid sequence set forth in SEQ ID NO: 19; and a CDR-H3 that is or comprises the amino acid sequence set forth in SEQ ID NO:20.

In some embodiments of the antibody or antigen-binding fragment thereof provided herein, the $V_H$ region comprises any of the CDR-H1, CDR-H2 and CDR-H3 as described and comprises a framework region 1 (FR1), a FR2, a FR3 and/or a FR4 having at least 90%, 91%, 92%, 93%, 94%, 95%, 96%, 97%, 98%, or 99% sequence identity, respectively, to a FR1, a FR2, a FR3 and/or a FR4 contained within the $V_H$ region amino acid sequence set forth in SEQ ID NO: 1. In some embodiments, the provided antibodies or antigen-binding fragment thereof can comprise a CDR-H1, CDR-H2 and CDR-H3, respectively, contained within the $V_H$ region amino acid sequence set forth in SEQ ID NO: 1, and a framework region (e.g., a FR1, a FR2, a FR3 and/or a FR4) that contains at least 90%, 91%, 92%, 93%, 94%, 95%, 96%, 97%, 98%, 99% sequence identity to a framework region (e.g., a FR1, a FR2, a FR3 and/or a FR4) contained within the $V_H$ region amino acid sequence set forth in SEQ ID NO: 1. In some embodiments, the $V_H$ region comprises a FR1, a FR2, a FR3 and/or a FR4 selected from a FR1 contained within the amino acid sequence set forth in SEQ ID NO:1; a FR2 contained within the amino acid sequence set forth in SEQ ID NO:1; a FR3 contained within the amino acid sequence set forth in SEQ ID NO:1 and/or a FR4 contained within the amino acid sequence set forth in SEQ ID NO: 1.

In some embodiments, the provided antibody or antigen-binding fragment thereof comprises a $V_H$ region comprising the amino acid sequence set forth in SEQ ID NO:1.

Also provided are antibodies and antigen-binding fragments thereof having sequences at least at or about at least 90%, 91%, 92%, 93%, 94%, 95%, 96%, 97%, 98%, or 99% identical to such sequences.

In some of any such embodiments, the antibody or antigen-binding fragment is a heavy chain only, a $V_H$-only, and/or does not include a $V_L$ or antigen-binding portion thereof and/or the antigen-binding site of the antibody or fragment includes residues from the heavy chain only and/or does not include residues from a light chain. In some of any such embodiments, the antibody or fragment does not contain a light chain variable ($V_L$) region, does not contain a CDR-L1, CDR-L2, and/or CDR-L3, and/or is a single-domain antibody (sdAb) containing only the $V_H$ region or an antigen-binding portion thereof. In some embodiments, the antibody or fragment is a sdAb that only contains a $V_H$ region from any as described or a sufficient antigen-binding portion thereof, such as any of the above described $V_H$ sequences (e.g., containing a CDR-H1, a CDR-H2, a CDR-H3).

In some embodiments, an antibody provided herein (e.g., an anti-CCT5 antibody) or antigen-binding fragment thereof comprising a $V_H$ region further comprises a light chain or a sufficient antigen binding portion thereof. For example, in some embodiments, the antibody or antigen-binding fragment thereof contains a $V_H$ region and a $V_L$ region, or a sufficient antigen-binding portion of a $V_H$ and $V_L$ region. In such embodiments, a $V_H$ region sequence can be any of the above described $V_H$ sequences.

In some embodiments, the antibody, e.g., antigen-binding fragment thereof, has a light chain variable ($V_L$) region having the amino acid sequence set forth in SEQ ID NO:2, or an amino acid sequence that has at least 90%, 91%, 92%, 93%, 94%, 95%, 96%, 97%, 98%, or 99% sequence identity to a $V_L$ region amino acid sequence set forth in SEQ ID NO:2.

In some embodiments, the $V_L$ region of a provided antibody or antigen-binding fragment thereof comprises a CDR-L1, CDR-L2, and/or CDR-L3 according to Kabat numbering as shown in Table 1. In some embodiments, the $V_L$ region of a provided antibody or antigen-binding fragment thereof comprises a CDR-L1, CDR-L2, and/or CDR-L3 according to Chothia numbering as shown in Table 1. In some embodiments, the $V_L$ region of a provided antibody or antigen-binding fragment thereof comprises a CDR-L1, CDR-L2, and/or CDR-L3 according to AbM numbering as shown in Table 1. In some embodiments, the $V_L$ region of a provided antibody or antigen-binding fragment thereof comprises a CDR-L1, CDR-L2, and/or CDR-L3 according to Contact numbering as shown in Table 1.

In some embodiments, the provided antibodies or antigen-binding fragments thereof that include a light chain variable ($V_L$) region comprising a light chain complementarity determining region 1 (CDR-L1), CDR-L2, and CDR-L3, wherein the CDR-L1 comprises the amino acid sequence set forth in SEQ ID NO: 21 or 24; the CDR-L2 comprises the amino acid sequence set forth in SEQ ID NO: 22 or 25; and/or the CDR-L3 comprises the amino acid sequence set forth in SEQ ID NO: 23 or 26. In some embodiments, provided are antibodies or antigen-binding fragments thereof that include a CDR-L1 having the amino acid sequence set forth in SEQ ID NO: 21 or 24; a CDR-L2 having the amino acid sequence set forth in SEQ ID NO: 22 or 25; and a CDR-L3 having the amino acid sequence set forth in SEQ ID NO: 23 or 26.

In some embodiments, the $V_L$ region of a provided antibody or antigen-binding fragment thereof comprises a CDR-L3 contained within the $V_L$ region amino acid sequence set forth in SEQ ID NO:2. In some embodiments, the provided antibody or antigen-binding fragment thereof contains a CDR-L3 comprising the amino acid sequence set forth in SEQ ID NO:23. In some embodiments, the provided antibody or antigen-binding fragment thereof contains a CDR-L3 comprising the amino acid sequence set forth in SEQ ID NO:26.

In some embodiments, the $V_L$ region of a provided antibody or antigen-binding fragment thereof comprises a CDR-L1 contained within the $V_L$ region amino acid sequence set forth in SEQ ID NO:2. In some embodiments, the provided antibody or antigen-binding fragment thereof contains a CDR-L1 comprising the amino acid sequence set forth in SEQ ID NO:21. In some embodiments, the provided antibody or antigen-binding fragment thereof contains a CDR-L1 comprising the amino acid sequence set forth in SEQ ID NO:24.

In some embodiments, the $V_L$ region of a provided antibody or antigen-binding fragment thereof comprises a CDR-L2 contained within the $V_L$ region amino acid sequence set forth in SEQ ID NO:2. In some embodiments, the provided antibody or antigen-binding fragment thereof contains a CDR-L2 comprising the amino acid sequence set forth in SEQ ID NO:22. In some embodiments, the provided antibody or antigen-binding fragment thereof contains a CDR-L2 comprising the amino acid sequence set forth in SEQ ID NO:25.

In some embodiments, the provided antibody or antigen-binding fragment thereof comprises a CDR-L1, CDR-L2 and CDR-L3, respectively, comprising the amino acid sequence of a CDR-L1, a CDR-L2, and a CDR-L3 contained within the $V_L$ region amino acid sequence set forth in SEQ ID NO:2. In some embodiments, the provided antibody or antigen-binding fragment thereof contains a CDR-L1 that is or comprises the amino acid sequence set forth in SEQ ID NO:21; a CDR-L2 that is or comprises the amino acid sequence set forth in SEQ ID NO:22; and a CDR-L3 that is or comprises the amino acid sequence set forth in SEQ ID NO:23. In some embodiments, the provided antibody or antigen-binding fragment thereof contains a CDR-L1 that is or comprises the amino acid sequence set forth in SEQ ID NO:24; a CDR-L2 that is or comprises the amino acid sequence set forth in SEQ ID NO:25; and a CDR-L3 that is or comprises the amino acid sequence set forth in SEQ ID NO:26.

In some embodiments of the antibody or antigen-binding fragment thereof provided herein, the $V_L$ region comprises any of the CDR-L1, CDR-L2 and CDR-L3 as described and comprises a framework region 1 (FR1), a FR2, a FR3 and/or a FR4 having at least 90%, 91%, 92%, 93%, 94%, 95%, 96%, 97%, 98%, or 99% sequence identity, respectively, to a FR1, a FR2, a FR3 and/or a FR4 contained within the $V_L$ region amino acid sequence set forth in SEQ ID NO:2. In some embodiments, the antibody or antigen-binding fragment thereof can comprise a CDR-L1, CDR-L2 and CDR-L3, respectively, contained within the $V_L$ region amino acid sequence set forth in SEQ ID NO:2, and a framework region (e.g., a FR1, a FR2, a FR3 and/or a FR4) that contains at least 90%, 91%, 92%, 93%, 94%, 95%, 96%, 97%, 98%, 99% sequence identity to a framework region (e.g., a FR1, a FR2, a FR3 and/or a FR4) contained within the $V_L$ region amino acid sequence set forth in SEQ ID NO:2. In some embodiments, the $V_L$ region comprises a FR1, a FR2, a FR3 and/or a FR4 selected from a FR1 contained within the amino acid sequence set forth in SEQ ID NO:2; a FR2 contained within the amino acid sequence set forth in SEQ ID NO:2; a FR3 contained within the amino acid sequence set forth in SEQ ID NO:2; and/or a FR4 contained within the amino acid sequence set forth in SEQ ID NO:2.

In some embodiments, the provided antibody or antigen-binding fragment thereof comprises a $V_L$ region comprising an amino acid sequence set forth in SEQ ID NO:2.

Also provided are antibodies having sequences at least at or or about at least 90%, 91%, 92%, 93%, 94%, 95%, 96%, 97%, 98%, or 99% identical to such sequences.

In some embodiments, the $V_H$ region of the antibody or antigen-binding fragment thereof comprises a CDR-H1, a CDR-H2, a CDR-H3, respectively, comprising the amino acid sequences of CDR-H1, CDR-H2, and CDR-H3 contained within the $V_H$ region amino acid sequence set forth in SEQ ID NO:1; and the $V_L$ region of the antibody or antigen-binding fragment thereof comprises a CDR-L1, a CDR-L2, a CDR-L3, respectively, comprising the amino acid sequences of CDR-L1, CDR-L2, and CDR-L3, respectively contained within the $V_L$ region amino acid sequence set forth in SEQ ID NO:2. In some embodiments, the $V_H$ and $V_L$ regions of the antibody or antigen-binding fragment thereof comprise the amino acid sequences of SEQ ID NOs:1 and 2, respectively, or any antibody or antigen-binding fragment thereof that has at least 90% sequence identity to any of the above $V_H$ and $V_L$, such as at least 90%, 91%, 92%, 93%, 94%, 95%, 96%, 97%, 98%, or 99% sequence identity thereto. In some embodiments, the provided antibody or antigen-binding fragment contains a $V_L$ region comprising an amino acid sequence having at least 90%, 91%, 92%, 93%, 94%, 95%, 96%, 97%, 98%, or 99% sequence identity to a $V_L$ region amino acid sequence set forth in SEQ ID NO:2 and/or contains a $V_H$ region comprising an amino acid sequence having at least 90%, 91%, 92%, 93%, 94%, 95%, 96%, 97%, 98%, or 99% sequence identity to a $V_H$ region amino acid sequence set forth in SEQ ID NO:1. In some embodiments, the $V_H$ region of the antibody or fragment comprises the amino acid sequence set forth in SEQ ID NO:1 and the $V_L$ region of the antibody or fragment comprises the amino acid sequence set forth in SEQ ID NO:2.

In some embodiments, the antibody or antigen binding fragment comprises one or more heavy chain variable ($V_H$) region and one or more light chain variable ($V_L$) region, in any order or orientation. In some embodiments, the antibody or antigen-binding fragment comprises a $V_H$ region and a $V_L$ region, and the $V_H$ region is amino-terminal to the $V_L$ region. In some embodiments, the antibody or antigen-binding fragment comprises a $V_H$ region and a $V_L$ region, and the $V_H$ region is carboxy-terminal to the $V_L$ region. In some embodiments, the $V_H$ region(s) and the $V_L$ region(s) are linked directly or indirectly, optionally via a linker.

In some embodiments, the anti-CCT5 antibody is an antigen-binding fragment. In some embodiments, the antigen-binding fragment is selected from the group consisting of fragment antigen binding (Fab) fragments, F(ab')2 fragments, Fab' fragments, Fv fragments, a single chain variable fragment (scFv) or a single domain antibody.

In some embodiments, the antibody or antigen-binding fragment thereof is a single-chain antibody fragment, such as a single chain variable fragment (scFv), comprising a heavy chain variable ($V_H$) region and a light chain variable ($V_L$) region. In some embodiments, the single-chain antibody fragment (e.g. scFv) includes one or more linkers joining two antibody domains or regions, such as a heavy chain variable ($V_H$) region and a light chain variable ($V_L$) region. In some embodiments, the antibody or antigen-binding fragment, e.g., scFv, may include a $V_H$ region or portion thereof, followed by the linker, followed by a $V_L$ region or portion thereof. In some embodiments, the antibody or antigen-binding fragment, e.g., the scFv, may include the $V_L$ region or portion thereof, followed by the linker, followed by the $V_H$ region or portion thereof. The linker typically is a peptide linker, e.g., a flexible and/or soluble peptide linker. Among the linkers are those rich in glycine and serine and/or in some cases threonine. In some embodiments, the linkers further include charged residues such as lysine and/or glutamate, which can improve solubility. In some embodiments, the linkers further include one or more proline.

In some aspects, the linkers rich in glycine and serine (and/or threonine) include at least 80%, 85%, 90%, 91%, 92%, 93%, 94%, 95%, 96%, 97%, 98%, or 99% such amino acid(s). In some embodiments, they include at least at or about 50%, 55%, 60%, 70%, or 75%, glycine, serine, and/or threonine. In some embodiments, the linker is comprised substantially entirely of glycine, serine, and/or threonine. The linkers generally are between about 5 and about 50 amino acids in length, typically between at or about 10 and at or about 30, e.g., 10, 11, 12, 13, 14, 15, 16, 17, 18, 19, 20, 21, 22, 23, 24, 25, 26, 27, 28, 29, or 30, and in some examples between 10 and 25 amino acids in length. Exemplary linkers include linkers having various numbers of repeats of the sequence GGGGS (4GS; SEQ ID NO:47) or GGGS (3GS; SEQ ID NO:48), such as between 2, 3, 4, and 5 repeats of such a sequence. Exemplary linkers include those having or consisting of an sequence set forth in SEQ ID NO:49 (GGGGSGGGGSGGGGS). Exemplary linkers further include those having or consisting of the sequence set forth in SEQ ID NO:50 (GSTSGSGKPGSGEGSTKG).

In some aspects, an scFv provided herein comprises the amino acid sequence set forth in SEQ ID NO: 52, or has an amino acid sequence having at least at or about 90%, 91%, 92%, 93%, 94%, 95%, 96%, 97%, 98%, or 99% sequence identity to the amino acid sequence set forth in SEQ ID NO: 52. In some embodiments, the scFv has the sequence set forth in SEQ ID NO:52.

In some embodiments, the antibody or antigen-binding fragment contains the $V_H$ and/or $V_L$ regions and may contain at least a portion of an immunoglobulin constant region, such as one or more constant region domains. In some embodiments, the constant regions include a light chain constant region (CL) and/or a heavy chain constant region 1 (CH1). In some embodiments, the anti-ID includes a CH2 and/or CH3 domain, such as an Fc region. In some embodiments, the Fc region is an Fc region of a human IgG, such as IgG1 or IgG4. In some embodiments, the antibody is an intact antibody or full-length antibody.

Among the provided antibodies, e.g. antigen-binding fragments, are human antibodies. In some embodiments of a provided human anti-CCT5 antibody, e.g., antigen-binding fragments, the human antibody contains a $V_H$ region that comprises a portion having at least 95%, 96%, 97%, 98%, 99%, or 100% sequence identity to an amino acid sequence encoded by a germline nucleotide human heavy chain V segment, a portion having at least 95%, 96%, 97%, 98%, 99%, or 100% sequence identity to an amino acid sequence encoded by a germline nucleotide human heavy chain D segment, and/or a portion having at least 95%, 96%, 97%, 98%, 99%, or 100% sequence identity to an amino acid sequence encoded by a germline nucleotide human heavy chain J segment; and/or contains a $V_L$ region that comprises a portion having at least 95%, 96%, 97%, 98%, 99%, or 100% sequence identity to an amino acid sequence encoded by a germline nucleotide human kappa or lambda chain V segment, and/or a portion having at least 95%, 96%, 97%, 98%, 99%, or 100% sequence identity to an amino acid sequence encoded by a germline nucleotide human kappa or lambda chain J segment. In some embodiments, the portion of the $V_H$ region corresponds to the CDR-H1, CDR-H2 and/or CDR-H3. In some embodiments, the portion of the $V_H$ region corresponds to the framework region 1 (FR1), FR2, FR2 and/or FR4. In some embodiments, the portion of the $V_L$ region corresponds to the CDR-L1, CDR-L2 and/or CDR-L3. In some embodiments, the portion of the $V_L$ region corresponds to the FR1, FR2, FR2 and/or FR4.

In some embodiments, the human antibody or antigen-binding fragment thereof, contains a CDR-H1 having at least 95%, 96%, 97%, 98%, 99%, or 100% sequence identity to an amino acid sequence of the corresponding CDR-H1 region within a sequence encoded by a germline nucleotide human heavy chain V segment. For example, the human antibody in some embodiments contains a CDR-H1 having a sequence that is 100% identical or with no more than one, two or three amino acid differences as compared to the corresponding CDR-H1 region within a sequence encoded by a germline nucleotide human heavy chain V segment.

In some embodiments, the human antibody or antigen-binding fragment thereof, contains a CDR-H2 having at least 95%, 96%, 97%, 98%, 99%, or 100% sequence identity to an amino acid sequence of the corresponding CDR-H2 region within a sequence encoded by a germline nucleotide human heavy chain V segment. For example, the human antibody in some embodiments contains a CDR-H2 having a sequence that is 100% identical or with no more than one, two or three amino acid difference as compared to the corresponding CDR-H2 region within a sequence encoded by a germline nucleotide human heavy chain V segment.

In some embodiments, the human antibody or antigen-binding fragment thereof, contains a CDR-H3 having at least 95%, 96%, 97%, 98%, 99%, or 100% sequence identity to an amino acid sequence of the corresponding CDR-H3 region within a sequence encoded by a germline nucleotide human heavy chain V segment, D segment and J segment. For example, the human antibody in some embodiments contains a CDR-H3 having a sequence that is 100% identical or with no more than one, two or three amino acid differences as compared to the corresponding CDR-H3 region within a sequence encoded by a germline nucleotide human heavy chain V segment, D segment and J segment.

In some embodiments, the human antibody or antigen-binding fragment thereof, contains a CDR-L1 having at least 95%, 96%, 97%, 98%, 99%, or 100% sequence identity to an amino acid sequence of the corresponding CDR-L1 region within a sequence encoded by a germline nucleotide human light chain V segment. For example, the human antibody in some embodiments contains a CDR-L1 having a sequence that is 100% identical or with no more than one, two or three amino acid differences as compared to the corresponding CDR-L1 region within a sequence encoded by a germline nucleotide human light chain V segment.

In some embodiments, the human antibody or antigen-binding fragment thereof, contains a CDR-L2 having at least 95%, 96%, 97%, 98%, 99%, or 100% sequence identity to an amino acid sequence of the corresponding CDR-L2 region within a sequence encoded by a germline nucleotide human light chain V segment. For example, the human antibody in some embodiments contains a CDR-L2 having a sequence that is 100% identical or with no more than one, two or three amino acid difference as compared to the corresponding CDR-L2 region within a sequence encoded by a germline nucleotide human light chain V segment.

In some embodiments, the human antibody or antigen-binding fragment thereof, contains a CDR-L3 having at least 95%, 96%, 97%, 98%, 99%, or 100% sequence identity to an amino acid sequence of the corresponding CDR-L3 region within a sequence encoded by a germline nucleotide human light chain V segment and J segment. For example, the human antibody in some embodiments contains a CDR-L3 having a sequence that is 100% identical or with no more than one, two or three amino acid differences as compared to the corresponding CDR-L3 region within a sequence encoded by a germline nucleotide human light chain V segment and J segment.

In some embodiments, the human antibody or antigen-binding fragment thereof, contains a framework region that contains human germline gene segment sequences. For example, in some embodiments, the human antibody contains a $V_H$ region in which the framework region, e.g. FR1, FR2, FR3 and FR4, has at least 95%, 96%, 97%, 98%, 99%, or 100% sequence identity to a framework region encoded by a human germline antibody segment, such as a V segment and/or J segment. In some embodiments, the human antibody contains a $V_L$ region in which the framework region e.g. FR1, FR2, FR3 and FR4, has at least 95%, 96%, 97%, 98%, 99%, or 100% sequence identity to a framework region encoded by a human germline antibody segment, such as a V segment and/or J segment. For example, in some such embodiments, the framework region sequence contained within the $V_H$ region and/or $V_L$ region differs by no more than 10 amino acids, such as no more than 9, 8, 7, 6, 5, 4, 3, 2 or 1 amino acid, compared to the framework region sequence encoded by a human germline antibody segment.

Also provided are nucleic acids, e.g., polynucleotides, encoding the antibodies and/or portions, e.g., chains, thereof. Among the provided nucleic acids are those encoding the any of the provided antibodies or antigen-binding fragments (e.g. anti-CCT5 antibodies antibodies or antigen-binding fragments) described herein. Also provided are nucleic acids, e.g., polynucleotides, encoding two or more antibodies and/or portions thereof, e.g., those encoding one or more of the anti-CCT5 antibodies or antigen-binding fragment described herein and another antibody and/or portions thereof, e.g., antibodies and/or portions thereof that binds other target antigens. The nucleic acids may include those encompassing natural and/or non-naturally occurring nucleotides and bases, e.g., including those with backbone modifications. The terms "nucleic acid molecule", "nucleic acid" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

The provided embodiments further include vectors and host cells and other expression systems for expressing and producing the antibodies and other antigen-binding proteins, including eukaryotic and prokaryotic host cells, including bacteria, filamentous fungi, and yeast, as well as mammalian cells such as human cells, as well as cell-free expression systems.

Also provided are vectors containing the nucleic acids, e.g., polynucleotides, and host cells containing the vectors, e.g., for producing the antibodies or antigen-binding fragments thereof. Also provided are methods for producing the antibodies or antigen-binding fragments thereof. The nucleic acid may encode an amino acid sequence comprising the $V_L$ region and/or an amino acid sequence comprising the $V_H$ region of the antibody (e.g., the light and/or heavy chains of the antibody). The nucleic acid may encode one or more amino acid sequence comprising the $V_L$ region and/or an amino acid sequence comprising the $V_H$ region of the antibody (e.g., the light and/or heavy chains of the antibody). In some embodiments, the nucleic acid, e.g., polynucleotide encodes one or more $V_H$ region and/or one or more $V_L$ region of the antibody, in any order or orientation. In some embodiments, the nucleic acid, e.g., polynucleotide encodes a $V_H$ region and a $V_L$ region, and the coding sequence for the $V_H$ region is upstream of the coding sequence for the $V_L$ region. In some embodiments, the nucleic acid, e.g., polynucleotide encodes a $V_H$ region and a $V_L$ region, and the coding sequence for the $V_L$ region is upstream of the coding sequence for the $V_H$ region.

In a further embodiment, one or more vectors (e.g., expression vectors) comprising such nucleic acids are provided. In a further embodiment, a host cell comprising such nucleic acids is provided. In one such embodiment, a host cell comprises (e.g., has been transformed with) a vector comprising a nucleic acid that encodes an amino acid sequence comprising the $V_H$ region of the antibody. In another such embodiment, a host cell comprises (e.g., has been transformed with) (1) a vector comprising a nucleic acid that encodes an amino acid sequence comprising the $V_L$ region of the antibody and an amino acid sequence comprising the $V_H$ region of the antibody, or (2) a first vector comprising a nucleic acid that encodes an amino acid sequence comprising the $V_L$ region of the antibody and a second vector comprising a nucleic acid that encodes an amino acid sequence comprising the $V_H$ region of the antibody. In some embodiments, a host cell comprises (e.g., has been transformed with) one or more vectors comprising one or more nucleic acid that encodes one or more an amino acid sequence comprising one or more antibodies and/or portions thereof, e.g., antigen-binding fragments thereof. In some embodiments, one or more such host cells are provided. In some embodiments, a composition containing one or more such host cells are provided. In some embodiments, the one or more host cells can express different antibodies, or the same antibody. In some embodiments, each of the host cells can express more than one antibody.

Also provided are methods of making the provided antibodies (including antigen-binding fragments). For recombinant production, a nucleic acid sequence or a polynucleotide encoding an antibody or fragment, e.g., as described above, may be isolated and inserted into one or more vectors for further cloning and/or expression in a host cell. Such nucleic acid sequences may be readily isolated and sequenced using conventional procedures (e.g., by using oligonucleotide probes that are capable of binding specifically to genes encoding the heavy and light chains of the antibody). In some embodiments, a method of making the antibody is provided, wherein the method comprises culturing a host cell comprising a nucleic acid sequence encoding the antibody, as provided above, under conditions suitable for expression of the antibody, and optionally recovering the antibody from the host cell (or host cell culture medium).

In addition to prokaryotes, eukaryotic microbes such as filamentous fungi or yeast are suitable cloning or expression hosts for antibody-encoding vectors, including fungi and yeast strains whose glycosylation pathways have been modified to mimic or approximate those in human cells, resulting in the production of an antibody with a partially or fully human glycosylation pattern. See Gerngross, Nat. Biotech. 22:1409-1414 (2004), and Li et al., Nat. Biotech. 24:210-215 (2006).

Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells; and NS0 cells. In some embodiments, the antibody heavy chains and/or light chains (e.g., $V_H$ region and/or $V_L$ region) may be expressed in yeast. See, e.g., U.S. Publication No. US 2006/0270045 A1. In some embodiments, a particular eukaryotic host cell is selected based on its ability to make desired post-translational modifications to the heavy chains and/or light chains (e.g., $V_H$ region and/or $V_L$ region). For example, in some embodiments, CHO cells produce polypeptides that have a higher level of sialylation than the same polypeptide produced in 293 cells.

In some embodiments, the antibody or antigen-binding fragment provided herein is produced in a cell-free system. Exemplary cell-free systems are described, e.g., in Sitaraman et al., Methods Mol. Biol. 498: 229-44 (2009); Spirin, Trends Biotechnol. 22: 538-45 (2004); Endo et al., Biotechnol. Adv. 21: 695-713 (2003).

1. Variants and Modifications

In certain embodiments, the antibodies (e.g., antigen-binding fragment) include one or more amino acid variations, e.g., substitutions, deletions, insertions, and/or mutations, compared to the sequence of an antibody described herein. Exemplary variants include those designed to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain embodiments, the antibodies (e.g. antigen-binding fragment) include one or more amino acid substitutions, e.g., as compared to an antibody sequence described herein and/or compared to a sequence of a natural repertoire, e.g., human repertoire. Sites of interest for substitutional mutagenesis include the CDRs and FRs. Amino acid substitutions may be introduced into an antibody of interest and the products screened for a desired activity, e.g., retained/improved antigen binding, decreased immunogenicity, improved half-life, and/or improved effector function, such as the ability to promote antibody-dependent cellular cytotoxicity (ADCC) or complement-dependent cytotoxicity (CDC).

In some embodiments, one or more residues within a CDR of a parent antibody (e.g. a humanized or human antibody) is/are substituted. In some embodiments, the substitution is made to revert a sequence or position in the sequence to a germline sequence, such as an antibody sequence found in the germline (e.g., human germline), for example, to reduce the likelihood of immunogenicity, e.g., upon administration to a human subject.

In some embodiments, alterations are made in CDR "hotspots," residues encoded by codons that undergo mutation at high frequency during the somatic maturation process (see, e.g., Chowdhury, Methods Mol. Biol. 207:179-196 (2008)), and/or residues that contact antigen, with the resulting variant $V_H$ or $V_L$ being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, NJ, (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. Such alterations may, for example, be outside of antigen contacting residues in the CDRs. In certain embodiments of the variant $V_H$ and $V_L$ sequences provided above, each CDR either is unaltered, or contains no more than one, two or three amino acid substitutions.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme or a polypeptide which increases the serum half-life of the antibody.

In certain embodiments, the antibody is altered to increase or decrease the extent to which the antibody is glycosylated, for example, by removing or inserting one or more glycosylation sites by altering the amino acid sequence and/or by modifying the oligosaccharide(s) attached to the glycosylation sites, e.g., using certain cell lines. In some embodiments, an N-linked glycosylation, which is a glycosylation site that occurs at asparagines in the consensus sequence -Asn-Xaa-Ser/Thr is removed or inserted.

Exemplary modifications, variants, and cell lines are described, e.g., in Patent Publication Nos. US 2003/0157108, US 2004/0093621, US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Ripka et al. Arch. Biochem. Biophys. 249:533-545 (1986); US Pat Appl No US 2003/0157108 A1, Presta, L; and WO 2004/056312 A1, Yamane-Ohnuki et al. Biotech. Bioeng. 87: 614 (2004); Kanda, Y. et al., Biotechnol. Bioeng., 94(4):680-688 (2006); and WO2003/085107); WO 2003/011878 (Jean-Mairet et al.); U.S. Pat. No. 6,602,684 (Umana et al.); and US 2005/0123546 (Umana et al.); WO 1997/30087 (Patel et al.); WO 1998/58964 (Raju, S.); and WO 1999/22764 (Raju, S.).

Among the modified antibodies are those having one or more amino acid modifications in the Fc region, such as those having a human Fc region sequence or other portion of a constant region (e.g., a human IgG1, IgG2, IgG3 or IgG4 Fc region) comprising an amino acid modification (e.g. a substitution) at one or more amino acid positions.

Such modifications can be made, e.g., to improve half-life, alter binding to one or more types of Fc receptors, and/or alter effector functions.

Also among the variants are cysteine engineered antibodies such as "thioMAbs" and other cysteine engineered variants, in which one or more residues of an antibody are substituted with cysteine residues, in order to generate reactive thiol groups at accessible sites, e.g., for use in conjugation of agents and linker-agents, to produce immunoconjugates. Cysteine engineered antibodies are described, e.g., in U.S. Pat. Nos. 7,855,275 and 7,521,541.

In some embodiments, the antibodies (e.g., antigen-binding fragment) are modified to contain additional non-proteinaceous moieties, including water soluble polymers. Exemplary polymers include, but are not limited to, polyethylene glycol (PEG), copolymers of ethylene glycol/propylene glycol, carboxymethylcellulose, dextran, polyvinyl alcohol, polyvinylpyrrolidone, poly-1, 3-dioxolane, poly-1, 3,6-trioxane, ethylene/maleic anhydride copolymer, polyamino acids (either homopolymers or random copolymers), and dextran or poly(n-vinyl pyrrolidone) polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

2. Exemplary Features

In some aspects, the provided binding molecules, including antibodies or antigen-binding fragments thereof or conjugates or chimeric antigen receptors containing such antibodies or antigen-binding fragments, have one or more specified functional features, such as binding properties, including binding to particular epitopes.

In some embodiments, the binding molecules, including antibodies or antigen-binding fragments thereof or conjugates or chimeric antigen receptors containing such antibodies or antigen-binding fragments, specifically bind to CCT5 protein. In some embodiments, CCT5 protein is a mammalian CCT5, such as or including human CCT5, a non-human primate (e.g., cynomolgus monkey) CCT5 protein or a rodent CCT5 protein (e.g. mouse or rat). In some embodiments, the antibody or antigen-binding fragment binds to a mammalian CCT5 protein, including to naturally occurring variants of CCT5, such as certain splice variants or allelic variants.

In some embodiments, the provided binding molecules, including antibodies or antigen-binding fragments thereof or conjugates or chimeric antigen receptors containing such antibodies or antigen-binding fragments, specifically bind to human CCT5 protein, such as to an epitope or region of human CCT5 protein, such as the human CCT5 protein comprising the amino acid sequence of SEQ ID NO:45 or SEQ ID NO: 46 (e.g. UniProt No. P48643), an allelic variant or splice variant thereof, a species variant or an epitope or region of such a human CCT5. In some embodiments, the antibodies specifically bind to a CCT5 protein that exhibits at least or about at least or 75%, 80%, 85%, 90%, 91%, 92%, 93%, 94%, 95%, 96%, 97%, 98%, 99% or more sequence identity to SEQ ID NO:45 or SEQ ID NO:46. In some embodiments, the provided binding molecules, including antibodies or antigen-binding fragments thereof or conjugates or chimeric antigen receptors containing such antibodies or antigen-binding fragments, specifically bind to a CCT5 protein set forth in SEQ ID NO:45 or SEQ ID NO:46.

In some embodiments, the provided binding molecules, including antibodies or antigen-binding fragments thereof or conjugates or chimeric antigen receptors containing such antibodies or antigen-binding fragments, bind to human CCT5 (e.g. set forth in SEQ ID NO:45 or SEQ ID NO:46), and, in some aspects, also bind to one or more other species of CCT5. CCT5 exhibits high sequence identity between and among mammalian species. Various sequences of primate CCT5, including cynomolgus monkey, exhibit 100% sequence identity to human CCT5, and rodent species of CCT5, such as rat or mouse CCT5, exhibit greater than 96% sequence identity to human CCT5. In some embodiments, the provided binding molecules, including antibodies or antigen-binding fragments thereof or conjugates or chimeric antigen receptors containing such antibodies or antigen-binding fragments, bind to a primate CCT5, such as cynomolgus monkey CCT5 (e.g. UniProt Q4R6V2; set forth in SEQ ID NO:45 or SEQ ID NO:46). In some embodiments, the provided binding molecules, including antibodies or antigen-binding fragments thereof or conjugates or chimeric antigen receptors containing such antibodies or antigen-binding fragments, bind to a rat CCT5 (e.g. UniProt P80316; set forth in SEQ ID NO:58 or SEQ ID NO:59). In some embodiments, the provided binding molecules, including antibodies or antigen-binding fragments thereof or conjugates or chimeric antigen receptors containing such antibodies or antigen-binding fragments, bind to a mouse CCT5 (e.g. UniProt P80316; set forth in SEQ ID NO:83 or SEQ ID NO:84).

The observation that an antibody or other binding molecule binds to CCT5 protein or specifically binds to CCT5 protein does not necessarily mean that it binds to a CCT5 protein of every species or with the same affinity to a CCT5 protein of different species. In some embodiments, features of binding to CCT5 protein, such as the ability to specifically bind thereto and/or to bind with a particular affinity or to a particular degree, in some embodiments, refers to the ability with respect to a human CCT5 protein and the antibody may not have this feature, or may not exhibit the same degree of binding, with respect to a CCT5 protein of another species, such as mouse.

In one embodiment, the extent of binding of an anti-CCT5 antibody to an unrelated, non-CCT5 protein, such as a non-human CCT5 protein or other non-CCT5 protein, is less than at or about 10% of the binding of the antibody to human CCT5 protein as measured, e.g., by a radioimmunoassay (RIA). In some embodiments, among provided antibodies are antibodies in which binding to mouse CCT5 protein is less than or at or about 10% of the binding of the antibody to human CCT5 protein. In some embodiments, among provided antibodies are antibodies in which binding to mouse CCT5 protein is similar to or about the same as the binding of the antibody to human CCT5 protein.

In some embodiments, the antibody specifically binds to and/or binds with a particular affinity to a particular degree, to a CCT5 protein, e.g., human CCT5 or a mouse CCT5 protein.

In some embodiments, the provided antibodies are capable of binding CCT5 protein, such as human CCT5 protein, with at least a certain affinity, as measured by any of a number of known methods. In some embodiments, the affinity is represented by an equilibrium dissociation constant ($K_D$); in some embodiments, the affinity is represented by $EC_{50}$.

A variety of assays are known for assessing binding affinity and/or determining whether a binding molecule (e.g., an antibody or fragment thereof) specifically binds to a particular ligand (e.g., an antigen, such as a CCT5 protein). Methods of determining the binding affinity of a binding molecule, e.g., an antibody, for an antigen, e.g., CCT5, such as human CCT5 or mouse CCT5, are known. For example, several binding assays are well-known. For example, in some embodiments, a BIAcore® instrument can be used to determine the binding kinetics and constants of a complex between two proteins (e.g., an antibody or fragment thereof, and an antigen, such as a CCT5 protein), using surface plasmon resonance (SPR) analysis (see, e.g., Scatchard et al., *Ann. N. Y. Acad. Sci.* 51:660, 1949; Wilson, Science 295:2103, 2002; Wolff et al., *Cancer Res.* 53:2560, 1993; and U.S. Pat. Nos. 5,283,173, 5,468,614, or the equivalent).

SPR measures changes in the concentration of molecules at a sensor surface as molecules bind to or dissociate from the surface. The change in the SPR signal is directly proportional to the change in mass concentration close to the surface, thereby allowing measurement of binding kinetics between two molecules. The dissociation constant for the complex can be determined by monitoring changes in the refractive index with respect to time as buffer is passed over the chip. Other suitable assays for measuring the binding of one protein to another include, for example, immunoassays such as enzyme linked immunosorbent assays (ELISA) and radioimmunoassays (RIA), or determination of binding by monitoring the change in the spectroscopic or optical properties of the proteins through fluorescence, UV absorption, circular dichroism, or nuclear magnetic resonance (NMR). Other exemplary assays include, but are not limited to, Western blot, ELISA, analytical ultracentrifugation, spectroscopy, flow cytometry, sequencing and other methods for detection of expressed nucleic acids or binding of proteins.

In some embodiments, the binding molecule, e.g., antibody or fragment thereof, binds, such as specifically binds, to an antigen, e.g., a CCT5 protein or an epitope therein, with an affinity or $K_A$ (i.e., an equilibrium association constant of a particular binding interaction with units of 1/M; equal to the ratio of the on-rate [$k_{on}$ or $k_a$] to the off-rate [$k_{off}$ or $k_d$] for this association reaction, assuming bimolecular interaction) equal to or greater than $10^5$ M$^{-1}$. In some embodiments, the antibody or fragment thereof exhibits a binding affinity for the peptide epitope with a $K_D$ (i.e., an equilibrium dissociation constant of a particular binding interaction with units of M; equal to the ratio of the off-rate [$k_{off}$ or $k_d$] to the on-rate [$k_{on}$ or $k_a$] for this association reaction, assuming bimolecular interaction) of equal to or less than $10^{-5}$ M. For example, the equilibrium dissociation constant $K_D$ ranges from $10^{-5}$ M to $10^{-13}$ M, such as $10^{-7}$ M to $10^{-11}$ M, $10^{-8}$ M to $10^{-10}$ M, or $10^{-9}$ M to $10^{-10}$ M. The on-rate (association rate constant; $k_{on}$ or $k_a$; units of 1/Ms) and the off-rate (dissociation rate constant; $k_{off}$ or $k_d$; units of 1/s) can be determined using any of the assay methods known, for example, surface plasmon resonance (SPR).

In some embodiments, the binding affinity ($EC_{50}$) and/or the dissociation constant of the antibody (e.g. antigen-binding fragment) to about CCT5 protein, such as human CCT5 protein, is from or from about 0.01 nM to about 500 nM, from or from about 0.01 nM to about 400 nM, from or from about 0.01 nM to about 100 nM, from or from about 0.01 nM to about 50 nM, from or from about 0.01 nM to about 10 nM, from or from about 0.01 nM to about 1 nM, from or from about 0.01 nM to about 0.1 nM, is from or from about 0.1 nM to about 500 nM, from or from about 0.1 nM to about 400 nM, from or from about 0.1 nM to about 100 nM, from or from about 0.1 nM to about 50 nM, from or from about 0.1 nM to about 10 nM, from or from about 0.1 nM to about 1 nM, from or from about 0.5 nM to about 200 nM, from or from about 1 nM to about 500 nM, from or from about 1 nM to about 100 nM, from or from about 1 nM to about 50 nM, from or from about 1 nM to about 10 nM, from or from about 2 nM to about 50 nM, from or from about 10 nM to about 500 nM, from or from about 10 nM to about 100 nM, from or from about 10 nM to about 50 nM, from or from about 50 nM to about 500 nM, from or from about 50 nM to about 100 nM or from or from about 100 nM to about 500 nM. In certain embodiments, the binding affinity ($EC_{50}$) and/or the equilibrium dissociation constant, $K_D$, of the antibody to a CCT5 protein, such as human CCT5 protein, is at or less than or about 400 nM, 300 nM, 200 nM, 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM or less. In some embodiments, the antibodies bind to a CCT5 protein, such as human CCT5 protein, with a sub-nanomolar binding affinity, for example, with a binding affinity less than about 1 nM, such as less than about 0.9 nM, about 0.8 nM, about 0.7 nM, about 0.6 nM, about 0.5 nM, about 0.4 nM, about 0.3 nM, about 0.2 nM or about 0.1 nM or less.

In some embodiments, the binding affinity may be classified as high affinity or as low affinity. In some cases, the binding molecule (e.g. antibody or fragment thereof) that exhibits low to moderate affinity binding exhibits a $K_A$ of up to $10^7$ M$^{-1}$, up to $10^6$ M$^{-1}$, up to $10^5$ M$^{-1}$. In some cases, a binding molecule (e.g. antibody or fragment thereof) that exhibits high affinity binding to a particular epitope interacts with such epitope with a $K_A$ of at least $10^7$ M$^{-1}$, at least $10^8$ M$^{-1}$, at least $10^9$ M$^{-1}$, at least $10^{10}$ M$^{-1}$, at least $10^{11}$ M$^{-1}$, at least $10^{12}$ M$^{-1}$, or at least $10^{13}$ M$^{-1}$. In some embodiments, the binding affinity ($EC_{50}$) and/or the equilibrium dissociation constant, $K_D$, of the binding molecule, e.g., anti-CCT5 antibody or fragment thereof, to a CCT5 protein, is from or from about 0.01 nM to about 1 µM, 0.1 nM to 1 µM, 1 nM to 1 µM, 1 nM to 500 nM, 1 nM to 100 nM, 1 nM to 50 nM, 1 nM to 10 nM, 10 nM to 500 nM, 10 nM to 100 nM, 10 nM to 50 nM, 50 nM to 500 nM, 50 nM to 100 nM or 100 nM to 500 nM. In certain embodiments, the binding affinity ($EC_{50}$) and/or the dissociation constant of the equilibrium dissociation constant, $K_D$, of the binding molecule, e.g., anti-CCT5 antibody or fragment thereof, to a CCT5 protein, is at or about or less than at or about 1 µM, 500 nM, 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM or less.

In some embodiments, the binding affinity of a binding molecule, such as an anti-CCT5 antibody, for different antigens, e.g., CCT5 proteins from different species can be compared to determine the species cross-reactivity. For example, species cross-reactivity can be classified as high cross reactivity or low cross reactivity. In some embodiments, the equilibrium dissociation constant, $K_D$, for different antigens, e.g., CCT5 proteins from different species, such as human or mouse, can be compared to determine species cross-reactivity. In some embodiments, the species cross-reactivity of an anti-CCT5 antibody can be high, e.g., the anti-CCT5 antibody binds to human CCT5 and a species variant CCT5 to a similar degree, e.g., the ratio of $K_D$ for human CCT5 and $K_D$ for the species variant CCT5 is or is about 1.

In some embodiments, the provided antibodies or antigen binding fragments thereof bind to a similar degree to a human CCT5 protein and a non-human CCT5 protein. For example, in some embodiments, the provided antibodies or antigen binding fragments thereof bind to a human CCT5 protein, such as the human CCT5 protein comprising the amino acid sequence of SEQ ID NO:45 or 46 (UniProt No. P48643), or an allelic variant or splice variant thereof, with a specific an equilibrium dissociation constant ($K_D$), and to a non-human CCT5, such as a mouse CCT5, such as the mouse CCT5 protein set forth in SEQ ID NO:83 or 84 (UniProt No. P80316), with a $K_D$ that is similar, or about the same, or less than 2-fold different, or less than 5-fold different.

For example, in some embodiments, the provided antibodies or antigen binding fragments thereof bind to a human CCT5 with a $K_D$ of about or less than at or about 1 µM, 500 nM, 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM or less. In some embodiments, the provided antibodies or antigen binding fragments thereof bind to a mouse CCT5 protein with a $K_D$ of about or less than at or about 1 µM, 500 nM, 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM or less. In some embodiments, the provided antibodies or antigen binding fragments thereof bind to a human CCT5 and a mouse CCT5 with high affinity. In some embodiments, the provided antibodies or antigen binding fragments thereof bind to a human CCT5 with a high affinity, and to a mouse CCT5 with low affinity. In some embodiments, the provided antibodies or antigen binding fragments thereof bind to a human CCT5 and CCT5 from other species, or other variants of the CCT5 protein, with high affinity.

In some embodiments, the total binding capacity ($R_{max}$), as measured using particular surface plasmon resonance (SPR) conditions, is used to determine the ability or capacity of binding of the provided antibody or antigen binding fragment thereof, to the antigen, e.g., a CCT5 protein, such as a human CCT5 protein. For SPR analysis, the "ligand" is the immobilized target molecule on the surface of the sensor, for example, a CCT5 protein, and the "analyte" is the tested molecule, e.g., antibody, for binding to the "ligand". For example, the "analyte" can be any of the provided antibodies or antigen binding fragments thereof that binds to a CCT5 protein. For a particular ligand and analyte pair in SPR, the $R_{max}$ can be determined assuming a 1:1 binding stoichiometry model, for a particular condition. In some embodiments, binding capacity ($R_{max}$) can be determined using the following formula: $R_{max}$ (RU)=(analyte molecular weight)/(ligand molecular weight)×immobilized ligand level (RU). In particular aspects of SPR conditions, the $R_{max}$ of binding between any of the provided antibody or antigen binding fragment thereof and a CCT5 protein, such as a human CCT5 or a mouse CCT5, is at least or at least about 50 resonance units (RU), such as about 25 RU, 20 RU, 15 RU, 10 RU, 5 RU or 1 RU.

In some embodiments, the antibodies or antigen-binding fragment thereof, binds, e.g., specifically binds, and/or recognizes, one or more epitopes in CCT5, e.g., human CCT5. In some embodiments, the epitopes include peptide epitopes. In some embodiments, the epitope includes linear epitopes and/or conformational epitopes or a combination thereof. In some embodiments, the epitope(s) on CCT5 that the e.g., anti-CCT5 antibody or antigen-binding fragment thereof provided herein binds, include(s) conformational epitopes, e.g., epitopes that include several peptide stretches from CCT5.

In some embodiments, the provided antibodies or antigen-binding fragment thereof specifically binds to a peptide sequence, or to an epitope that is or is contained within the peptide sequence, having the sequence XSVEXXKX (SEQ ID NO: 68), wherein X can be any amino acid. In some embodiments, the peptide sequence is set forth in sequence $X_1SVEX_5X_6KX_8$ (SEQ ID NO: 69), wherein $X_1$ is T, S or D; $X_5$ is D or A; $X_6$ is Y, F, or I; and $X_8$ is A or R, or an amino acid sequence contained within the amino acid sequence set forth in SEQ ID NO: 69. In some embodiments, the peptide sequence is or includes TSVEDYKA (SEQ ID NO: 70), SSVEAFKR (SEQ ID NO: 71), or DSVEAIKA (SEQ ID NO: 72), or an amino acid sequence contained within any of the amino acid sequences set forth in SEQ ID NOs: 70-72.

In some embodiments, the antibodies (e.g., antigen-binding fragment) display a binding preference for CCT5-expressing cells as compared to CCT5-negative cells, such as particular cells known and/or described herein to express CCT5 and known not to express CCT5. In some embodiments, the antibodies (e.g., antigen-binding fragment) display a binding preference for cells expressing CCT5 on the surface as compared to cells not expressing CCT5 on the surface, such as particular cells known and/or described herein to express surface CCT5 and known not to express surface CCT5. In some embodiments, the antibodies display a binding preference for cells that exhibit increased expression of one or more subunits of the TRiC complex. In some embodiments, the provided antibodies display a binding preference for cancer cells or tumor cells. In some embodiments, the binding preference is observed where a significantly greater degree of binding is measured to the CCT5 surface-expressing, as compared to the non-surface-expressing cells. In some embodiments, the fold change in degree of binding detected, for example, as measured by mean fluorescence intensity in a flow cytometry-based assay and/or dissociation constant or $EC_{50}$, to the CCT5-expressing cells as compared to the non-CCT5-expressing cells, is at least at or about 1.5, 2, 3, 4, 5, 6, or more, and/or is about as great, about the same, at least as great or at least about as great, or greater, than the fold change observed for the corresponding form of a reference antibody known to bind CCT5, such as a reference antibody containing a VH set forth in SEQ ID NO:1 and a VL set forth in SEQ ID NO:2. In some cases, the total degree of observed binding to CCT5 or to the CCT5-expressing cells is approximately the same, at least as great as, or greater than that observed for the corresponding form of the reference antibody known to bind CCT5, such as a reference antibody containing a VH set forth in SEQ ID NO:1 and a VL set forth in SEQ ID NO:2.

In some embodiments, the provided binding molecules, including antibodies or antigen-binding fragments thereof or conjugates or chimeric antigen receptors containing such antibodies or antigen-binding fragments, bind to cells that aberrantly express CCT5, such as overexpress CCT5, express misfolded CCT5, surface expressed CCT5 or to CCT5 that is associated with or localized to the membrane. In some embodiments, the binding is to certain cancer cell lines, such as epithelial cells. In some embodiments, the cancer cell line is a tumor cell line from among breast cancer (SK-BR-3, MCF7, HCC 1806, HCC 2218, BT549, and MDA-MB-231), pancreatic cancer (MIA PaCa-2, PANC-1, BxPC-3, SU86.86, and Panc10.05), ovarian cancer (OVCAR-8, Caov-3, ES-2, NIH:OVCAR-3, and OVCAR-4), lung cancer (A549, NCI-H1975, NCI H1299, NCI H1573, and NCI H1915), head and neck squamous cell carcinoma (HNSCC; UPCI:SCC152), cervical cancer (CaSki), dermal cancer (SV-80), acute myeloid leukemia (AML; Kasumi-1, SH-2, HT-93, HL60, ML-2, BDCM, KG-1, SKM-1, THP-1, and OCI-M1) or chronic myeloid leukemia (CML; K-562).

In some aspects, the provided antibodies or antigen-binding fragments, such as anti-CCT5 antibodies (e.g., antigen-binding fragments) provided herein may be identified, screened for, or characterized for their physical/chemical properties and/or biological activities by various known assays. In one aspect, the antibody is tested for its antigen binding activity, e.g., by known methods such as ELISA, Western blotting, and/or flow cytometric assays, including cell-based binding assays, for example, assessing binding of the antibody (e.g., conjugated to a fluorescent marker or tagged) to a cell expressing the target antigen on its surface, e.g., surface CCT5, in some cases compared to results using cells that do not express the target antigen on its surface. Binding affinity may be measured as $K_D$ or $EC_{50}$. In some examples, binding affinity, binding kinetics, and/or binding constants can be measured using assays to determine molecular interaction, such as surface plasmon resonance analysis.

Competition assays may be used to identify an antibody that competes with any of the antibodies (e.g., antigen-binding fragments) described herein. Assays for mapping epitopes bound by the antibodies and reference antibodies also may be used and are known.

B. Immunoconjugates

Also provided herein are antibody conjugates or immunoconjugates. In some embodiments, the antibody (e.g., antigen-binding fragment) is or is part of an immunoconjugate, in which the antibody is conjugated directly or indirectly, such as via a linker, to one or more heterologous molecule(s) or moiety. The provided conjugates can be used for targeted delivery of cytotoxic or cytostatic agents, i.e., drugs, to kill or inhibit target cells expressing CCT5, such as aberrantly expressing CCT5 and/or a polypeptide containing the sequence set forth in SEQ ID NO: 68 or 69 (e.g. the sequence set forth in any of SEQ ID NO:70-72). In some embodiments, such conjugates can be used to kill or inhibit tumor target cells, such as in the treatment of cancer. In some embodiments the provided conjugates are referred to as antibody-drug conjugates, or ADCs. Such conjugates exhibit selectivity to tumor cells that are desired to be eliminated over non-diseased cells, and thereby do not result in unacceptable levels of toxicity to normal cells. Hence, such compounds can be used in the methods described herein of diagnosis or treatment of cancer and other diseases or disorders.

In some embodiment, the heterologous molecule or moiety is a targeted agent. Exemplary heterologous molecules or moieties include, but are not limited to, cytotoxic or imaging agent(s). In some aspects, such conjugates contain the following components: antibody (Ab), (linker (L))$_q$, (targeted agent)$_m$ and are represented by the formula: Ab-(L)$_q$-(targeted agent)$_m$, where q is 0 or more and m is at least 1. Among the conjugates provided herein are conjugates that contain one or more targeted agents covalently linked to an antibody provided herein.

In some embodiments, the number of targeted agents is designated by the variable m, where m is an integer of 1 or greater. In some embodiments, the targeted agent is conjugated to an antibody provided herein by the number of linkers designated by the variable q, where q is 0 or any integer. The variables q and m are selected such that the resulting conjugate interacts with the target antigen, e.g. CCT5, such as aberrantly expressed CCT5, and/or a polypeptide containing the sequence motif set forth in SEQ ID NO:68 or 69 (e.g. the sequence set forth in any of SEQ ID NO:70-72), such as on the surface of target cells, in particular, tumor cells. In some aspects such interaction delivers the targeted agent to the target cell and/or causes or brings about internalization of the targeted agent by the target cell. In some embodiments, following internalization all or a portion of the internalized protein traffics to the cytoplasm of such cells In some embodiments, m is between 1 and 8. In some embodiments, q is 0 or more, depending upon the number of linked targeting and targeted agents and/or functions of the linker; q is generally 0 to 4. When more than one targeted agent is present in a conjugate, the targeted agents may be the same or different.

The targeted agents can be covalently linked to the antibody directly or by one or more linkers. Any suitable association among the elements of the conjugate is contemplated as long as the resulting conjugates interact with the target antigen, e.g. CCT5, such as aberrantly expressed CCT5, and/or a polypeptide containing the sequence motif set forth in SEQ ID NO:68 or 69 (e.g. the sequence set forth in any of SEQ ID NO:70-72). The conjugates provided herein can be produced as fusion proteins, can be chemically coupled, or can include a fusion protein portion and a chemically linked portion or any combination thereof.

The targeted agents also can be modified to render them more suitable for conjugation with the linker and/or the provided antibody or to increase their intracellular activity. For example, in the case of polypeptide targeted agents, such modifications include, but are not limited to, the introduction of a Cys residue at or near the N-terminus or C-terminus, derivatization to introduce reactive groups, such as thiol groups, and/or addition of sorting signals, such as (Xaa-Asp-Glu-Leu)$_n$ (SEQ ID NO: 85) where Xaa is Lys or Arg, such as Lys, and n is 1 to 6, such as 1-3. In some embodiments, such modifications are at, the carboxy-terminus of the targeted agent (see, e.g., Seetharam et al. (1991) J. Biol. Chem. 266:17376-17381; and Buchner et al. (1992) Anal. Biochent. 205:263-270), which, in some aspects, directs the targeted agent to the endoplasmic reticulum.

In some embodiments, the targeted agent can be modified to eliminate one or more cysteine residues, for example, to provide more predictable thiol conjugation at preferred locations. In some cases, care must be taken to avoid altering specificity of the resulting modified targeted agent, unless such alteration is desired. In all instances, particular modifications can be determined empirically.

In some embodiments, the linker, L, attaches the antibody to the targeted agent through covalent bond(s). The linker can be a peptide or a non-peptide. In some embodiments, the linker can be selected to relieve or decrease steric hindrance caused by proximity of the targeted agent to the antibody and/or to increase or alter other properties of the conjugate, such as the specificity, toxicity, solubility, serum stability and/or intracellular availability of the targeted moiety and/or to increase the flexibility of the linkage between the antibody and the targeted agent.

When fusion proteins are contemplated, the linker is selected such that the resulting nucleic acid molecule encodes a fusion protein that binds to, and, in some cases, is internalized by cells that express or overexpress the target antigen, e.g. CCT5, such as aberrantly expressed CCT5, and/or a polypeptide containing the sequence motif set forth in SEQ ID NO:68 or 69 (e.g. the sequence set forth in any of SEQ ID NO:70-72). It also is contemplated that several linkers can be joined in order to employ the advantageous properties of each linker. In such instances, the linker portion of a conjugate may contain more than 50 amino acid residues. The number of residues is not important as long as the resulting fusion protein binds to the target antigen, e.g. CCT5, such as aberrantly expressed CCT5, and/or a polypeptide containing the sequence motif set forth in SEQ ID NO:68 or 69 (e.g. the sequence set forth in any of SEQ ID NO:70-72) on the surface of the target cell and internalizes the linked targeted agent via a pathway that traffics the targeted agent to the cytoplasm and/or nucleus.

The targeted agent can be a protein, peptide, nucleic acid, small molecule, therapeutic moiety, or other agent in which targeted delivery to a selected population of tumor cells is desired. Such targeted agents include, but are not limited to, cytotoxic agents, DNA and RNA nucleases, toxins, drugs or other agents. Therapeutic moieties include, but are not limited to, cytotoxic moieties, radioisotopes, chemotherapeutic agents, lytic peptides and cytokines.

Exemplary therapeutic moieties include, but are not limited to, taxol; cytochalasin B; gramicidin D; ethidium bromide; emetine; mitomycin; etoposide; teniposide; vincristine; vinblastine; colchicine; doxorubicin; daunorubicin; dihydroxy anthracin dione; maytansine or an analog or derivative thereof, an auristatin or a functional peptide analog or derivative thereof, dolastatin 10 or 15 or an analog thereof, irinotecan or an analog thereof, mitoxantrone; mithramycin; actinomycin D; 1-dehydrotestosterone; a glucocorticoid; procaine; tetracaine; lidocaine; propranolol; puromycin; calicheamicin or an analog or derivative thereof, an antimetabolite; an alkylating agent; a platinum derivative; duocarmycin A, duocarmycin SA, rachelmycin (CC-1065), or an analog or derivative thereof, an antibiotic; pyrrolo[2,1-c][1,4]-benzodiazepine (PDB); a toxin; ribonuclease (RNase); DNase I, Staphylococcal enterotoxin A; and pokeweed antiviral protein.

Drugs also can be used as a targeted agent in the provided conjugates. Such drugs include 5-fluorouracil, vinca alkaloids, and antibiotics such as dactinomycin, bleomycin, daunorubicin, doxorubicin, idarubicin, methotrexate, mithramycin, mitomycin, mitoxantrone, plicamycin and anthramycin (AMC), neocarzinostatin and vindesine.

Toxins used in antibody-toxin conjugates include bacterial toxins such as diphtheria toxin, and active fragments thereof and hybrid molecules, plant toxins, such as ricin toxin, small molecule toxins such as geldanamycin, maytansinoids, such as DM1, DM3 and DM4, and calicheamicin. Finally, the auristatin peptides, auristatin E (AE), monomethyl auristatin E (MMAE), and monomethyl auristatin F (MMAF), synthetic analogs of dolastatin can be employed. Other toxins include cholera toxin, a Shiga-like toxin, LT toxin, C3 toxin, Shiga toxin, pertussis toxin, tetanus toxin, soybean Bowman-Birk protease inhibitor, *Pseudomonas* exotoxin, alorin, saporin, modeccin, galanin, abrin A chain, modeccin A chain, alpha-sarcin, *Aleurites fordii* proteins, dianthin proteins, *Phytolacca americana* proteins, *Momordica charantia* inhibitor, curcin, crotin, gelonin, mitogillin, restrictocin, phenomycin, and enomycin toxins. The toxins can effect their cytotoxic and cytostatic activity by mechanisms including tubulin binding, DNA binding, or topoisomerase inhibition.

1. Targeted Agents

In some embodiments, the targeted agent can be a protein, peptide, nucleic acid, small molecule, therapeutic moiety, radioactive isotope, or other agent in which targeted delivery to a selected population of tumor cells is desired. Such targeted agents include, but are not limited to, cytotoxic agents, DNA and RNA nucleases, toxins, drugs or other agents.

a. Radioactive Moieties

In some embodiments, radioactive isotopes can be employed as a target agent in the provided conjugates, in which the antibody (e.g., antigen-binding fragment) is conjugated to a radioactive atom to form a radioconjugate. Exemplary radioactive isotopes include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu.

b. Maytansinoid Drug Moieties

In some embodiments, a cytotoxic moiety as a targeted agent in the conjugates include Maytansinoid drug moieties, including those described in U.S. Pat. No. 8,142,784. In some embodiments, maytansine compounds inhibit cell proliferation by inhibiting the formation of microtubules during mitosis through inhibition of polymerization of the microtubule protein, tubulin (Remillard et al. (1975) Science 189:1002-1005; U.S. Pat. No. 5,208,020). Maytansine and maytansinoids are highly cytotoxic but their clinical use in cancer therapy has been limited by their systemic side-effects, which is attributed, in some aspects, to their poor selectivity for tumors. Clinical trials with maytansine had been discontinued due to serious adverse effects on the central nervous system and gastrointestinal system (Issell et al. (1978) Can. Treatment. Rev. 5:199-207).

In some aspects, maytansinoid drug moieties are attractive drug moieties in antibody-drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Among maytansine compounds suitable for use as maytansinoid drug moieties are those that can be isolated from natural sources according to known methods, produced using genetic engineering techniques (see Yu et al. (2002) PNAS 99:7968-7973), or maytansinol and maytansinol analogs prepared synthetically according to known methods.

Exemplary maytansinoid drug moieties include those having a modified aromatic ring, such as: C-19-dechloro (U.S. Pat. No. 4,256,746) (prepared by lithium aluminum hydride reduction of ansamitocin P2); C-20-hydroxy (or C-20-demethyl)+/−C-19-dechloro (U.S. Pat. Nos. 4,361,650 and 4,307,0.16) (prepared by demethylation using *Streptomyces* or *Actinomyces* or dechlorination using LAH); and C-20-demethoxy, C-20-acyloxy (−OOR), +/− dechloro (U.S. Pat. No. 4,294,757) (prepared by acylation using acyl chlorides); and those having modifications at other positions.

Exemplary maytansinoid drug moieties also include those having modifications such as: C-9-SH, prepared by the reaction of maytansinol with H2S or P2S5 (U.S. Pat. No. 4,424,219); C-14-alkoxymethyl(demethoxy/CH2OR)(U.S. Pat. No. 4,331,598); C-14-hydroxymethyl or acyloxymethyl (CH2OH or CH20Ac) prepared from *Nocardia* (U.S. Pat. No. 4,450,234); C-15-hydroxy/acyloxy, prepared by the conversion of maytansinol by Streptotnyces (U.S. Pat. No. 4,364,866); C-15-methoxy, isolated from Trewia nudijlora (U.S. Pat. Nos. 4,313,946 and 4,315,929); C-18-N-demethyl, prepared by the demethylation of maytansinol by *Streptomyces* (U.S. Pat. Nos. 4,362,663 and 4,322,348); and 4,5-deoxy, prepared by the titanium trichloride/LAH reduction of maytansinol (U.S. Pat. No. 4,371,533).

Many positions on maytansine compounds are known to be useful as the linkage—position, depending upon the type of link. For example, for forming an ester linkage, the C-3 position having a hydroxyl group, the C-14 position modified with hydroxymethyl, the C-15 position modified with a hydroxyl group and the C-20 position having a hydroxyl group are all suitable.

In some embodiments, maytansinoid drug moieties can be linked to a provided antibody or fragment by direct conjugation or using a linker, such as any as described herein. In particular examples, the cytotoxic or drug agent is mertansine, also known as DM1 (N2t-deacetyl-N2'-(3-mercapto-1-oxopropyl)-maytansine). Mertansine can be linked via 4-mercaptovaleric acid.

In some embodiments, an emtansine conjugate also can be formed with the antibodies herein using the linker 4-(3-mercapto-2,5-dioxo-1-pyrrolidinylmethyl)-cylohexanecarboxylic acid (MCC).

c. Auristatins and Dolastatins Drug Moieties

In some embodiments, a cytotoxic moiety as a targeted agent in the conjugates include auristatins and dolastatins, including those described in U.S. Publication No. US2011/0217321. Dolastatins and auristatins have been shown to interfere with microtubule dynamics, GTP hydrolysis, and nuclear and cellular division (Woyke et al. (2001) Antimicrob. Agents and Chemother. 45(12):3580-3584) and have anticancer (U.S. Pat. No. 5,663,149) and/or antifungal activity (Pettit et al. (1998) Antimicrob. Agents Chemother. 42:2961-2965). Further, auristatins are highly potent, synthetic, stable, and amenable to chemical modification to allow for linker attachment (Senter (2009) CUPT Opin Chem Biol 13:235-244).

Because auristatins are synthetic, integral structural modifications can be made to significantly alter the properties of the parent drug. For example, monomethyl auristatin F (MMAF) terminates with the amino acid residue phenylalanine, which impairs cell membrane permeability (Doronina et al., (2006) Bioconjug Chem. 17:114-124). In some embodiments, conjugation of MMAF to an ADC can facilitate selective drug uptake by antigen-positive cells (Doronina et al., (2006) Bioconjug Chem. 17:114-124; Doronina et al., (2003) Nat Biotechnol. 21:778-784).

In some embodiments, the dolastatin or auristatin drug moiety can be attached to antibodies through the N (amino) terminus or the C (carboxyl) terminus of the peptidic drug moiety, (WO 2002/088172). Exemplary auristatin embodiments include N-terminally and C-terminally linked monomethyl auristatin drug moieties MMAE and MMAF (Senter et at (2004) "Proceedings of the American Association for Cancer Research," Volume 45, Abstract Number 623, and presented Mar. 28, 2004; U.S. Publication No. 2011/0020343).

Dolastatin or auristatin can be linked to an antibody or fragment by direct conjugation or using a linker, such as any of the linkers as described. In particular examples, dolastatin or auristatin can be linked to an antibody or fragment with a peptide linker, such as a valine-citrulline (Val-Cit) linker.

d. Pyrrolobenzodiazepines (PBDs)

In some embodiments, a cytotoxic moiety as a targeted agent in the conjugates include pyrrolobenzodiazepines (PBDs) (or pyrrolo[2,1-c][1, 4]-benzodiazepines), which are sequence-selective DNA alkylating antibiotics with antitumor properties. PBDs have the ability to recognize and bond specific sequences of DNA. In some embodiment the DNA sequence of a PBD is or comprises PuGPu (Purine-Guanine-Purine). PBDs also can bond to PuGPy (Purine-Guanine-Pyrimidine) or PyGPu sequences, generally over PyGPy sequences.

PBDS can be naturally occurring or synthetic. Naturally occurring PBDs include abbeymycin (Hochlowski, et al., J. Antibiotics, 40, 145-148 (1987)), anthramycin=(Leimgruber, et al., J. Am. Chem. Soc, 87, 5793-5795 (1965); Leimgruber, et al., J. Am. Chem. Soc, 87, 5791-5793 (1965)), chicamycin (Konishi, et al., J. Antibiotics, 37, 200-206 (1984)), DC-81 (Thurston, et al., Chem. Brit, 26, 767-772 (1990); Bose, et al., Tetrahedron, 48, 751-758 (1992)), mazethramycin (Kunimoto, et al., J. Antibiotics, 33, 665-667(1980)), neothramycins A and B (Takeuchi, et al., J. Antibiotics, 29, 93-96 (197.6)), porothramycin (Tsunakawa, et al., J. Antibiotics, 41, 1366-1373 (1988)), prothracarcin (Shimizu, et al, J. Antibiotics, 29, 2492-2503 (1982); Langley and Thurston, J. Org. Chem., 52, 91-91 (1987)), sibanomicin (DC-102)(Hara, et alõ J. Antibiotics, 41, 702-704 (1988); hob, et al., J. Antibiotics, 41, 1281-1284 (1988)), sibiromycin (Leber, et al., J, Am. Chem. Soc, 110, 2992-2993 (1988)), and tomamycin (Arima, et al., J. Antibiotics, 25, 437-444 (1972)). Synthesis of PBDs and generation of synthetic analogs also have been described (see, e.g., U.S. Pat. Nos. 6,562,806, 6,608,192 6,747,144, and 7,049,311, 7,528,126).

PBDs differ in the number, type and position of substituents, in both their aromatic A rings and pyrrolo C rings, and in the degree of saturation of the C ring. In the B-ring there is either an imine (N=C), a carbinolamine (NH—CH(OH)), or a carbinolamine methyl ether (NH-5 CH(Olvle)) at the N10-C11 position which is the electrophilic center responsible for alkylating DNA. All of the known natural products have an (S)-configuration at the chiral C11 a position which provides them with a right-handed twist when viewed from the C ring towards the A ring. This gives them the appropriate three-dimensional shape for isohelicity with the minor groove of B-form DNA (Kohn, In Antibiotics III. Springer-Verlag, New York, 10 pp. 3-11 (1975); Hurley and Needham-VanDevanter, Acc. Chem. Res., 19,230-237 (1986)).

In some embodiments, PBDs form a covalent, aminal linkage with the exocyclic N2 of the guanine' in the PuGPu consensus sequence, forming a PBD/DNA adduct which interferes with DNA processing and leads to cell cycle arrest and apoptosis. Thus PBDs are effective antitumor agents.

In some embodiments, dimers of PBDs can be effective antitumor agents. In some aspects, PBD dimers cover six base pairs instead of three base pairs covered by the PBD monomer. Further, the PBDs in the dimer can bond sequences in the complementary strands of DNA (i.e., an interstrand guanine-guanine cross-link), leading to sequence-selective DNA cross-linking. PBD dimer-induced cross-linking prevents strand separation, thereby preventing DNA replication. In some aspects, this results in cell cycle arrest and apoptosis in the G2/M interface In some embodiments, the increased coverage of PBD-dimers compared to PBD monomers, in addition to DNA cross-linking, can lead to substantially increased efficacy as anticancer agents.

In some embodiments, PBD dimers can be homodimers or heterodimers, and are synthesized by joining the two monomer PBD units together through their C8 positions via a flexible linker. Commonly used linkers include propyldioxy (PBD-C8-0-(C1-12)3-0-C8'-PBD) and pentyldioxy (PBD-C8-0-(CH2)5-0-C8'-PBD'). The properties of the linker, such as the length of the linker, can be selected to target the dimer to specific DNA sequences (Rahman et al., (2011) Nucleic Acids Res. 39(13): 5800-5812 and Gregson et al., (2004) J Med Chem 47:1161-1174).

Exemplary inter-PBD linkers are described in Bose et al., (1992) J Am Chem Soc. 114:4939-4941, Bose et al., (1992) J Chem Soc Chem Commun. 14:1518-1520, Thurston et al., (1996) J Org Chem. 61:8141-8147, Gregson et al., (2001) 0.1 Med Chem. 44:737-748, and Gregson et al., J Med Chem 2004; 47:1161-1174. Exemplary PBD dimers have been described (see, e.g., U.S. Pat. Nos. 6,562,806, 6,608,192 6,747,144, 7,049,311, 7,528,126, 7,741,319, 8,592,576) and include, but are not limited to, compounds designated DSB-120 (U.S. Pat. No. 7,049,311), DRH-165 (U.S. Pat. No. 7,049,311), ELB21 (Rahman et al., (2011) Nucleic Acids Res. 39(13): 5800-5812), 5G2000/5JG136 (Rahman et al., (2011) Nucleic Acids Res. 39(13):5800-5812; U.S. Pat. No. 7,049,311), 5G2057/DRG16 (Rahman et al., (2011) Nucleic Acids Res. 39(13): 5800-5812), 5G2202 (U.S. Pat. No. 7,741,319; Hartley et al., (2010) Cancer Res. 70(17):6849-6858), 5G2285 (Hartley et al., (2010) Cancer Res. 70(17): 6849-6858), 5G3132 (US 20130028919).

In some embodiments, PBDs and PBD dimers can be conjugated to any of the antibodies provided herein by any method, including, but not limited to thiol, amine and phenol conjugation. Typically, the PBD or PBD dimer is conjugated to the antibody using a cleavable linker, that is stable in in vivo circulation, such that the PBD or PBD dimer is released from the antibody following cleavage of the linker inside the target cell. In some examples, PBD or PBD dimer can be conjugated to inter-chain cysteines. In some examples, the antibody can be modified to replace amino acid(s) to insert or remove an inter-chain cysteine to facilitate directed thiol linkage of the PBD or PBD dimer.

e. Cell Toxin Moieties

In some embodiments, toxins in the provided conjugates include small molecules, such as DNA cleaving agents, and proteinaceous cell toxins, including, but not limited to, bacterial, fungal, plant, insect, snake and spider toxins. Exemplary cell toxins contemplated for incorporation in the conjugates provided herein include Bryodin (SEQ ID NO:73), Saporin-6 (SEQ ID NO: 75), Anti-Viral Protein MAP (SEQ ID NO: 77), Shiga Toxin A-Chain (SEQ ID NO: 79), Shiga-Like Toxin Subunit A (Verotoxin 2) (SEQ ID NO: 80), Trichosanthin (SEQ ID NO:86).

(i) DNA Cleaving Agents

Examples of DNA cleaving agents suitable for inclusion as a toxin in the provided conjugates include, but are not limited to, anthraquinone-oligopyrrol-carboxamide, benzimidazole, leinamycin; dynemycin A; enediyne; as well as biologically active analogs or derivatives thereof (i.e., those having a substantially equivalent biological activity). Known analogs and derivatives are disclosed, for examples in Islam et al., J. Med. Chem. 342954-61, 1991; Skibo et al., J. Med. Chem. 37:78-92, 1994; Behroozi et al., Biochemistry 35:1768-74, 1996; Helissey et al., Anticancer Drug Des. 11:527-551, 1996; Unno et al., Chem. Pharm. Bull. 45:125-133, 1997; Unno et al., Bioorg. Med. Chem., 5:903-919, 1997; Unno et al., Bioorg. Med. Chem., 5: 883-901, 1997; and Xu et al., Biochemistry 37:1890-1897, 1998). Other examples include, but are not limited to, endiyne quinone imines (U.S. Pat. No. 5,622,958); 2,2r-bis (2-aminoethyl)-4-4'-bithiazole (Lee et al., Biochem. Mot. Biol. Int. 40:151-7, 1996); ellipticine-salen=copper conjugates (Routier et al., Bioconjug. Chem., 8: 789-92, 1997).

(ii) Antimetabolites

Examples of antimetabolites useful for inclusion as a cell toxin in the provided conjugates include, but are not limited to, 5-fluorouracil, methotrexate, melphalan, daunomycin, doxorubicin, nitrogen mustard and mitomycin c.

(iii) Proteinaceous Cell Toxins

Examples of proteinaceous toxins in the provided conjugates include, but are not limited to, type one and type two ribosome inactivating proteins (RIP). Useful type one plant RIPs include, but are not limited to, dianthin 30, dianthin 32, lychnin, saporins 1-9, pokeweed activated protein (PAP), PAP II, PAP-R, PAP-S, PAP-C, mapalmin, dodecandrin, bryodin-L, bryodin, Colicin 1 and 2, luffin-A, luffin-B, luffin-S, 19K-protein synthesis inhibitory protein (PSI), 15K-PSI, 9K-PSI, alpha-kirilowin, beta-kirilowin, gelonin, momordin, momordin-II, momordin-Ic, MAP-30, alpha-momorcharin, beta-momorcharin, trichosanthin, TAP-29, trichokirin; barley RIP; flax RIP, tritin, corn RIP, Asparin 1 and 2. Useful type two RIPs include, but are not limited to, volkensin, ricin, nigrin-b, CIP-29, abrin, modeccin, ebulitin-a, ebulitin-13, vircumin, porrectin, as well as the biologically active enzymatic subunits thereof (Stirpe et al., Bio/Technology 10:405-12, 1992; Pastan et al., Annu. Rev. Biochem. 61:331-54; Brinkmann and Pastan, Biochim. et Biophys. Acta 1198:27-45, 1994; and Sandvig and Van Deurs, Physiol. Rev. 76:949-66, 1996).

(iv) Bacterial Toxins

Examples of bacterial toxins in the provided conjugates include, but are not limited to, shiga toxin and shiga-like toxins (i.e., toxins that have the same activity or structure), as well as the catalytic subunits and biologically functional fragments thereof. These bacterial toxins also are type two RIPs (Sandvig and Van Deurs, Physiol. Rev. 76:949-66, 1996; Armstrong, J. Infect. Dis., 171:1042-5, 1995; Kim et al., Microbiol. Immunol. 41:805-8, 1997, and Skinner et al., Microb. Pathog. 24:117-22, 1998). Additional examples of useful bacterial toxins include, but are not limited to, *Pseudomonas* exotoxin and Diphtheria toxin (Pastan et al., Annu. Rev. Biochem. 61:331-54; and Brinkmann and Pastan, Biochim. et Biophys. Acta 1198:27-45, 1994). Truncated forms and mutants of the toxin enzymatic subunits also can be used as a cell toxin moiety (Pastan et al., Annu. Rev. Biochem. 61:331-54; Brinkmann and Pastan, Biochim. et Biophys. Acta 1198:27-45, 1994; Mesri et al., J. Biol. Chem. 268:4853-62, 1993; Skinner et al., Microb. Pathog. 24:117-22, 1998; and U.S. Pat. No. 5,082,927). Other targeted agents include, but are not limited to a toxin of the Colicin family of RNase toxins which include colicins A, B, D, ET-9, cloacin DF13 and the fungal RNase, a-sarcin (Ogawa et al. Science 283: 2097-100, 1999; Smarda et al., Folia Microbiol (Praha) 43:563-82, 1998; Wool et al., Trends Biochem. Sci., 17: 266-69, 1992).

(v) Porphyrins and Other Light Activated Toxins

In some embodiments, the toxin in the provided conjugates is a porphyrin, which are are light activatable toxins that can be readily cross-linked to proteins (see, e.g., U.S. Pat. Nos. 5,257,970; 5,252,720; 5,238,940; 5,192,788; 5,171,749; 5,149,708; 5,202,317; 5,217,966; 5,053,423; 5,109,016; 5,087,636; 5,028,594; 5,093,349; 4,968,715; 4,920,143 and International Publication No. WO 93/02192).

f. Nucleic Acids for Targeted Delivery

In some embodiments, the conjugates provided herein also can be used to deliver nucleic acids to targeted cells. In some embodiments, the nucleic acids include DNA to modify the genome of a cell and thereby effect genetic therapy, and DNA and RNA for use as antisense agents. The nucleic acids include antisense RNA, DNA, ribozymes and other oligonucleotides that are intended to be used as antisense agents. The nucleic acids can also include RNA trafficking signals, such as viral packaging sequences (see, e.g., Sullenger et al. (1994) Science 262:1566-1569). In some cases, the nucleic acids also include DNA molecules that encode intact genes or that encode proteins intended to be used in gene therapy.

In some embodiments, DNA (or RNA) that may be delivered to a cell to effect genetic therapy includes DNA that encodes tumor-specific cytotoxic molecules, such as tumor necrosis factor, viral antigens and other proteins to render a cell susceptible to anti-cancer agents, and DNA encoding genesto replace defective genes.

Nucleic acids and oligonucleotides for use as described herein can be synthesized by any method known (see, e.g., WO 93/01286 and U.S. Pat. Nos. 5,218,088; 5,175,269; and 5,109,124). Identification of oligonucleotides and ribozymes for use as antisense agents are known. DNA encoding genes for targeted delivery for genetic therapy can be selected by known methods. For example, the desirable properties, lengths and other characteristics of such oligonucleotides are well-known. Antisense oligonucleotides are designed to resist degradation by endogenous nucleolytic enzymes and include, but are not limited to: phosphorothioate, methylphosphonate, sulfone, sulfate, ketyl, phosphorodithioate, phosphoramidate, phosphate esters, and other such linkages (see, e.g., Agrawal et al. (1987) Tetrahedron Lett. 28:3539-3542; Miller et al. (1971) J. Am. Chem. Soc. 93:6657-6665; Stec et al. (1985) Tetrahedron Lett. 26:2191-2194; Moody et al. (1989) NucL Acids Res. 17:4769-4782; Letsinger et al. (1984) Tetrahedron 40:137-143; Eckstein (1985) Annu. Rev. Biochem. 54:367-402; Eckstein (1989) Trends Biochem. Sci.14:97-100; Stein (1989) In: Oligodeoxynucleotides. Antisense Inhibitors of Gene Expression, Cohen, ed, Macmillan Press, London, pp. 97-117; Jager et al. (1988) Biochemistry 27:7237-7246).

In some embodiments, to effect chemical conjugation herein, the targeting agent is linked to the nucleic acid either directly or via one or more linkers. Methods for conjugating nucleic acids, at the 5' ends, 3' ends and elsewhere, to the amino and carboxyl termini and other sites in proteins are known (for a review see e.g., Goodchild, (1993) In: Perspectives in Bioconjugate Chemistry, Mears, Ed., American Chemical Society, Washington, D.C. pp. 77-99). For example, proteins have been linked to nucleic acids using ultraviolet irradiation (Sperling et al. (1978) Nucleic Acids Res. 5:2755-2773; Fiser et al. (1975) FEBS Lett. 52:281. 283), bifunctional chemicals (Baumert et al. (1978) Eur. J. Biochem. 89:353-359; and Oste et al. (1979) Mol. Gen. Genet. 168:81-86), and photochemical cross-linking (Vanin et al. (1981) FEBS Lett. 124:89-92; Rinke et al. (1980) 1Mol.Biol. /37:301-304; Millon et al. (1980) Eur.J. Biochetn. 110:485-492). In some embodiments, various reactive groups can be introduced into nucleic acids to carry out linkage, such as sulfhydrul groups, amine groups, bromoacetyl groups or thiol groups.

(i) Antisense Nucleotides, Including: Antisense Oligonucleotides; Triplex Molecules; Dumbbell Oligonucleotides; DNA; Extracellular Protein Binding Oligonucleotides; and Small Nucleotide Molecules In some embodiments, the nucleic acid is an antisense nucleotides, including oligonucleotides that specifically bind to mRNA that has complementary sequences, which, in some aspects, can prevent translation of the mRNA (see, e.g., U.S. Pat. No. 5,168,053 to Altman et al. U.S. Pat. No. 5,190,931 to Inouye, U.S. Pat. No. 5,135,917 to Burch; U.S. Pat. No. 5,087,617 to Smith and Clusel et al. (1993) NucL Acids Res. 21:3405-3411, which describes dumbbell antisense oligonucleotides). Triplex molecules refer to single DNA strands that target duplex DNA and thereby prevent transcription (see, e.g., U.S. Pat. No. 5,176,996, which describes methods for making synthetic oligonucleotides that bind to target sites on duplex DNA).

(ii) Ribozymes

In some embodiment, the nucleic acids include ribozymes, such as RNA constructs that specifically cleave messenger RNA. Such ribozymes can include any of at least five classes of ribozymes that are known that are involved in the cleavage and/or ligation of RNA chains. Ribozymes can be targeted to any RNA transcript and can catalytically cleave such transcript (see, e.g., U.S. Pat. Nos. 5,272,262; 5,144,019 5,168,053; 5,180,818; 5,116,742 and 5,093,246, which describe ribozymes and methods for production thereof). Any such ribosome may be linked to a provided antibody or fragment for delivery to target cells.

In some embodiments, he ribozymes may be delivered to the targeted cells as DNA encoding the ribozyme linked to a eukaryotic promoter, such as a eukaryotic viral promoter, generally a late promoter, such that upon introduction into the nucleus, the ribozyme will be directly transcribed. In such instances, the construct will also include a nuclear translocation sequence, generally as part of the targeting agent or as part of a linker in order to render it suitable for delivering linked nucleic acids to the nucleus.

(iii) Nucleic Acids Encoding Therapeutic Products for Targeted Delivery

In some embodiments, among the DNA that encodes therapeutic products contemplated for use is DNA encoding correct copies of anticancer agents, such as cytokines (e.g. tumor necrosis factors), and cytotoxic agents (e.g. shiga A1 toxin or saporin) or other therapeutic agents. In some embodiments, such conjugates include a nuclear translocation sequence (NTS). In some aspects, if the conjugate is designed such that the targeting agent and linked DNA is cleaved in the cytoplasm, then the NTS is included in a portion of the linker that remains bound to the DNA, so that, upon internalization, the conjugate will be trafficked to the nucleus. In some aspects, the nuclear translocation sequence (NTS) may be a heterologous sequence or a may be derived from the selected chemokine receptor targeting agent. A typical consensus NTS sequence contains an amino-terminal proline or glycine followed by at least three basic residues in an array of seven to nine amino acids (see, e.g., Dang et al. (1989)1 Biol. Chem. 264:18019-18023).

2. Linkers

In some embodiments, the antibody or antigen-binding fragment is linked indirectly to the moiety, e.g. targeted agent, such as a toxin, indirectly via a linker. In some embodiments, the linker, L, attaches the antibody or fragment to a targeted agent through covalent bond(s). In some embodiments, the linker is a bifunctional or multifunctional moiety which can be used to link one or more targeted agent(s) to an antibody or fragment to form an antibody-drug conjugate (ADC).

In some embodiments, ADCs can be readily prepared using a linker having reactive functionality for binding to the targeted agent and to an antibody or fragment. A cysteine thiol group, or an amine group, e.g., N-terminus or lysine side chain, of an antibody can form a bond with a functional group of a linker reagent, targeted agent or targeted agent-linker reagent.

In some embodiment, the linker is stable in the extracellular environment so that the antibody-drug conjugate (ADC) is stable and remains intact, i.e., the antibody remains linked to the targeted agent, before transport or delivery into the target cell. In some cases, the linkers are stable outside the target cell and may be cleaved or enable dissociation of the antibody and targeted agent at some efficacious rate once inside the cell. Among contemplated linkers are linkers that (i) do not or generally do not interfere with the specific binding properties of the antibody; (ii) permit intracellular delivery of the conjugate or targeted agent; (iii) remain stable and intact, i.e., not cleaved, until the conjugate has been delivered or transported to its targeted site; and (iv) do not or generally do not interfere with the cytotoxic, cell-killing effect or a cytostatic effect of the targeted agent. Stability of the ADC may be measured by standard analytical techniques such as mass spectrometry and/or HPLC.

In some embodiments, a linker has two reactive functional groups to permit covalent attachment to both the antibody and the targeted agent, and thus exhibits bivalency in a reactive sense. Such chemical cross-linking reagents, which are useful for attaching two or more functional or biologically active moieties, such as peptides, nucleic acids, drugs, toxins, antibodies, haptens, and reporter groups, are known, and methods have been described for their use in generating conjugates (Hermanson, G. T. (1996) Bioconjugate Techniques; Academic Press: New York, p 234-242).

In some embodiments, a linker has a reactive functional group which has a nucleophilic group that is reactive to an electrophilic group present on an antibody. Useful electrophilic groups on an antibody include, but are not limited to, aldehyde and ketone carbonyl groups. The heteroatom of a nucleophilic group of a linker can react with an electrophilic group on an antibody and form a covalent bond to an antibody unit. Useful nucleophilic groups on a linker include, but are not limited to, hydrazide, oxime, amino, hydrazine, thiosemicarbazone, hydrazine carboxylate, and arylhydrazide. The electrophilic group on an antibody provides a convenient site for attachment to a linker.

a. Peptide Linkers

In some embodiments, linkers can be peptidic, comprising one or more amino acid units. Peptide linker reagents may be prepared by solid phase or liquid phase synthesis methods (E. Schroder and K. Lubke, The Peptides, volume 1, pp. 76-136 (1965) Academic Press) that are well-known in the field of peptide chemistry, including t-BOC chemistry (Geiser et al. "Automation of solid-phase peptide synthesis" in Macromolecular Sequencing and Synthesis, Alan R. Liss, Inc., 1988, pp. 199-218) and Fmoc/HBTU chemistry (Fields, G. and Noble, R. (1990) "Solid phase peptide synthesis utilizing 9-fluorenylmethoxycarbonyl amino acids", Int. J. Peptide Protein Res. 35:161-214), on an automated synthesizer such as the Rainin Symphony Peptide Synthesizer (Protein Technologies, Inc.), or Model 433 (Applied Biosystems). In some cases, peptide-based linkers offer advantages over linkers that are hydrolytically or reductively labile, since proteolysis is enzymatic, and the enzymes can be selected for preferential expression within tumor cells. The cathepsin B-cleavable peptide linker, valine-citrulline (Val-Cit), and modifications thereof such as maleimidocaproyl-valine-citrulline (mc-vc), phenylalanine-lysine, Ala-Leu-Ala-Ala (SEQ ID NO: 64), other tri/tetra-peptides are exemplary peptide linkers that have been employed in ADCs (Dosio et al., (2010) Toxins 3:848-883; Doronina et al., (2006) Bioconjug Chem. 17:114-124; Doronina et al., (2003) Nat Biotechnot. 21:778-784; Sanderson et al., (2005) Clin Cancer Res 11:843-852; Ducry and Stump (2010) Bioconjug Chem. 21:5-13). Exemplary non-cleavable peptide linkers include N-methyl-valine-citrulline. Other peptide linkers are described in U.S. Publication No. 2011/0020343.

In some embodiments, a peptide linker includes those that can be incorporated in fusion proteins and expressed in a host cell, such as E. coli. Such linkers include: enzyme substrates, such as cathepsin B substrate, cathepsin D substrate, trypsin substrate, thrombin substrate, subtilisin substrate, Factor Xa substrate, and enterokinase substrate; linkers that increase solubility, flexibility, and/or intracellular cleavability include linkers, such as (glymser)ii and (sermgly)ii, where m is 1 to 6, preferably 1 to 4, more preferably 2 to 4, and n is 1 to 6, preferably 1 to 4, more preferably 2 to 4 (see, e.g., International PCT application No. WO 96/06641, which provides exemplary linkers for use in conjugates). In some embodiments, several linkers may be included in order to take advantage of desired properties of each linker.

b. Chemical Linkers

In some embodiments, conjugates, such as ADCs, also can be prepared using linkers that are non-cleavable moieties or chemical cross-linking reagents. Exemplary non-cleavable linkers include amide linkers and amide and ester linkages with succinate spacers (Dosio et al., (2010) Toxins 3:848-883). Exemplary chemical cross-linking linkers include, but are not limited to, SMCC (Succinimidyl-4-(N-maleimidomethyl)cyclohexane-1-carboxylate) and SIAB (Succinimidyl (4-iodoacetyl)aminobenzoate). SMCC is an amine-to-sulfhydryl crosslinker that contains NHS-ester and maleimide reactive groups at opposite ends of a medium-length cyclohexane-stabilized spacer arm. SIAB is a short, NHS-ester and iodoacetyl crosslinker for amine-to-sulfhydryl conjugation. Other exemplary cross-linking reagents include, but are not limited to, thioether linkers, chemically labile hydrazone linkers, 4-mercaptovaleric acid, BMPEO, BMPS, EMCS, GMBS, HBVS, LC-SMCC, MBS, MPBH, SBAP, SIA, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate), and bis-maleimide reagents, such as DTME, BMB, BMDB, BMH, BMOE, BM(PEO)3, and BM(PEO)4, which are commercially available (Pierce Biotechnology, Inc.). Bis-maleimide reagents allow the attachment of a free thiol group of a cysteine residue of an antibody to a thiol-containing targeted agent, or linker intermediate, in a sequential or concurrent fashion. Other thiol-reactive functional groups, besides maleimide, include iodoacetamide, bromoacetamide, vinyl pyridine, disulfide, pyridyl disulfide, isocyanate, and isothiocyanate. Other exemplary linkers and methods of use are described in U.S. Publication No. 2005/0276812 and in Ducry and Stump (2010) Bioconjug Chem. 21:5-13.

Linkers optionally can be substituted with groups which modulate solubility or reactivity. For example, a sulfonate substituent may increase water solubility of the reagent and facilitate the coupling reaction of the linker reagent with the antibody or the drug moiety, or facilitate the coupling reaction of an antibody-linker (Ab-L) with the targeted agent, or targeted agent-L with the antibody, depending on the synthetic route employed to prepare the conjugate, e.g. ADC.

In some cases, linker reagents can be obtained via commercial sources, such as Molecular Biosciences Inc. (Boulder, Colo.), or synthesized in accordance with procedures described in Toki et al. (2002) J. Org. Chem. 67:1866-1872; U.S. Pat. No. 6,214,345; WO 02/088172; U.S. 2003130189; U.S. 2003096743; WO 03/026577; WO 03/043583; and WO 04/032828. For example, linker reagents such as DOTA-maleimide (4-maleimidobutyramidobenzyl-DOTA) can be prepared by the reaction of aminobenzyl-DOTA with 4-maleimidobutyric acid (Fluka) activated with isopropylchloroformate (Aldrich), following the procedure of Axworthy et al. (2000) Proc. Natl. Acad. Sci. USA 97(4):1802-1807). DOTA-maleimide reagents react with the free cysteine amino acids of the cysteine engineered antibodies and provide a metal complexing ligand on the antibody (Lewis et al. (1998) Bioconj. Chem. 9:72-86). Chelating linker labelling reagents such as DOTA-NHS (1,4,7,10-tetraazacyclododecane-1,4,7,10-tetraacetic acid mono (N-hydroxysuccinimide ester) are commercially available (Macrocyclics, Dallas, Tex.).

In some embodiments, the Linker can be a dendritic type linker for covalent attachment of more than one drug moiety through a branching, multifunctional linker moiety to an antibody (Sun et al. (2002) Bioorganic & Medicinal Chemistry Letters 12:2213-2215; Sun et al. (2003) Bioorganic & Medicinal Chemistry 11:1761-1768; King et al. (2002) Tetrahedron Letters 43:1987-1990). In some cases, dendritic linkers can increase the molar ratio of targeted agent to antibody, i.e., loading, which can increase the potency of the ADC. Thus, where an antibody bears only one reactive cysteine thiol group, a multitude of drug moieties may be attached through a dendritic linker. Exemplary dendritic linker reagents are described in U.S. Patent Publication No. 2005/0276812.

C. Multispecific Antibodies

In certain embodiments, the provided binding molecules, e.g., antibodies or polypeptides such as chimeric receptors containing the same, are multispecific. Among the multispecific binding molecules are multispecific antibodies, including, e.g. bispecific or trispecific antibodies. Multispecific binding partners, e.g., antibodies, have binding specificities for at least two different sites, which may be in the same or different antigens.

In some embodiments, one of the binding specificities is for CCT5 such as aberrantly expressed CCT5, or a polypeptide containing the sequence set forth in SEQ ID NO:68 or 69 (e.g., any of SEQ ID NOs: 70-72) and the other is for another antigen. In some embodiments, additional binding molecules bind to and/or recognize a third, or more antigens. In certain embodiments, bispecific antibodies may bind to two different epitopes of CCT5, such as two or more epitopes of an aberrantly expressed CCT5, or two or more epitopes of a polypeptide containing the sequence set forth in SEQ ID NO:68 or 69, such as set forth in any of SEQ ID NOs: 70-72. In some embodiments, at least one epitope contains the sequence set forth in SEQ ID NO:68 or 69, such as set forth in any of SEQ ID NOS:70-72. Bispecific antibodies may also be used to localize cytotoxic agents to cells which express CCT5, such as aberrantly expressed CCT5, e.g. CCT5 expressed on the surface or localized to the cell membrane, or to a polypeptide containing the sequence set forth in SEQ ID NO:68.

Bispecific antibodies can be prepared as full length antibodies or antibody fragments. Among the multispecific antibodies are multispecific single-chain antibodies, e.g., diabodies, triabodies, and tetrabodies, tandem di-scFvs, and tandem tri-scFvs. Also provided are multispecific chimeric receptors, such as multispecific CARs, containing the antibodies (e.g., antigen-binding fragments). In certain embodiments, multispecific binding molecules, e.g., multispecific chimeric receptors, such as multispecific CARs, can contain any of the multispecific antibodies, including, e.g. bispecific antibodies, multispecific single-chain antibodies, e.g., diabodies, triabodies, and tetrabodies, tandem di-scFvs, and tandem tri-scFvs, such as any described above in Section I.A.

Among other antigens for targeting by provided multispecific, such as bispecific antibodies, are antigens that are associated with the same disease or condition as targeted by CCT5, e.g. a tumor antigen. Exemplary antigens include antigens that are universal tumor antigens, or family members thereof. In some embodiments, the second or additional antigen is an antigen expressed on a tumor. In some embodiments, the second or additional antigen targets an antigen on the same tumor type as targeted by the provided binding molecules, e.g. CCT5, such as aberrantly expressed CCT5, and/or a polypeptide containing the sequence set forth in SEQ ID NO:68 or 69 (e.g., any of SEQ ID NOs: 70-72). In some embodiments, the second or additional antigen may be a universal tumor antigen or may be a tumor antigen specific to a tumor type.

Exemplary antigens include CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, MUC-1, Ia, HM1.24, HLA-DR, tenascin, an angiogenesis factor, VEGF, PIGF, ED-B fibronectin, an oncogene, an oncogene product, CD66a-d, necrosis antigens, Ii, IL-2, T101, TAC, IL-6, ROR1, TRAIL-R1 (DR4), TRAIL-R2 (DR5), B cell maturation antigen (BCMA), tEGFR, Her2, L1-CAM, mesothelin, CEA, hepatitis B surface antigen, anti-folate receptor, CD24, CD30, CD44, EGFR, EGP-2, EGP-4, EPHa2, ErbB2, ErbB3, ErbB4, erbB dimers, EGFR viii, FBP, FCRL5, FCRH5, fetal acetylcholine receptor, GD2, GD3, HMW-MAA, IL-22R-alpha, IL-13R-alpha2, kdr, kappa light chain, Lewis Y, L1-cell adhesion molecule (L1-CAM), Melanoma-associated antigen (MAGE)-A1, MAGE-A3, MAGE-A6, Preferentially expressed antigen of melanoma (PRAME), survivin, EGP2, EGP40, TAG72, B7-H6, IL-13 receptor a2 (IL-13Ra2), CA9, CD171, G250/CAIX, HLA-A1 MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, dual antigen, an antigen associated with a universal tag, a cancer-testes antigen, MUC1, MUC16, NY-ESO-1, MART-1, gp100, oncofetal antigen, VEGF-R2, carcinoembryonic antigen (CEA), prostate specific antigen, PSMA, Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, hTERT, MDM2, CYP1B, WT1, livin, AFP, p53, cyclin (D1), CS-1, BCMA, BAFF-R, TACI, CD56, TIM-3, CD123, L1-cell adhesion molecule, MAGE-A1, MAGE A3, a cyclin, such as cyclin A1 (CCNA1) and/or a pathogen-specific antigen, biotinylated molecules, molecules expressed by HIV, HCV, HBV and/or other pathogens, and/or in some aspects, neoepitopes or neoantigens thereof. In some embodiments, the antigen is associated with or is a universal tag.

In some embodiments, the second or additional antigen is an antigen specific to an epithelial cell cancer. In some embodiments, the antigen is one that is specific to or expressed on a carcinoma. Exemplary second or additional antigens include, but are not limited to, Ca-1, TA-4, SQM1, 3H-1, squamous cell carcinoma antigen (SCC-ag), and cancer antigen (CA) 125.

In some embodiments, the second or additional antigen is a molecule expressed on a T cell. In some embodiments, the surface molecule is an activating component of a T cell, such as a component of the T cell receptor complex. In some embodiments, the surface molecule is CD3 or is CD2. In some embodiments, the multi-specific, such as a bispecific antibody contains at least one antigen-binding domain binding that binds to a molecule expressed on a T cells, such as an activating component of the T cell (e.g. a T cell surface molecule, e.g. CD3 or CD2) and at least one antigen-binding domain that binds to CCT5, such as aberrantly expressed CCT5, and/or a polypeptide containing the sequence set forth in SEQ ID NO:68 or 69 (e.g. containing the sequence set forth in any of SEQ ID NOS: 70-72) as described herein. In some embodiments, the simultaneous or near simultaneous binding of such an antibody to both of its targets can result in a temporary interaction between the target cell and T cell, thereby resulting in activation, e.g. cytotoxic activity, of the T cell and subsequent lysis of the target cell.

D. Recombinant Receptors and Engineered Cells

Also among the binding molecules are polypeptides containing such antibodies, including single chain cell surface proteins, e.g., recombinant receptors, such as chimeric antigen receptors containing such antibodies. Also provided are engineered cells, such as immune cells, such as T cells, that express such recombinant receptors, including CARs.

1. Recombinant Receptors

Among the provided binding molecules are single chain cell surface proteins, such as recombinant receptors (e.g., antigen receptors), that include one of the provided antibodies (e.g., antigen-binding fragment). The recombinant receptors include antigen receptors that specifically bind to CCT5, such as aberrantly expressed CCT5, and/or a polypeptide containing the sequence set forth in SEQ ID NO:68 or 69 (e.g. containing the sequence set forth in any of SEQ ID NOS: 70-72), including antigen receptors containing any of the provided antibodies, e.g., antigen-binding fragments. Among the antigen receptors are functional non-TCR antigen receptors, such as chimeric antigen receptors (CARs). Also provided are cells expressing the recombinant receptors and uses thereof in adoptive cell therapy, such as treatment of diseases and disorders associated with CCT5 expression.

Exemplary antigen receptors, including CARs, and methods for engineering and introducing such antigen receptors into cells, include those described, for example, in international patent application publication nos. WO200014257, WO2013126726, WO2012/129514, WO2014031687, WO2013/166321, WO2013/071154, WO2013/123061 U.S. patent application publication Nos. US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application No. EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 Mar. 18(2): 160-75. In some aspects, the antigen receptors include a CAR as described in U.S. Pat. No. 7,446,190, and those described in International Patent Application Publication No. WO/2014055668 A1. Exemplary CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, e.g., and in which the antigen-binding portion, e.g., scFv, is replaced by an antibody or an antigen-binding fragment thereof, e.g., as provided herein.

Among the chimeric receptors are chimeric antigen receptors (CARs). In some embodiments, the chimeric antigen receptor includes an extracellular portion containing the antibody or fragment described herein, e.g. an scFv, an intracellular signaling region containing an intracellular signaling domain, such as an intracellular signaling domain containing an ITAM (e.g. CD3zeta signaling domain), and a transmembrane domain linking the extracellular domain and intracellular signaling region. In some embodiments, the chimeric antigen receptor contains an intracellular domain of a co-stimulatory molecule (e.g., T cell costimulatory molecule), such as between the transmembrane domain and intracellular signaling domain.

The chimeric receptors, such as CARs, generally include in their extracellular portion an extracellular antigen binding domain, of a provided binding molecule, such as one or more antigen-binding fragment, domain, or portion, or one or more antibody variable regions, and/or antibody molecules, such as those described herein. In some embodiments, the CAR includes a binding portion or portions of an antibody molecule, such as a heavy chain variable ($V_H$) region and/or light chain variable ($V_L$) region of the antibody, e.g., an scFv antibody fragment. In some embodiments, the antigen-binding domain, such as a binding portion or antigen-binding fragment of an antibody, specifically binds to CCT5, such as aberrantly expressed CCT5, and/or a polypeptide containing the sequence set forth in SEQ ID NO:68 or 69 (e.g. containing the sequence set forth in any of SEQ ID NOS: 70-72).

In some embodiments, the recombinant receptor such as a CAR comprising an antibody (e.g., antigen-binding fragment) provided herein, further includes a spacer, which may be or include at least a portion of an immunoglobulin constant region or variant or modified version thereof, such as a hinge region, e.g., an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component (e.g., scFv) and transmembrane domain. The spacer can be of a length that provides for increased responsiveness of the cell following antigen binding, as compared to in the absence of the spacer. Exemplary spacers include those having at least about 10 to 250 amino acids, such as 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, about 10 to 15 amino acids, about 40 to 229 amino acids, about 40 to 200 amino acids, about 40 to 175 amino acids, about 40 to 150 amino acids, about 40 to 100 amino acids, about 40 to 75 amino acids, about 75 to 250 amino acids, about 75 to 200 amino acids, about 75 to 175 amino acids, about 75 to 150 amino acids, about 75 to 100 amino acids, about 100 to 250 amino acids, about 100 to 200 amino acids, about 100 to 150 amino acids, about 150 to 250 amino acids, and including any integer between the endpoints of any of the listed ranges. In some embodiments, a spacer region has about 12 amino acids or less, such as is at or about 12 amino acids in length or is no more than 12 amino acids in length. Exemplary spacers include those that are at least or at least about or are or about 10, 12, 14, 16, 18, 20, 25, 30, 40, 50, 60, 70, 80, 90, 100, 110, 115, 120, 130, 140, 150, 160, 170, 180, 190, 200, 210, 220, 230 or more. In some embodiments, a spacer region has about 119 amino acids or less, such as is at or about 119 amino acids in length or is no more than 119 amino acids in length. In some embodiments, a spacer region has about 229 amino acids or less, such as is at or about 229 amino acids in length or is no more than 229 amino acids in length. Exemplary spacers include IgG4 hinge alone, IgG4 hinge linked to CH2 and CH3 domains, or IgG4 hinge linked to the CH3 domain. Exemplary spacers include, but are not limited to, those described in Hudecek et al. (2013) *Clin. Cancer Res.*, 19:3153, Hudecek et al. (2015) *Cancer Immunol. Res.*, 3(2):125-135 or international patent application publication number WO2014031687.

In some embodiments, the spacer has the sequence set forth in SEQ ID NO:6. In some embodiments, the spacer has the sequence set forth in SEQ ID NO:81. In some embodiments, the spacer has the sequence set forth in SEQ ID NO:5. In some embodiments, the spacer has the sequence set forth in SEQ ID NO:74.

The antigen-recognition component generally is linked to one or more intracellular signaling components, such as signaling components that mimic activation through an antigen receptor complex, such as a TCR complex, in the case of a CAR, and/or signal via another cell surface receptor. Thus, in some embodiments, the binding molecule (e.g., antibody or antigen binding fragment thereof) is linked to one or more transmembrane domains such as those described herein and intracellular signaling domains comprising one or more intracellular components such as those described herein. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane domains include those derived from (i.e. comprise at least the transmembrane domain(s) of) the alpha, beta or zeta chain of the T-cell receptor, CD3 epsilon, CD4, CD5, CD8, CD9, CD16, CD22, CD28, CD33, CD37, CD45, CD64, CD80, CD86, CD134, CD137, and/or CD154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the intracellular signaling domain of the CAR.

The receptor, e.g., the CAR, generally includes an intracellular signaling domain comprising at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the CCT5-binding antibody is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR includes a chimeric molecule between CD3-zeta (CD3-ζ) or Fc receptor γ and CD8, CD4, CD25 or CD16.

In some embodiments, upon ligation of the CAR, the cytoplasmic domain or intracellular signaling domain of the CAR activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such classes of cytoplasmic signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR or CD3 zeta, FcR gamma, CD3 gamma, CD3 delta and CD3 epsilon. In some embodiments, the intracellular signaling domain in the CAR contain(s) a cytoplasmic signaling domain, portion thereof, or sequence derived from CD3 zeta.

In some embodiments, the CAR includes a signaling region (e.g., an intracellular signaling domain) and/or transmembrane portion of a costimulatory molecule, such as a T cell costimulatory molecule. Exemplary costimulatory molecules include CD28, 4-1BB, OX40, DAP10, and ICOS. In some aspects, the same CAR includes both the activating or stimulatory components (e.g., cytoplasmic signaling sequence) and costimulatory components. In some embodiments, the costimulatory region is derived from an intracellular signaling domain of 4-1BB.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR in some aspects is one that includes multiple costimulatory domains of different costimulatory receptors.

In some embodiments, the chimeric antigen receptor includes an extracellular portion containing an antibody or fragment described herein (e.g. anti-CCT5 antibody). In some aspects, the chimeric antigen receptor includes an extracellular portion containing the antibody or fragment described herein and an intracellular signaling region or domain. In some embodiments, the antibody or fragment includes an scFv or a single-domain antibody comprising only the $V_H$ region and the intracellular signaling domain contains an ITAM. In some aspects, the intracellular signaling domain includes a signaling domain of a zeta chain of a CD3-zeta (CD3ζ) chain. In some embodiments, the chimeric antigen receptor includes a transmembrane domain linking the extracellular domain and the intracellular signaling domain. In some aspects, the transmembrane domain contains a transmembrane portion of CD28. The extracellular domain and transmembrane can be linked directly or indirectly. In some embodiments, the extracellular domain and transmembrane are linked by a spacer, such as any described herein. In some embodiments, the chimeric antigen receptor contains an intracellular domain of a co-stimulatory molecule (e.g., T cell costimulatory molecule), such as between the transmembrane domain and intracellular signaling domain. In some aspects, the T cell costimulatory molecule is CD28 or 4-1BB.

In some embodiments, the CAR contains an antibody, e.g., an antibody fragment, as described herein (e.g. anti-CCT5 antibody), a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, as described herein (e.g. anti-CCT5 antibody), a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, IgG4 hinge linked to CH2 and CH3 domains, or IgG4 hinge linked to the CH3 domain.

In some embodiments, the CAR includes an antibody or fragment specific to, or that specifically binds to, CCT5, such as aberrantly expressed CCT5, and/or to a polypeptide containing the sequence set forth in SEQ ID NO:68 or 69 (e.g. containing the sequence set forth in any of SEQ ID NOS: 70-72), including any of the provided antibodies or antigen-binding fragments (e.g. scFv); a spacer such as any of the Ig-hinge containing spacers; a CD28 transmembrane domain; a CD28 intracellular signaling domain; and a CD3 zeta signaling domain. In some embodiments, the CAR includes an antibody or fragment specific to, or that specifically binds to, CCT5, such as aberrantly expressed CCT5, and/or to a polypeptide containing the sequence set forth in SEQ ID NO:68 or 69 (e.g. containing the sequence set forth in any of SEQ ID NOS: 70-72), including any of the provided antibodies or antigen-binding fragments (e.g. scFv); a spacer such as any of the Ig-hinge containing spacers, a CD28 transmembrane domain, a 4-1BB intracellular signaling domain, and a CD3 zeta signaling domain.

In some embodiments, the transmembrane domain of the receptor, e.g., the CAR is a transmembrane domain of human CD28 or variant thereof, e.g., a 27-amino acid transmembrane domain of a human CD28 (GenBank Accession No.: P10747.1), or is a transmembrane domain that comprises the sequence of amino acids set forth in SEQ ID NO: 7 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO:7; in some embodiments, the transmembrane-domain containing portion of the recombinant receptor comprises the sequence of amino acids set forth in SEQ ID NO:78 or a sequence of amino acids having at least or at least about 85%, 86%, 87%, 88%, 89%, 90%, 91%, 92%, 93%, 94%, 95%, 96%, 97%, 98%, 99% or more sequence identity thereto.

In some embodiments, the chimeric antigen receptor contains an intracellular domain of a T cell costimulatory molecule. In some aspects, the T cell costimulatory molecule is CD28 or 4-1BB.

In some embodiments, the intracellular signaling region comprises an intracellular costimulatory signaling domain of human CD28 or functional variant or portion thereof, such as a 41 amino acid domain thereof and/or such a domain with an LL to GG substitution at positions 186-187 of a native CD28 protein. In some embodiments, the intracellular signaling domain can comprise the sequence of amino acids set forth in SEQ ID NO: 61 or 63 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO: 61 or 63. In some embodiments, the intracellular region comprises an intracellular costimulatory signaling domain of 4-1BB or functional variant or portion thereof, such as a 42-amino acid cytoplasmic domain of a human 4-1BB (Accession No. Q07011.1) or functional variant or portion thereof, such as the sequence of amino acids set forth in SEQ ID NO: 8 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO: 8.

In some embodiments, the intracellular signaling region comprises a human CD3 chain, optionally a CD3 zeta stimulatory signaling domain or functional variant thereof, such as an 112 AA cytoplasmic domain of isoform 3 of human CD3ζ ((Accession No.: P20963.2) or a CD3 zeta signaling domain as described in U.S. Pat. No. 7,446,190 or U.S. Pat. No. 8,911,993. In some embodiments, the intracellular signaling region comprises the sequence of amino acids set forth in SEQ ID NO: 9, 60, 62 or 67 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO: 9, 60, 62 or 67.

In some aspects, the spacer contains only a hinge region of an IgG, such as only a hinge of IgG4 or IgG1, such as the hinge only spacer set forth in SEQ ID NO:6. In other embodiments, the spacer is an Ig hinge, e.g., and IgG4 hinge, linked to a $C_H2$ and/or $C_H3$ domains. In some embodiments, the spacer is an Ig hinge, e.g., an IgG4 hinge, linked to $C_H2$ and $C_H3$ domains, such as set forth in SEQ ID NO:5. In some embodiments, the spacer is an Ig hinge, e.g., an IgG4 hinge, linked to a $C_H3$ domain only, such as set forth in SEQ ID NO:81. In some embodiments, the spacer is or comprises a glycine-serine rich sequence or other flexible linker such as known flexible linkers.

2. Multi-Targeting

Also provided are multispecific cells containing the antibodies or antigen-binding fragments provided herein, or polypeptides including the same, including such binding molecules that specifically bind to CCT5, such as an aberrantly expressed CCT5, or to a polypeptide that contains the sequence set forth in SEQ ID NO:68 or 69 (e.g. containing the sequence set forth in any of SEQ ID NOs:70-72). In some embodiments, such cells contain a cell surface protein including a receptor, e.g. CAR, containing an antibody or antigen-binding fragment as provided, and an additional cell surface protein, such as an additional chimeric receptor, which binds to a different antigen or a different epitope of CCT5.

In some embodiments, the cells and methods include multi-targeting strategies, such as expression of two or more genetically engineered receptors on the cell, each recognizing the same of a different antigen and typically each including a different intracellular signaling component. Such multi-targeting strategies are described, for example, in International Patent Application Publication No: WO 2014055668 A1 (describing combinations of activating and costimulatory CARs, e.g., targeting two different antigens present individually on off-target, e.g., normal cells, but present together only on cells of the disease or condition to be treated) and Fedorov et al., Sci. Transl. Medicine, 5(215) (December, 2013) (describing cells expressing an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat).

In some embodiments, the CARs include activating or stimulatory CARs, and costimulatory CARs, both expressed on the same cell (see WO2014/055668). In some embodiments, the cells include a receptor expressing a first genetically engineered antigen receptor (e.g., CAR or TCR) which is capable of inducing an activating or stimulating signal to the cell, generally upon specific binding to the antigen recognized by the first receptor, e.g., the first antigen. In some embodiments, the cell further includes a second genetically engineered antigen receptor (e.g., CAR or TCR), e.g., a chimeric costimulatory receptor, which is capable of inducing a costimulatory signal to the immune cell, generally upon specific binding to a second antigen recognized by the second receptor. In some embodiments, the first antigen and second antigen are the same.

In some embodiments, the first antigen and second antigen are different. In some aspects, the CAR targeting or specifically binding CCT5, such as aberrantly expressed CCT5, and/or a polypeptide containing the sequence set forth in SEQ ID NO:68 or 69 (e.g. containing the sequence set forth in any of SEQ ID NOS: 70-72) is the stimulatory or activating CAR; in other aspects, it is the costimulatory CAR. In some embodiments, the second genetically engineered antigen receptor includes the other of the stimulatory CAR or costimulatory CAR, and is specific to a second or different antigen. In some embodiments, the second or additional antigen is an antigen expressed on a tumor, such as an antigen on the same tumor type as targeted by the provided binding molecules, e.g. on the same tumor as CCT5, such as aberrantly expressed CCT5, and/or a polypeptide containing the sequence set forth in SEQ ID NO:68 or 69 (e.g. containing the sequence set forth in any of SEQ ID NOS: 70-72). In some embodiments, the second or different antigen is any antigen as described above in connection with multi-targeting strategies, e.g. Section I.D.2. In some embodiments, the second or different antigen is an antigen specific to an epithelial cell cancer, such as a carcinoma, e.g., a carcinoma of the colon, breast, ovarian, prostate, pancreatic, bladder, or lung cancer. In some embodiments, the second or different antigen is a universal tumor antigen.

In some embodiments, the first and/or second genetically engineered antigen receptor (e.g. CAR or TCR) is capable of inducing an activating or stimulating signal to the cell. In some embodiments, the receptor includes an intracellular signaling component containing ITAM or ITAM-like motifs. In some embodiments, the activation induced by the first receptor involves a signal transduction or change in protein expression in the cell resulting in initiation of an immune response, such as ITAM phosphorylation and/or initiation of ITAM-mediated signal transduction cascade, formation of an immunological synapse and/or clustering of molecules near the bound receptor (e.g. CD4 or CD8, etc.), activation of one or more transcription factors, such as NF-κB and/or AP-1, and/or induction of gene expression of factors such as cytokines, proliferation, and/or survival.

In some embodiments, the first and/or second receptor includes intracellular signaling domains of costimulatory receptors such as CD28, CD137 (4-1BB), OX40, and/or ICOS. In some embodiments, the first and second receptor include an intracellular signaling domain of a costimulatory receptor that are different. In one embodiment, the first receptor contains a CD28 costimulatory signaling region and the second receptor contain a 4-1BB co-stimulatory signaling region or vice versa.

In some embodiments, the first and/or second receptor includes both an intracellular signaling domain containing ITAM or ITAM-like motifs and an intracellular signaling domain of a costimulatory receptor.

In some embodiments, the first receptor contains an intracellular signaling domain containing ITAM or ITAM-like motifs and the second receptor contains an intracellular signaling domain of a costimulatory receptor. The costimulatory signal in combination with the activating or stimulating signal induced in the same cell is one that results in an immune response, such as a robust and sustained immune response, such as increased gene expression, secretion of cytokines and other factors, and T cell mediated effector functions such as cell killing.

In some embodiments, neither ligation of the first receptor alone nor ligation of the second receptor alone induces a robust immune response. In some aspects, if only one receptor is ligated, the cell becomes tolerized or unresponsive to antigen, or inhibited, and/or is not induced to proliferate or secrete factors or carry out effector functions. In some such embodiments, however, when the plurality of receptors are ligated, such as upon encounter of a cell expressing the first and second antigens, a desired response is achieved, such as full immune activation or stimulation, e.g., as indicated by secretion of one or more cytokine, proliferation, persistence, and/or carrying out an immune effector function such as cytotoxic killing of a target cell.

In some embodiments, the genetically engineered cells express two receptors, which induce, respectively, an activating and an inhibitory signal to the cell, such that binding by one of the receptor to its antigen activates the cell or induces a response, but binding by the second inhibitory receptor to its antigen induces a signal that suppresses or dampens that response. Examples are combinations of activating CARs and inhibitory CARs or iCARs. Such a strategy may be used, for example, in which the activating CAR binds an antigen expressed in a disease or condition but which is also expressed on normal cells, and the inhibitory receptor binds to a separate antigen which is expressed on the normal cells but not cells of the disease or condition.

In some embodiments, the multi-targeting strategy is employed in a case where an antigen associated with a particular disease or condition is expressed on a non-diseased cell and/or is expressed on the engineered cell itself, either transiently (e.g., upon stimulation in association with genetic engineering) or permanently. In such cases, by requiring ligation of two separate and individually specific antigen receptors, specificity, selectivity, and/or efficacy may be improved. In some embodiments, the plurality of antigens, e.g., the first and, in some cases, second antigens, are expressed on the cell, tissue, or disease or condition being targeted, such as on the cancer cell. In some embodiments, one or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy is achieved.

In some embodiments, the genetically engineered cells include a CAR targeting or specifically binding CCT5, such as aberrantly expressed CCT5, and/or a polypeptide containing the sequence set forth in SEQ ID NO:68 or 69 (e.g. containing the sequence set forth in any of SEQ ID NOS: 70-72) that is a stimulatory or activating CAR and also expresses an inhibitory CARs (iCARs, see Fedorov et al., Sci. Transl. Medicine, 5(215) (December, 2013), such as a CAR recognizing an antigen other than CCT5, such as other than aberrantly expressed CCT5, and/or other than a polypeptide containing the sequence set forth in SEQ ID NO:68 or 69 (e.g. containing the sequence set forth in any of SEQ ID NOS:70-72). In some of such embodiments, an activating or stimulatory signal delivered through the CAR targeting CCT5, such as aberrantly expressed CCT5, and/or a polypeptide containing the sequence set forth in SEQ ID NO:68 or 69 (e.g. containing the sequence set forth in any of SEQ ID NOS:70-72) is diminished or inhibited by binding of the inhibitory CAR to its ligand, e.g., to reduce off-target effects. In some embodiments, the iCAR is specific to a second or different antigen that is not expressed on an epithelial cell cancer. In some embodiments, the iCAR is specific to a second or different antigen that is a prostate or mammary epithelial antigen.

3. Engineered Cells and Methods of Generating Engineered Cells

Also provided are cells such as engineered cells that contain a recombinant receptor (e.g., a chimeric antigen receptor) such as one that contains an extracellular domain including an anti-CCT5 antibody or fragment as described herein. Also provided are populations of such cells, compositions containing such cells and/or enriched for such cells, such as in which cells expressing the CCT5-binding molecule make up at least 50, 60, 70, 80, 90, 91, 92, 93, 94, 95, 96, 97, 98, 99, or more percent of the total cells in the composition or cells of a certain type such as T cells or CD8+ or CD4+ cells. Among the compositions are pharmaceutical compositions and formulations for administration, such as for adoptive cell therapy. Also provided are therapeutic methods for administering the cells and compositions to subjects, e.g., patients.

Thus also provided are genetically engineered cells expressing the recombinant receptors containing the antibodies, e.g., cells containing the CARs. The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types. In some embodiments, the cells (e.g., engineered cells) comprise a vector (e.g., a viral vector, expression vector, etc.) as described herein such as a vector comprising a nucleic acid encoding a recombinant receptor described herein.

a. Vectors and Methods for Genetic Engineering

Also provided are methods, nucleic acids, compositions, and kits, for expressing the binding molecules (e.g., anti-CCT5 binding molecules or antibodies), including recombinant receptors (e.g., CARs) comprising the binding molecules, and for producing the genetically engineered cells expressing such binding molecules. In some embodiments, one or more binding molecules, including recombinant receptors (e.g., CARs) can be genetically engineered into cells or plurality of cells. The genetic engineering generally involves introduction of a nucleic acid encoding the recombinant or engineered component into the cell, such as by retroviral transduction, transfection, or transformation. Also provided are polynucleotides encoding a recombinant receptor, and vectors or constructs containing such nucleic acids and/or polynucleotides.

In some cases, the nucleic acid sequence encoding the recombinant receptor contains a signal sequence that encodes a signal peptide. In some aspects, the signal sequence may encode a signal peptide derived from a native polypeptide. In other aspects, the signal sequence may encode a heterologous or non-native signal peptide.

In some embodiments, the vector backbone contains a nucleic acid sequence encoding one or more marker(s). In some embodiments, the one or more marker(s) is a transduction marker, surrogate marker and/or a selection marker.

In some embodiments, the marker is a transduction marker or a surrogate marker. A transduction marker or a surrogate marker can be used to detect cells that have been introduced with the polynucleotide, e.g., a polynucleotide encoding a recombinant receptor. In some embodiments, the transduction marker can indicate or confirm modification of a cell. In some embodiments, the surrogate marker is a protein that is made to be co-expressed on the cell surface with the recombinant receptor, e.g. CAR. In particular embodiments, such a surrogate marker is a surface protein that has been modified to have little or no activity. In certain embodiments, the surrogate marker is encoded on the same polynucleotide that encodes the recombinant receptor. In some embodiments, the nucleic acid sequence encoding the recombinant receptor is operably linked to a nucleic acid sequence encoding a marker, optionally separated by an internal ribosome entry site (IRES), or a nucleic acid encoding a self-cleaving peptide or a peptide that causes ribosome skipping, such as a 2A sequence, such as a T2A, a P2A, an E2A or an F2A. Extrinsic marker genes may in some cases be utilized in connection with engineered cell to permit detection or selection of cells and, in some cases, also to promote cell suicide.

Exemplary surrogate markers can include truncated forms of cell surface polypeptides, such as truncated forms that are non-functional and to not transduce or are not capable of transducing a signal or a signal ordinarily transduced by the full-length form of the cell surface polypeptide, and/or do not or are not capable of internalizing. Exemplary truncated cell surface polypeptides including truncated forms of growth factors or other receptors such as a truncated human epidermal growth factor receptor 2 (tHER2), a truncated epidermal growth factor receptor (tEGFR, exemplary tEGFR sequence set forth in SEQ ID NO:65 or 66) or a prostate-specific membrane antigen (PSMA) or modified form thereof tEGFR may contain an epitope recognized by the antibody cetuximab (Erbitux®) or other therapeutic anti-EGFR antibody or binding molecule, which can be used to identify or select cells that have been engineered with the tEGFR construct and an encoded exogenous protein, and/or to eliminate or separate cells expressing the encoded exogenous protein. See U.S. Pat. No. 8,802,374 and Liu et al., Nature Biotech. 2016 April; 34(4): 430-434). In some aspects, the marker, e.g. surrogate marker, includes all or part (e.g., truncated form) of CD34, a NGFR, a CD19 or a truncated CD19, e.g., a truncated non-human CD19, or epidermal growth factor receptor (e.g., tEGFR).

In some embodiments, the marker is or comprises a fluorescent protein, such as green fluorescent protein (GFP), enhanced green fluorescent protein (EGFP), such as superfold GFP (sfGFP), red fluorescent protein (RFP), such as tdTomato, mCherry, mStrawberry, AsRed2, DsRed or DsRed2, cyan fluorescent protein (CFP), blue green fluorescent protein (BFP), enhanced blue fluorescent protein (EBFP), and yellow fluorescent protein (YFP), and variants thereof, including species variants, monomeric variants, and codon-optimized and/or enhanced variants of the fluorescent proteins. In some embodiments, the marker is or comprises an enzyme, such as a luciferase, the lacZ gene from *E. coli*, alkaline phosphatase, secreted embryonic alkaline phosphatase (SEAP), chloramphenicol acetyl transferase (CAT).

Exemplary light-emitting reporter genes include luciferase (luc), β-galactosidase, chloramphenicol acetyltransferase (CAT), β-glucuronidase (GUS) or variants thereof.

In some embodiments, the marker is a selection marker. In some embodiments, the selection marker is or comprises a polypeptide that confers resistance to exogenous agents or drugs. In some embodiments, the selection marker is an antibiotic resistance gene. In some embodiments, the selection marker is an antibiotic resistance gene confers antibiotic resistance to a mammalian cell. In some embodiments, the selection marker is or comprises a Puromycin resistance gene, a Hygromycin resistance gene, a Blasticidin resistance gene, a Neomycin resistance gene, a Geneticin resistance gene or a Zeocin resistance gene or a modified form thereof.

In some embodiments, one or more binding molecules, including antibodies and/or recombinant receptors (e.g., CARs), can be genetically engineered to be expressed in cells or plurality of cells. In some embodiments, a first recombinant receptor and a second binding molecule, e.g., recombinant receptor, are encoded by the same or separate nucleic acid molecules. In some embodiments, additional binding molecules are engineered to be expressed in cells or a plurality of cells.

In some embodiments, the vector or construct can contain a single promoter that drives the expression of one or more nucleic acid molecules. In some embodiments, such nucleic acid molecules, e.g., transcripts, can be multicistronic (bicistronic or tricistronic, see e.g., U.S. Pat. No. 6,060,273). For example, in some embodiments, transcription units can be engineered as a bicistronic unit containing an IRES (internal ribosome entry site), which allows coexpression of gene products (e.g. encoding a first and second chimeric receptor) by a message from a single promoter. Alternatively, in some cases, a single promoter may direct expression of an RNA that contains, in a single open reading frame (ORF), two or three genes (e.g. encoding the molecule involved in modulating a metabolic pathway and encoding the recombinant receptor) separated from one another by sequences encoding a self-cleavage peptide (e.g., 2A sequences) or a protease recognition site (e.g., furin). The ORF thus encodes a single polypeptide, which, either during (in the case of 2A) or after translation, is processed into the individual proteins. In some cases, the peptide, such as T2A, can cause the ribosome to skip (ribosome skipping) synthesis of a peptide bond at the C-terminus of a 2A element, leading to separation between the end of the 2A sequence and the next peptide downstream (see, for example, de Felipe. *Genetic Vaccines and Ther.* 2:13 (2004) and deFelipe et al. *Traffic* 5:616-626 (2004)). Many 2A elements are known. Examples of 2A sequences that can be used in the methods and nucleic acids disclosed herein, without limitation, 2A sequences from the foot-and-mouth disease virus (F2A, e.g., SEQ ID NO: 39 or 40), equine rhinitis A virus (E2A, e.g., SEQ ID NO: 37 or 38), Thosea asigna virus (T2A, e.g., SEQ ID NO: 31-34), and porcine teschovirus-1 (P2A, e.g., SEQ ID NO: 35 or 36) as described in U.S. Patent Publication No. 20070116690. In some embodiments, the one or more different or separate promoters drive the expression of one or more nucleic acid molecules encoding the one or more binding molecules, e.g., recombinant receptors.

Any of the binding molecules, e.g., antibodies and/or recombinant receptors provided herein, e.g., CCT5-binding molecules and/or the additional recombinant receptors, can be encoded by polynucleotides containing one or more nucleic acid molecules encoding the receptors, in any combinations or arrangements. For example, one, two, three or more polynucleotides can encode one, two, three or more different receptors or domains. In some embodiments, one vector or construct contains nucleic acid molecules encoding one or more binding molecules, e.g., antibody and/or recombinant receptor, and a separate vector or construct contains nucleic acid molecules encoding an additional binding molecule, e.g., antibody and/or recombinant receptor. Each of the nucleic acid molecule can also encode one or more marker, such as a surface marker, e.g., truncated EGFR (tEGFR).

Also provided are compositions containing one or more of the nucleic acid molecules, vectors or constructs, such as any described above. In some embodiments, the nucleic acid molecules, vectors, constructs or compositions can be used to engineer cells, such as T cells, to express any of the binding molecules, e.g., antibody or recombinant receptor, and/or the additional binding molecules.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some contexts, overexpression of a stimulatory factor (for example, a lymphokine or a cytokine) may be toxic to a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell 2:223, 1977) which confers ganciclovir sensitivity; the cellular hypoxanthine phosphoribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some aspects, the cells further are engineered to promote expression of cytokines or other factors. Various methods for the introduction of genetically engineered components, e.g., antigen receptors, e.g., CARs, are well known and may be used with the provided methods and compositions. Exemplary methods include those for transfer of nucleic acids encoding the receptors, including via viral, e.g., retroviral or lentiviral, transduction, transposons, and electroporation.

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 November 29(11): 550-557).

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), human immunodeficiency virus type 1 (HIV-1) or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) J. Immunother. 35(9): 689-701; Cooper et al. (2003) Blood. 101: 1637-1644; Verhoeyen et al. (2009) Methods Mol Biol. 506: 97-114; and Cavalieri et al. (2003) Blood. 102(2): 497-505.

In some embodiments, recombinant nucleic acids are transferred into T cells via electroporation (see, e.g., Chicaybam et al, (2013) PLoS ONE 8(3): e60298 and Van Tedeloo et al. (2000) Gene Therapy 7(16): 1431-1437). In some embodiments, recombinant nucleic acids are transferred into T cells via transposition (see, e.g., Manuri et al. (2010) Hum Gene Ther 21(4): 427-437; Sharma et al. (2013) Molec Ther Nucl Acids 2, e74; and Huang et al. (2009) Methods Mol Biol 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., Mol. and Cell Biol., 11:6 (1991); and Riddell et al., Human Gene Therapy 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

b. Preparation of Cells for Engineering

In some embodiments, preparation of the engineered cells includes one or more culture and/or preparation steps. The cells for introduction of the recombinant receptor (e.g., CAR) may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, or pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contain cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques.

For example, CD3+, CD28+ T cells can be positively selected using anti-CD3/anti-CD28 conjugated magnetic beads (e.g., DYNABEADS® M-450 CD3/CD28 T Cell Expander, MACSiBeads, etc.).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker$^+$) at a relatively higher level (marker$^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations.

In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) Blood.1:72-82; Wang et al. (2012) J Immunother. 35(9):689-701. In some embodiments, combining $T_{CM}$-enriched CD8+ T cells and CD4+ T cells further enhances efficacy.

In embodiments, memory T cells are present in both CD62L+ and CD62L-subsets of CD8+ peripheral blood lymphocytes. PBMC can be enriched for or depleted of CD62L-CD8+ and/or CD62L+CD8+ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a CD8+ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or subpopulation, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of CD4+ cells, where both the negative and positive fractions are retained. The negative fraction then is subjected to negative selection based on expression of CD14 and CD45RA, and positive selection based on a marker characteristic of central memory T cells, such as CD62L or CCR7, where the positive and negative selections are carried out in either order.

CD4+T helper cells are sorted into naïve, central memory, and effector cells by identifying cell populations that have cell surface antigens. CD4+ lymphocytes can be obtained by standard methods. In some embodiments, naive CD4+T lymphocytes are CD45RO−, CD45RA+, CD62L+, CD4+ T cells. In some embodiments, central memory CD4+ cells are CD62L+ and CD45RO+. In some embodiments, effector CD4+ cells are CD62L− and CD45RO−.

In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In vitro and In vivo, p 17-25 Edited by: S. A. Brooks and U. Schumacher© Humana Press Inc., Totowa, NJ).

In some aspects, the sample or composition of cells to be separated is incubated with small, magnetizable or magnetically responsive material, such as magnetically responsive particles or microparticles, such as paramagnetic beads (e.g., such as Dynabeads™ or MACS® beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084, are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the affinity-based selection is via magnetic-activated cell sorting (MACS®) (Miltenyi Biotec, Auburn, CA). Magnetic Activated Cell Sorting (MACS®) systems are capable of high-purity selection of cells having magnetized particles attached thereto. In certain embodiments, MACS® operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS® system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS® system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy® system (Miltenyi Biotec). The CliniMACS Prodigy® system in some aspects is equipped with a cell processing unity that permits automated washing and fractionation of cells by centrifugation. The CliniMACS Prodigy® system can also include an onboard camera and image recognition software that determines the optimal cell fractionation endpoint by discerning the macroscopic layers of the source cell product. For example, peripheral blood may be automatically separated into erythrocytes, white blood cells and plasma layers. The CliniMACS Prodigy® system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) J Immunother. 35(9): 651-660, Terakura et al. (2012) Blood.1:72-82, and Wang et al. (2012) J Immunother. 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) Lab Chip 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80° C. at a rate of 1° per minute and stored in the vapor phase of a liquid nitrogen storage tank.

In some embodiments, the provided methods include cultivation, incubation, culture, and/or genetic engineering steps. For example, in some embodiments, provided are methods for incubating and/or engineering the depleted cell populations and culture-initiating compositions.

Thus, in some embodiments, the cell populations are incubated in a culture-initiating composition. The incubation and/or engineering may be carried out in a culture vessel, such as a unit, chamber, well, column, tube, tubing set, valve, vial, culture dish, bag, or other container for culture or cultivating cells.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2, IL-15 and/or IL-7. In some aspects, the IL-2 concentration is at least about 10 units/mL.

In some aspects, incubation is carried out in accordance with techniques such as those described in U.S. Pat. No.

6,040,177 to Riddell et al., Klebanoff et al. (2012) J Immunother. 35(9): 651-660, Terakura et al. (2012) Blood.1:72-82, and/or Wang et al. (2012) J Immunother. 35(9):689-701.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

c. Engineered Cells, Vectors and Compositions for Multi-Targeting

Also provided are cells such as engineered cells that can bind to and/or target multiple antigens. In some embodiments, improved selectivity and specificity is achieved through strategies targeting multiple antigens. Such strategies generally involve multiple antigen-binding domains, which typically are present on distinct genetically engineered antigen receptors and specifically bind to distinct antigens. In some embodiments, the cells are engineered with the ability to bind more than one antigen. For example, in some embodiments, the cells are engineered to express multispecific binding molecules. In some embodiments, the cells express multiple binding molecules, e.g., recombinant receptors, each of which can target one antigen or multiple antigens, e.g., one receptor that targets CCT5, such as any described herein, and another receptor that targets another antigen, e.g., tumor antigen. In some aspects, a plurality of genetically engineered antigen receptors are introduced into the cell, which specifically bind to different antigens, each expressed in or on the disease or condition to be targeted with the cells or tissues or cells thereof. Such features can in some aspects address or reduce the likelihood of off-target effects or increase efficacy. For example, where a single antigen expressed in a disease or condition is also expressed on or in non-diseased or normal cells, such multi-targeting approaches can provide selectivity for desired cell types by requiring binding via multiple antigen receptors in order to activate the cell or induce a particular effector function. In some embodiments, a plurality of cells can be engineered to express one or more different binding molecules, e.g., recombinant receptors, each of which can target one antigen or multiple antigens.

Also provided are multispecific cells containing any of the binding molecules described herein, such as cells containing a cell surface protein including the anti-CCT5 antibody and an additional cell surface protein, such as an additional chimeric receptor, which binds to a different antigen or a different epitope on CCT5. In some embodiments, provided are compositions of cells that express recombinant receptors, wherein one or more of the binding molecules, multispecific binding molecules and/or recombinant receptors bind and/or target CCT5. Also provided are compositions of cells containing a plurality of cells that express one or more different binding molecules, e.g., recombinant receptors that can target one or multiple antigens. In some embodiments, the multispecific binding molecules and/or recombinant receptors target one or more different epitopes on CCT5.

In some embodiments, provided are composition of cells, wherein each type of cell expresses one or more binding molecules, e.g., recombinant receptors. In some embodiments, the cell comprises (e.g., has been transformed with) one or more vectors comprising one or more nucleic acid that encodes one or more an amino acid sequence comprising one or more antibodies and/or portions thereof, e.g., antigen-binding fragments thereof. In some embodiments, one or more such cells are provided. In some embodiments, a composition containing one or more such cells is provided. In some embodiments, the one or more cells can express different antibodies, or the same antibody. In some embodiments, each of the cells expresses one or more antibodies, such as more than one antibody. In some embodiments, each of the cells expresses a multispecific binding molecule, e.g., a multispecific receptor, e.g., CAR.

In some embodiments, the cells include multi-targeting strategies that target CCT5 and a second or additional antigen associated with a particular disease or condition. In some embodiments, the second or additional antigen is targeted by a multispecific binding molecule and/or multiple binding molecules and/or a plurality of cells, e.g., one or more cells, each engineered to express one or more recombinant receptors. In some embodiments, a recombinant receptor targeting a second or additional antigen is expressed on the same cell as a CCT5 binding molecule, or on a different cell.

In some embodiments, among the second or additional antigens for multi-targeting strategies includes those in which at least one of the antigens is a universal tumor antigen, or a family member thereof. In some embodiments, the second or additional antigen is an antigen expressed on a tumor. In some embodiments, the CCT5-binding molecules provided herein target an antigen on the same tumor type as the second or additional antigen. In some embodiments, the second or additional antigen may also be a universal tumor antigen or may be a tumor antigen specific to a tumor type. In some embodiments, the cell further comprises an additional genetically engineered antigen receptor that recognizes a second or additional antigen expressed on a disease or condition to be treated and induces a stimulatory or activating signal.

Exemplary antigens include CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, MUC-1, Ia, HM1.24, HLA-DR, tenascin, an angiogenesis factor, VEGF, PlGF, ED-B fibronectin, an oncogene, an oncogene product, CD66a-d, necrosis antigens, Ii, IL-2, T101, TAC, IL-6, ROR1, TRAIL- R1 (DR4), TRAIL-R2 (DR5), B cell maturation antigen (CCT5), tEGFR, Her2, L1-CAM, mesothelin, CEA, hepatitis B surface antigen, anti-folate receptor, CD24, CD30, CD44, EGFR, EGP-2, EGP-4, EPHa2, ErbB2, ErbB3, ErbB4, erbB dimers, EGFR viii, FBP, FCRL5, FCRH5, fetal acetylcholine receptor, GD2, GD3, HMW-MAA, IL-22R-alpha, IL-13R-alpha2, kdr, kappa light chain, Lewis Y, L1-cell adhesion molecule (L1-CAM), Melanoma-associated antigen (MAGE)-A1, MAGE-A3, MAGE-A6, Preferentially expressed antigen of melanoma (PRAME), survivin, EGP2, EGP40, TAG72, B7-H6, IL-13 receptor a2 (IL-13Ra2), CA9, CD171, G250/CAIX, HLA-A1 MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, dual antigen, an antigen associated with a universal tag, a cancer-testes antigen, MUC1, MUC16, NY-ESO-1, MART-1, gp100, oncofetal antigen, VEGF-R2, carcinoembryonic antigen (CEA), prostate specific antigen, PSMA, Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, hTERT, MDM2, CYP1B, WT1, livin, AFP, p53, cyclin (DI), CS-1, CCT5, BAFF-R, TACI, CD56, TIM-3, CD123, L1-cell adhesion molecule, MAGE-A1, MAGE A3, a cyclin, such as cyclin A1 (CCNA1) and/or a pathogen-specific antigen, biotinylated molecules, molecules expressed by HIV, HCV, HBV and/or other pathogens, and/or in some aspects, neoepitopes or neoantigens thereof. In some embodiments, the antigen is associated with or is a universal tag.

In some embodiments, the plurality of antigens, e.g., the first antigen, e.g., CCT5, and the second or additional antigens, are expressed on the cell, tissue, or disease or condition being targeted, such as on the cancer cell. In some aspects, the cell, tissue, disease or condition is multiple myeloma or a multiple myeloma cell. One or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy is/are achieved.

In some embodiments, the cells and methods include multi-targeting strategies, such as expression of two or more genetically engineered receptors on the cell, each recognizing a different antigen and typically each including a different intracellular signaling component. Such multi-targeting strategies are described, for example, in International Patent Application, Publication No.: WO 2014055668 A1 (describing combinations of activating and costimulatory CARs, e.g., targeting two different antigens present individually on off-target, e.g., normal cells, but present together only on cells of the disease or condition to be treated) and Fedorov et al., *Sci. Transl. Medicine,* 5(215) (December, 2013) (describing cells expressing an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat).

In some embodiments, a plurality of cells, each engineered to express one or more recombinant receptors, are provided. For example, in some embodiments, one cell is engineered to express a binding molecule that binds and/or targets CCT5, and another cell is engineered to express a binding molecule that binds and/or targets an additional or second antigen. In some embodiments, the cells can each express a multispecific binding molecule, e.g., a multispecific recombinant receptor, where one or more of the target antigen is CCT5. In some of such embodiments, the plurality of cells can be administered together or separately. In some embodiments, some of the plurality of cells are administered simultaneously or concurrently with other cells, e.g., administered on the same day, and/or sequentially with or intermittently with, in any order, another engineered cell in the plurality. For example, in some embodiments, an engineered cell expressing a CCT5-binding molecule, e.g., CAR, is administered simultaneously with or sequentially with, in any order, another engineered cell expressing a binding molecule that binds a different target antigen or a different epitope on CCT5. In some embodiments, the plurality of cells can be in the same composition or in different compositions. Exemplary compositions of the cells include compositions described in Section II below.

II. PHARMACEUTICAL COMPOSITIONS

Also provided are compositions including the CCT5-binding molecules (e.g. antibody), immunoconjugates, recombinant receptors, and engineered cells, including pharmaceutical compositions and formulations.

Provided are pharmaceutical formulations comprising a CCT5-binding molecule (e.g., antibody), an immunoconjugate, a recombinant receptor (e.g., chimeric antigen receptor), engineered cells expressing said molecules (e.g., recombinant receptor), a plurality of engineered cells expressing said molecules (e.g., recombinant receptor) and/or additional agents for combination treatment or therapy. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell, binding molecule, and/or antibody, and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

Formulations of the antibodies described herein can include lyophilized formulations and aqueous solutions.

The formulation or composition may also contain more than one active ingredient useful for the particular indication, disease, or condition being treated with the binding molecules or cells, preferably those with activities complementary to the binding molecule or cell, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the cells or antibodies are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

Active ingredients may be entrapped in microcapsules, in colloidal drug delivery systems (for example, liposomes, albumin microspheres, microemulsions, nano-particles and nanocapsules) or in macroemulsions. In certain embodiments, the pharmaceutical composition is formulated as an inclusion complex, such as cyclodextrin inclusion complex, or as a liposome. Liposomes can serve to target the host cells (e.g., T-cells or NK cells) to a particular tissue. Many methods are available for preparing liposomes, such as those described in, for example, Szoka et al., Ann. Rev. Biophys. Bioeng., 9: 467 (1980), and U.S. Pat. Nos. 4,235,871, 4,501,728, 4,837,028, and 5,019,369.

The pharmaceutical composition in some aspects can employ time-released, delayed release, and sustained release delivery systems such that the delivery of the composition occurs prior to, and with sufficient time to cause, sensitization of the site to be treated. Many types of release delivery systems are available and known. Such systems can avoid repeated administrations of the composition, thereby increasing convenience to the subject and the physician.

The pharmaceutical composition in some embodiments contains the binding molecules and/or cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

In certain embodiments, in the context of genetically engineered cells containing the binding molecules, a subject is administered the range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges, and/or such a number of cells per kilogram of body weight of the subject.

The may be administered using standard administration techniques, formulations, and/or devices. Provided are formulations and devices, such as syringes and vials, for storage and administration of the compositions. Administration of the cells can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, intracranial, intrathoracic, and intraperitoneal administration. In some embodiments, the cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the binding molecule in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

Also provided are pharmaceutical compositions for combination therapy. Any of the additional agents for combination therapy described herein, such as agents described in Section III.B, can be prepared and administered as one or more pharmaceutical compositions, with the CCT5-binding molecule (e.g., antibody), immunoconjugate, recombinant receptor (e.g., chimeric antigen receptor) and/or engineered cells expressing said molecules (e.g., recombinant receptor) described herein. The combination therapy can be administered in one or more pharmaceutical compositions, e.g., where the binding molecules, recombinant receptors and/or cells are in the same pharmaceutical composition as the additional agent, or in separate pharmaceutical compositions. For example, in some embodiments, the additional agent is an additional engineered cell, e.g., cell engineered to express a different recombinant receptor that targets a different antigen or a different epitope on CCT5, and is administered in the same composition or in a separate composition. In some embodiments, each of the pharmaceutical composition is formulated in a suitable formulation according to the particular binding molecule, recombinant receptor, cell, e.g., engineered cell, and/or additional agent, and the particular dosage regimen and/or method of delivery.

III. METHODS AND USES

Also provided methods of using and uses of the CCT5-binding molecules (e.g. antibody), immunoconjugates, recombinant receptors, engineered cells, and pharmaceutical compositions and formulations thereof, such as in the treatment of diseases, conditions, and disorders in which CCT5 is expressed, and/or detection, diagnostic, and prognostic methods. Also provided are methods of combination therapy and/or treatment.

A. Therapeutic and Prophylactic Methods and Uses

Also provided are methods of administering and uses, such as therapeutic and prophylactic uses, of the CCT5-binding molecules, including the anti-CCT5 antibodies, e.g., antibody fragments and proteins containing the same such as the recombinant receptors (e.g., CARs), engineered cells expressing the recombinant receptors (e.g., CARs), plurality of engineered cells expressing the receptors, and/or compositions comprising the same. Such methods and uses include therapeutic methods and uses, for example, involving administration of the molecules (e.g., CCT5-binding molecules, conjugates, and recombinant receptors), cells (e.g., engineered cells), or compositions containing the same, to a subject having a disease, condition, or disorder associated with CCT5 such as a disease, condition, or disorder associated with CCT5 expression, and/or in which cells or tissues express, e.g., specifically express CCT5. In some embodiments, the molecule, cell, and/or composition is administered in an effective amount to effect treatment of the disease or disorder. Provided herein are uses of the binding molecules (e.g., anti-CCT5 antibodies or antigen-binding fragments thereof), recombinant receptors (e.g., CARs), and cells (e.g., engineered cells) in such methods and treatments, and in the preparation of a medicament in order to carry out such therapeutic methods. In some embodiments, the methods are carried out by administering the binding molecules or cells, or compositions comprising the same, to the subject having, having had, or suspected of having the disease or condition. In some embodiments, the methods thereby treat the disease or condition or disorder in the subject.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or subject being treated. It is known that a sufficient or significant delay can, in effect, encompass prevention, in that the subject does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided molecules and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, an antibody or composition or cell which suppresses tumor growth reduces the rate of growth of the tumor compared to the rate of growth of the tumor in the absence of the antibody or composition or cell.

An "effective amount" of an agent, e.g., a pharmaceutical formulation, binding molecule, antibody, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation, binding molecule, antibody, cells, or composition refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered. In some embodiments, the provided methods involve administering the molecules, antibodies, cells, and/or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

As used herein, a "subject" or an "individual" is a mammal. In some embodiments, a "mammal" includes humans, non-human primates, domestic and farm animals, and zoo, sports, or pet animals, such as dogs, horses, rabbits, cattle, pigs, hamsters, gerbils, mice, ferrets, rats, cats, monkeys, etc. In some embodiments, the subject is human.

In certain diseases and conditions, CCT5 is expressed on malignant cells and cancers. In some embodiments, the cancer (e.g., a CCT5-expressing cancer) is a solid tumor. In some embodiments, the cancer (e.g., a CCT5-expressing cancer) is a diffuse or circulating cancer or tumor. In some embodiments, the cancer is an adrenal cancer, bladder cancer, brain cancer, breast cancer, cervical cancer, colon cancer, colorectal cancer, epithelial squamous cell cancer, head and neck cancer, leukemia, liver cancer, lung cancer, lymphoma, melanoma, myeloma (e.g., multiple myeloma), neuroblastoma, ovarian cancer, pancreatic cancer, prostate cancer, renal cancer, renal cell carcinoma, skin cancer, stomach cancer, testicular cancer, thyroid cancer, urothelial cancer, uterine cancer, and the like.

In some embodiments, the cancer is an epithelial cell cancer, such as a carcinoma originating in cells derived from the endodermal, mesodermal or ectodermal germ layers. In some embodiments the carcinoma is a squamous cell carcinoma (skin), basal cell carcinoma, gastric carcinoma, (e.g., intestinal type gastric carcinoma or diffuse type (mucinous) gastric carcinoma), an adenocarcinoma, adenosquamous carcinoma, anaplastic carcinoma, transitional cell carcinoma, large cell carcinoma, small cell carcinoma, hepatocellular carcinoma, renal cell carcinoma, endometrial carcinoma, invasive carcinoma of the breast, or a carcinoma metastasis (e.g., lymph node). In some embodiments, the epithelial cell cancer is colon, breast, ovarian, prostate, pancreatic, bladder, or lung cancer.

In some embodiments, the disease or disorder associated with CCT5 is an autoimmune disease or disorder. Autoimmune diseases or disorders include, but are not limited to, systemic lupus erythematosus (SLE), lupus nephritis, inflammatory bowel disease, rheumatoid arthritis (e.g., juvenile rheumatoid arthritis), ANCA associated vasculitis, idiopathic thrombocytopenia purpura (ITP), thrombotic thrombocytopenia purpura (TTP), autoimmune thrombocytopenia, Chagas' disease, Grave's disease, Wegener's granulomatosis, poly-arteritis nodosa, Sjogren's syndrome, pemphigus vulgaris, scleroderma, multiple sclerosis, psoriasis, IgA nephropathy, IgM polyneuropathies, vasculitis, diabetes mellitus, Reynaud's syndrome, anti-phospholipid syndrome, Goodpasture's disease, Kawasaki disease, autoimmune hemolytic anemia, myasthenia gravis, or progressive glomerulonephritis.

In some embodiments, the methods may identify a subject who has, is suspected to have, or is at risk for developing a CCT5-associated disease or disorder. Hence, provided are methods for identifying subjects with diseases or disorders associated with elevated CCT5 expression and selecting them for treatment with a provided CCT5-binding molecule, including any of the anti-CCT5 antibodies, e.g., antibody fragments and proteins containing the same such as the recombinant receptors (e.g., CARs), and/or engineered cells expressing the recombinant receptors.

For example, a subject may be screened for the presence of a disease or disorder associated with elevated CCT5 expression, such as a CCT5-expressing cancer. In some embodiments, the methods include screening for or detecting the presence of a CCT5-associated disease, e.g. a tumor. Thus, in some aspects, a sample may be obtained from a patient suspected of having a disease or disorder associated with elevated CCT5 expression and assayed for the expression level of CCT5. In some aspects, a subject who tests positive for a CCT5-associated disease or disorder may be selected for treatment by the present methods, and may be administered a therapeutically effective amount of a CCT5-binding molecule (e.g., anti-CCT5 antibody or antigen-binding fragment thereof), recombinant receptor (e.g., CAR) comprising a CCT5-binding molecule, cells containing a recombinant receptor or a pharmaceutical composition thereof as described herein. In some embodiments, the methods can be used to monitor the size or density of a CCT5-expressing tissue, e.g. tumor, over time, e.g., before, during, or after treatment by the methods.

In some embodiments, the subject has persistent or relapsed disease, e.g., following treatment with another CCT5-specific antibody and/or cells expressing a CCT5-targeting chimeric receptor and/or other therapy, including chemotherapy, radiation, and/or hematopoietic stem cell transplantation (HSCT), e.g., allogenic HSCT. In some embodiments, the administration effectively treats the subject despite the subject having become resistant to another CCT5-targeted therapy. In some embodiments, the subject has not relapsed but is determined to be at risk for relapse, such as at a high risk of relapse, and thus the compound or composition is administered prophylactically, e.g., to reduce the likelihood of or prevent relapse.

In some embodiments, the treatment does not induce an immune response by the subject to the therapy, and/or does not induce such a response to a degree that prevents effective treatment of the disease or condition. In some aspects, the degree of immunogenicity and/or graft versus host response is less than that observed with a different but comparable treatment. For example, in the case of adoptive cell therapy using cells expressing CARs including the provided anti-CCT5 antibodies, the degree of immunogenicity in some embodiments is reduced compared to CARs including a different antibody that binds to a similar, e.g., overlapping epitope and/or that competes for binding to CCT5 with the provided antibody, such as a mouse or monkey or rabbit or humanized antibody.

In some embodiments, the methods include adoptive cell therapy, whereby genetically engineered cells expressing the provided recombinant receptors comprising a CCT5-binding molecule (e.g., CARs comprising anti-CCT5 antibody or antigen-binding fragment thereof) are administered to subjects. Such administration can promote activation of the cells (e.g., T cell activation) in a CCT5-targeted manner, such that the cells of the disease or disorder are targeted for destruction.

Thus, the provided methods and uses include methods and uses for adoptive cell therapy. In some embodiments, the methods include administration of the cells, the plurality of cells a composition containing the cells or the plurality of cells to a subject, tissue, or cell, such as one having, at risk for, or suspected of having the disease, condition or disorder. In some embodiments, the cells, populations, and compositions are administered to a subject having the particular disease or condition to be treated, e.g., via adoptive cell therapy, such as adoptive T cell therapy. In some embodiments, the cells or compositions are administered to the subject, such as a subject having or at risk for the disease or condition. In some aspects, the methods thereby treat, e.g., ameliorate one or more symptom of the disease or condition, such as by lessening tumor burden in a CCT5-expressing cancer.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

In some embodiments, the cell therapy, e.g., adoptive cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject, to whom the cells, cell populations, or compositions are administered is a primate, such as a human. In some embodiments, the subject, to whom the cells, cell populations, or compositions are administered is a non-human primate. In some embodiments, the non-human primate is a monkey (e.g., cynomolgus monkey) or an ape. The subject can be male or female and can be any suitable age, including infant, juvenile, adolescent, adult, and geriatric subjects. In some embodiments, the subject is a non-primate mammal, such as a rodent (e.g., mouse, rat, etc.). In some examples, the patient or subject is a validated animal model for disease, adoptive cell therapy, and/or for assessing toxic outcomes such as cytokine release syndrome (CRS).

In some embodiments, the RNA expression profile of a tumor cell can be used to predict the response of an anti-CCT5 CAR-expressing T cell to the tumor cell. In some aspects, RNA-seq data, for example, the Quantified Cancer Cell Line Encyclopedia (CCLE) RNA-seq data, can be mined for upregulated transcripts that could be predictive of anti-CCT5 CAR T cell activation. For example, RNA-seq databases that include data for cell lines known to be capable of activating anti-CCT5 CAR T cells and cell lines known to be incapable of activating anti-CCT5 CAR T cells, can be used to identify factors that correlate with predicted anti-CCT5 CAR T cell activation. In some embodiments CCT5 RNA expression may not correlate with anti-CCT5 CAR T cell activation based on RNA-seq data. In some embodiments, expression of T-complex protein 1 (TCP1), a member of the TCP1 complex (CCT), may correlate with predicted anti-CCT5 CAR T cell activation. In some aspects, CCT5 and other members of the TCP complex are upregulated by the myc pathway, and the TCP complex may be associated with myc-dependent cancers. In some embodiments, pathways or genes that correlate with anti-CCT5 CAR T cell activation include MYC, estrogen receptor, INSR, miR-124-3p, ESRRA, miR-199a-5p, MYCN, mir-210, and TFAP2C pathways In some embodiments, these pathways may be used to predict anti-CCT5 CAR activation in tumor cell lines including breast, ovary and lung cancer cell lines.

The CCT5-binding molecules such as antibodies, recombinant receptors (e.g., CARs) containing the antibodies and cells expressing the same, can be administered by any suitable means, for example, by injection, e.g., intravenous or subcutaneous injections, intraocular injection, periocular injection, subretinal injection, intravitreal injection, transseptal injection, subscleral injection, intrachoroidal injection, intracameral injection, subconjunctival injection, subconjunctival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, intracranial, intrathoracic, or subcutaneous administration. Dosing and administration may depend in part on whether the administration is brief or chronic. Various dosing schedules include but are not limited to single or multiple administrations over various time-points, bolus administration, and pulse infusion.

For the prevention or treatment of disease, the appropriate dosage of the binding molecule, recombinant receptor or cell may depend on the type of disease to be treated, the type of binding molecule or recombinant receptor, the severity and course of the disease, whether the binding molecule or recombinant receptor is administered for preventive or therapeutic purposes, previous therapy, the patient's clinical history and response to the binding molecule, recombinant receptor or cell, and the discretion of the attending physician. The compositions and molecules and cells are in some embodiments suitably administered to the patient at one time or over a series of treatments.

Depending on the type and severity of the disease, dosages of binding molecules (e.g., anti-CCT5 antibody or antigen-binding fragment thereof) or recombinant receptors may include about 1 µg/kg to about 15 mg/kg (e.g. 0.1 mg/kg-10 mg/kg), about 1 µg/kg to about 100 mg/kg, about 0.05 mg/kg to about 10 mg/kg, about 0.5 mg/kg, about 2.0 mg/kg, about 4.0 mg/kg or about 10 mg/kg. Multiple doses may be administered intermittently, e.g. every week or every three weeks. An initial higher loading dose, followed by one or more lower doses may be administered.

In certain embodiments, in the context of genetically engineered cells containing the binding molecules or recombinant receptors, a subject is administered the range of about one million to about 100 billion cells and/or that amount of cells per kilogram of body weight, such as, e.g., about 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Again, dosages may vary depending on attributes particular to the disease or disorder and/or patient and/or other treatments.

In some embodiments, for example, where the subject is a human, the dose includes fewer than about $1\times10^8$ total recombinant receptor (e.g., CAR)-expressing cells, T cells, or peripheral blood mononuclear cells (PBMCs), e.g., in the range of about $1\times10^6$ to $1\times10^8$ such cells, such as $2\times10^6$, $5\times10^6$, $1\times10^7$, $5\times10^7$, or $1\times10^8$ or total such cells, or the range between any two of the foregoing values.

In some aspects, the size of the dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some aspects, the size of the dose is determined by the burden of the disease or condition in the subject. For example, in some aspects, the number of cells administered in the dose is determined based on the tumor burden that is present in the subject immediately prior to administration of the initiation of the dose of cells. In some embodiments, the size of the first and/or subsequent dose is inversely correlated with disease burden. In some aspects, as in the context of a large disease burden, the subject is administered a low number of cells. In other embodiments, as in the context of a lower disease burden, the subject is administered a larger number of cells.

In some embodiments, the cells, binding molecules, or recombinant receptors are administered as part of a combination treatment, such as simultaneously with or sequentially with, in any order, another therapeutic intervention, such as another antibody or engineered cell or receptor or agent, such as a cytotoxic or therapeutic agent, such as any described in Section I.E or III.B.

The cells, binding molecules and/or recombinant receptors in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells, binding molecules and/or recombinant receptors are administered prior to the one or more additional therapeutic agents. In some embodiments, the cells, binding molecules and/or recombinant receptors are administered after to the one or more additional therapeutic agents.

Once the cells are administered to a mammal (e.g., a human), the biological activity of the engineered cell populations and/or antibodies in some aspects is measured by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method, such as cytotoxicity assays described in, for example, Kochenderfer et al., *J. Immunotherapy*, 32(7): 689-702 (2009), and Herman et al. *J. Immunological Methods*, 285(1): 25-40 (2004). In certain embodiments, the biological activity of the cells also can be measured by assaying expression and/or secretion of certain cytokines, such as CD 107a, IFNγ, IL-2, and TNF. In some aspects the biological activity is measured by assessing clinical outcome, such as reduction in tumor burden or load.

In certain embodiments, engineered cells are modified in any number of ways, such that their therapeutic or prophylactic efficacy is increased. For example, the engineered CAR or TCR expressed by the population in some embodiments are conjugated either directly or indirectly through a linker to a targeting moiety. The practice of conjugating compounds, e.g., the CAR or TCR, to targeting moieties is known. See, for instance, Wadwa et al., *J. Drug Targeting*, 3(2):111 (1995), and U.S. Pat. No. 5,087,616.

B. Combination Therapy

Also provided are methods of combination therapy that includes administering and uses, such as therapeutic and prophylactic uses, of the CCT5-binding molecules, including the anti-CCT5 antibodies, e.g., antibody fragments and proteins containing the same such as the recombinant receptors (e.g., CARs), engineered cells expressing the recombinant receptors (e.g., CARs), plurality of engineered cells expressing the receptors, and/or compositions comprising the same.

In some embodiments, the CCT5-binding molecule (e.g., antibody), immunoconjugate, recombinant receptor (e.g., chimeric antigen receptor) and/or engineered cells expressing said molecules (e.g., recombinant receptor) described herein are administered as part of a combination treatment or combination therapy, such as simultaneously with, sequentially with or intermittently with, in any order, one or more additional therapeutic intervention. In some embodiments, the one or more additional therapeutic intervention includes, for example, an antibody, an engineered cell, a receptor and/or an agent, such as a cell expressing a recombinant receptor, and/or cytotoxic or therapeutic agent, e.g., a chemotherapeutic agent. In some embodiments, the combination therapy includes administration of one or more additional agents, therapies and/or treatments, e.g., any of the additional agents, therapy and/or treatments described herein. In some embodiments, the combination therapy includes administration of one or more additional agents for treatment or therapy, such as an immunomodulatory agent, immune checkpoint inhibitor, adenosine pathway or adenosine receptor antagonist or agonist and kinase inhibitors. In some embodiments, the combination treatment or combination therapy includes an additional treatment, such as a surgical treatment, transplant, and/or radiation therapy. Also provided are methods of combination treatment or combination therapy that includes administering the binding molecules (e.g., CCT5-binding molecules), recombinant receptors, cells and/or compositions described herein and one or more additional therapeutic interventions.

In some embodiments, the additional agent for combination treatment or combination therapy enhances, boosts and/or promotes the efficacy and/or safety of the therapeutic effect of binding molecules, recombinant receptors, cells and/or compositions. In some embodiments, the additional agent enhances or improves the efficacy, survival or persistence of the administered cells, e.g., cells expressing the binding molecule or a recombinant receptor. In some embodiments, the additional agent is selected from among a protein phosphatase inhibitor, a kinase inhibitor, a cytokine, an immunomodulator, or an agent that decreases the level or activity of a regulatory T (Treg) cell. In some embodiments, the additional agent enhances safety, by virtue of reducing or ameliorating adverse effects of the administered binding molecules, recombinant receptors, cells and/or compositions. In some embodiments, the additional agent can treat the same disease, condition or a comorbidity. In some embodiments, the additional agent can ameliorate, reduce or eliminate one or more toxicities, adverse effects or side effects that are associated with administration of the binding molecules, recombinant receptors, cells and/or compositions, e.g., CAR-expressing cells.

In some embodiments, the additional therapy, treatment or agent includes chemotherapy, radiation therapy, surgery, transplantation, adoptive cell therapy, antibodies, cytotoxic agents, chemotherapeutic agents, cytokines, growth inhibitory agents, anti-hormonal agents, kinase inhibitors, anti-angiogenic agents, cardioprotectants, immunostimulatory agents, immunosuppressive agents, immune checkpoint inhibitors, antibiotics, angiogenesis inhibitors, metabolic modulators or other therapeutic agents or any combination thereof. In some embodiments, the additional agent is a protein, a peptide, a nucleic acid, a small molecule agent, a cell, a toxin, a lipid, a carbohydrate or combinations thereof, or any other type of therapeutic agent, e.g. radiation. In some embodiments, the additional therapy, agent or treatment includes surgery, chemotherapy, radiation therapy, transplantation, administration of cells expressing a recombinant receptor, e.g., CAR, kinase inhibitor, immune checkpoint inhibitor, mTOR pathway inhibitor, immunosuppressive agents, immunomodulators, antibodies, immunoablative agents, antibodies and/or antigen binding fragments thereof, antibody conjugates, other antibody therapies, cytotoxins, steroids, cytokines, peptide vaccines, hormone therapy, anti-metabolites, metabolic modulators, drugs that inhibit either the calcium dependent phosphatase calcineurin or the p70S6 kinase FK506) or inhibit the p70S6 kinase, alkylating agents, anthracyclines, vinca alkaloids, proteasome inhibitors, GITR agonists, protein tyrosine phosphatase inhibitors, protein kinase inhibitors, an oncolytic virus, and/or other types of immunotherapy. In some embodiments, the additional agent or treatment is bone marrow transplantation, T cell ablative therapy using chemotherapy agents such as, fludarabine, external-beam radiation therapy (XRT), cyclophosphamide, and/or antibody therapy.

In some embodiments, the cells, binding molecules (e.g., CCT5-binding molecules), conjugates, recombinant receptors and/or compositions, e.g., CAR-expressing cells, are administered in combination with other binding molecules, such as antibodies, conjugates, recombinant receptors, and/or engineered cells, e.g., other CAR-expressing cells. In some embodiments, the additional agent is another CCT5-binding molecule, such as an anti-CCT5 antibody, conjugate, recombinant receptor, and/or anti-CCT5 CAR-expressing cell. In some embodiments, the additional CCT5-binding molecule or agent containing the CCT5-binding molecule binds a different or overlapping epitope as the CCT5 biding molecule, e.g., antibody or CAR, provided herein.

In some embodiments, the additional agent is a kinase inhibitor, e.g., an inhibitor of Bruton's tyrosine kinase (Btk), e.g., ibrutinib. In some embodiments, the additional agent is an adenosine pathway or adenosine receptor antagonist or agonist. In some embodiments, the additional agent is an immunomodulator such as thalidomide or a thalidomide derivative (e.g., lenalidomide). In some embodiments, the additional therapy, agent or treatment is a cytotoxic or chemotherapy agent, a biologic therapy (e.g., antibody, e.g., monoclonal antibody, or cellular therapy), or an inhibitor (e.g., kinase inhibitor).

In some embodiments, a chemotherapeutic agent (sometimes referred to as a cytotoxic agent) is administered to the subject to disrupt a lesion. In certain embodiments, the lesion is tumor. In particular embodiments, the lesion is cancerous. In particular embodiments, the chemotherapeutic agent is any agent known to be effective for the treatment, prevention or amelioration of hyperproliferative disorders such as cancer. Chemotherapeutic agents include, but are not limited to, small molecules, synthetic drugs, peptides, polypeptides, proteins, nucleic acids (e.g., DNA and RNA polynucleotides including, but not limited to, antisense nucleotide sequences, triple helices and nucleotide sequences encoding biologically active proteins, polypeptides or peptides), antibodies, synthetic or natural inorganic molecules, mimetic agents, and synthetic or natural organic molecules. In particular embodiments, chemotherapeutic drugs include alkylating agents, anthracyclines, cytoskeletal disruptors (taxanes), epothilones, histone deacetylase inhibitors, topoisomerase inhibitors, topoisomerase II inhibitors, kinase inhibitors, nucleotide analogs and precursor analogs, peptide antibiotics, platinum-based agents, and *vinca* alkaloids and derivatives.

In certain embodiments, a lesion is disrupted by administering a chemotherapeutic agent to modulate genetically engineered cells in vivo. Chemotherapeutic agents may include, but are not limited to, abarelix, aldesleukin, alemtuzumab, alitretinoin, allopurinol, altretamine, amifostine, anastrozole, arsenic trioxide, asparaginase, BCG live, bevaceizumab, bexarotene, bleomycin, bortezomib, busulfan, calusterone, camptothecin, capecitabine, carboplatin, carmustine, celecoxib, cetuximab, chlorambucil, cinacalcet, cisplatin, cladribine, cyclophosphamide, cytarabine, dacarbazine, dactinomycin, darbepoetin alfa, daunorubicin, denileukin diftitox, dexrazoxane, docetaxel, doxorubicin, dromostanolone, Elliott's B solution, epirubicin, epoetin alfa, estramustine, etoposide, exemestane, filgrastim, floxuridine, fludarabine, fluorouracil, fulvestrant, gemcitabine, gemtuzumab ozogamicin, gefitinib, goserelin, hydroxyurea, ibritumomab tiuxetan, idarubicin, ifosfamide, imatinib, interferon alfa-2a, interferon alfa-2b, irinotecan, letrozole, leucovorin, levamisole, lomustine, meclorethamine, megestrol, melphalan, mercaptopurine, mesna, methotrexate, methoxsalen, methylprednisolone, mitomycin C, mitotane, mitoxantrone, nandrolone, nofetumomab, oblimersen, oprelvekin, oxaliplatin, paclitaxel, pamidronate, pegademase, pegaspargase, pegfilgrastim, pemetrexed, pentostatin, pipobroman, plicamycin, polifeprosan, porfimer, procarbazine, quinacrine, rasburicase, rituximab, sargramostim, streptozocin, talc, tamoxifen, tarceva, temozolomide, teniposide, testolactone, thioguanine, thiotepa, topotecan, toremifene, tositumomab, trastuzumab, tretinoin, uracil mustard, valrubicin, vinblastine, vincristine, vinorelbine, and zoledronate.

In some embodiments, exemplary chemotherapeutic agents include an anthracycline (e.g., doxorubicin, such as liposomal doxorubicin); a *vinca* alkaloid (e.g., vinblastine, vincristine, vindesine, vinorelbine); an alkylating agent (e.g., cyclophosphamide, decarbazine, melphalan, ifosfamide, temozolomide); an immune cell antibody (e.g., alemtuzumab, gemtuzumab, rituximab, tositumomab); an antimetabolite (including, e.g., folic acid antagonists, pyrimidine analogs, purine analogs and adenosine deaminase inhibitors such as fludarabine); a TNFR glucocorticoid induced TNFR related protein (GITR) agonist; a proteasome inhibitor (e.g., aclacinomycin A, gliotoxin or bortezomib); an immunomodulatory such as thalidomide or a thalidomide derivative (e.g., lenalidomide).

In some embodiments, the additional therapy or treatment is cell therapy, e.g., adoptive cell therapy. In some embodiments, the additional therapy includes administration of engineered cells, e.g., additional CAR-expressing cell. In some embodiments, the additional engineered cell is a CAR-expressing cell that expresses the same or different recombinant receptor as the engineered cells provided herein, e.g., anti-CCT5 CAR-expressing cells. In some embodiments, the recombinant receptor, e.g., CAR, expressed on the additional engineered cell, recognizes a different antigen and/or epitope. In some embodiments, the recombinant receptor, e.g., CAR, expressed on the additional engineered cell, recognizes a different epitope of the same antigen as the recombinant receptors described herein, e.g., CCT5. In some embodiments, the recombinant receptor, e.g., CAR, expressed on the additional engineered cell, recognizes a different antigen, e.g., a different tumor antigen or combination of antigens. For example, in some embodiments, the recombinant receptor, e.g., CAR, expressed on the additional engineered cell, targets cancer cells that express early lineage markers, e.g., cancer stem cells, while other CAR-expressing cells target cancer cells that express later lineage markers. In such embodiments, the additional engineered cell is administered prior to, concurrently with, or after administration (e.g., infusion) of the CAR-expressing cells described herein. In some embodiments, the additional engineered cell expresses allogeneic CAR.

In some embodiments, the configurations of one or more of the CAR molecules comprise a primary intracellular signaling domain and two or more, e.g., 2, 3, 4, or 5 or more, costimulatory signaling domains. In some embodiments, the one or more of the CAR molecules may have the same or a different primary intracellular signaling domain, the same or different costimulatory signaling domains, or the same number or a different number of costimulatory signaling domains. In some embodiments, the one or more of the CAR molecules can be configured as a split CAR, in which one of the CAR molecules comprises an antigen binding domain and a costimulatory domain (e.g., 4-1BB), while the other CAR molecule comprises an antigen binding domain and a primary intracellular signaling domain (e.g., CD3 zeta).

In some embodiments, the additional agent is any of the multispecific binding molecules and/or cells engineered to express one or more of the binding molecules described herein and/or cells engineered to express additional binding molecules, e.g., recombinant receptors, e.g., CAR, that target a different antigen. In some embodiments, the additional agent includes any of the cells or plurality of cells described herein, e.g., in Section I.E. In some embodiments, the additional agent is a cell engineered to express a recombinant receptor, e.g., CAR, targeting a different epitope and/or antigen, e.g., a different antigen associated with a disease or condition.

In some embodiments, the additional agent is an immunomodulatory agent. In some embodiments, the combination therapy includes an immunomodulatory agent that can stimulate, amplify and/or otherwise enhance an anti-tumor immune response, e.g. anti-tumor immune response from the administered engineered cells, such as by inhibiting immunosuppressive signaling or enhancing immunostimulant signaling. In some embodiments, the immunomodulatory agent is a peptide, protein or is a small molecule. In some embodiments, the protein can be a fusion protein or a recombinant protein. In some embodiments, the immunomodulatory agent binds to an immunologic target, such as a cell surface receptor expressed on immune cells, such a T cells, B cells or antigen-presenting cells. For example, in some embodiments, the immunomodulatory agent is an antibody or antigen-binding antibody fragment, a fusion protein, a small molecule or a polypeptide. In some embodiments, the binding molecules, recombinant receptors, cells and/or compositions are administered in combination with an additional agent that is an antibody or an antigen-binding fragment thereof, such as a monoclonal antibody.

In some embodiments, the immunomodulatory agent blocks, inhibits or counteracts a component of the immune checkpoint pathway. The immune system has multiple inhibitory pathways that are involved in maintaining self-tolerance and for modulating immune responses. Tumors can use certain immune-checkpoint pathways as a major mechanism of immune resistance, particularly against T cells that are specific for tumor antigens (Pardoll (2012) Nature Reviews Cancer 12:252-264), e.g., engineered cells such as CAR-expressing cells. Because many such immune checkpoints are initiated by ligand-receptor interactions, they can be readily blocked by antibodies against the ligands and/or their receptors.

Therefore, therapy with antagonistic molecules blocking an immune checkpoint pathway, such as small molecules, nucleic acid inhibitors (e.g., RNAi) or antibody molecules, are becoming promising avenues of immunotherapy for cancer and other diseases. In contrast to the majority of anti-cancer agents, checkpoint inhibitors do not necessarily target tumor cells directly, but rather target lymphocyte receptors or their ligands in order to enhance the endogenous antitumor activity of the immune system.

As used herein, the term "immune checkpoint inhibitor" refers to molecules that totally or partially reduce, inhibit, interfere with or modulate one or more checkpoint proteins. Checkpoint proteins regulate T-cell activation or function. These proteins are responsible for co-stimulatory or inhibitory interactions of T-cell responses. Immune checkpoint proteins regulate and maintain self-tolerance and the duration and amplitude of physiological immune responses. In some embodiments, the subject can be administered an additional agent that can enhance or boost the immune response, e.g., immune response effected by the binding molecules (e.g., CCT5-binding molecules), recombinant receptors, cells and/or compositions provided herein, against a disease or condition, e.g., a cancer, such as any described herein.

Immune checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors, ligands and/or receptor-ligand interaction. In some embodiments, modulation, enhancement and/or stimulation of particular receptors can overcome immune checkpoint pathway components. Illustrative immune checkpoint molecules that may be targeted for blocking, inhibition, modulation, enhancement and/or stimulation include, but are not limited to, PD-1 (CD279), PD-L1 (CD274, B7-H1), PDL2 (CD273, B7-DC) CTLA-4, LAG-3 (CD223), TIM-3, 4-1BB (CD137), 4-1BBL (CD137L), GITR (TNFRSF18, AITR), CD40, OX40 (CD134, TNFRSF4), CXCR2, tumor associated antigens (TAA), B7-H3, B7-H4, BTLA, HVEM, GAL9, B7H3, B7H4, VISTA, KIR, 2B4 (belongs to the CD2 family of molecules and is expressed on all NK, γδ, and memory CD8+(αβ) T cells), CD160 (also referred to as BY55), CGEN-15049, CEACAM (e.g., CEACAM-1, CEACAM-3 and/or CEACAM-5), TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and a transforming growth factor receptor (TGFR; e.g., TGFR beta). Immune checkpoint inhibitors include antibodies, or antigen binding fragments thereof, or other binding proteins that bind to and block or inhibit and/or enhance or stimulate the activity of one or more of any of the said molecules.

Exemplary immune checkpoint inhibitors include Tremelimumab (CTLA-4 blocking antibody, also known as ticilimumab, CP-675,206), anti-OX40, PD-L1 monoclonal antibody (Anti-B7-H1; MEDI4736), MK-3475 (PD-1 blocker), nivolumab (anti-PD-1 antibody), CT-011 (anti-PD-1 antibody), BY55 monoclonal antibody, AMP224 (anti-PD-L1 antibody), BMS-936559 (anti-PD-L1 antibody), MPLDL3280A (anti-PD-L1 antibody), MSB0010718C (anti-PD-L1 antibody) and ipilimumab (anti-CTLA-4 antibody, also known as Yervoy®, MDX-010 and MDX-101). Exemplary of immunomodulatory antibodies include, but are not limited to, Daclizumab (Zenapax), Bevacizumab (Avastin®), Basiliximab, Ipilimumab, Nivolumab, pembrolizumab, MPDL3280A, Pidilizumab (CT-011), MK-3475, BMS-936559, MPDL3280A (Atezolizumab), tremelimumab, IMP321, BMS-986016, LAG525, urelumab, PF-05082566, TRX518, MK-4166, dacetuzumab (SGN-40), lucatumumab (HCD122), SEA-CD40, CP-870, CP-893, MEDI6469, MEDI6383, MOXR0916, AMP-224, MSB0010718C (Avelumab), MEDI4736, PDR001, rHIgM12B7, Ulocuplumab, BKT140, Varlilumab (CDX-1127), ARGX-110, MGA271, lirilumab (BMS-986015, IPH2101), IPH2201, ARGX-115, Emactuzumab, CC-90002 and MNRP1685A or an antibody-binding fragment thereof. Other exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon .gamma., CAS 951209-71-5, available from IRX Therapeutics).

Programmed cell death 1 (PD-1) is an immune checkpoint protein that is expressed in B cells, NK cells, and T cells (Shinohara et al., 1995, Genomics 23:704-6; Blank et al., 2007, Cancer Immunol Immunother 56:739-45; Finger et al., 1997, Gene 197:177-87; Pardoll (2012) Nature Reviews Cancer 12:252-264). The major role of PD-1 is to limit the activity of T cells in peripheral tissues during inflammation in response to infection, as well as to limit autoimmunity. PD-1 expression is induced in activated T cells and binding of PD-1 to one of its endogenous ligands acts to inhibit T-cell activation by inhibiting stimulatory kinases. PD-1 also acts to inhibit the TCR "stop signal". PD-1 is highly expressed on Treg cells and may increase their proliferation in the presence of ligand (Pardoll (2012) Nature Reviews Cancer 12:252-264). Anti-PD 1 antibodies have been used for treatment of melanoma, non-small-cell lung cancer, bladder cancer, prostate cancer, colorectal cancer, head and neck cancer, triple-negative breast cancer, leukemia, lymphoma and renal cell cancer (Topalian et al., 2012, N Engl J Med 366:2443-54; Lipson et al., 2013, Clin Cancer Res 19:462-8; Berger et al., 2008, Clin Cancer Res 14:3044-51; Gildener-Leapman et al., 2013, Oral Oncol 49:1089-96; Menzies & Long, 2013, Ther Adv Med Oncol 5:278-85). Exemplary anti-PD-1 antibodies include nivolumab (Opdivo by BMS), pembrolizumab (Keytruda by Merck), pidilizumab (CT-011 by Cure Tech), lambrolizumab (MK-3475 by Merck), and AMP-224 (Merck), nivolumab (also referred to as Opdivo, BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are described in U.S. Pat. No. 8,008,449 and WO2006/121168. Pidilizumab (CT-011; Cure Tech) is a humanized IgG1k monoclonal antibody that binds to PD-1. Pidilizumab and other humanized anti-PD-1 monoclonal antibodies are described in WO2009/101611. Pembrolizumab (formerly known as lambrolizumab, and also referred to as Keytruda, MK03475; Merck) is a humanized IgG4 monoclonal antibody that binds to PD-1. Pembrolizumab and other humanized anti-PD-1 antibodies are described in U.S. Pat. No. 8,354,509 and WO2009/114335. Other anti-PD-1 antibodies include AMP 514 (Amplimmune), among others, e.g., anti-PD-1 antibodies described in U.S. Pat. No. 8,609,089, US 2010028330, US 20120114649 and/or US 20150210769. AMP-224 (B7-DCIg; Amplimmune; e.g., described in WO2010/027827 and WO2011/066342), is a PD-L2 Fc fusion soluble receptor that blocks the interaction between PD-1 and B7-H1.

PD-L1 (also known as CD274 and B7-H1) and PD-L2 (also known as CD273 and B7-DC) are ligands for PD-1, found on activated T cells, B cells, myeloid cells, macrophages, and some types of tumor cells. Anti-tumor therapies have focused on anti-PD-L1 antibodies. The complex of PD-1 and PD-L1 inhibits proliferation of CD8+ T cells and reduces the immune response (Topalian et al., 2012, N Engl J Med 366:2443-54; Brahmer et al., 2012, N Eng J Med 366:2455-65). Anti-PD-L1 antibodies have been used for treatment of non-small cell lung cancer, melanoma, colorectal cancer, renal-cell cancer, pancreatic cancer, gastric cancer, ovarian cancer, breast cancer, and hematologic malignancies (Brahmer et al., 2012, N Eng J Med 366:2455-65; Ott et al., 2013, Clin Cancer Res 19:5300-9; Radvanyi et al., 2013, Clin Cancer Res 19:5541; Menzies & Long, 2013, Ther Adv Med Oncol 5:278-85; Berger et al., 2008, Clin Cancer Res 14:13044-51). Exemplary anti-PD-L1 antibodies include MDX-1105 (Medarex), MED14736 (Medimmune) MPDL3280A (Genentech), BMS-935559 (Bristol-Myers Squibb) and MSB0010718C. MEDI4736 (Medimmune) is a human monoclonal antibody that binds to PD-L1, and inhibits interaction of the ligand with PD-1. MDPL3280A (Genentech/Roche) is a human Fc optimized IgG1 monoclonal antibody that binds to PD-L1. MDPL3280A and other human monoclonal antibodies to PD-L1 are described in U.S. Pat. No. 7,943,743 and U.S Publication No. 20120039906. Other anti-PD-L1 binding agents include YW243.55.570 (see WO2010/077634) and MDX-1105 (also referred to as BMS-936559, and, e.g., anti-PD-L1 binding agents described in WO2007/005874).

Cytotoxic T-lymphocyte-associated antigen (CTLA-4), also known as CD152, is a co-inhibitory molecule that functions to regulate T-cell activation. CTLA-4 is a member of the immunoglobulin superfamily that is expressed exclusively on T-cells. CTLA-4 acts to inhibit T-cell activation and is reported to inhibit helper T-cell activity and enhance regulatory T-cell immunosuppressive activity. Although the precise mechanism of action of CTLA-4 remains under investigation, it has been suggested that it inhibits T cell activation by outcompeting CD28 in binding to CD80 and CD86, as well as actively delivering inhibitor signals to the T cell (Pardoll (2012) Nature Reviews Cancer 12:252-264). Anti-CTLA-4 antibodies have been used in clinical trials for the treatment of melanoma, prostate cancer, small cell lung cancer, non-small cell lung cancer (Robert & Ghiringhelli, 2009, Oncologist 14:848-61; Ott et al., 2013, Clin Cancer Res 19:5300; Weber, 2007, Oncologist 12:864-72; Wada et al., 2013, J Transl Med 11:89). A significant feature of anti-CTLA-4 is the kinetics of anti-tumor effect, with a lag period of up to 6 months after initial treatment required for physiologic response. In some cases, tumors may actually increase in size after treatment initiation, before a reduction is seen (Pardoll (2012) Nature Reviews Cancer 12:252-264). Exemplary anti-CTLA-4 antibodies include ipilimumab (Bristol-Myers Squibb) and tremelimumab (Pfizer). Ipilimumab has recently received FDA approval for treatment of metastatic melanoma (Wada et al., 2013, J Transl Med 11:89).

Lymphocyte activation gene-3 (LAG-3), also known as CD223, is another immune checkpoint protein. LAG-3 has been associated with the inhibition of lymphocyte activity and in some cases the induction of lymphocyte anergy. LAG-3 is expressed on various cells in the immune system including B cells, NK cells, and dendritic cells. LAG-3 is a natural ligand for the MHC class II receptor, which is substantially expressed on melanoma-infiltrating T cells including those endowed with potent immune-suppressive activity. Exemplary anti-LAG-3 antibodies include BMS-986016 (Bristol-Myers Squib), which is a monoclonal antibody that targets LAG-3. IMP701 (Immutep) is an antagonist LAG-3 antibody and IMP731 (Immutep and GlaxoSmithKline) is a depleting LAG-3 antibody. Other LAG-3 inhibitors include IMP321 (Immutep), which is a recombinant fusion protein of a soluble portion of LAG-3 and Ig that binds to MHC class II molecules and activates antigen presenting cells (APC). Other antibodies are described, e.g., in WO2010/019570 and US 2015/0259420

T-cell immunoglobulin domain and mucin domain-3 (TIM-3), initially identified on activated Th1 cells, has been shown to be a negative regulator of the immune response. Blockade of TIM-3 promotes T-cell mediated anti-tumor immunity and has anti-tumor activity in a range of mouse tumor models. Combinations of TIM-3 blockade with other immunotherapeutic agents such as TSR-042, anti-CD137 antibodies and others, can be additive or synergistic in increasing anti-tumor effects. TIM-3 expression has been associated with a number of different tumor types including melanoma, NSCLC and renal cancer, and additionally, expression of intratumoral TIM-3 has been shown to correlate with poor prognosis across a range of tumor types including NSCLC, cervical, and gastric cancers. Blockade of TIM-3 is also of interest in promoting increased immunity to a number of chronic viral diseases. TIM-3 has also been shown to interact with a number of ligands including galectin-9, phosphatidylserine and HMGB1, although which of these, if any, are relevant in regulation of anti-tumor responses is not clear at present. In some embodiments, antibodies, antibody fragments, small molecules, or peptide inhibitors that target TIM-3 can bind to the IgV domain of TIM-3 to inhibit interaction with its ligands. Exemplary antibodies and peptides that inhibit TIM-3 are described in US 2015/0218274, WO2013/006490 and US 2010/0247521. Other anti-TIM-3 antibodies include humanized versions of RMT3-23 (Ngiow et al., 2011, Cancer Res, 71:3540-3551), and clone 8B.2C12 (Monney et al., 2002, Nature, 415:536-541). Bi-specific antibodies that inhibit TIM-3 and PD-1 are described in US 2013/0156774.

In some embodiments, the additional agent is a CEACAM inhibitor (e.g., CEACAM-1, CEACAM-3, and/or CEACAM-5 inhibitor). In some embodiments, the inhibitor of CEACAM is an anti-CEACAM antibody molecule. Exemplary anti-CEACAM-1 antibodies are described in WO 2010/125571, WO 2013/082366 WO 2014/059251 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In some embodiments, the anti-CEACAM antibody binds to CEACAM-5 as described in, e.g., Zheng et al. PLoS One. (2011) 6(6): e21146), or cross-reacts with CEACAM-1 and CEACAM-5 as described in, e.g., WO 2013/054331 and US 2014/0271618.

4-1BB, also known as CD137, is transmembrane glycoprotein belonging to the TNFR superfamily. 4-1BB receptors are present on activated T cells and B cells and monocytes. An exemplary anti-4-1BB antibody is urelumab (BMS-663513), which has potential immunostimulatory and antineoplastic activities.

Tumor necrosis factor receptor superfamily, member 4 (TNFRSF4), also known as OX40 and CD134, is another member of the TNFR superfamily. OX40 is not constitutively expressed on resting naïve T cells and acts as a secondary co-stimulatory immune checkpoint molecule. Exemplary anti-OX40 antibodies are MEDI6469 and MOXR0916 (RG7888, Genentech).

In some embodiments, the additional agent includes a molecule that decreases the regulatory T cell (Treg) population. Methods that decrease the number of (e.g., deplete) Treg cells are known and include, e.g., CD25 depletion, cyclophosphamide administration, and modulating Glucocorticoid-induced TNFR family related gene (GITR) function. GITR is a member of the TNFR superfamily that is upregulated on activated T cells, which enhances the immune system. Reducing the number of Treg cells in a subject prior to apheresis or prior to administration of engineered cells, e.g., CAR-expressing cells, can reduce the number of unwanted immune cells (e.g., Tregs) in the tumor microenvironment and reduces the subject's risk of relapse. In some embodiments, the additional agent includes a molecule targeting GITR and/or modulating GITR functions, such as a GITR agonist and/or a GITR antibody that depletes regulatory T cells (Tregs). In some embodiments, the additional agent includes cyclophosphamide. In some embodiments, the GITR binding molecule and/or molecule modulating GITR function (e.g., GITR agonist and/or Treg depleting GITR antibodies) is administered prior to the engineered cells, e.g., CAR-expressing cells. For example, in some embodiments, the GITR agonist can be administered prior to apheresis of the cells. In some embodiments, cyclophosphamide is administered to the subject prior to administration (e.g., infusion or re-infusion) of the engineered cells, e.g., CAR-expressing cells or prior to apheresis of the cells. In some embodiments, cyclophosphamide and an anti-GITR antibody are administered to the subject prior to administration (e.g., infusion or re-infusion) of the engineered cells, e.g., CAR-expressing cells or prior to apheresis of the cells.

In some embodiments, the additional agent is a GITR agonist. Exemplary GITR agonists include, e.g., GITR fusion proteins and anti-GITR antibodies (e.g., bivalent anti-GITR antibodies) such as, e.g., a GITR fusion protein described in U.S. Pat. No. 6,111,090, European Patent No. 090505B 1, U.S. Pat. No. 8,586,023, PCT Publication Nos.: WO 2010/003118 and 2011/090754, or an anti-GITR antibody described, e.g., in U.S. Pat. No. 7,025,962, European Patent No. 1947183B 1, U.S. Pat. Nos. 7,812,135, 8,388, 967, 8,591,886, European Patent No. EP 1866339, PCT Publication No. WO 2011/028683, PCT Publication No. WO 2013/039954, PCT Publication No. WO2005/007190, PCT Publication No. WO 2007/133822, PCT Publication No. WO2005/055808, PCT Publication No. WO 99/40196, PCT Publication No. WO 2001/03720, PCT Publication No. WO99/20758, PCT Publication No. WO2006/083289, PCT Publication No. WO 2005/115451, U.S. Pat. No. 7,618,632, and PCT Publication No. WO 2011/051726. An exemplary anti-GITR antibody is TRX518.

In some embodiments, the additional agent enhances tumor infiltration or transmigration of the administered cells, e.g., CAR-expressing cells. For example, in some embodiments, the additional agent stimulates CD40, such as CD40L, e.g., recombinant human CD40L. Cluster of differentiation 40 (CD40) is also a member of the TNFR superfamily. CD40 is a costimulatory protein found on antigen-presenting cells and mediates a broad variety of immune and inflammatory responses. CD40 is also expressed on some malignancies, where it promotes proliferation. Exemplary anti-CD40 antibodies are dacetuzumab (SGN-40), lucatumumab (Novartis, antagonist), SEA-CD40 (Seattle Genetics), and CP-870,893. In some embodiments, the additional agent that enhances tumor infiltration includes tyrosine kinase inhibitor sunitnib, heparanase, and/or chemokine receptors such as CCR2, CCR4, and CCR7.

In some embodiments, the additional agent is a structural or functional analog or derivative of thalidomide and/or an inhibitor of E3 ubiquitin ligase. In some embodiments, the immunomodulatory agent binds to cereblon (CRBN). In some embodiments, the immunomodulatory agent binds to the CRBN E3 ubiquitin-ligase complex. In some embodiments, the immunomodulatory agent binds to CRBN and the CRBN E3 ubiquitin-ligase complex. In some embodiments, the immunomodulatory agent up-regulates the protein or gene expression of CRBN. In some aspects, CRBN is the substrate adaptor for the $CRL4^{CRBN}$ E3 ubiquitin ligase, and modulates the specificity of the enzyme. In some embodiments, binding to CRB or the CRBN E3 ubiquitin ligase complex inhibits E3 ubiquitin ligase activity. In some embodiments, the immunomodulatory agent induces the ubiquitination of KZF1 (Ikaros) and IKZF3 (Aiolos) and/or induces degradation of IKZF1 (Ikaros) and IKZF3 (Aiolos). In some embodiments, the immunomodulatory agent induces the ubiquitination of casein kinase 1A1 (CK1α) by the $CRL4^{CRBN}$ E3 ubiquitin ligase. In some embodiments, the ubiquitination of CK1α results in CK1α degradation.

In some embodiments, the additional agent is an inhibitor of the Ikaros (IKZF1) transcription factor. In some embodiments, the additional agent enhances ubiquitination of Ikaros. In some embodiments, the additional agent enhances the degradation of Ikaros. In some embodiments, the additional agent down-regulates the protein or gene expression of Ikaros. In some embodiments, administration of the additional agent causes a decrease in Ikaros protein levels.

In some embodiments, the additional agent is an inhibitor of the Aiolos (IKZF3) transcription factor. In some embodiments, the additional agent enhances ubiquitination of Aiolos. In some embodiments, the additional agent enhances the degradation of Aiolos. In some embodiments, the additional agent down-regulates the protein or gene expression of Aiolos. In some embodiments, administration of the additional agent causes a decrease in Aiolos protein levels.

In some embodiments, the additional agent is an inhibitor of both the Ikaros (IKZF1) and Aiolos (IKZF3) transcription factors. In some embodiments, the additional agent enhances ubiquitination of both Ikaros and Aiolos. In some embodiments, the additional agent enhances the degradation of both Ikaros and Aiolos. In some embodiments, the additional agent enhances ubiquitination and degradation of both Ikaros and Aiolos. In some embodiments, administration of the additional agent causes both Aiolos protein levels and Ikaros protein levels to decrease.

In some embodiments, the additional agent is a selective cytokine inhibitory drug (SelCID). In some embodiments, the additional agent inhibits the activity of phosphodiesterase-4 (PDE4). In some embodiments, the additional agent suppresses the enzymatic activity of the CDC25 phosphatases. In some embodiments, the additional agent alters the intracellular trafficking of CDC25 phosphatases.

In some embodiments, the additional agent is thalidomide (2-(2,6-dioxopiperidin-3-yl)-1H-isoindole-1,3(2H)-dione) or an analog or derivative of thalidomide. In certain embodiments, a thalidomide derivative includes structural variants of thalidomide that have a similar biological activity. Exemplary thalidomide derivatives include, but are not limited to lenalidomide (REVLIMMUNOMODULATORY COMPOUND™; Celgene Corporation), pomalidomide (also known as ACTIMMUNOMODULATORY COMPOUND™ or POMALYST™ (Celgene Corporation)), CC-1088, CDC-501, and CDC-801, and the compounds disclosed in U.S. Pat. Nos. 5,712,291; 7,320,991; and 8,716,315; U.S. Appl. No. 2016/0313300; and PCT Pub. Nos. WO 2002/068414 and WO 2008/154252.

In some embodiments, the additional agent is 1-oxo- and 1,3 dioxo-2-(2,6-dioxopiperldin-3-yl) isoindolines substituted with amino in the benzo ring as described in U.S. Pat. No. 5,635,517 which is incorporated herein by reference.

In some embodiments, the additional agent is a compound of the following formula:

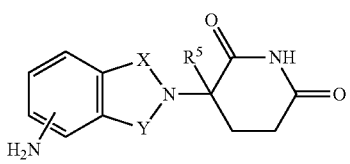

wherein one of X and Y is —C(O)— and the other of X and Y is —C(O)— or —CH₂—, and R⁵ is hydrogen or lower alkyl, or a pharmaceutically acceptable salt thereof. In some embodiments, X is —C(O)— and Y is —CH₂—. In some embodiments, both X and Y are —C(O)—. In some embodiments, R⁵ is hydrogen. In other embodiments, R⁵ is methyl.

In some embodiments, the additional agent is a compound that belongs to a class of substituted 2-(2, 6-dioxopiperidin-3-yl)phthalate immunomodulatory compounds and substituted 2-(2,6-dioxopiperldin-3-yl)-1-oxoisoindoles, such as those described in U.S. Pat. Nos. 6,281,230; 6,316,471; 6,335,349; and 6,476,052, and International Patent Application No. PCT/US97/13375 (International Publication No. WO 98/03502), each of which is incorporated herein by reference.

In some embodiments, the additional agent is a compound of the following formula:

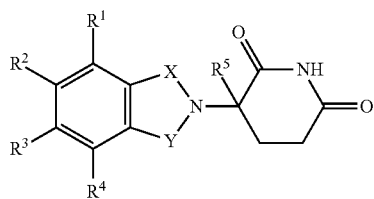

wherein one of X and Y is —C(O)— and the other of X and Y is —C(O)— or —CH2—; (1) each of R¹, R², R³, and R⁴ are independently halo, alkyl of 1 to 4 carbon atoms, or alkoxy or 1 to 4 carbon atoms, or (2) one of R¹, R³, R4, and R⁵ is —NHRᵃ and the remaining of R¹, R², R³, and R⁴ is are hydrogen, wherein Rᵃ is hydrogen or alkyl of 1 to 8 carbon atoms; R⁵ is hydrogen or alkyl of 1 to 8 carbon atoms, benzyl, or halo; provided that R⁵ is other than hydrogen if X and Y are —C(O)— and (i) each of R¹, R², R³, and R⁴ is fluoro; or (ii) one of R¹, R², R³, and R⁴ is amino; or a pharmaceutically acceptable salt thereof.

In some embodiments, the additional agent is a compound that belongs to a class of isoindole-immunomodulatory compounds disclosed in U.S. Pat. No. 7,091,353, U.S. Patent Publication No. 2003/0045552, and International Application No. PCT/USOI/50401 (International Publication No. WO02/059106), each of which are incorporated herein by reference. For example, in some embodiments, the additional agent is [2-(2,6-dioxo-piperidin-3-yl)-1,3-dioxo-2,3-dihydro-1H-isoindol-4-ylmethyl]-amide; (2-(2,6-dioxo-piperidin-3-yl)-1,3-dioxo-2,3-dihydro-1H-isoindol-4-ylmethyl)-carbamic acid tert-butyl ester; 4-(aminomethyl)-2-(2,6-dioxo(3-piperidyl))-isoindoline-1,3-dione; N-(2-(2,6-dioxo-piperidin-3-yl)-1,3-dioxo-2,3-dihydro-1H-isoindol-4-yl-methyl)-acetamide; N-{(2-(2,6-dioxo(3-piperidyl)-1,3-dioxoisoindolin-4-yl)methyl}cyclopropyl-carboxamide; 2-chloro-N-{(2-(2,6-dioxo(3-piperidyl))-1,3-dioxoisoindolin-4-yl)methyl}acetamide; N-(2-(2,6-dioxo(3-piperidyl))-1,3-dioxoisoindolin-4-yl)-3-pyridylcarboxamide; 3-{1-oxo-4-(benzylamino)isoindolin-2-yl}piperidine-2,6-dione; 2-(2,6-dioxo(3-piperidyl))-4-(benzylamino)isoindoline-1,3-dione; N-{(2-(2,6-dioxo(3-piperidyl))-1,3-dioxoisoindolin-4-yl)methyl}propanamide; N-{(2-(2,6-dioxo(3-piperidyl))-1,3-dioxoisoindolin-4-yl)methyl}-3-pyridylcarboxamide; N-{(2-(2,6-dioxo(3-piperidyl))-1,3-dioxoisoindolin-4-yl)methyl}heptanamide; N-{(2-(2,6-dioxo(3-piperidyl))-1,3-dioxoisoindolin-4-yl)methyl}-2-furylcarboxamide; {N-(2-(2,6-dioxo(3-piperidyl))-1,3-dioxoisoindolin-4-yl)carbamoyl}methyl acetate; N-(2-(2,6-dioxo(3-piperidyl))-1,3-dioxoisoindolin-4-yl)pentanamide; N-(2-(2,6-dioxo(3-piperidyl))-1,3-dioxoisoindolin-4-yl)-2-thienylcarboxamide; N-{[2-(2,6-dioxo(3-piperidyl))-1,3-dioxoisoindolin-4-yl]methyl}(butylamino)carboxamide; N-{[2-(2,6-dioxo(3-piperidyl))-1,3-dioxoisoindolin-4-yl]methyl}(octylamino)carboxamide; or N-{[2-(2,6-dioxo(3-piperidyl))-1,3-dioxoisoindolin-4-yl]methyl}(benzylamino)carboxamide.

In some embodiments, the additional agent is a compound that belongs to a class of isoindole-immunomodulatory compounds disclosed in U.S. Patent Application Publication Nos. 2002/0045643, International Publication No. WO 98/54170, and U.S. Pat. No. 6,395,754, each of which is incorporated herein by reference. In some embodiments, the additional agent is a tetra substituted 2-(2,6-dioxopiperdin-3-yl)-1-oxoisoindolines described in U.S. Pat. No. 5,798,368, which is incorporated herein by reference. In some embodiments, the additional agent is 1-oxo and 1,3-dioxo-2-(2,6-dioxopiperidin-3-yl) isoindolines disclosed in U.S. Pat. No. 6,403,613, which is incorporated herein by reference. In some embodiments the additional agent is a 1-oxo or 1,3-dioxoisoindoline substituted in the 4- or 5-position of the indoline ring as described in U.S. Pat. Nos. 6,380,239 and 7,244,759, both of which are incorporated herein by reference.

In some embodiments, the additional agent is 2-(4-amino-1-oxo-1,3-dihydro-isoindol-2-yl)-4-carbamoyl-butyric acid or 4-(4-amino-1-oxo-1,3-dihydro-isoindol-2-yl)-4-carbamoyl-butyric acid. In some embodiments, the immunomodulatory compound is 4-carbamoyl-4-{4-[(furan-2-yl-methyl)-amino]-1,3-dioxo-1,3-dihydro-isoindol-2-yl}-butyric acid, 4-carbamoyl-2-{4-[(furan-2-yl-methyl)-amino]-1,3-dioxo-1,3-dihydro-isoindol-2-yl}-butyric acid, 2-{4-[(furan-2-yl-methyl)-amino]-1,3-dioxo-1,3-dihydro-isoindol-2-yl}-4-phenylcarbamoyl-butyric acid, or 2-{4-[(furan-2-yl-methyl)-amino]-1,3-dioxo-1,3-dihydro-isoindol-2-yl}-pentanedioic acid.

In some embodiments, the additional agent is a isoindoline-1-one or isoindoline-1,3-dione substituted in the 2-position with 2,6-dioxo-3-hydroxypiperidin-5-yl as described in U.S. Pat. No. 6,458,810, which is incorporated herein by reference. In some embodiments, the immunomodulatory compound is 3-(5-amino-2-methyl-4-oxo-4H-quinazolin-3-yl)-piperidine-2,6-dione, or an enantiomer or a mixture of enantiomers thereof; or a pharmaceutically acceptable salt, solvate, hydrate, co-crystal, clathrate, or polymorph thereof. In some embodiments, the immunomodulatory compound is 3-[4-(4-morpholin-4-ylmethyl-benzyloxy)-1-oxo-1,3-dihydro-isoindol-2-yl]-piperidine-2,6-dione.

In some embodiments, the additional agent is as described in Oshima, K. et al., *Nihon Rinsho.,* 72(6):1130-5 (2014); Millrine, D. et al., *Trends Mol Med.,* 23(4):348-364 (2017); and Collins, et al., *Biochem J,* 474(7):1127-1147 (2017).

In some embodiments, the additional agent is lenalidomide, pomalidomide, avadomide, a stereoisomer of lenalidomide, pomalidomide, avadomide or a pharmaceutically acceptable salt, solvate, hydrate, co-crystal, clathrate, or polymorph thereof. In some embodiments, the immunomodulatory compound is lenalidomide, a stereoisomer of lenalidomide or a pharmaceutically acceptable salt, solvate, hydrate, co-crystal, clathrate, or polymorph thereof. In some embodiments, the immunomodulatory compound is lenalidomide, or ((RS)-3-(4-Amino-1-oxo-1,3-dihydro-2H-isoindol-2-yl)piperidine-2,6-dione).

In certain embodiments, the lesion is disrupted by administering the thalidomide derivative lenalidomide, ((RS)-3-(4-Amino-1-oxo-1,3-dihydro-2H-isoindol-2-yl)piperidine-2,6-dione) to the subject. Lenalidomide is FDA approved for the treatment of multiple myeloma, myelodysplastic syndrome associated with deletion 5q, and most recently in relapsed/refractory mantle-cell lymphoma (MCL). Lenalidomide generally is a synthetic derivative of thalidomide, and is currently understood to have multiple immunomodulatory effects, including enforcement of immune synapse formation between T cell and antigen presenting cells (APCs). For example, in some cases, lenalidomide modulates T cell responses and results in increased interleukin (IL)-2 production in CD4+ and CD8+ T cells, induces the shift of T helper (Th) responses from Th2 to Th1, inhibits expansion of regulatory subset of T cells (Tregs), and improves functioning of immunological synapses in follicular lymphoma and chronic lymphocytic leukemia (CLL) (Otahal et al., Oncoimmunology (2016) 5(4):e1115940). Lenalidomide also has direct tumoricidal activity in patients with multiple myeloma (MM) and directly and indirectly modulates survival of CLL tumor cells by affecting supportive cells, such as nurse-like cells found in the microenvironment of lymphoid tissues. Lenalidomide also can enhance T-cell proliferation and interferon-γ production in response to activation of T cells via CD3 ligation or dendritic cell-mediated activation. In addition, lenalidomide is thought to decrease proliferation of pro-inflammatory cytokines including TNF-a, IL-1, IL-6, and IL-12 and enhance antibody-dependent cellular cytotoxicity (ADCC) via increased NK cell activation. Lenalidomide can also induce malignant B cells to express higher levels of immunostimulatory molecules such as CD80, CD86, HLA-DR, CD95, and CD40 (Fecteau et al., Blood (2014) 124(10):1637-1644). Cereblon, an E3 ubiquitin ligase, was identified as the primary target for thalidomide-induced teratogenesis (Ito et al., T., (2010) Science 327: 1345-1350). Lenalidomide also targets cereblon and it has been shown that this leads to the reduction of c-Myc and IRF4 expression while also increasing expression of p21 that leads to G1 cell-cycle arrest (Lopez-Girona et al., (2012) Leukemia 26: 2326-2335).

In some embodiments, the additional agent includes thalidomide drugs or analogs thereof and/or derivatives thereof, such as lenalidomide, pomalidomide or apremilast. See, e.g., Bertilaccio et al., Blood (2013) 122:4171, Otahal et al., Oncoimmunology (2016) 5(4):e1115940; Fecteau et al., Blood (2014) 124(10):1637-1644 and Kuramitsu et al., Cancer Gene Therapy (2015) 22:487-495). Lenalidomide ((RS)-3-(4-Amino-1-oxo-1,3-dihydro-2H-isoindol-2-yl)piperidine-2,6-dione; also known as Revlimid) is a synthetic derivative of thalidomide, and has multiple immunomodulatory effects, including enforcement of immune synapse formation between T cell and antigen presenting cells (APCs). For example, in some cases, lenalidomide modulates T cell responses and results in increased interleukin (IL)-2 production in CD4+ and CD8+ T cells, induces the shift of T helper (Th) responses from Th2 to Th1, inhibits expansion of regulatory subset of T cells (Tregs), and improves functioning of immunological synapses in follicular lymphoma and chronic lymphocytic leukemia (CLL) (Otahal et al., Oncoimmunology (2016) 5(4):e1115940). Lenalidomide also has direct tumoricidal activity in patients with multiple myeloma (MM) and directly and indirectly modulates survival of CLL tumor cells by affecting supportive cells, such as nurse-like cells found in the microenvironment of lymphoid tissues. Lenalidomide also can enhance T-cell proliferation and interferon-γ production in response to activation of T cells via CD3 ligation or dendritic cell-mediated activation. Lenalidomide can also induce malignant B cells to express higher levels of immunostimulatory molecules such as CD80, CD86, HLA-DR, CD95, and CD40 (Fecteau et al., Blood (2014) 124(10): 1637-1644).

In some embodiments, the additional agent is a B-cell inhibitor. In some embodiments, the additional agent is one or more B-cell inhibitors selected from among inhibitors of CD10, CD19, CD20, CD22, CD34, CD123, CD79a, CD79b, CD179b, FLT-3, or ROR1, or a combination thereof. In some embodiments, the B-cell inhibitor is an antibody (e.g., a mono- or bispecific antibody) or an antigen binding fragment thereof. In some embodiments, the additional agent is an engineered cell expressing recombinant receptors that target B-cell targets, e.g., CD10, CD19, CD20, CD22, CD34, CD123, CD79a, CD79b, CD179b, FLT-3, or ROR1.

In some embodiments, the additional agent is a CD20 inhibitor, e.g., an anti-CD20 antibody (e.g., an anti-CD20 mono- or bi-specific antibody) or a fragment thereof. Exemplary anti-CD20 antibodies include but are not limited to rituximab, ofatumumab, ocrelizumab (also known as GA101 or R05072759), veltuzumab, obinutuzumab, TRU-015 (Trubion Pharmaceuticals), ocaratuzumab (also known as AME-133v or ocaratuzumab), and Pro131921 (Genentech). See, e.g., Lim et al. Haematologica. (2010) 95(1):135-43. In some embodiments, the anti-CD20 antibody comprises rituximab. Rituximab is a chimeric mouse/human monoclonal antibody IgG1 kappa that binds to CD20 and causes cytolysis of a CD20 expressing cell. In some embodiments, the additional agent includes rituximab. In some embodiments, the CD20 inhibitor is a small molecule.

In some embodiments, the additional agent is a CD22 inhibitor, e.g., an anti-CD22 antibody (e.g., an anti-CD22 mono- or bi-specific antibody) or a fragment thereof. Exemplary anti-CD22 antibodies include epratuzumab and RFB4. In some embodiments, the CD22 inhibitor is a small molecule. In some embodiments, the antibody is a monospecific antibody, optionally conjugated to a second agent such as a chemotherapeutic agent. For instance, in some embodiments, the antibody is an anti-CD22 monoclonal antibody-MMAE conjugate (e.g., DCDT2980S). In some embodiments, the antibody is an scFv of an anti-CD22 antibody, e.g., an scFv of antibody RFB4. In some embodiments, the scFv is fused to all of or a fragment of *Pseudomonas* exotoxin-A (e.g., BL22). In some embodiments, the scFv is fused to all of or a fragment of (e.g., a 38 kDa fragment of) *Pseudomonas* exotoxin-A (e.g., moxetumomab pasudotox). In some embodiments, the anti-CD22 antibody is an anti-CD19/CD22 bispecific antibody, optionally conjugated to a toxin. For instance, in some embodiments, the anti-CD22 antibody comprises an anti-CD19/CD22 bispecific portion, (e.g., two scFv ligands, recognizing human CD19 and CD22) optionally linked to all of or a portion of diphtheria toxin (DT), e.g., first 389 amino acids of diphtheria toxin (DT), DT 390, e.g., a ligand-directed toxin such as DT2219ARL). In some embodiments, the bispecific portion (e.g., anti-CD 19/anti-CD22) is linked to a toxin such as deglycosylated ricin A chain (e.g., Combotox).

In some embodiments, the immunomodulatory agent is a cytokine. In some embodiments, the immunomodulatory agent is a cytokine or is an agent that induces increased expression of a cytokine in the tumor microenvironment. Cytokines have important functions related to T cell expansion, differentiation, survival, and homeostasis. Cytokines that can be administered to the subject receiving the binding molecules (e.g., CCT5-binding molecules), recombinant receptors, cells and/or compositions provided herein include one or more of IL-2, IL-4, IL-7, IL-9, IL-15, IL-18, and IL-21. In some embodiments, the cytokine administered is IL-7, IL-15, or IL-21, or a combination thereof. In some embodiments, administration of the cytokine to the subject that has sub-optimal response to the administration of the engineered cells, e.g., CAR-expressing cells improves efficacy and/or anti-tumor activity of the administered cells, e.g., CAR-expressing cells.

By "cytokine" is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and —II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines. For example, the immunomodulatory agent is a cytokine and the cytokine is IL-4, TNF-α, GM-CSF or IL-2.

In some embodiments, the additional agent includes an interleukin-15 (IL-15) polypeptide, an interleukin-15 receptor alpha (IL-15Ru) polypeptide, or combination thereof, e.g., hetIL-15 (Admune Therapeutics, LLC). hetIL-15 is a heterodimeric non-covalent complex of IL-15 and IL-15Rα. hetIL-15 is described in, e.g., U.S. Pat. No. 8,124,084, U.S. 2012/0177598, U.S. 2009/0082299, U.S. 2012/0141413, and U.S. 2011/0081311. In some embodiments, the immunomodulatory agent can contain one or more cytokines. For example, the interleukin can include leukocyte interleukin injection (Multikine), which is a combination of natural cytokines. In some embodiments, the immunomodulatory agent is a Toll-like receptor (TLR) agonist, an adjuvant or a cytokine.

In some embodiments, the additional agent is an agent that ameliorates or neutralizes one or more toxicities or side effects associated with the cell therapy. In some embodiments, the additional agent is selected from among a steroid (e.g., corticosteroid), an inhibitor of TNFα, and an inhibitor of IL-6. An example of a TNFα inhibitor is an anti-TNFα antibody molecule such as, infliximab, adalimumab, certolizumab pegol, and golimumab. Another example of a TNFα inhibitor is a fusion protein such as entanercept. Small molecule inhibitors of TNFα include, but are not limited to, xanthine derivatives (e.g. pentoxifylline) and bupropion. An example of an IL-6 inhibitor is an anti-IL-6 antibody molecule such as tocilizumab, sarilumab, elsilimomab, CNTO 328, ALD518/BMS-945429, CNTO 136, CPSI-2364, CDP6038, VX30, ARGX-109, FE301, and FM101. In some embodiments, the anti-IL-6 antibody molecule is tocilizumab. In some embodiments, the additional agent is an IL-1R inhibitor, such as anakinra.

In some embodiments, the additional agent is a modulator of adenosine levels and/or an adenosine pathway component. Adenosine can function as an immunomodulatory agent in the body. For example, adenosine and some adenosine analogs that non-selectively activate adenosine receptor subtypes decrease neutrophil production of inflammatory oxidative products (Cronstein et al., Ann. N.Y. Acad. Sci. 451:291, 1985; Roberts et al., Biochem. J., 227:669, 1985; Schrier et al., J. Immunol. 137:3284, 1986; Cronstein et al., Clinical Immunol. Immunopath. 42:76, 1987). In some cases, concentration of extracellular adenosine or adenosine analogs can increase in specific environments, e.g., tumor microenvironment (TME). In some cases, adenosine or adenosine analog signaling depends on hypoxia or factors involved in hypoxia or its regulation, e.g., hypoxia inducible factor (HIF). In some embodiments, increase in adenosine signaling can increase in intracellular cAMP and cAMP-dependent protein kinase that results in inhibition of proin-flammatory cytokine production, and can lead to the synthesis of immunosuppressive molecules and development of Tregs (Sitkovsky et al., Cancer Immunol Res (2014) 2(7): 598-605). In some embodiments, the additional agent can reduce or reverse immunosuppressive effects of adenosine, adenosine analogs and/or adenosine signaling. In some embodiments, the additional agent can reduce or reverse hypoxia-driven A2-adenosinergic T cell immunosuppression. In some embodiments, the additional agent is selected from among antagonists of adenosine receptors, extracellular adenosine-degrading agents, inhibitors of adenosine generation by CD39/CD73 ectoenzymes, and inhibitors of hypoxia-HIF-1α signaling. In some embodiments, the additional agent is an adenosine receptor antagonist or agonist.

Inhibition or reduction of extracellular adenosine or the adenosine receptor by virtue of an inhibitor of extracellular adenosine (such as an agent that prevents the formation of, degrades, renders inactive, and/or decreases extracellular adenosine), and/or an adenosine receptor inhibitor (such as an adenosine receptor antagonist) can enhance immune response, such as a macrophage, neutrophil, granulocyte, dendritic cell, T- and/or B cell-mediated response. In addition, inhibitors of the Gs protein mediated cAMP dependent intracellular pathway and inhibitors of the adenosine receptor-triggered Gi protein mediated intracellular pathways, can also increase acute and chronic inflammation.

In some embodiments, the additional agent is an adenosine receptor antagonist or agonist, e.g., an antagonist or agonist of one or more of the adenosine receptors A2a, A2b, A1, and A3. A1 and A3 inhibit, and A2a and A2b stimulate, respectively, adenylate cyclase activity. Certain adenosine receptors, such as A2a, A2b, and A3, can suppress or reduce the immune response during inflammation. Thus, antagonizing immunosuppressive adenosine receptors can augment, boost or enhance immune response, e.g., immune response from administered cells, e.g., CAR-expressing T cells. In some embodiments, the additional agent inhibits the production of extracellular adenosine and adenosine-triggered signaling through adenosine receptors. For example, enhancement of an immune response, local tissue inflammation, and targeted tissue destruction can be enhanced by inhibiting or reducing the adenosine-producing local tissue hypoxia; by degrading (or rendering inactive) accumulated extracellular adenosine; by preventing or decreasing expression of adenosine receptors on immune cells; and/or by inhibiting/antagonizing signaling by adenosine ligands through adenosine receptors.

An antagonist is any substance that tends to nullify the action of another, as an agent that binds to a cell receptor without eliciting a biological response. In some embodiments, the antagonist is a chemical compound that is an antagonist for an adenosine receptor, such as the A2a, A2b, or A3 receptor. In some embodiments, the antagonist is a peptide, or a peptidomimetic, that binds the adenosine receptor but does not trigger a Gi protein dependent intracellular pathway. Exemplary antagonists are described in U.S. Pat. Nos. 5,565,566; 5,545, 627, 5,981,524; 5,861,405; 6,066,642; 6,326,390; 5,670,501; 6,117,998; 6,232,297; 5,786,360; 5,424,297; 6,313,131, 5,504,090; and 6,322,771.

In some embodiments, the additional agent is an A2 receptor (A2R) antagonist, such as an A2a antagonist. Exemplary A2R antagonists include KW6002 (istradefyline), SCH58261, caffeine, paraxanthine, 3,7-dimethyl-1-propargylxanthine (DMPX), 8-(m-chlorostyryl) caffeine (CSC), MSX-2, MSX-3, MSX-4, CGS-15943, ZM-241385, SCH-442416, preladenant, vipadenant (B11014), V2006, ST-1535, SYN-115, PSB-1115, ZM241365, FSPTP, and an inhibitory nucleic acid targeting A2R expression, e.g., siRNA or shRNA, or any antibodies or antigen-binding fragment thereof that targets an A2R. In some embodiments, the additional agent is an A2R antagonist described in, e.g., Ohta et al., Proc Natl Acad Sci USA (2006) 103:13132-13137; Jin et al., *Cancer Res*. (2010) 70(6):2245-2255; Leone et al., Computational and Structural Biotechnology Journal (2015) 13:265-272; Beavis et al., Proc Natl Acad Sci USA (2013) 110:14711-14716; and Pinna, A., Expert Opin Investig Drugs (2009) 18:1619-1631; Sitkovsky et al., Cancer Immunol Res (2014) 2(7):598-605; U.S. Pat. Nos. 8,080, 554; 8,716,301; US 20140056922; WO2008/147482; U.S. Pat. No. 8,883,500; US 20140377240; WO02/055083; U.S. Pat. Nos. 7,141,575; 7,405,219; 8,883,500; 8,450,329 and 8,987,279).

In some embodiments, the antagonist is an antisense molecule, inhibitory nucleic acid molecule (e.g., small inhibitory RNA (siRNA)) or catalytic nucleic acid molecule (e.g. a ribozyme) that specifically binds mRNA encoding an adenosine receptor. In some embodiments, the antisense molecule, inhibitory nucleic acid molecule or catalytic nucleic acid molecule binds nucleic acids encoding A2a, A2b, or A3. In some embodiments, an antisense molecule, inhibitory nucleic acid molecule or catalytic nucleic acid targets biochemical pathways downstream of the adenosine receptor. For example, the antisense molecule or catalytic nucleic acid can inhibit an enzyme involved in the Gs protein- or Gi protein-dependent intracellular pathway. In some embodiments, the additional agent includes dominant negative mutant form of an adenosine receptor, such as A2a, A2b, or A3.

In some embodiments, the additional agent that inhibits extracellular adenosine includes agents that render extracellular adenosine non-functional (or decrease such function), such as a substance that modifies the structure of adenosine to inhibit the ability of adenosine to signal through adenosine receptors. In some embodiments, the additional agent is an extracellular adenosine-generating or adenosine-degrading enzyme, a modified form thereof or a modulator thereof. For example, in some embodiments, the additional agent is an enzyme (e.g. adenosine deaminase) or another catalytic molecule that selectively binds and destroys the adenosine, thereby abolishing or significantly decreasing the ability of endogenously formed adenosine to signal through adenosine receptors and terminate inflammation.

In some embodiments, the additional agent is an adenosine deaminase (ADA) or a modified form thereof, e.g., recombinant ADA and/or polyethylene glycol-modified ADA (ADA-PEG), which can inhibit local tissue accumulation of extracellular adenosine. ADA-PEG has been used in treatment of patients with ADA SCID (Hershfield (1995) Hum Mutat. 5:107). In some embodiments, an agent that inhibits extracellular adenosine includes agents that prevent or decrease formation of extracellular adenosine, and/or prevent or decrease the accumulation of extracellular adenosine, thereby abolishing, or substantially decreasing, the immunosuppressive effects of adenosine. In some embodiments, the additional agent specifically inhibits enzymes and proteins that are involved in regulation of synthesis and/or secretion of pro-inflammatory molecules, including modulators of nuclear transcription factors. Suppression of adenosine receptor expression or expression of the Gs protein- or Gi protein-dependent intracellular pathway, or the cAMP dependent intracellular pathway, can result in an increase/enhancement of immune response.

In some embodiments, the additional agent can target ectoenzymes that generate or produce extracellular adenosine. In some embodiments, the additional agent targets CD39 and CD73 ectoenzymes, which function in tandem to generate extracellular adenosine. CD39 (also called ectonucleoside triphosphate diphosphohydrolase) converts extracellular ATP (or ADP) to 5'AMP. Subsequently, CD73 (also called 5'nucleotidase) converts 5'AMP to adenosine. The activity of CD39 is reversible by the actions of NDP kinase and adenylate kinase, whereas the activity of CD73 is irreversible. CD39 and CD73 are expressed on tumor stromal cells, including endothelial cells and Tregs, and also on many cancer cells. For example, the expression of CD39 and CD73 on endothelial cells is increased under the hypoxic conditions of the tumor microenvironment. Tumor hypoxia can result from inadequate blood supply and disorganized tumor vasculature, impairing delivery of oxygen (Carroll and Ashcroft (2005), Expert. Rev. Mol. Med. 7(6): 1-16). Hypoxia also inhibits adenylate kinase (AK), which converts adenosine to AMP, leading to very high extracellular adenosine concentration. Thus, adenosine is released at high concentrations in response to hypoxia, which is a condition that frequently occurs the tumor microenvironment (TME), in or around solid tumors. In some embodiments, the additional agent is one or more of anti-CD39 antibody or antigen binding fragment thereof, anti-CD73 antibody or antigen binding fragment thereof, e.g., MEDI9447 or TY/23, α-β-methylene-adenosine diphosphate (ADP), ARL 67156, POM-3, IPH52 (see, e.g., Allard et al. Clin Cancer Res (2013) 19(20):5626-5635; Hausler et al., Am J Transl Res (2014) 6(2):129-139; Zhang, B., *Cancer Res*. (2010) 70(16):6407-6411).

In some embodiments, the additional agent is an inhibitor of hypoxia inducible factor 1 alpha (HIF-1α) signaling. Exemplary inhibitors of HIF-1α include digoxin, acriflavine, sirtuin-7 and ganetespib.

In some embodiments, the additional agent includes a protein tyrosine phosphatase inhibitor, e.g., a protein tyrosine phosphatase inhibitor described herein. In some embodiments, the protein tyrosine phosphatase inhibitor is an SHP-1 inhibitor, e.g., an SHP-1 inhibitor described herein, such as, e.g., sodium stibogluconate. In some embodiments, the protein tyrosine phosphatase inhibitor is an SHP-2 inhibitor, e.g., an SHP-2 inhibitor described herein.

In some embodiments, the additional agent is a kinase inhibitor. Kinase inhibitors, such as a CDK4 kinase inhibitor, a BTK kinase inhibitor, a MNK kinase inhibitor, or a DGK kinase inhibitor, can regulate the constitutively active survival pathways that exist in tumor cells and/or modulate the function of immune cells. In some embodiments, the kinase inhibitor is a Bruton's tyrosine kinase (BTK) inhibitor, e.g., ibrutinib. In some embodiments, the kinase inhibitor is a phosphatidylinositol-4,5-bisphosphate 3-kinase (PI3K) inhibitor. In some embodiments, the kinase inhibitor is a CDK4 inhibitor, e.g., a CDK4/6 inhibitor. In some embodiments, the kinase inhibitor is an mTOR inhibitor, such as, e.g., rapamycin, a rapamycin analog, OSI-027. The mTOR inhibitor can be, e.g., an mTORC1 inhibitor and/or an mTORC2 inhibitor, e.g., an mTORC1 inhibitor and/or mTORC2 inhibitor. In some embodiments, the kinase inhibitor is an MNK inhibitor, or a dual PI3K/mTOR inhibitor. In some embodiments, other exemplary kinase inhibitors include the AKT inhibitor perifosine, the mTOR inhibitor temsirolimus, the Src kinase inhibitors dasatinib and fostamatinib, the JAK2 inhibitors pacritinib and ruxolitinib, the PKCβ inhibitors enzastaurin and bryostatin, and the AAK inhibitor alisertib.

In some embodiments, the kinase inhibitor is a BTK inhibitor selected from ibrutinib (PCI-32765); GDC-0834; RN-486; CGI-560; CGI-1764; HM-71224; CC-292; ONO-4059; CNX-774; and LFM-A13. In some embodiments, the BTK inhibitor does not reduce or inhibit the kinase activity of interleukin-2-inducible kinase (ITK), and is selected from GDC-0834; RN-486; CGI-560; CGI-1764; HM-71224; CC-292; ONO-4059; CNX-774; and LFM-A13.

In some embodiments, the kinase inhibitor is a BTK inhibitor, e.g., ibrutinib (1-[(3R)-3-[4-Amino-3-(4-phenoxyphenyl)-1H-pyrazolo[3,4-d]pyrimidin-1-yl]piperidin-1-yl] prop-2-en-1-one; also known as PCI-32765). In some embodiments, the kinase inhibitor is a BTK inhibitor, e.g., ibrutinib (PCI-32765). In some embodiments, 1, 2, 3, 4, 5, 6, 7, 8, 9, 10, 11, 12 or more cycles of ibrutinib are administered. In some embodiments, the BTK inhibitor is a BTK inhibitor described in International Application WO 2015/079417.

In some embodiments, the kinase inhibitor is a PI3K inhibitor. PI3K is central to the PI3K/Akt/mTOR pathway involved in cell cycle regulation and lymphoma survival. Exemplary PI3K inhibitor includes idelalisib (PI3Kδ inhibitor). In some embodiments, the additional agent is idelalisib and rituximab.

In some embodiments, the additional agent is an inhibitor of mammalian target of rapamycin (mTOR). In some embodiments, the kinase inhibitor is an mTOR inhibitor selected from temsirolimus; ridaforolimus (also known as AP23573 and MK8669); everolimus (RAD001); rapamycin (AY22989); simapimod; AZD8055; PF04691502; SF1126; and XL765. In some embodiments, the additional agent is an inhibitor of mitogen-activated protein kinase (MAPK), such as vemurafenib, dabrafenib, and trametinib.

In some embodiments, the additional agent is an agent that regulates pro- or anti-apoptotic proteins. In some embodiments, the additional agent includes a B-cell lymphoma 2 (BCL-2) inhibitor (e.g., venetoclax, also called ABT-199 or GDC-0199; or ABT-737). Venetoclax is a small molecule (4-(4-{[2-(4-Chlorophenyl)-4,4-dimethyl-1-cyclohexen-1-yl]methyl}-1-piperazinyl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide) that inhibits the anti-apoptotic protein, BCL-2. Other agents that modulate pro- or anti-apoptotic protein include BCL-2 inhibitor ABT-737, navitoclax (ABT-263); Mcl-1 siRNA or Mcl-1 inhibitor retinoid N-(4-hydroxyphenyl) retinamide (4-HPR) for maximal efficacy. In some embodiments, the additional agent provides a pro-apoptotic stimuli, such as recombinant tumor necrosis factor-related apoptosis-inducing ligand (TRAIL), which can activate the apoptosis pathway by binding to TRAIL death receptors DR-4 and DR-5 on tumor cell surface, or TRAIL-R2 agonistic antibodies.

In some embodiments, the additional agent includes an indoleamine 2,3-dioxygenase (IDO) inhibitor. IDO is an enzyme that catalyzes the degradation of the amino acid, L-tryptophan, to kynurenine. Many cancers overexpress IDO, e.g., prostatic, colorectal, pancreatic, cervical, gastric, ovarian, head, and lung cancer. Plasmacytoid dendritic cells (pDCs), macrophages, and dendritic cells (DCs) can express IDO. In some aspects, a decrease in L-tryptophan (e.g., catalyzed by IDO) results in an immunosuppressive milieu by inducing T-cell anergy and apoptosis. Thus, in some aspects, an IDO inhibitor can enhance the efficacy of the binding molecules (e.g., CCT5-binding molecules), recombinant receptors, cells and/or compositions described herein, e.g., by decreasing the suppression or death of the administered CAR-expressing cell. Exemplary inhibitors of IDO include but are not limited to 1-methyl-tryptophan, indoximod, and INCB024360 (epacadostat).

In some embodiments, the additional agent includes a cytotoxic agent, e.g., CPX-351 (Celator Pharmaceuticals), cytarabine, daunorubicin, vosaroxin (Sunesis Pharmaceuticals), sapacitabine (Cyclacel Pharmaceuticals), idarubicin, or mitoxantrone. In some embodiments, the additional agent includes a hypomethylating agent, e.g., a DNA methyltransferase inhibitor, e.g., azacitidine or decitabine.

In another embodiment, the additional therapy is a transplantation, e.g., allogeneic stem cell transplant.

In some embodiments, the additional therapy is a lymphodepleting therapy. In some embodiments, lymphodepletion is performed on a subject, e.g., prior to administering engineered cells, e.g., CAR-expressing cells. In some embodiments, the lymphodepletion comprises administering one or more of melphalan, Cytoxan, cyclophosphamide, and fludarabine. In some embodiments, a lymphodepleting chemotherapy is administered to the subject prior to, concurrently with, or after administration (e.g., infusion) of engineered cells, e.g., CAR-expressing cells. In an example, the lymphodepleting chemotherapy is administered to the subject prior to administration of engineered cells, e.g., CAR-expressing cells.

In some embodiments, the additional agent is an oncolytic virus. In some embodiments, oncolytic viruses are capable of selectively replicating in and triggering the death of or slowing the growth of a cancer cell. In some cases, oncolytic viruses have no effect or a minimal effect on non-cancer cells. An oncolytic virus includes but is not limited to an oncolytic adenovirus, oncolytic Herpes Simplex Viruses, oncolytic retrovirus, oncolytic parvovirus, oncolytic vaccinia virus, oncolytic Sinbis virus, oncolytic influenza virus, or oncolytic RNA virus (e.g., oncolytic reovirus, oncolytic Newcastle Disease Virus (NDV), oncolytic measles virus, or oncolytic vesicular stomatitis virus (VSV)).

Other exemplary combination therapy, treatment and/or agents include anti-allergenic agents, anti-emetics, analgesics and adjunct therapies. In some embodiments, the additional agent includes cytoprotective agents, such as neuroprotectants, free-radical scavengers, cardioprotectors, anthracycline extravasation neutralizers and nutrients.

In some embodiments, an antibody used as an additional agent is conjugated or otherwise bound to a therapeutic agent, e.g., a chemotherapeutic agent (e.g., Cytoxan, fludarabine, histone deacetylase inhibitor, demethylating agent, peptide vaccine, anti-tumor antibiotic, tyrosine kinase inhibitor, alkylating agent, anti-microtubule or anti-mitotic agent), anti-allergic agent, anti-nausea agent (or anti-emetic), pain reliever, or cytoprotective agent described herein. In some embodiments, the additional agent is an antibody-drug conjugate.

In some embodiments, the additional agent can modulate, inhibit or stimulate particular factors at the DNA, RNA or protein levels, to enhance or boost the efficacy of the binding molecules (e.g., CCT5-binding molecules), recombinant receptors, cells and/or compositions provided herein. In some embodiments, the additional agent can modulate the factors at the nucleic acid level, e.g., DNA or RNA, within the administered cells, e.g., cells engineered to express recombinant receptors, e.g., CAR. In some embodiments, an inhibitory nucleic acid, e.g., an inhibitory nucleic acid, e.g., a dsRNA, e.g., an siRNA or shRNA, or a clustered regularly interspaced short palindromic repeats (CRISPR), a transcription-activator like effector nuclease (TALEN), or a zinc finger endonuclease (ZFN), can be used to inhibit expression of an inhibitory molecule in the engineered cell, e.g., CAR-expressing cell. In some embodiments the inhibitor is an shRNA. In some embodiments, the inhibitory molecule is inhibited within the engineered cell, e.g., CAR-expressing cell. In some embodiments, a nucleic acid molecule that encodes a dsRNA molecule that inhibits expression of the molecule that modulates or regulates, e.g., inhibits, T-cell function is operably linked to a promoter, e.g., a HI- or a U6-derived promoter such that the dsRNA molecule that inhibits expression of the inhibitory molecule is expressed within the engineered cell, e.g., CAR-expressing cell. See, e.g., Brummelkamp T R, et al. (2002) Science 296: 550-553; Miyagishi M, et al. (2002) Nat. Biotechnol. 19: 497-500.

In some embodiments, the additional agent is capable of disrupting the gene encoding an inhibitory molecule, such as any immune checkpoint inhibitors described herein. In some embodiments, disruption is by deletion, e.g., deletion of an entire gene, exon, or region, and/or replacement with an exogenous sequence, and/or by mutation, e.g., frameshift or missense mutation, within the gene, typically within an exon of the gene. In some embodiments, the disruption results in a premature stop codon being incorporated into the gene, such that the inhibitory molecule is not expressed or is not expressed in a form that is capable of being expressed on the cells surface and/or capable of mediating cell signaling. The disruption is generally carried out at the DNA level. The disruption generally is permanent, irreversible, or not transient.

In some aspects, the disruption is carried out by gene editing, such as using a DNA binding protein or DNA-binding nucleic acid, which specifically binds to or hybridizes to the gene at a region targeted for disruption. In some aspects, the protein or nucleic acid is coupled to or complexed with a nuclease, such as in a chimeric or fusion protein. For example, in some embodiments, the disruption is effected using a fusion comprising a DNA-targeting protein and a nuclease, such as a Zinc Finger Nuclease (ZFN) or TAL-effector nuclease (TALEN), or an RNA-guided nuclease such as a clustered regularly interspersed short palindromic nucleic acid (CRISPR)-Cas system, such as CRISPR-Cas9 system, specific for the gene being disrupted. In some embodiments, methods of producing or generating genetically engineered cells, e.g., CAR-expressing cells, include introducing into a population of cells nucleic acid molecules encoding a genetically engineered antigen receptor (e.g. CAR) and nucleic acid molecules encoding an agent targeting an inhibitory molecule that is a gene editing nuclease, such as a fusion of a DNA-targeting protein and a nuclease such as a ZFN or a TALEN, or an RNA-guided nuclease such as of the CRISPR-Cas9 system, specific for an inhibitory molecule.

Any of the additional agents described herein can be prepared and administered as combination therapy with the CCT5-binding molecule (e.g., antibody), immunoconjugate, recombinant receptor (e.g., chimeric antigen receptor) and/or engineered cells expressing said molecules (e.g., recombinant receptor) described herein, such as in pharmaceutical compositions comprising one or more agents of the combination therapy and a pharmaceutically acceptable carrier, such as any described herein. In some embodiments, the CCT5-binding molecule (e.g., antibody), immunoconjugate, recombinant receptor (e.g., chimeric antigen receptor), engineered cells expressing said molecules (e.g., recombinant receptor), plurality of engineered cells expressing said molecules (e.g., recombinant receptor) can be administered simultaneously, concurrently or sequentially, in any order with the additional agents, therapy or treatment, wherein such administration provides therapeutically effective levels each of the agents in the body of the subject. The agents can be co-administered with the binding molecules (e.g., CCT5-binding molecules), recombinant receptors, cells and/or compositions described herein, for example, as part of the same pharmaceutical composition or using the same method of delivery. In some embodiments, the additional agent is incubated with the engineered cell, e.g., CAR-expressing cells, prior to administration of the cells.

In some examples, the one or more additional agents are administered subsequent to or prior to the administration of the binding molecules (e.g., CCT5-binding molecules), recombinant receptors, cells and/or compositions described herein, separated by a selected time period. In some examples, the time period is 1 day, 2 days, 3 days, 4 days, 5 days, 6 days, 1 week, 2 weeks, 3 weeks, 1 month, 2 months, or 3 months. In some examples, the one or more additional agents are administered multiple times and/or the binding molecules (e.g., CCT5-binding molecules), recombinant receptors, cells and/or compositions described herein, is administered multiple times. For example, in some embodiments, the additional agent is administered prior to the binding molecules (e.g., CCT5-binding molecules), recombinant receptors, cells and/or compositions described herein, e.g., two weeks, 12 days, 10 days, 8 days, one week, 6 days, 5 days, 4 days, 3 days, 2 days or 1 day before the administration. For example, in some embodiments, the additional agent is administered after the binding molecules (e.g., CCT5-binding molecules), recombinant receptors, cells and/or compositions described herein, e.g., two weeks, 12 days, 10 days, 8 days, one week, 6 days, 5 days, 4 days, 3 days, 2 days or 1 day after the administration.

The dose of the additional agent can be any therapeutically effective amount, e.g., any dose amount described herein, and the appropriate dosage of the additional agent may depend on the type of disease to be treated, the type, dose and/or frequency of the binding molecule, recombinant receptor, cell and/or composition administered, the severity and course of the disease, whether the binding molecule, recombinant receptor, cell and/or composition is administered for preventive or therapeutic purposes, previous therapy, the patient's clinical history and response to the binding molecule, recombinant receptor, cell and/or composition, and the discretion of the attending physician. The binding molecule, recombinant receptor, cell and/or composition and/or the additional agent and/or therapy can be administered to the patient at one time, repeated or administered over a series of treatments.

C. Diagnostic and Detection Methods

Also provided are methods involving use of the provided binding molecules, e.g., antibodies or antigen-binding fragments thereof, in detection of CCT5, for example, in diagnostic and/or prognostic methods in association with a CCT5-expressing disease or condition. The methods in some embodiments include incubating a biological sample with the antibody or antigen-binding fragment thereof and/ or administering the antibody or antigen-binding fragment thereof to a subject. In certain embodiments, a biological sample includes a cell or tissue, such as tumor or cancer tissue. In certain embodiments, the contacting is under conditions permissive for binding of the anti-CCT5 antibody to CCT5, and detecting whether a complex is formed between the anti-CCT5 antibody and CCT5. Such a method may be an in vitro or in vivo method. In one embodiment, an anti-CCT5 antibody (e.g., antigen-binding fragment) is used to select subjects eligible for therapy with an anti-CCT5 antibody (e.g., antigen-binding fragment) or recombinant receptor, e.g. where CCT5 is a biomarker for selection of patients.

In some embodiments, a sample, such as a cell, tissue sample, lysate, composition, or other sample derived therefrom is contacted with the anti-CCT5 antibody (e.g., antigen-binding fragment) and binding or formation of a complex between the antibody and the sample (e.g., CCT5 in the sample) is determined or detected. When binding in the test sample is demonstrated or detected as compared to a reference cell of the same tissue type, it may indicate the presence of an associated disease or condition. In some embodiments, the sample is from human tissues.

Various methods known for detecting specific antibody-antigen binding can be used. Exemplary immunoassays include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radio-immunoassay (RIA). An indicator moiety, or label group, can be attached to the subject antibodies and is selected so as to meet the needs of various uses of the method which are often dictated by the availability of assay equipment and compatible immunoassay procedures. Exemplary labels include radionuclides (e.g. $^{125}$I, $^{131}$I, $^{35}$S, $^{3}$H, or $^{32}$P), enzymes (e.g., alkaline phosphatase, horseradish peroxidase, luciferase, or β-galactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). General techniques to be used in performing the various immunoassays noted above are known.

For purposes of diagnosis, the antibodies (e.g., antigen-binding fragments) can be labeled with a detectable moiety including but not limited to radioisotopes, fluorescent labels, and various other enzyme-substrate labels. Methods of conjugating labels to an antibody are known.

In some embodiments, antibodies (e.g., antigen-binding fragments) need not be labeled, and the presence thereof can be detected using a labeled antibody which binds to the antibodies.

The provided antibodies (e.g., antigen-binding fragments) in some embodiments can be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987).

The antibodies (e.g., antigen-binding fragments) and polypeptides can also be used for in vivo diagnostic assays, such as in vivo imaging. Generally, the antibody is labeled with a radionuclide (such as $^{111}$In, $^{99}$Tc, $^{14}$C, $^{131}$I, $^{125}$I, or $^{3}$H) so that the cells or tissue of interest can be localized in vivo following administration to a subject.

The antibody (e.g., antigen-binding fragment) may also be used as staining reagent in pathology, e.g., using known techniques.

IV. ARTICLES OF MANUFACTURE OR KITS

Also provided are articles of manufacture or kit containing the provided binding molecules (e.g., antibodies), recombinant receptors (e.g., CARs), genetically engineered cells, and/or compositions comprising the same. The articles of manufacture may include a container and a label or package insert on or associated with the container. Suitable containers include, for example, bottles, vials, syringes, test tubes, IV solution bags, etc. The containers may be formed from a variety of materials such as glass or plastic. In some embodiments, the container has a sterile access port. Exemplary containers include an intravenous solution bags, vials, including those with stoppers pierceable by a needle for injection. The article of manufacture or kit may further include a package insert indicating that the compositions can be used to treat a particular condition such as a condition described herein (e.g., multiple myeloma). Alternatively, or additionally, the article of manufacture or kit may further include another or the same container comprising a pharmaceutically-acceptable buffer. It may further include other materials such as other buffers, diluents, filters, needles, and/or syringes.

The label or package insert may indicate that the composition is used for treating the CCT5-expressing or CCT5-associated disease, disorder or condition in an individual. The label or a package insert, which is on or associated with the container, may indicate directions for reconstitution and/or use of the formulation. The label or package insert may further indicate that the formulation is useful or intended for subcutaneous, intravenous, or other modes of administration for treating or preventing a CCT5-expressing or CCT5-associated disease, disorder or condition in an individual.

The container in some embodiments holds a composition which is by itself or combined with another composition effective for treating, preventing and/or diagnosing the condition. The article of manufacture or kit may include (a) a first container with a composition contained therein (i.e., first medicament), wherein the composition includes the antibody (e.g., anti-CCT5 antibody) or antigen-binding fragment thereof or recombinant receptor (e.g., CAR); and (b) a second container with a composition contained therein (i.e., second medicament), wherein the composition includes a further agent, such as a cytotoxic or otherwise therapeutic agent, and which article or kit further comprises instructions on the label or package insert for treating the subject with the second medicament, in an effective amount.

V. DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, reference to a "corresponding form" of an antibody means that when comparing a property or activity of two antibodies, the property is compared using the same form of the antibody. For example, if it is stated that an antibody has greater activity compared to the activity of the corresponding form of a first antibody, that means that a particular form, such as an scFv of that antibody, has greater activity compared to the scFv form of the first antibody.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, M D, 1991.

The terms "full length antibody," "intact antibody," and "whole antibody" are used herein interchangeably to refer to an antibody having a structure substantially similar to a native antibody structure or having heavy chains that contain an Fc region, such as defined herein.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-CCT5 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The terms "polypeptide" and "protein" are used interchangeably to refer to a polymer of amino acid residues, and are not limited to a minimum length. Polypeptides, including the provided antibodies and antibody chains and other peptides, e.g., linkers and CCT5-binding peptides, may include amino acid residues including natural and/or non-natural amino acid residues. The terms also include post-expression modifications of the polypeptide, for example, glycosylation, sialylation, acetylation, phosphorylation, and the like. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

As used herein, "percent (%) amino acid sequence identity" and "percent identity" and "sequence identity" when used with respect to an amino acid sequence (reference polypeptide sequence) is defined as the percentage of amino acid residues in a candidate sequence (e.g., the subject antibody or fragment) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways, such as, using publicly available computer software such as BLAST, BLAST-2, ALIGN or Megalign (DNASTAR) software. Appropriate parameters can be determined for aligning sequences, including any algorithms needed to achieve maximal alignment over the full length of the sequences being compared.

An amino acid substitution may include replacement of one amino acid in a polypeptide with another amino acid. Amino acid substitutions may be introduced into a binding molecule, e.g., antibody, of interest and the products screened for a desired activity, e.g., retained/improved antigen binding, decreased immunogenicity, or improved ADCC or CDC.

Amino acids generally can be grouped according to the following common side-chain properties:
 (1) hydrophobic: Norleucine, Met, Ala, Val, Leu, Ile;
 (2) neutral hydrophilic: Cys, Ser, Thr, Asn, Gln;
 (3) acidic: Asp, Glu;
 (4) basic: His, Lys, Arg;
 (5) residues that influence chain orientation: Gly, Pro;
 (6) aromatic: Trp, Tyr, Phe.

Non-conservative amino acid substitutions will involve exchanging a member of one of these classes for another class.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, the singular forms "a," "an," and "the" include plural referents unless the context clearly dictates otherwise. For example, "a" or "an" means "at least one" or "one or more." It is understood that aspects, embodiments, and variations described herein include "comprising," "consisting," and/or "consisting essentially of" aspects, embodiments and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a "composition" refers to any mixture of two or more products, substances, or compounds, including cells. It may be a solution, a suspension, liquid, powder, a paste, aqueous, non-aqueous or any combination thereof.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

VI. EXEMPLARY EMBODIMENTS

Among the provided embodiments are:
1. 1. An antibody or antigen-binding fragment thereof, wherein the antibody or antigen-binding fragment specifically binds to a peptide comprising an amino acid sequence set forth in SEQ ID NO:68 ($X_1SVEX_5X_6KX_8$) and/or a peptide sequence set forth in SEQ ID NO:68 ($X_1SVEX_5X_6KX_8$), wherein X is any amino acid.
2. An antibody or antigen-binding fragment thereof, wherein the antibody or antigen-binding fragment specifically binds to an epitope that is or is contained within the peptide sequence set forth in SEQ ID NO:68 ($X_1SVEX_5X_6KX_8$), wherein X is any amino acid.
3. The antibody or antigen-binding fragment of embodiment 1 or embodiment 2, wherein $X_1$ is threonine, serine or aspartic acid, $X_5$ is aspartic acid or alanine, $X_6$ is tyrosine, phenylalanine, or isoleucine and $X_8$ is alanine or arginine.
4. The antibody or antigen-binding fragment of any of embodiments 1-3, wherein the peptide sequence consists of the sequence TSVEDYKA (SEQ ID NO:70), SSVEAFKR (SEQ ID NO:71) or DSVEAIKA (SEQ ID NO:72).
5. The antibody or antigen-binding fragment of any of embodiments 1-4, wherein the antibody or antigen-binding fragment comprises:
a heavy chain variable ($V_H$) region having at least 90%, 91%, 92%, 93%, 94%, 95%, 96%, 97%, 98% or 99% sequence identity to the $V_H$ region amino acid sequence set forth in SEQ ID NO:1; and a light chain variable ($V_L$) region having at least 90%, 91%, 92%, 93%, 94%, 95%, 96%, 97%, 98% or 99% sequence identity to the $V_L$ region amino acid sequence set forth in SEQ ID NO:2.
6. An antibody or antigen-binding fragment thereof, wherein the antibody or antigen-binding fragment comprises:
a heavy chain variable ($V_H$) region having at least 90%, 91%, 92%, 93%, 94%, 95%, 96%, 97%, 98% or 99% sequence identity to the $V_H$ region amino acid sequence set forth in SEQ ID NO:1; and
a light chain variable ($V_L$) region having at least 90%, 91%, 92%, 93%, 94%, 95%, 96%, 97%, 98% or 99% sequence identity to the $V_L$ region amino acid sequence set forth in SEQ ID NO:2.

7. The antibody or antigen-binding fragment of any of embodiments 1-6, wherein:
the $V_H$ region comprises a CDR-H3 comprising the amino acid sequence set forth in SEQ ID NO:13 or a CDR-H3 contained within the $V_H$ region amino acid sequence set forth in SEQ ID NO:1; and/or
the $V_L$ region comprises a CDR-L3 comprising the amino acid sequence set forth in SEQ ID NO: 23, or a CDR-L3 contained within the $V_L$ region amino acid sequence set forth in SEQ ID NO:2.

8. The antibody or antigen-binding fragment of any of embodiments 1-7, wherein:
the $V_H$ region comprises a CDR-H1 and a CDR-H2 contained within the $V_H$ region amino acid sequence set forth in SEQ ID NO:1; and/or
the $V_L$ region comprises a CDR-L1 and a CDR-L2 contained within the $V_L$ region amino acid sequence set forth in SEQ ID NO:2.

9. An antibody or antigen-binding fragment thereof comprising:
a heavy chain variable ($V_H$) region comprising a heavy chain complementarity determining region 1 (CDR-H1) 1, a CDR-H2, and a CDR-H3, respectively, comprising the amino acid sequences of CDR-H1, CDR-H2, and CDR-H3 sequences contained within the $V_H$ region amino acid sequence set forth in SEQ ID NO: 1; and/or
a light chain variable ($V_L$) region comprising a light chain complementarity determining region 1 (CDR-L1), a CDR-L2, and a CDR-L3, respectively, comprising the amino acid sequences of CDR-L1, CDR-L2, and CDR-L3 sequences contained within the light chain variable ($V_L$) region amino acid sequence set forth in SEQ ID NO: 2.

10. The antibody or antigen-binding fragment thereof of any of embodiments 1-9, wherein:
the $V_H$ region comprises a CDR-H1 comprising the amino acid sequence set forth in SEQ ID NO:11; a CDR-H2 comprising the amino acid sequence set forth in SEQ ID NO: 12; and a CDR-H3 comprising the amino acid sequence set forth in SEQ ID NO: 13; and/or
the $V_L$ region comprises a CDR-L1 comprising the amino acid sequence set forth in SEQ ID NO:21; a CDR-L 2 comprises the amino acid sequence set forth in SEQ ID NO: 22; and a CDR-L3 comprising the amino acid sequence set forth in SEQ ID NO: 23.

11. An antibody or antigen-binding fragment thereof, wherein the antibody or antigen-binding fragment comprises:
a heavy chain variable ($V_H$) region comprising a CDR-H1 comprising the amino acid sequence set forth in SEQ ID NO:11; a CDR-H2 comprising the amino acid sequence set forth in SEQ ID NO: 12; and a CDR-H3 comprising the amino acid sequence set forth in SEQ ID NO: 13; and/or
a light chain variable ($V_L$) region comprising a CDR-L1 comprising the amino acid sequence set forth in SEQ ID NO:21; a CDR-L 2 comprises the amino acid sequence set forth in SEQ ID NO: 22; and a CDR-L3 comprising the amino acid sequence set forth in SEQ ID NO: 23.

12. The antibody or antigen-binding fragment of any of embodiments 1-11, comprising a $V_H$ region comprising a CDR-H1, CDR-H2, and CDR-H3 comprising the amino acid sequence of SEQ ID NOs: 11, 12, and 13, respectively and a $V_L$ region comprising a CDR-L1, CDR-L2, and CDR-L3 comprising the amino acid sequence of SEQ ID NOs: 21, 22, and 23, respectively.

13. The antibody or antigen-binding fragment of any one of embodiments 1-12, wherein the $V_H$ region comprises the amino acid sequence set forth in SEQ ID NO: 1.

14. The antibody or antigen-binding fragment of any one of embodiments 1-13, wherein the $V_L$ region comprises the amino acid sequence set forth in SEQ ID NO: 2.

15. The antibody or antigen-binding fragment of any of embodiments 1-14, wherein the $V_H$ and $V_L$ regions of the antibody or antigen-binding fragment thereof comprise the amino acid sequences of SEQ ID NOs:1 and 2, respectively.

16. An antibody or antigen-binding fragment, wherein the antibody or antigen-binding fragment specifically binds to the same or an overlapping epitope as specifically bound by the antibody or antigen-binding fragment of any of embodiments 6-15.

17. An antibody or antigen-binding fragment, wherein the antibody or antigen-binding fragment competes for binding to CCT5 or to a peptide set forth in SEQ ID NO:68 ($X_1SVEX_5X_6KX_8$), wherein X is any amino acid.

18. The antibody or antigen-binding fragment of any one of embodiments 1-17, wherein said antibody or antigen-binding fragment specifically binds to a chaperonin containing TCP1 subunit 5 (CCT5) protein.

19. The antibody or antigen-binding fragment of embodiment 17 or embodiment 18, wherein the CCT5 protein is a human CCT5 protein, a mouse CCT5 protein, or a non-human primate CCT5 protein.

20. The antibody or antigen-binding fragment of any of embodiments 17-19, wherein the CCT5 protein is a human CCT5 protein.

21. The antibody or antigen-binding fragment of any of embodiments 17-20, wherein the CCT5 comprises the sequence set forth in SEQ ID NO:45 or 46 or a sequence of amino acids that exhibits at least or about at least 90%, 91%, 92%, 93%, 94%, 95%, 96%, 97%, 98%, 99% or more sequence identity to SEQ ID NO:45 or 46.

22. The antibody or antigen-binding fragment of any of embodiments 17-22, wherein the CCT5 protein comprises the amino acid sequence set forth in SEQ ID NO:45 or 46.

23. The antibody or antigen-binding fragment of any of embodiments 6-22, wherein the antibody or antigen-binding fragment specifically binds to a peptide sequence set forth in SEQ ID NO:68 ($X_1SVEX_5X_6KX_8$), wherein X is any amino acid.

24. The antibody or antigen-binding fragment of embodiment 17 or embodiment 23, wherein $X_1$ is threonine, serine or aspartic acid, $X_5$ is aspartic acid or alanine, $X_6$ is tyrosine, phenylalanine, or isoleucine and $X_8$ is alanine or arginine.

25. The antibody or antigen-binding fragment of embodiment 17, embodiment 23 or embodiment 24, wherein the peptide sequence consists of the sequence TSVEDYKA (SEQ ID NO:70), SSVEAFKR (SEQ ID NO:71) or DSVEAIKA (SEQ ID NO:72).

26. The antibody or antigen-binding fragment of any one of embodiments 1-25, wherein the antibody or antigen-binding fragment is human.

27. The antibody or antigen-binding fragment thereof of any of embodiments 1-26, wherein the antibody is a human antibody.

28. The antibody or antigen-binding fragment of embodiment 26 or embodiment 27, wherein:

the antibody or antigen-binding fragment comprises a heavy chain variable ($V_H$) region, said $V_H$ region comprises a portion having at least 95%, 96%, 97%, 98%, 99%, or 100% sequence identity to an amino acid sequence encoded by a germline nucleotide human heavy chain V segment, a portion with at least 95%, 96%, 97%, 98%, 99%, or 100% sequence identity to an amino acid sequence encoded by a germline nucleotide human heavy chain D segment, and/or a portion having at least 95%, 96%, 97%, 98%, 99%, or 100% sequence identity to an amino acid sequence encoded by a germline nucleotide human heavy chain J segment; and/or the antibody or antigen-binding fragment comprises a light chain variable ($V_L$) region, said $V_L$ region comprises a portion with at least 95%, 96%, 97%, 98%, 99%, or 100% sequence identity to an amino acid sequence encoded by a germline nucleotide human kappa or lambda chain V segment, and/or a portion with at least 95%, 96%, 97%, 98%, 99%, or 100% sequence identity to an amino acid sequence encoded by a germline nucleotide human kappa or lambda chain J segment.

29. The antibody or antigen-binding fragment of any one of embodiments 26-28, wherein:

the CDR-H1 and/or CDR-H2 comprises a sequence 100% identical or with no more than one amino acid difference as compared to an amino acid sequence of a CDR-H1 and/or CDR-H2, respectively, within a sequence encoded by a germline nucleotide human heavy chain V segment; and/or the CDR-L1 and/or CDR-L2 comprises a sequence 100% identical or with no more than one amino acid difference as compared to an amino acid sequence of a CDR-L1 and/or CDR-L2, respectively, within a sequence encoded by a germline nucleotide human kappa or lambda v segment.

30. The antibody or antigen-binding fragment of any one of embodiments 1-29, wherein the antibody or antigen-binding fragment is recombinant.

31. The antibody or antigen-binding fragment of any one of embodiments 1-30, wherein the antibody or antigen-binding fragment is monoclonal.

32. The antibody or antigen-binding fragment of any one of embodiments 1-31, that is an antigen-binding fragment.

33. The antibody or antigen-binding fragment of any one of embodiments 1-32, that is a single chain fragment.

34. The antibody or antigen-binding fragment of embodiment 32 or embodiment 33, wherein the fragment comprises an scFv.

35. The antibody or antigen-binding fragment of any of embodiments 32-34, wherein the $V_H$ region is amino-terminal to the $V_L$ region.

36. The antibody or antigen-binding fragment of any of embodiments 32-34, wherein the $V_H$ region is carboxy-terminal to the $V_L$ region.

37. The antibody or antigen-binding fragment of any one of embodiments 32-36, that is a fragment comprising antibody $V_H$ and $V_L$ regions joined by a flexible linker.

38. The antibody or antigen-binding fragment of any of embodiments 34-37, wherein the scFv comprises a linker comprising the amino acid sequence GGGGSGGGGSGGGGS (SEQ ID NO:49).

39. The antibody or antigen-binding fragment of any of embodiments 34-38, wherein the scFv comprises the amino acid sequence set forth in SEQ ID NO:52, or an amino acid sequence having at least 90%, 91%, 92%, 93%, 94%, 95%, 96%, 97%, 98%, or 99% sequence identity to the amino acid sequence set forth in SEQ ID NO:52.

40. The antibody or antigen-binding fragment of any one of embodiments 1-39, which further comprises at least a portion of an immunoglobulin constant region.

41. The antibody or antigen-binding fragment of any of embodiments 1-31 and 40, that is a whole or intact antibody.

42. The antibody or antigen-binding fragment of any of embodiments 1-41 that is a bispecific antibody.

43. The antibody or antigen-binding fragment of embodiment 42, that further specifically binds to a second antigen.

44. The antibody or antigen-binding fragment of embodiment 43, wherein the second antigen is expressed on a tumor cell, optionally a tumor cell that expresses or aberrantly expresses CCT5, or a T cell.

45. The antibody or antigen-binding fragment of embodiment 43 or embodiment 44, wherein the second antigen is expressed on a tumor cell and the tumor cell is of an epithelial cell cancer.

46. The antibody or antigen-binding fragment of embodiment 43 or embodiment 44, wherein the second antigen is expressed on a T cell antigen and the T cell antigen is CD2 or CD3.

47. A single chain cell-surface protein, comprising the antibody or antigen-binding fragment of any one of embodiments 1-46, and optionally a transmembrane domain.

48. A single chain cell-surface protein, comprising an antibody or antigen-binding fragment that specifically binds to CCT5, and optionally a transmembrane domain.

49. The single chain cell surface protein of embodiment 47 or embodiment 48 that is an antigen-binding fragment, optionally an scFv.

50. The single chain cell surface protein of embodiment 49, wherein the antigen-binding fragment is an scFv and the scFv comprises the amino acid sequence set forth in SEQ ID NO: 52 or a sequence of amino acids that exhibits at least 85%, 90%, 91%, 92%, 93%, 94%, 95%, 96%, 97%, 98% or 99% sequence identity to SEQ ID NO:52 and that binds CCT5 or a peptide comprising the sequence set forth in SEQ ID NO:68, optionally a peptide set forth in any of SEQ ID NOS: 70-72.

51. A conjugate, comprising the antibody or antigen-binding fragment of any one of embodiments 1-46 and a heterologous molecule or moiety.

52. A conjugate, comprising an antibody or antigen-binding fragment that specifically binds to CCT5 and a heterologous molecule or moiety.

53. The conjugate of embodiment 51 or embodiment 52, wherein the heterologous molecule or moiety is a protein, peptide, nucleic acid or small molecule.

54. The conjugate of any of embodiments 51-53, wherein the heterologous molecule or moiety is a cytotoxic agent, a toxin, a radioisotope, a chemotherapeutic agent, a lytic peptide or a cytokine.

55. The conjugate of any of embodiments 51-54, wherein the antibody or antigen-binding fragment and moiety are linked directly or indirectly via a linker.

56. The conjugate of any of embodiments 51-55, wherein the antibody or antigen-binding fragment and the moiety are covalently or chemically linked.
57. The conjugate of any of embodiments 51-55, wherein the moiety is a protein or peptide and the conjugate is a fusion protein.
58. A chimeric antigen receptor (CAR) comprising an extracellular portion comprising the antibody or antigen-binding fragment of any one of embodiments 1-46 and an intracellular signaling region.
59. A chimeric antigen receptor (CAR) comprising an extracellular portion comprising an antibody or antigen-binding fragment that specifically binds CCT5 and an intracellular signaling region.
60. The chimeric antigen receptor of embodiment 58 or embodiment 59, wherein the extracellular portion comprises an antigen-binding fragment and the antigen-binding fragment is an scFv.
61. The chimeric antigen receptor of embodiment 60, wherein the scFv comprises the amino acid sequence set forth in SEQ ID NO: 52 or a sequence of amino acids that exhibits at least 85%, 90%, 91%, 92%, 93%, 94%, 95%, 96%, 97%, 98% or 99% sequence identity to SEQ ID NO:52 and that binds CCT5 or a peptide comprising the sequence set forth in SEQ ID NO:68, optionally a peptide set forth in any of SEQ ID NOS: 70-72.
62. The chimeric antigen receptor of any of embodiments 58-61, wherein the intracellular signaling region is or comprises a primary signaling domain, an signaling domain that is capable of inducing a primary activation signal in a T cell, a signaling domain of a T cell receptor (TCR) component, and/or a signaling domain comprising an immunoreceptor tyrosine-based activation motif (ITAM).
63. The chimeric antigen receptor of embodiment 62, wherein the intracellular signaling region is or comprises an intracellular signaling domain of a CD3 chain, optionally a CD3-zeta (CD3ζ) chain, or a signaling portion thereof.
64. The chimeric antigen receptor of any of embodiments 58-63, wherein the CAR further comprises a transmembrane domain disposed between the extracellular domain and the intracellular signaling region.
65. The chimeric antigen receptor of embodiment 64, wherein the transmembrane domain comprises a transmembrane portion of CD28.
66. The chimeric antigen receptor of any of embodiments 58-65, wherein the intracellular signaling region further comprises a costimulatory signaling domain.
67. The chimeric antigen receptor of embodiment 66, wherein the costimulatory signaling domain comprises an intracellular signaling domain of a T cell costimulatory molecule or a signaling portion thereof.
68. The chimeric antigen receptor of embodiment 66 or embodiment 67, wherein the costimulatory signaling domain comprises an intracellular signaling domain of a CD28, a 4-1BB or an ICOS or a signaling portion thereof.
69. The chimeric antigen receptor of any of embodiments 66-68, wherein the costimulatory signaling domain comprises an intracellular signaling domain of a 4-1BB or a signaling portion thereof.
70. The chimeric antigen receptor of any of embodiments 66-69, wherein the costimulatory signaling domain is between the transmembrane domain and the intracellular signaling domain.
71. A polynucleotide encoding the antibody or antigen-binding fragment thereof of any one of embodiments 1-46, a single chain cell surface protein of any of embodiments 47-50, a conjugate of any of embodiments 51-57 or the chimeric antigen receptor of any one of embodiments 58-70.
72. The polynucleotide of embodiment 71, further encoding a signal sequence, optionally wherein the signal sequence is a GM-CSF signal sequence, a CD8 signal sequence, an Ig kappa signal sequence or a CD33 signal sequence.
73. A vector, comprising the polynucleotide of embodiment 71 or embodiment 72.
74. The vector of embodiment 73, wherein the vector is an expression vector.
75. The vector of embodiment 73 or embodiment 74, wherein the vector is a viral vector.
76. The vector of embodiment 75, wherein the viral vector is a retroviral vector.
77. The vector of embodiment 75 or embodiment 76, wherein the viral vector is a lentiviral vector.
78. The vector of embodiment 77, wherein the lentiviral vector is derived from HIV-1.
79. An engineered cell comprising the vector of any one of embodiments 73-78.
80. An engineered cell expressing a receptor comprising the antibody or antigen-binding fragment of any one of embodiments 1-46, a single chain cell surface protein of any of embodiments 47-50, a conjugate of any of embodiments 51-57 or the chimeric antigen receptor of any one of embodiments 58-70.
81. The engineered cell of embodiment 79 or embodiment 80, wherein the cell is an immune cell.
82. The engineered cell of embodiment 81, wherein the immune cell is a T cell.
83. The engineered cell of embodiment 82, wherein the T cell is a CD4+ or CD8+ T cell.
84. The engineered cell of embodiment 79 or embodiment 80, wherein the cell is an induced pluripotent stem cell (iPS cell).
85. The engineered cell of any of embodiments 79-84, further comprising another genetically engineered antigen receptor that is a chimeric costimulatory receptor that specifically binds to another antigen and is capable of inducing a costimulatory signal to the cell, optionally wherein the another antigen is expressed on the same cell as CCT5 or is a tumor antigen.
86. The engineered cell of any of embodiments 79-85, further comprising another generally engineered antigen receptor that is a inhibitory chimeric antigen receptor that specifically binds to another antigen and is capable of inducing an inhibitory or immunosuppressive or repressive signal to the cell upon recognition of the second antigen, optionally wherein the second antigen is expressed on a normal cell or is expressed on a prostate or mammary epithelial cell.
87. A composition comprising the antibody or antigen-binding fragment thereof of any one of embodiments 1-46, a single chain cell surface protein of any of embodiments 47-50, a conjugate of any of embodiments 51-57, a chimeric antigen receptor of any one of embodiments 58-70 or an engineered cell of any of embodiments 71-86.
88. The composition of embodiment 87, further comprising a pharmaceutically acceptable excipient.
89. A method of treatment, comprising administering the antibody or antigen-binding fragment thereof of any one of embodiments 1-46, a single chain cell surface protein of any of embodiments 47-50, a conjugate of any of embodiments 51-57, a chimeric antigen receptor of any one of embodiments 58-70, an engineered cell of any of embodiments 71-86 or the composition of embodiment 87 or embodiment 88 to a subject having a disease or disorder.
90. A method of treatment, the method comprising administering to a subject a binding molecule comprising an antibody or antigen-binding fragment that specifically binds CCT5 for treating a disease or disorder.
91. The method of embodiment 90, wherein the binding molecule is a conjugate, optionally an antibody-drug conjugate (ADC).
92. The method of embodiment 90, wherein the binding molecule is a chimeric antigen receptor and engineered cells expressing the chimeric antigen receptor are administered to the subject.
93. The method of treatment of any of embodiments 89-92, wherein the disease or disorder is associated with CCT5, optionally aberrantly expressed CCT5, optionally surface CCT5 or membrane localized CCT5.
94. The method of treatment of any of embodiments 89-93, wherein the disease or disorder is a tumor or a cancer.
95. The method of treatment of any of embodiments 89-94, wherein the disease or disorder is a leukemia, lymphoma, or a solid tumor, optionally a sarcoma or a carcinoma.
96. The method of treatment of any of embodiments 89-95, wherein the disease or condition is a pancreatic cancer, bladder cancer, colorectal cancer, breast cancer, prostate cancer, renal cancer, hepatocellular cancer, lung cancer, ovarian cancer, cervical cancer, pancreatic cancer, rectal cancer, thyroid cancer, uterine cancer, gastric cancer, esophageal cancer, head and neck cancer, melanoma, neuroendocrine cancers, CNS cancers, brain tumors, bone cancer, or soft tissue sarcoma.
97. The method of treatment of any of embodiments 89-96, wherein the disease or disorder is a carcinoma or epithelial cell cancer.
98. The method of treatment of embodiment 96, wherein the carcinoma or epithelial cell cancer is selected from a squamous cell carcinoma (skin), basal cell carcinoma, gastric carcinoma, an adenocarcinoma, adenosquamous carcinoma, anaplastic carcinoma, transitional cell carcinoma, large cell carcinoma, small cell carcinoma, hepatocellular carcinoma, renal cell carcinoma, endometrial carcinoma, invasive carcinoma of the breast, or a carcinoma metastasis.
99. The method of treatment of any of embodiments 89-98, wherein the disease or condition is a colon cancer, breast cancer, ovarian cancer, prostate cancer, pancreatic cancer, bladder cancer, or a lung cancer.

VII. EXAMPLES

The following examples are included for illustrative purposes only and are not intended to limit the scope of the invention.

Example 1: Isolation of Antibody Against Tumor Antigen

Tumor infiltrated lymphocytes (TILs) were harvested from pancreatic cancer patients, and B-cells were isolated using a negative selection-based human B-cell enrichment kit (Stem Cell Technologies). Selected B cells were then subjected to single-cell IgG sequencing, generally as described in WO2016044227, WO2016176322 and WO2012048340, using IgG-specific primers, to determine the sequences of paired variable heavy (VH) and variable light (VL) chains of IgG molecules in the B cells isolated from the tumors.

The sequenced antibodies were then cloned, expressed, and tested for binding reactivity to six different cancer-derived cell lines, SK-BR-3, MiaPaCa2, Panc1, Panc10.05, SU8686, and BxPC3, using surface and intracellular flow cytometry. An exemplary antibody that exhibited positive reactivity to the cancer cell lines contained a variable heavy (VH) chain set forth in SEQ ID NO:1 (encoded by a sequence of nucleotides set forth in SEQ ID NO:3) and a variable light (VL) chain set forth in SEQ ID NO: 2 (encoded by a sequence of nucleotides set forth in SEQ ID NO:4). The exemplary antibody was selected for further investigation.

Example 2: Identification of the Target Antigen

A. Immunoprecipitation and Mass Spectrometry to Identify Candidate Target Proteins Whole cell lysates of exemplary ovarian or leukemia cell lines were used for immunoprecipitation experiments with the antibody identified in Example 1. The identified antibody was covalently conjugated to magnetic epoxy beads, and 10 µg of bead-bound antibody were incubated with 1-2 mL whole cell lysate (at 1 mg protein/mL lysate) of ovarian carcinoma cell line (OvCar8) or acute myeloid leukemia cell line (SKM1). The cell lysates were also incubated with control antibodies known to bind the cell line, or beads alone. The immunoprecipitates were then washed and eluted first with low pH, and second with a cationic detergent elution buffer. The eluates were resolved by SDS-PAGE and stained with a protein stain to visualize the bands.

The immunoprecipitation produced multiple bands. Bands at approximately 220 kDa and 70-80 kDa were enriched in the immunoprecipitation with the identified antibody. The bands were excised, separately in-gel digested with trypsin, and analyzed by tandem mass spectrometry. The spectra generated from each sample were analyzed for protein identification. Protein abundance was estimated by summing the spectral counts (total peptide count per protein). The top 10 proteins that were enriched with the antibody identified in Example 1, in the immunoprecipitations from the Ovcar8 and SKM1 lysates, were selected for further evaluation.

B. Target Validation by Immunoprecipitation and Western Blot

The immunoprecipitation with the identified antibody was repeated, with OvCar8 cells and also SKBR3 (breast cancer) and MIAPACA2 (pancreas carcinoma) cell lines. The eluates were resolved by SDS-PAGE, transferred for Western blot analysis using rabbit polyclonal antibodies specific to the top 10 candidate proteins identified in part A: RalGapa2, RalGapB, SPTAN1, IMPDH2, DNAJC13, SPTAN1, SNRNP200, PRPF8, CCT4, and CCT2. CCT2 and CCT4 were specifically detected in the immunoprecipitates from all assessed cancer cell lines. No bands corresponding to the other proteins were detected. CCT2 and CCT4 are both part of the TCP1 ring complex (TRiC).

C. Target Validation by Mass Spectrometry of Total Immunoprecipitation Eluate Immunoprecipitation eluates from OvCar8, MIAPaCa2, SKM-1, and SKBR3 cell lines, using the antibody identified in Example 1, control antibodies with known targets or beads only, were resolved by SDS-PAGE. Each lane was divided into two fractions, digested, and analyzed by tandem mass spectrometry as described above. Proteins specifically enriched by the antibody identified in Example 1 were determined after eliminating peptides identified from the bead only or control antibody conditions.

The majority of the proteins enriched with the antibody identified in Example 1 were part of the TRiC protein complex, indicating the antibody specifically immunoprecipitates this complex.

D. Target Validation by Peptide Array

Peptide array analysis using peptide arrays covering all human proteins was employed for the analysis of antibody specificity (Forsström et al., Mol Cell Proteomics. 2014 June; 13(6): 1585-1597). The top identified epitope peptide was from human CCT5, which is a protein present in the TRiC ring complex. In this assay, the antibody appeared to bind preferentially to a CCT5 peptide comprising the sequence TSVEDYKA (SEQ ID NO: 70). A pattern of binding to peptides comprising a similar sequence emerged, all comprising the sequence XSVEXXKX (SEQ ID NO: 68), wherein X could be any amino acid.

E. Target Confirmation by ELISA

Figure 1B:
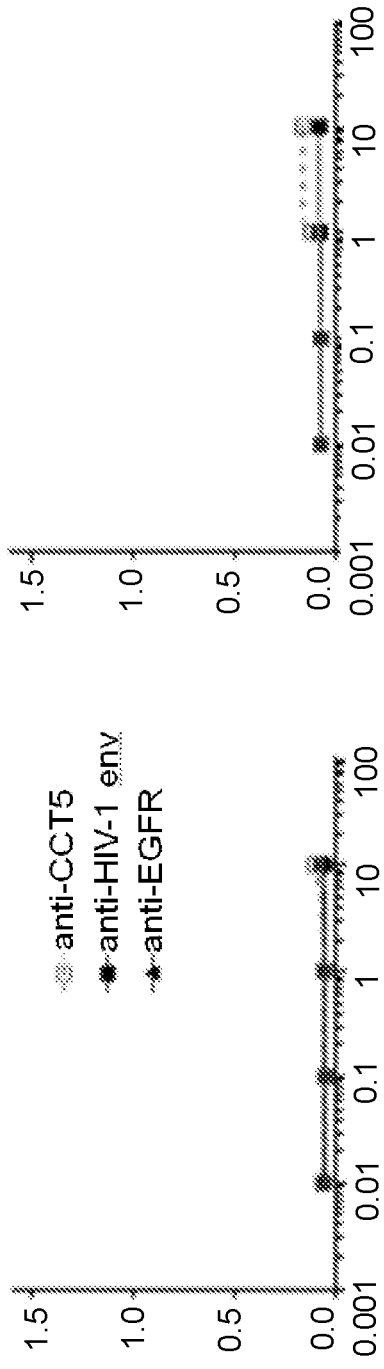
Figure 1B:
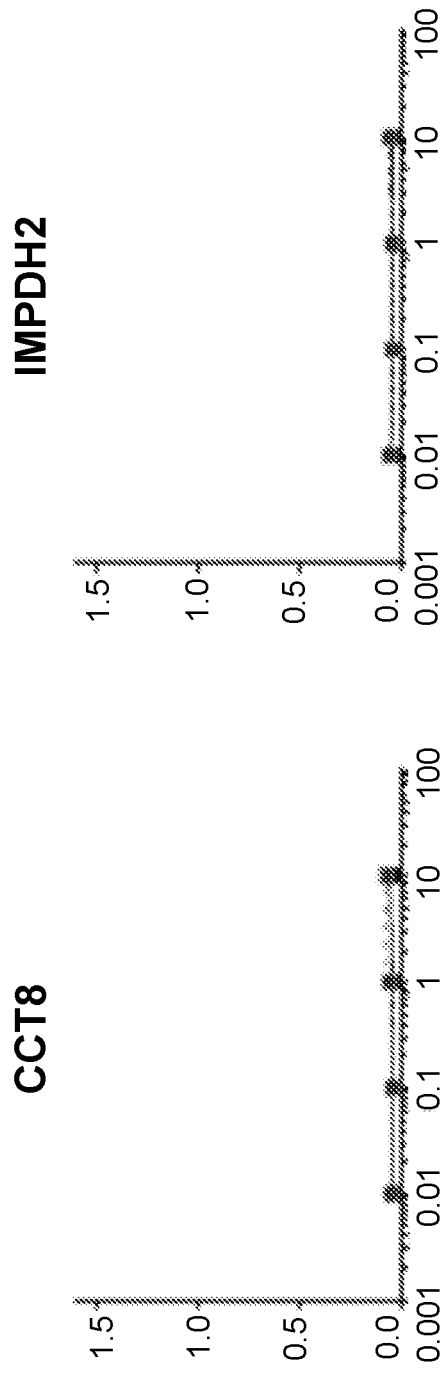

Recombinant proteins from the TriC ring complex were immobilized and probed with the antibody identified in Example 1 or control non-target antibodies. As shown in FIG. 1A and FIG. 1B, the antibody identified in Example 1 only bound to protein CCT5, in a dose-dependent manner, but did not bind to any other proteins from the complex. The negative control antibodies did not bind any of the immobilized recombinant proteins from the TriC ring complex.

F. Target Confirmation by Western Blot

Figure 2:
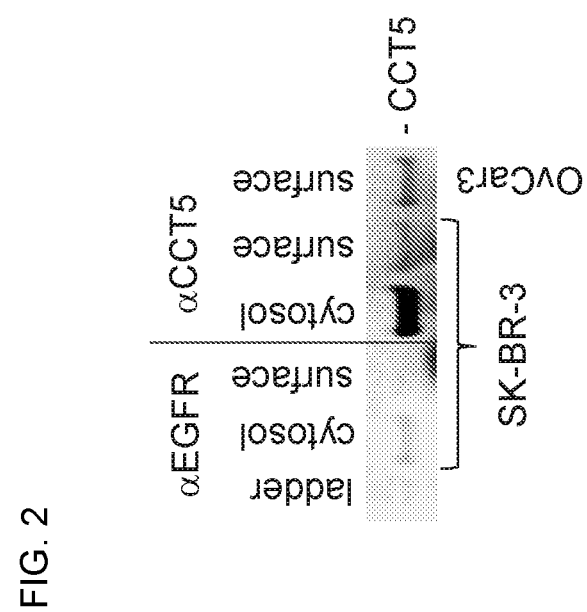
FIG. 2 depicts detection of TRiC proteins on the cell surface by immunoprecipitation.

Cytosolic and plasma membrane (surface) lysate preparations of SK-BR-3 and OvCar3 cells were probed by Western blot for CCT5 after immunoprecipitation with the antibody identified Example 1, or a negative control antibody, Panitumumab. As shown in FIG. 2, TRiC protein CCT5 was detected by immunoprecipitation with the exemplary antibody from Example 1 in both the plasma membrane and cytosolic lysate fractions of SK-BR-3, as well as the plasma membrane fraction in OvCar3. The negative control antibody showed slight CCT5 detection in the cytosolic lysate fraction of SK-BR-3, but none in the plasma membrane lysate fraction.

Example 3: Generation of CARs Against CCT5

The VH and VL chains of the exemplary anti-CCT5 antibody identified in Example 1 were cloned into a lentiviral backbone containing the coding sequence for a chimeric antigen receptor (CAR), under the regulation of an EF1a promoter (SEQ ID NO: 82) or an MND promoter (SEQ ID NO:27). Six formats of CARs were generated, including two orientations of the VH and VL chains and three different spacers, each having different lengths. The encoded CARs contained an antigen-binding domain containing the variable heavy chain and variable light chain in either VH/VL or VL/VH orientations, separated by a (Gly$_4$Ser)$_4$ linker (SEQ ID NO: 10); an extracellular spacer having: an IgG4/IgG2 hinge-IgG2/IgG4 CH2-IgG4 CH3 (SEQ ID NO: 5), an IgG4 hinge-CH3 (SEQ ID NO: 81), or an IgG4 hinge (SEQ ID NO: 6); a human CD28 transmembrane domain (SEQ ID NO: 7); a human 4-1BB-derived intracellular co-signaling sequence (SEQ ID NO: 8); and a human CD3-zeta derived intracellular signaling domain (SEQ ID NO: 9). The constructs also contained a coding sequence for green fluorescent protein reporter for use as a transduction marker, which was separated from the CAR via a T2A ribosomal skip element-encoding sequence.

Example 4: Jurkat CAR Screening Assay

An exemplary Jurkat reporter cell line, containing a nucleic acid encoding a red fluorescent protein reporter under the control of a Nur77 promoter, was used to assess activity of T cells expressing the exemplary CARs described in Example 3 under various conditions.

Various compositions of cells of the exemplary Nur77 reporter cell line were transduced with lentiviral vectors individually encoding the CAR constructs as described in Example 3.

The reporter T cells were transduced with lentiviral constructs encoding the various anti-CCT5 CAR, each differing in the extracellular spacer having either: an IgG4 hinge, IgG4 hinge-CH3, or IgG4/IgG2 hinge-IgG2/IgG4 CH2-IgG4 CH3. In addition, reporter T cells also were transduced with an anti-EGFR CAR with an extracellular spacer having an IgG4/IgG2 hinge-IgG2/IgG4 CH2-IgG4 CH3 (control). Expression of all constructs was under an EF1a promoter. The CAR-expressing reporter cells were co-cultured with a tumor cell line for which the antibody had been shown to be reactive. Nur77 reporter and surface expression of CD69 was then assessed by flow cytometry. For each condition, percentage of cells observed to be positive for surface expression of CD69 and the Nur77 reporter signal, above the percentage observed in cells cultured with media alone (i.e., no target cells), was determined as an indicator of level of activation was calculated.

All CAR-expressing Jurkat T cells were observed to exhibit increased levels of activation (as indicated by reporter and CD69 levels) in response to increased numbers of target cells. The anti-CCT5 CAR-expressing Jurkat cells exhibited maximum activation at about 20,000 target cells per well, when the well reached confluency. Reporter cells expressing the anti-CCT5 CAR with the IgG4 hinge spacer exhibited the highest level of activation. Anti-EGFR CAR-expressing cells achieved 100% activation at 2,500 target cells per well. Reporter cells expressing anti-EGFR CAR with an IgG4 hinge spacer approached 100% activation at approximately 750 target cells/well.

Example 5: CAR-Expressing T-Cell Function Following Incubation with Cancer Cell Lines and Primary Cells Jurkat reporter T cells containing cells that had been transduced with the various anti-CCT5 CARs, each expressed under the control of the EF1a promoter were incubated with various cell lines or primary cells. Expression of the reporter and CD69 were determined using flow cytometry. CAR positive cells were determined by flow cytometry based on GFP expression and/or anti-IgG staining. Percentage of CAR-expressing cells detected as positive for both surface CD69 expression and the reporter signal (and the difference of this percentage above signal observed for cells cultured in media alone (i.e., in the absence of target cells), was calculated for each condition as an indicator of activation.

A. Human Cells

Anti-CCT5 CAR Jurkat reporter cells were incubated for 2 days in 96-well cell culture plates with exemplary human tumor cell lines: breast cancer (SK-BR-3, MCF7, HCC 1806, HCC 2218, BT549, and MDA-MB-231), pancreatic cancer (MIA PaCa-2, PANC-1, BxPC-3, SU86.86, and Panc10.05), ovarian cancer (OVCAR-8, Caov-3, ES-2, NIH: OVCAR-3, and OVCAR-4), lung cancer (A549, NCI-H1975, NCI H1299, NCI H1573, and NCI H1915), head and neck squamous cell carcinoma (HNSCC; UPCI:SCC152), cervical cancer (CaSki), dermal cancer (SV-80), acute myeloid leukemia (AML; Kasumi-1, SH-2, HT-93, HL60, ML-2, BDCM, KG-1, SKM-1, THP-1, and OCI-M1) or chronic myeloid leukemia (CML; K-562). In this experiment, adherent cells were used at confluence and incubated with transduced cells. For non-adherent cells, a target 1:1 E:T ratio was used. Anti-CCT5 CAR-expressing Jurkat reporter cells exhibited response following incubation with at least one cell line representing each indication.

In another study, anti-CCT5 CAR Jurkat reporter cells were incubated with normal human cells: primary dermal fibroblasts, human umbilical vein cells (HUVEC), pancreatic endothelial, brain endothelial, and a panel of epithelial cell samples, including those generated from epidermal keratinocytes, renal, mammary, prostate, cervical, colonic, pancreatic, ovarian surface, pulmonary alveolar, and esophageal. Anti-CCT5 CAR Jurkat reporter cells also were incubated with primary cells obtained from a healthy human donor, including cells from an apheresis sample, peripheral blood mononuclear cells (PBMCs) therefrom, or CD4+ T cells, CD8+ T cells, or cells from the negative blood fraction (e.g. CD4- and CD8- T cells) that had been enriched by immunoaffinity-based selection. In this assay, an increase in surface CD69 and Nur77 reporter signal were observed in CAR-expressing T cells when incubated with six out of ten human primary epithelial cell samples, including epidermal keratinocytes and mammary, prostate, cervical, colonic, and ovarian surface epithelial cells. No activity of the CAR-expressing T cells against the other human cells tested was observed.

B. Non-Human Cells

In a further study, binding of the anti-CCT5 antibody to murine CCT5, in B16-F10 (melanoma) cells, was also confirmed by immunoprecipitation and Western blot. To further assess binding to murine cells, Jurkat reporter cells that had been transduced to express the anti-CCT5 CARs were incubated with exemplary murine cells lines, including: primary mouse renal epithelial cells, primary mouse mammary epithelial cells and the A20 (B lymphoma), CT26 (colon), LL/2 (lung), B16-F10 (melanoma), B16-F1 (melanoma), NIH3T3 (embryonic fibroblast), ID8 (ovarian), and EpH4-1424 (mammary epithelial tumor) immortalized mouse lines. In this reporter assay, no or a low level of increased reporter signal (compared to CAR-containing Jurkat cells incubated without target cells) was observed following incubation with the various assessed target cells.

Anti-CCT5 CAR Jurkat reporter cells described above were also incubated with exemplary non-human primate (NHP) cells, including 4MBr-5 Rhesus (*Macaca mulatta*) lung epithelial line and a panel of Cynomolgus (*Macaca fascicularis*) primary epithelial cell samples, including those generated from renal, small airway, and large airway epithelial cells. A substantially higher reporter signal was observed following incubation with Cynomolgus small airway and large airway epithelial cells, but compared to 4MBr-5 or Cynomolgus renal epithelial cells. These results are consistent with a finding that the anti-CCT5 CAR-expressing cells exhibit some reactivity against certain non-human cells.

Example 6: Assessment of Target Specificity CAR-Expressing T-Cells

Activation of anti-CCT5 CAR-expressing T cells was tested in response to other members of from the TRiC Ring. Jurkat reporter T cells that had been transduced with various anti-CCT5 CAR, as described in Example 4 above, were plated in uncoated wells or in wells containing immobilized recombinant proteins from the TRiC ring complex, CCT1, CCT2, CCT3, CCT4, CCT5, CCT8 and CCTr1. Expression of the reporter and CAR positive cells based on GFP expression were determined by flow cytometry. Only incubation with recombinant CCT5 yielded activation of the anti-CCT5 CAR-expressing reporter T cells above baseline.

Example 7: Localization of CCT5 in Cell Lines

Cells from a breast cancer cell line that resulted in anti-CCT5 CAR activity, as determined by reporter/CD69 levels, in Example 5 and an ovarian cancer cell line to which anti-CCT5 CAR-expressing reporter T cells did not respond in Example 5 were examined for CCT5 localization by confocal fluorescent microscopy. CCT5 was detected using a polyclonal anti-CCT5 antibody, the membrane was labeled with wheat germ agglutinin (WGA), and the nuclei were identified using DAPI (4',6-diamidino-2-phenylindole). Cells to which the anti-CCT5 CAR was not observed to respond in Example 5 exhibited diffuse cytoplasmic and/or perinuclear localization of CCT5. Cells that induced a response from the anti-CCT5 CAR cells exhibited increased CCT5 staining that was distributed as small aggregates that may be associated with or localized to the membrane over the surface of the entire cell. Some diffuse cytoplasmic staining of CCT5 was also observed in these cells.

Example 8: Anti-CCT5 CAR Expression on Primary T Cells

Primary human T cells (CD4+ and CD8+ T cells) from human donors were stimulated and transduced with lentiviral constructs encoding anti-CCT5 CAR, generated as described in Example 3, which included constructs under the regulation of an EF1a or MND promoter, and with an IgG4 hinge spacer, IgG4 hinge-CH3 spacer, or IgG4/IgG2 hinge-IgG2/IgG4 CH2-IgG4 CH3 extracellular spacer. Transduction efficiency and CAR expression were assessed by flow cytometry at 5 and 14 days post infection. Transduction efficiency and CAR expression were also tested in primary human T cells, which were stimulated and transduced with lentiviral constructs encoding an anti-EGFR CAR, with a IgG4/IgG2 hinge-IgG2/IgG4 CH2-IgG4 CH3 spacer, under the regulation of an EF1a or MND promoter, as a control.

Figure 3A:
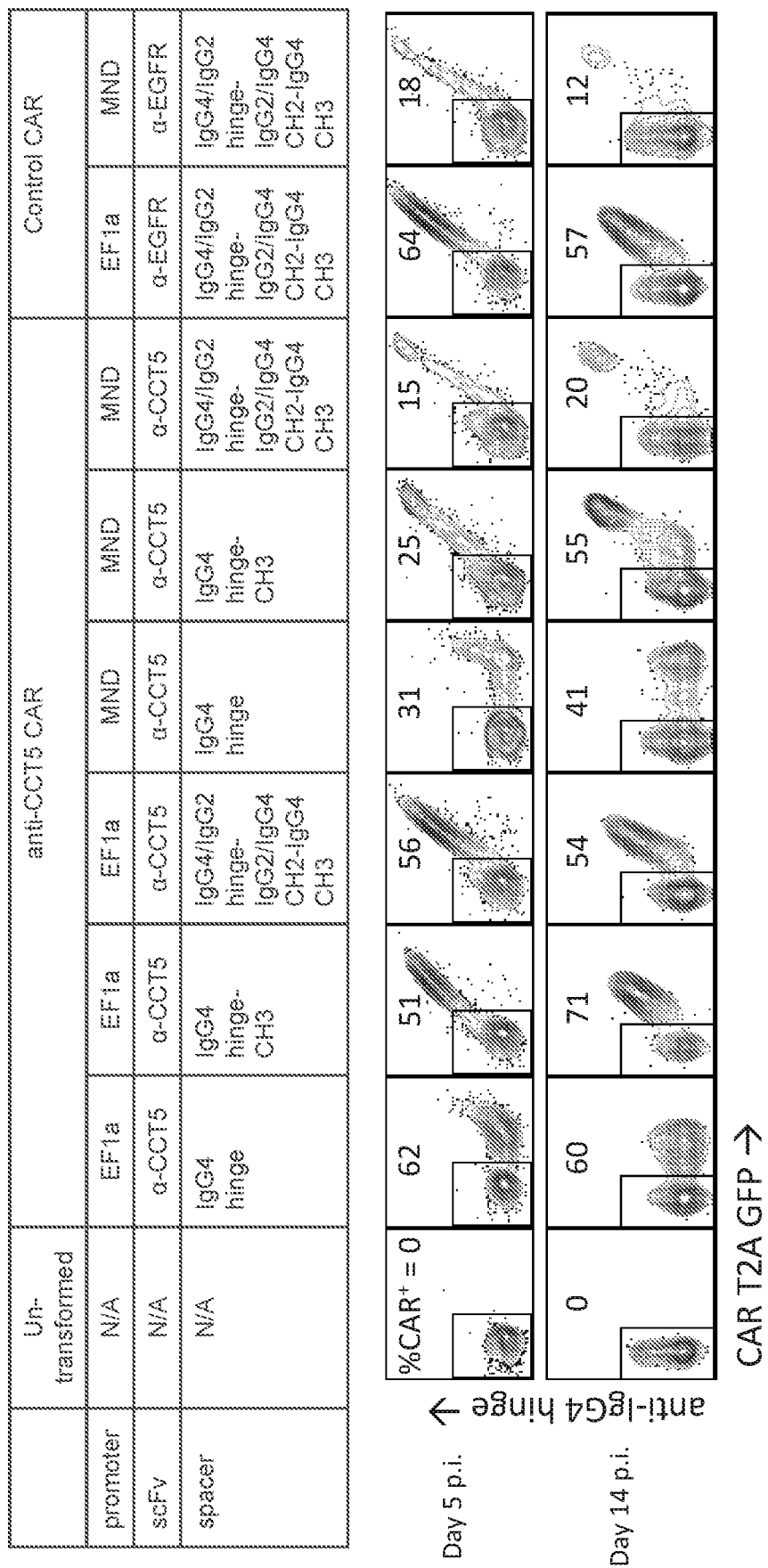
FIG. 3A depicts the expression of various anti-CCT5 CARs, indicated by GFP expression and IgG4 hinge detection.
Figure 3B:
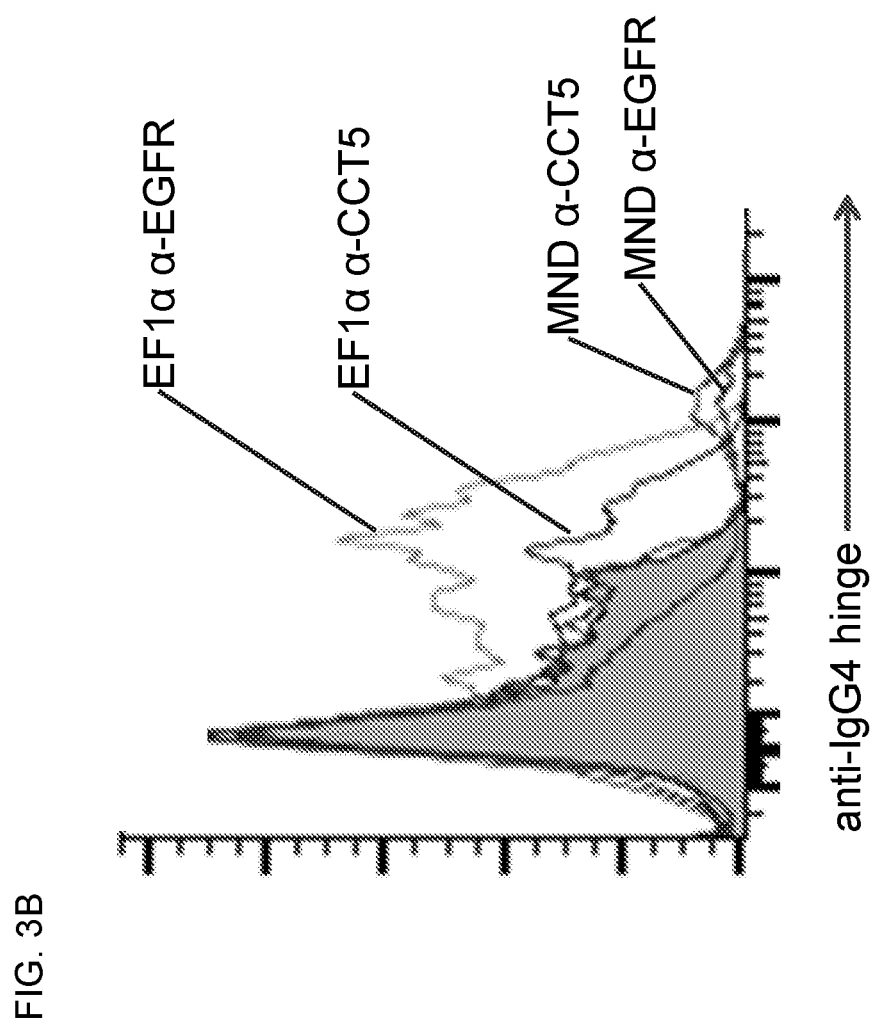
FIG. 3B depicts the transduction efficiency of the indicated CAR constructs.

The lentiviral constructs contained a GFP sequence that was separated from the CAR sequence by a T2A self-cleaving peptide, which served as a marker for transduction. CAR expression was detected by a fluorescently labeled anti-IgG4 hinge antibody. Events were plotted as GFP (infection) vs. anti-IgG4 hinge (CAR expression). Expression of the CARs in primary human T cells is shown in FIG. 3A. As shown in FIG. 3B, in this assay, certain MND promoter constructs exhibited lower transduction efficiency, but expressed higher levels of CAR.

Example 9: Cytolytic Activity of Anti-CCT5 CAR-Expressing T Cells

Anti-CCT5 and anti-EGFR CAR-expressing primary human T cells, from Example 8 above, were incubated with SK-BR-3 (breast cancer), MIA PaCA-2 (pancreatic cancer), and OvCar4 (ovarian cancer) target cells. Anti-CCT5 and anti-EGFR CAR-expressing primary human T cells, from Example 9 above, were also incubated with UPCI:SCC152 (head and neck squamous cell carcinoma) at effector to target (E:T) ratios of 4:1 and 1:1. Target cells were also incubated with mock-processed T cells or no cells as controls. To perform the cytolytic assay, the target cells were labeled with NucLight Red (NLR) to permit tracking of target cells by microscopy. Cytolytic activity was assessed by measuring the loss of viable target cells over a period of 92 hours, as determined by red fluorescent signal (using the INCUCYTE® Live Cell Analysis System, Essen Bioscience).

SK-BR-3 and MIA PaCa-2 target cells that were untreated or incubated with mock-processed CAR T cells exhibited progressive growth over the course of the study. OvCar4 target cells that were untreated or incubated with mock-processed CAR T cells exhibited growth that peaked at about 30 hours, and returned to at or below baseline at about 48 hours, and remained at a steady level for the remainder of the study. UPCI:SCC152 target cells that were untreated or incubated with mock-processed CAR T cells exhibited growth that peaked at about 60 hours.

Target cells incubated with CAR T cells expressing anti-CCT5 CAR with an IgG4 hinge spacer, IgG4 hinge-CH3 spacer or IgG4/IgG2 hinge-IgG2/IgG4 CH2-IgG4 CH3 spacer, under the regulation of an EF1a promoter, exhibited similar or slightly reduced growth compared to untreated or mock-processed T cell-treated conditions. Incubation with anti-EGFR CAR-expressing T cells resulted in progressive decreases in the number of target cells for all three target cell lines.

MIA PaCa-2 target cells incubated with anti-CCT5 CAR with an IgG4 hinge spacer, IgG4 hinge-CH3 spacer or IgG4/IgG2 hinge-IgG2/IgG4 CH2-IgG4 CH3 spacer, under the regulation of an MND promoter exhibited reduced growth compared to the untreated or mock-processed T cell-treated conditions. SK-BR-3, UPCI:SCC152 and OvCar4 target cells incubated with anti-CCT5 CAR with an IgG4 hinge spacer, IgG4 hinge-CH3 spacer, or IgG4/IgG2 hinge-IgG2/IgG4 CH2-IgG4 CH3 spacer, under the regulation of an MND promoter exhibited a decline in the number of target cells, demonstrative of cell death under these conditions. In this assay, among the assessed anti-CCT5 CARs, the anti-CCT5 CAR with an IgG4 hinge-CH3 spacer, under the regulation of an MND promoter was most effective at reducing proliferation of or killing target cells, compared with CARs comprising other spacers or under the control of a different promoter.

Example 10: Characteristics of Anti-CCT5 CAR-Expressing Cells Following Incubation with Target Cells CD4+ and CD8+ primary human T cells expressing anti-CCT5 CAR or anti-EGFR, as described in Example 8 above, were incubated with A549 (adenocarcinoma), SK-BR-3 (breast cancer), MIA PaCA-2 (pancreatic cancer), OvCar4 (ovarian cancer), and UPCI:SCC152 (head and neck squamous cell carcinoma) target cells and media only for 2.5 days. Target tumor cells were also incubated with non-processed T cells as a control. Following incubation, the T cells were analyzed for shifts in phenotype corresponding to naïve T ($T_N$) cells (CD45RA+, CD26L−), central memory T ($T_{CM}$) cells (CD45RA−, CD26L+), and effector memory T ($T_{EM}$) cells (CD45RA−, CD26L−). Cells were also assessed for activation (CD25+) and exhaustion markers (PD-1). When incubated with tumor cell lines, anti-CCT5 CAR-expressing T cells expressed phenotypic activation markers (CD25+, CD45RA+CD62Llo) without exhaustion markers (PD-1).

After 24 hours of co-culture, supernatants were collected and analyzed for IL-2, IFNγ, and TNFα release. All three cytokines were detected in the supernatant of co-cultures containing all five cancer cell types incubated with T cells expressing anti-CCT5 CAR with the IgG4 hinge-CH3 spacer, under the regulation of the MND promoter. Detectable cytokine production also was observed in supernatants of co-cultures containing cancer cells that had been incubated with T cells expressing anti-CCT5 CAR with the IgG4-hinge spacer under the regulation of the MND promoter.

CD4+ and CD8+ primary human T cells expressing anti-CCT5 CAR or anti-EGFR, generated as described in Example 8 above under the regulation of the MND promoter, were stained with the proliferation dye CellTrace™ Violet (ThermoFisher Scientific) and then incubated with UPCI.SCC152 (head and neck squamous cell carcinoma)-target cells and media only for 4 days. Target tumor cells were also incubated with non-processed T cells as a control. Following incubation, the T cells were analyzed for dilution of the CellTrace™ Violet dye as distinct peaks indicating successive generations of cell division. When incubated with SCC152, anti-CCT5 CAR-expressing CD4+ and CD8+ T cells showed dilution of the CellTrace™ Violet dye, indicating proliferation, compared to the untransduced T cells in the same culture. When incubated in media without tumor cell lines, both anti-CCT5 CAR-expressing and untransduced CD4+ and CD8+ T cells exhibited a similar maintained intensity of the dye, consistent with the effect being target specific.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

| # | SEQUENCE | ANNOTATION |
|---|---|---|
| 1 | EVQLVESGGGLVQPGGSLRLSCAASGFTFSSYSMNWVRQAPGKGLEWVSYISSSSSTIYYADSVKGRFTISRDNAKNSLYLQMNSLRDEDTAVYYCARDFKGDCSSTSCYRGGYYYYYGMDVWGQGTTVTVSS | Antibody variable heavy (VH) chain (aa) |
| 2 | SYELTQPPSVSVSPGQTASITCFGDQLGDKYVSWYQKKPGQSPVLVIYQDANRPSGIPERFSGSNSGNTATLTIRGTQNLDEADYYCQTWGTTTALFGGGTKLTVL | Antibody variable light (VL) chain (aa) |
| 3 | gaggtgcagcttgtggagtcaggcggagggcttgtacagcccggcggcagtcttagactcagttgtgccgcctctggctttacttttctcatcttactccatgaactgggtgagacaggcccctggaaaaggacttgagtgggttagttatatttcatcttcaagcagcacaatatattatgcagactcagtgaagggcagattcaccattagtcgggacaatgcaaaaaacagtctgtacttgcagatgaattccctcagggatgaagatacagcagtgtactattgtgccagagacttcaaaggcgattgctcctctacgtcctgctatcgcggtggatactactattattatggaatggacgtttggggccagggtaccacagtgaccgtgtcttcc | Antibody variable heavy (VH) chain (nt) |
| 4 | agctatgagctgacccagcccccctccgttagcgtcagtcccggtcaaaccgccagcatcacctgtttcggggaccagctgggagataagtatgtgagctggtatcagaaaaaaccaggtcagtctcccgtgcttgtcatttatcaggatgccaacagaccaagcgggatccctgaacgattctcagggagcaacagcgggaatactgccacgcttactatcaggggcaccagaatctggacgaggccgattactactgccaaacctgggggacaacaactgcgctgttcggcgggggcacaaagctgaccgttctg | Antibody variable light (VL) chain (nt) |
| 5 | ESKYGPPCPPCPAPPVAGPSVFLFPPKPKDTLMISRTPEVTCVVVDVSQEDPEVQFNWYVDGVEVHNAKTKPREEQFQSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK | IgG4/IgG2 hinge-IgG2/IgG4 CH2-IgG4 CH3 extracellular spacer |
| 6 | ESKYGPPCPPCP | Human IgG4 hinge extracellular spacer (aa) |
| 7 | FWVLVVVGGVLACYSLLVTVAFIIFWV | Human CD28 transmembrane domain (aa) |
| 8 | KRGRKKLLYIFKQPFMRPVQTTQEEDGCSCRFPEEEEGGCEL | Human 4-1BB-derived intracellular co-signaling sequence (aa) |
| 9 | RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | Human CD3-zeta derived intracellular signaling domain (aa) |
| 10 | GGGGSGGGGSGGGGSGGGGS | (Gly$_4$Ser)$_4$ linker |
| 11 | SYSMN | CDR-H1 |
| 12 | YISSSSSTIYYADSVKG | CDR-H2 |
| 13 | DFKGDCSSTSCYRGGYYYYYGMDV | CDR-H3 |
| 14 | GFTFSSY | CDR-H1 |
| 15 | SSSSST | CDR-H2 |
| 16 | GFTFSSYSMN | CDR-H1 |
| 17 | WVRQAPGKGLEWVS | CDR-H2 |
| 18 | SSYSMN | CDR-H1 |
| 19 | WVSYISSSSSTIY | CDR-H2 |
| 20 | ARDFKGDCSSTSCYRGGYYYYYGMD | CDR-H3 |
| 21 | FGDQLGDKYVS | CDR-L1 |
| 22 | QDANRPS | CDR-L2 |
| 23 | QTWGTTTAL | CDR-L3 |
| 24 | DKYVSWY | CDR-L1 |
| 25 | LVIYQDANRP | CDR-L2 |

| # | SEQUENCE | ANNOTATION |
|---|---|---|
| 26 | QTWGTTTA | CDR-L3 |
| 27 | tttatttagtctccagaaaaggggggaatgaaagaccccacctgt aggtttggcaagctaggatcaaggttaggaacagagagacagcaga atatgggccaaacaggatatctgtggtaagcagttcctgccccggc tcagggccaagaacagttggaacagcagaatatgggccaaacagga tatctgtggtaagcagttcctgccccggctcagggccaagaacaga tggtccccagatgcggtcccgccctcagcagtttctagagaaccat cagatgtttccagggtgccccaaggacctgaaatgaccctgtgcct tatttgaactaaccaatcagttcgcttctcgcttctgttcgcgcgc ttctgctccccgagctcaataaaagagccca | MND promoter |
| 28 | CAUGAAGAUCUUGUCAAUGA | Human Nur77 gRNA 1 targeting domain |
| 29 | UGCACACGUGUUCCCAGGC | Human Nur77 gRNA 2 targeting domain |
| 30 | cagcctcctaaagtgctgggattacaggtgtgagccaccacgccta gcccttcactgtgacttctgacagtgcagatcagattggttgtgcc tgttttggactttatgtaaatgtagttctgcaggatggaatctggt gttgaatgcagaggttttcagatttctctgttttttaaaggaaaga atccaccctcgttcattttttcacttaaattgcacaggggacccaa cgatatagaacacaatcagaggtactctgggctgagggagtgctga gttctgaggctgggtttctcagaacagtctagattttaaaaaccca atgatctagccagaaaacgtaggttaggattttatttcccgtttgt gaccctgggcaagtcattagcctcctgggcctcgggttctcacttg gagtatgaggataatgagggttactgcttctcagacttgtgacgat gcttactaatggccaacatgtgaatgcgcttttgtgaagtgccagc agagcatgaggggtggtcaggggcagcagttttagggggctggggg aggctgggcctttgggggcctggttctcagatgtacagctaatcct gtacccttcccgcagaccggcatgggctgcaggagccgcggcgggt ggaggagctgcagaaccgcatcgccagctgcctgaaggagcacgtg gcagctgtggcgggcgagcccagccagccagctgcctgtcacgtc tgttgggcaaactgcccgagctgcggaccctgtgcacccagggcct gcagcgtatcttctacctcaagctggaggacttggtgccccctcca cctatcatcgacaagatcttcatggacacgctgcccttcggatccg gagaaggcagaggctctctcctcacatgtggggatgttgaagaaaa tccaggtcccggtgtgagcaagggcgaggaggtgatcaaggagttt atgagattcaaagtccggatggagggcagcatgaacggacatgagt tcgaaattgagggagaaggcgagggacgaccttacgagggaacaca gaccgccaaactgaaagtgacaaaaggcggacctctgccatttgct tgggacatcctgagtccacagttcatgtatggctctaaggcttacg tgaaacaccctgccgatattcccgactacaaaaaactgagtttccc tgaaggcttcaaatgggaacgagtgatgaactttgaggacggaggc ctggtgacagtgacacaggactctagtctccaggacggcacactca tctacaaagtgaaaatgaggggcaccaatttccctcccgatggacc tgtcatgcagaaaaaaacaatgggatgggaggcttctaccgaacga ctgtacccacgggatggagtgctgaaaggcgagatccatcaggcac tgaaactgaaggatggcggccattacctggtcgagttcaaaaccat ctatatggccaaaaaacccgtccagctgcctggctactattacgtg gataccaaactggacattacctctcacaatgaagactacacaatcg tcgagcagtacgagaggagtgagggccgacaccacctcttcctcgg gcatggcaccggcagcaccggcagcggcagctccggcaccgctagt tccgaggacaacaacatggccgtcatcaaagagttcatgcgcttca aggtgcgcatggagggctccatgaacggccacgagttcgagatcga gggcgagggcgagggccgcccctacgagggcacccagaccgccaag ctgaaggtgaccaaggcggccccctgcccttcgcctgggacatcc tgtcccccagttcatgtacggctccaaggcgtacgtgaagcaccc cgccgacatccccgattacaagaagctgtccttccccgagggcttc aagtgggagcgcgtgatgaacttcgaggacggcggtctggtgaccg tgacccaggactcctccctgcaggacggcacgctgatctacaaggt gaagatgcgcggcaccaacttccccccgacggcccccgtaatgcag aagaagaccatgggctgggaggcctccaccgagcgcctgtaccccc gcgacggcgtgctgaagggcgagatccaccaggccctgaagctgaa ggacggcggccactacctggtggagttcaagaccatctacatggcc aagaagcccgtgcaactgcccggctactactacgtggacaccaagc tggacatcacctcccacaacgaggactacaccatcgtggaacagta cgagcgctccgagggccgccaccacctgttcctgtacggcatggac gagctgtacaaatgactgagcctgggaacacgtgtgcacatgcgc actctcatatgccaccccatgtgcctttagtccacggaccccccaga gcaccccaagcctgggcttgagctgcagaatgactccaccttctc acctgctccaggaggtttgcagggagctcaagccctggggagggg gatgccttcatgggggtgaccccacgatttgtcttatccccccag | Nur77 knock-in construct sequence |

| # | SEQUENCE | ANNOTATION |
|---|---|---|
| | cctggccccggcctttatgttttttgtaagataaaccgtttttaac<br>acatagcgccgtgctgtaaataagcccagtgctgctgtaaatacag<br>gaagaaagagcttgaggtgggagcggggctggaggaagggatggg<br>ccccgccttcctgggcagcctttccagcctcctgctggctctctct<br>tcctaccctccttccacatgtacataaactgtcactctaggaagaa<br>gacaaatgacagattctgacatttatatttgtgtattttcctggat<br>ttatagtatgtgacttttctgattaatatatttaatatattgaata<br>aaaaatagacatgtagttggaactgagattcagtctgtctctgatg<br>cccctccccactccccaccagacacaccccatcattacataaga<br>gatgggctgctcaagatgaaacttggatgttaccagcctgagctgt<br>caggcctcagtgtactcatttgtaaaaggcggataataatgacacc<br>tgcttcacgaggttgttatgcaaagcacttagactaatttctaaca<br>cgtgggaagcctgcattagctgtgcctggctagctgtgcctggctc<br>attgctggggtctgcagtggctgactagcccaggggtcactgcagg<br>gccctagcaatagacttagccgcagatctcaggttgtcatgtttc<br>ctaaactggacatatattctctgattcttgatttccacatccataa<br>aacaagaatagacccagcctcacagagct | |
| 31 | gaaggcagaggctctctcctcacatgtggggatgttgaagaaaatc<br>caggtccc | T2A DNA |
| 32 | EGRGSLLTCGDVEENPGP | T2A peptide (aa) |
| 33 | GSGEGRGSLLTCGDVEENPGP | T2A peptide (aa) |
| 34 | LEGGGEGRGSLLTCGDVEENPGPR | T2A peptide (aa) |
| 35 | ATNFSLLKQAGDVEENPGP | P2A peptide (aa) |
| 36 | GSGATNFSLLKQAGDVEENPGP | P2A peptide (aa) |
| 37 | QCTNYALLKLAGDVESNPGP | E2A peptide (aa) |
| 38 | GSGQCTNYALLKLAGDVESNPGP | E2A peptide (aa) |
| 39 | VKQTLNFDLLKLAGDVESNPGP | F2A peptide (aa) |
| 40 | GSGVKQTLNFDLLKLAGDVESNPGP | F2A peptide (aa) |
| 41 | gtgagcaagggcgaggaggtgatcaaggagtttatgagattcaaag<br>tccgaatggagggcagcatgaacggacatgagttcgaaattgaggg<br>agaaggcgagggacgaccttacgagggaacacagaccgccaaactg<br>aaagtgacaaaaggcggacctctgccatttgcttgggacatcctga<br>gtccacagttcatgtatggctctaaggcttacgtgaaacaccctgc<br>cgatattcccgactacaaaaaaactgagttttccctgaaggcttcaaa<br>tgggaacgagtgatgaactttgaggacggaggcctggtgacagtga<br>cacaggactctagtctccaggacggcacactcatctacaaagtgaa<br>aatgaggggcaccaatttccctcccgatggacctgtcatgcagaaa<br>aaaacaatgggatgggaggcttctaccgaacgactgtacccacggg<br>atggagtgctgaaaggcgagatccatcaggcactgaaactgaagga<br>tggcggccattacctggtcgagttcaaaaccatctatatggccaaa<br>aaacccgtccagctgcctggctactattacgtggataccaaactgg<br>acattacctctcacaatgaagactacacaatcgtcgagcagtacga<br>gaggagtgagggccgacaccacctcttcctcgggcatggcaccggc<br>agcaccggcagcggcagctccggcaccgctagttccgaggacaaca<br>acatggccgtcatcaaagagttcatgcgcttcaaggtgcgcatgga<br>gggctccatgaacggccacgagttcgagatcgagggcgagggcgag<br>ggccgcccctacgagggcacccagaccgccaagctgaaggtgacca<br>agggcggccccctgcccttcgcctgggacatcctgtcccccagtt<br>catgtacggctccaaggcgtacgtgaagcaccccgccgacatcccc<br>gattacaagaagctgtccttccccgagggcttcaagtgggagcgcg<br>tgatgaacttcgaggacggcggtctggtgaccgtgacccaggactc<br>ctccctgcaggacggcacgctgatctacaaggtgaagatgcgcggc<br>accaacttccccccgacggccccgtaatgcagaagaagaccatgg<br>gctgggaggcctccaccgagcgcctgtacccccgcgacggcgtgct<br>gaagggcgagatccaccaggccctgaagctgaaggacggcggccac<br>tacctggtggagttcaagaccatctacatggccaagaagcccgtgc<br>aactgcccggctactactacgtggacaccaagctggacatcacctc<br>ccacaacgaggactacaccatcgtggaacagtacgagcgctccgag<br>ggccgccaccacctgttcctgtacggcatggacgagctgtac | tdTomato DNA |
| 42 | VSKGEEVIKEFMRFKVRMEGSMNGHEFEIEGEGEGRPYEGTQTAKL<br>KVTKGGPLPFAWDILSPQFMYGSKAYVKHPADIPDYKKLSFPEGFK<br>WERVMNFEDGGLVTVQDSSLQDGTLIYKVKMRGTNFPPDGPVMQK<br>KTMGWEASTERLYPRDGVLKGEIHQALKLKDGGHYLVEFKTIYMAK | tdTomato protein |

| # | SEQUENCE | ANNOTATION |
|---|---|---|
| | KPVQLPGYYYVDTKLDITSHNEDYTIVEQYERSEGRHHLFLGHGTG<br>STGSGSSGTASSEDNNMAVIKEFMRFKVRMEGSMNGHEFEIEGEGE<br>GRPYEGTQTAKLKVTKGGPLPFAWDILSPQFMYGSKAYVKHPADIP<br>DYKKLSFPEGFKWERVMNFEDGGLVTVTQDSSLQDGTLIYKVKMRG<br>TNFPPDGPVMQKKTMGWEASTERLYPRDGVLKGEIHQALKLKDGGH<br>YLVEFKTIYMAKKPVQLPGYYYVDTKLDITSHNEDYTIVEQYERSE<br>GRHHLFLYGMDELY | |
| 43 | AATCTCACTATGTTGCCCGAGCTGGTCTCGAACTCCTGGGCTCAAA<br>TGATCCTCCTGTCTCAGCCTCCTAAAGTGCTGGGATTACAGGTGTG<br>AGCCACCACGCCTAGCCCTTCACTGTGACTTCTGACAGTGCAGATC<br>AGATTGGTTGTGCCTGTTTTGGACTTTATGTAAATGTAGTTCTGCA<br>GGATGGAATCTGGTGTTGAATGCAGAGGTTTTCAGATTTCTCTGTT<br>TTTTAAAGGAAAGAATCCACCCTCGTTCATTTTTTCACTTAAATTG<br>CACAGGGGACCCAACGATATAGAACACAATCAGAGGTACTCTGGGC<br>TGAGGGAGTGCTGAGTTCTGAGGCTGGGTTTCTCAGAACAGTCTAG<br>ATTTTAAAAACCCAATGATCTAGCCAGAAAACGTAGGTTAGGATTT<br>TATTTCCCGTTTGTGACCCTGGGCAAGTCATTAGCCTCCTGGGCCT<br>CGGGTTCTCACTTGGAGTATGAGGATAATGAGGGTTACTGCTTCTC<br>AGACTTGTGACGATGCTTACTAATGGCCAACATGTGAATGCGCTTT<br>TGTGAAGTGCCAGCAGAGCATGAGGGGTGGTCAGGGGCAGCAGTTT<br>TAGGGGCCTGGGGGAGGCTGGGGCTTTGGGGGCCTGGTTCTCAGAT<br>GTACAGCTAATCCTGTACCCTTCCCGCAGACCGGCATGGGCTGCAG<br>GAGCCGCGGCGGGTGGAGGAGCTGCAGAACCGCATCGCCAGCTGCC<br>TGAAGGAGCACGTGGCAGCTGTGGCGGGCGAGCCCCAGCCAGCCAG<br>CTGCCTGTCACGTCTGTTGGGCAAACTGCCCGAGCTGCGGACCCTG<br>TGCACCCAGGGCCTGCAGCGTATCTTCTACCTCAAGCTGGAGGACT<br>TGGTGCCCCCTCCACCtATCATcGACAAGATCTTCATGGACACGCT<br>GCCCTTC | Nur77 left homology arm<br>(chr12:52,058,015-52,058,941<br>hg38 assembly), with silent<br>mutations |
| 44 | GCCTGGGAACACGTGTGCACATGCGCACTCTCATATGCCACCCCAT<br>GTGCCTTTAGTCCACGGACCCCCAGAGCACCCCAAGCCTGGGCTT<br>GAGCTGCAGAATGACTCCACCTTCTCACCTGCTCCAGGAGGTTTGC<br>AGGGGAGCTCAAGCCCTTGGGGAGGGGGATGCCTTCATGGGGGTGAC<br>CCCACGATTTGTCTTATCCCCCCCAGCCTGGCCCCGGCCTTTATGT<br>TTTTTGTAAGATAAACCGTTTTTAACACATAGCGCCGTGCTGTAAA<br>TAAGCCCAGTGCTGCTGTAAATACAGGAAGAAAGAGCTTGAGGTGG<br>GAGCGGGGCTGGGAGGAAGGGATGGGCCCCGCCTTCCTGGGCAGCC<br>TTTCCAGCCTCCTGCTGGCTCTCTCTTCCTACCCTCCTTCCACATG<br>TACATAAACTGTCACTCTAGGAAGAAGACAAATGACAGATTCTGAC<br>ATTTATATTTGTGTATTTTCCTGGATTTATAGTATGTGACTTTTCT<br>GATTAATATATTTAATATATTGAATAAAAAATAGACATGTAGTTGG<br>AACTGAGATTCAGTCTGTCTCTGATGCCCCCTCCCCACTCCCCCAC<br>CAGACACACCCCATCATTACATAAGAGATGGGCTGCTCAAGATGAA<br>ACTTGGATGTTACCAGCCTGAGCTGTCAGGCCTCAGTGTACTCATT<br>TGTAAAAGGCGGATAATAATGACACCTGCTTCACGAGGTTGTTATG<br>CAAAGCACTTAGACTAATTTCTAACACGTGGGAAGCCTGCATTAGC<br>TGTGCCTGGCTAGCTGTGCCTGGCTCATTGCTGGGGTCTGCAGTGG<br>CTGACTAGCCCAGGGGTCACTGCAGGGCCCTAGCAATAGACTTAGC<br>CGCAGATCTCAGGGTTGTCATGTTTCCTAAACTGGACATATATTCT<br>CTGATTCTTGATTTCCACATCCATAAAACAAGAATAGACCCAGCCT<br>CACAGAGCT | Nur77 right homology arm<br>(chr12:52,058,950-52,059,924<br>hg38 assembly): |
| 45 | MASMGTLAFDEYGRPFLIIKDQDRKSRLMGLEALKSHIMAAKAVAN<br>TMRTSLGPNGLDKMMVDKDGDVTVTNDGATILSMMDVDHQIAKLMV<br>ELSKSQDDEIGDGTTGVVVLAGALLEEAEQLLDRGIHPIRIADGYE<br>QAARVAIEHLDKISDSVLVDIKDTEPLIQTAKTTLGSKVVNSCHRQ<br>MAEIAVNAVLTVADMERRDVDFELIKVEGKVGGRLEDTKLIKGVIV<br>DKDFSHPQMPKKVEDAKIAILTCPFEPPKPKTKHKLDVTSVEDYKA<br>LQKYEKEKFEEMIQQIKETGANLAICQWGFDDEANHLLLQNNLPAV<br>RWVGGPEIELIAIATGGRIVPRFSELTAEKLGFAGLVQEISFGTTK<br>DKMLVIEQCKNSRAVTIFIRGGNKMIIEEAKRSLHDALCVIRNLIR<br>DNRVVYGGGAAEISCALAVSQEADKCPTLEQYAMRAFADALEVIPM<br>ALSENSGMNPIQTMTEVRARQVKEMNPALGIDCLHKGTNDMKQQHV<br>IETLIGKKQQISLATQMVRMILKIDDIRKPGESEE | Human CCT5<br>(Uniprot P48643) |
| 46 | ASMGTLAFDEYGRPFLIIKDQDRKSRLMGLEALKSHIMAAKAVANT<br>MRTSLGPNGLDKMMVDKDGDVTVTNDGATILSMMDVDHQIAKLMVE<br>LSKSQDDEIGDGTTGVVVLAGALLEEAEQLLDRGIHPIRIADGYEQ<br>AARVAIEHLDKISDSVLVDIKDTEPLIQTAKTTLGSKVVNSCHRQM<br>AEIAVNAVLTVADMERRDVDFELIKVEGKVGGRLEDTKLIKGVIVD<br>KDFSHPQMPKKVEDAKIAILTCPFEPPKPKTKHKLDVTSVEDYKAL<br>QKYEKEKFEEMIQQIKETGANLAICQWGFDDEANHLLLQNNLPAVR<br>WVGGPEIELIAIATGGRIVPRFSELTAEKLGFAGLVQEISFGTTKD<br>KMLVIEQCKNSRAVTIFIRGGNKMIIEEAKRSLHDALCVIRNLIRD | Human CCT5<br>(Uniprot P48643) |

| # | SEQUENCE | ANNOTATION |
|---|---|---|
| | NRVVYGGGAAEISCALAVSQEADKCPTLEQYAMRAFADALEVIPMA<br>LSENSGMNPIQTMTEVRARQVKEMNPALGIDCLHKGTNDMKQQHVI<br>ETLIGKKQQISLATQMVRMILKIDDIRKPGESEE | |
| 47 | GGGGS | 4GS linker (aa) |
| 48 | GGGS | 3GS linker (aa) |
| 49 | GGGGSGGGGSGGGGS | (4GS)$_3$ linker (aa) |
| 50 | GSTSGSGKPGSGEGSTKG | Linker (aa) |
| 51 | ggaggcggaggatctggtggcggaggaagtggcggaggcggtagtg<br>gtggtggtggatct | (4GS)$_3$ linker (nt) |
| 52 | SYELTQPPSVSVSPGQTASITCFGDQLGDKYVSWYQKKPGQSPVLV<br>IYQDANRPSGIPERFSGSNSGNTATLTIRGTQNLDEADYYCQTWGT<br>TTALFGGGTKLTVLGGGGSGGGGSGGGGSEVQLVESGGGLV<br>QPGGSLRLSCAASGFTFSSYSMNWVRQAPGKGLEWVSYISSSSSTI<br>YYADSVKGRFTISRDNAKNSLYLQMNSLRDEDTAVYYCARDFKGDC<br>SSTSCYRGGYYYYGMDVWGQGTTVTVSS | CCT5 scFv (aa) |
| 53 | agctatgagctgacccagccccctccgttagcgtcagtcccggtc<br>aaaccgccagcatcacctgtttcggggaccaactgggagataaata<br>tgtgagctggtatcagaaaaaaccaggccagtctcccgtgcttgtc<br>atttatcaagacgccaacagaccaagcgggatcctgaacgattct<br>cagggagcaacagcgggaatactgccacgcttactatccgggggac<br>ccagaatctggacgaggccgattactactgccaaacctggggaca<br>caactgcgctgttcggcggggggcacaaagctgaccgttctggag<br>gcggaggatctggtggcggaggaagtggcggaggcggtagtggtgg<br>tggtggatctgaggtgcagcttgtggagtcaggcggagggcttgta<br>cagcccggcggcagtcttagactcagttgtgccgcctctggcttta<br>ctttctcatcttactccatgaactgggtcagacaggcccctggaaa<br>aggacttgagtgggttagttatatttcatcttcaagcagcacaata<br>tattatgcagactcagtgaagggcagattcaccattagtcgggaca<br>atgcaaaaaacagcctgtacttgcaaatgaattcctccgggatga<br>agatacagcagtgtactattgtgccagagacttcaaaggcgattgc<br>tcctctacgtcctgctatcgcggtggatactactattattatggaa<br>tggacgtttggggccagggtaccacagtgaccgtgtcttcc | CCT5 scFv (nt) |
| 54 | MPLLLLLPLLWAGALASYELTQPPSVSVSPGQTASITCFGDQLGDK<br>YVSWYQKKPGQSPVLVIYQDANRPSGIPERFSGSNSGNTATLTIRG<br>TQNLDEADYYCQTWGTTTALFGGGTKLTVLGGGGSGGGGSGGGGS<br>GGGSEVQLVESGGGLVQPGGSLRLSCAASGFTFSSYSMNWVRQAPG<br>KGLEWVSYISSSSSTIYYADSVKGRFTISRDNAKNSLYLQMNSLRD<br>EDTAVYYCARDFKGDCSSTSCYRGGYYYYGMDVWGQGTTVTVSSE<br>SKYGPPCPPCPAPPVAGPSVFLFPPKPKDTLMISRTPEVTCVVVDV<br>SQEDPEVQFNWYVDGVEVHNAKTKPREEQFQSTYRVVSVLTVLHQD<br>WLNGKEYKCKVSNKGLPSSIEKTISKAKGQPREPQVYTLPPSQEEM<br>TKNQVSLTCLVKGFYPSDIAVEWESNGQPENNYKTTPPVLDSDGSF<br>FLYSRLTVDKSRWQEGNVFSCSVMHEALHNHYTQKSLSLSLGKMFW<br>VLVVVGGVLACYSLLVTVAFIIFWVKRGRKKLLYIFKQPFMRPVQT<br>TQEEDGCSCRFPEEEEGGCELRVKFSRSADAPAYQQGQNQLYNELN<br>LGRREEYDVLDKRRGRDPEMGGKPRRKNPQEGLYNELQKDKMAEAY<br>SETGMKGERRRGKGHDGLYQGLSTATKDTYDALHMQALPPR | CCT5 CAR (aa) |
| 55 | atgccgctgctgctactgctgcccctgctgtgggcaggggctctag<br>ccagctatgagctgacccagccccctccgttagcgtcagtcccgg<br>tcaaaccgccagcatcacctgtttcggggaccaactgggagataaa<br>tatgtgagctggtatcagaaaaaaccaggccagtctcccgtgcttg<br>tcatttatcaagacgccaacagaccaagcgggatcctgaacgatt<br>ctcagggagcaacagcgggaatactgccacgcttactatccggggg<br>acccagaatctggacgaggccgattactactgccaaacctggggga<br>caacaactgcgctgttcggcggggggcacaaagctgaccgttctggg<br>aggcggaggatctggtggcggaggaagtggcggaggcggtagtggt<br>ggtggtggatctgaggtgcagcttgtggagtcaggcggagggcttg<br>tacagcccggcggcagtcttagactcagttgtgccgcctctggctt<br>tactttctcatcttactccatgaactgggtcagacaggcccctgga<br>aaaggacttgagtgggttagttatatttcatcttcaagcagcacaa<br>tatattatgcagactcagtgaagggcagattcaccattagtcggga<br>caatgcaaaaaacagcctgtacttgcaaatgaattcctccgggat<br>gaagatacagcagtgtactattgtgccagagacttcaaaggcgatt<br>gctcctctacgtcctgctatcgcggtggatactactattattatgg<br>aatggacgtttggggccagggtaccacagtgaccgtgtcttccgaa<br>tctaaatacggaccgccttgtcctccatgtcctgctcctccagttg | CCT5 CAR (nt) |

| # | SEQUENCE | ANNOTATION |
|---|---|---|
| | ccggaccttccgtgttcctgtttcctccaaagcctaaggacaccct<br>gatgatcagcagaacccctgaagtgacctgcgtggtggtggacgtg<br>tcccaagaggatcctgaggtgcagttcaactggtatgtggacggcg<br>tggaagtgcacaacgccaagaccaagcctagagaggaacagttcca<br>gagcacctacagagtggtgtccgtgctgacagtgctgcaccaggat<br>tggctgaacggcaaagagtacaagtgcaaggtgtccaacaagggcc<br>tgcctagcagcatcgagaaaaccatcagcaaggccaagggccagcc<br>aagagaacccaggtgtacacactgcctccaagccaagaggaaatg<br>accaagaaccaggtgtccctgacctgcctggtcaagggcttctacc<br>cttccgatatcgccgtggaatgggagagcaatggccagcctgaga<br>caactacaagaccacacctcctgtgctggacagcgacggctcattc<br>ttcctgtacagccggctgaccgtggacaagagcagatggcaagagg<br>gcaacgtgttcagctgcagcgtgatgcacgaggccctgcacaacca<br>ctacacccagaagtctctgagcctgagcctgggcaagatgttctgg<br>gtgctcgttgttgttggcggcgtgctggcctgttactccctgctgg<br>ttaccgtggccttcatcatcttttgggtcaagcggggcagaaagaa<br>gctgctctacatcttcaagcagcccttcatgcggcccgtgcagacc<br>acacaagaggaagatggctgctcctgcagattccccgaggaagaag<br>aaggcggctgcgagctgagagtgaagttcagcagatccgccgacgc<br>tccagcctatcagcagggacagaaccagctgtacaacgagctgaac<br>ctggggagaagagaagagtacgacgtgctggataagcggagaggca<br>gagatcctgagatgggcggcaagcccagacggaagaatcctcaaga<br>gggcctgtataatgagctgcagaaagacaagatggccgaggcctac<br>agcgagatcggaatgaagggcgagcgcagaagaggcaagggacacg<br>atggactgtaccagggactgagcaccgccaccaaggatacctatga<br>cgcactgcacatgcaggccctgccacctaga | |
| 56 | MVLQTQVFISLLLWISGAYG | Human IgG-kappa signaling sequence (aa) |
| 57 | atggtgctgcagacccaggtgttcatcagcctgctgctgtggatct ccggagcatacgga | Human IgG-kappa signaling sequence (nt) |
| 58 | MASVGTLAFDEYGRPFLIIKDQDRKSRLMGLEALKSHIMAAKAVAN<br>TMRTSLGPNGLDKMMVDKDGDVTVTNDGATILSMMDVDHQIAKLMV<br>ELSKSQDDEIGDGTTGVVVLAGALLEEAEQLLDRGIHPIRIADGYE<br>QAARIAIQHLDKISDNVLVDINNPEPLIQTAKTTLGSKVVNSCHRQ<br>MAEIAVNAVLTVADMERRDVDFELIKVEGKVGGRLEDTKLIKGVIV<br>DKDFSHPQMPKEVLNAKIAILTCPFEPPKPKTKHKLDVTSVEDYKA<br>LQKYEKEKFEEMIAQIKETGANLAICQWGFDDEANHLLLQNGLPAV<br>RWVGGPEIELIAIATGGRIVPRFSELTSEKLGFAGVVREISFGTTK<br>DKMLVIEQCKNSRAVTIFIRGGNKMIIEEAKRSLHDALCVIRNLIR<br>DNRVVYGGGAAEISCALAVSQEADKCPTLEQYAMRAFADALEVIPM<br>ALSENSGMNPIQTMTEVRARQVKESNPALGIDCLHKGSNDMQYQHV<br>IETLIGKKQQISLATQMVRMILKIDDIRKPGESEE | Rat CCT5 (aa) (UniProt Q68FQ0) |
| 59 | ASVGTLAFDEYGRPFLIIKDQDRKSRLMGLEALKSHIMAAKAVANT<br>MRTSLGPNGLDKMMVDKDGDVTVTNDGATILSMMDVDHQIAKLMVE<br>LSKSQDDEIGDGTTGVVVLAGALLEEAEQLLDRGIHPIRIADGYEQ<br>AARIAIQHLDKISDNVLVDINNPEPLIQTAKTTLGSKVVNSCHRQM<br>AEIAVNAVLTVADMERRDVDFELIKVEGKVGGRLEDTKLIKGVIVD<br>KDFSHPQMPKEVLNAKIAILTCPFEPPKPKTKHKLDVTSVEDYKAL<br>QKYEKEKFEEMIAQIKETGANLAICQWGFDDEANHLLLQNGLPAVR<br>WVGGPEIELIAIATGGRIVPRFSELTSEKLGFAGVVREISFGTTKD<br>KMLVIEQCKNSRAVTIFIRGGNKMIIEEAKRSLHDALCVIRNLIRD<br>NRVVYGGGAAEISCALAVSQEADKCPTLEQYAMRAFADALEVIPMA<br>LSENSGMNPIQTMTEVRARQVKESNPALGIDCLHKGSNDMQYQHVI<br>ETLIGKKQQISLATQMVRMILKIDDIRKPGESEE | Rat CCT5 (aa) (UniProt Q68FQ0) |
| 60 | RVKFSRSADAPAYKQGQNQLYNELNLGRREEYDVLDKRRGRDPEMG<br>GKPRRKNPQEGLYNELQKDKMAEAYSETGMKGERRRGKGHDGLYQG<br>LSTATKDTYDALHMQALPPR | Human CD3-zeta derived intracellular signaling domain (aa) |
| 61 | RSKRSRLLHSDYMNMTPRRPGPTRKHYQPYAPPRDFAAYRS | Human CD28 (amino acids 180-220 of P10747) |
| 62 | MPLLLLLPLLWAGALA | CD3-zeta derived intracellular signaling domain (aa) |
| 63 | RSKRSRGGHSDYMNMTPRRPGPTRKHYQPYAPPRDFAAYRS | Human CD28 (LL to GG) |
| 64 | ALAA | peptide linker |

-continued

Sequences

| # | SEQUENCE | ANNOTATION |
|---|---|---|
| 65 | MLLLVTSLLLCELPHPAFLLIPRKVCNGIGIGEFKDSLSINATNIK HFKNCTSISGDLHILPVAFRGDSFTHTPPLDPQELDILKTVKEITG FLLIQAWPENRTDLHAFENLEIIRGRTKQHGQFSLAVVSLNITSLG LRSLKEISDGDVIISGNKNLCYANTINWKKLFGTSGQKTKIISNRG ENSCKATGQVCHALCSPEGCWGPEPRDCVSCRNVSRGRECVDKCNL LEGEPREFVENSECIQCHPECLPQAMNITCTGRGPDNCIQCAHYID GPHCVKTCPAGVMGENNTLVWKYADAGHVCHLCHPNCTYGCTGPGL EGCPTNGPKIPSIATGMVGALLLLLVVALGIGLFM | EGFRt |
| 66 | RKVCNGIGIGEFKDSLSINATNIKHFKNCTSISGDLHILPVAFRGD SFTHTPPLDPQELDILKTVKEITGFLLIQAWPENRTDLHAFENLEI IRGRTKQHGQFSLAVVSLNITSLGLRSLKEISDGDVIISGNKNLCY ANTINWKKLFGTSGQKTKIISNRGENSCKATGQVCHALCSPEGCWG PEPRDCVSCRNVSRGRECVDKCNLLEGEPREFVENSECIQCHPECL PQAMNITCTGRGPDNCIQCAHYIDGPHCVKTCPAGVMGENNTLVWK YADAGHVCHLCHPNCTYGCTGPGLEGCPTNGPKIPSIATGMVGALL LLLVVALGIGLFM | EGFRt |
| 67 | RVKFSRSAEPPAYQQGQNQLYNELNLGRREEYDVLDKRRGRDPEMG GKPRRKNPQEGLYNELQKDKMAEAYSETGMKGERRRGKGHDGLYQG LSTATKDTYDALHMQALPPR | CD3-zeta derived intracellular signaling domain (aa) |
| 68 | XSVEXXKX | epitope, where X is any amino acid |
| 69 | XSVEXXKX | epitope, X1 = T, S, or D; X5 = D or A; X6 = Y, F or I; X8 = A or R |
| 70 | TSVEDYKA | epitope |
| 71 | SSVEAFKR | epitope |
| 72 | DSVEAIKA | epitope |
| 73 | DVSFRLSGATTTSYGVFIKNLREALPYERKVYNIPLLRSSISGRYT LLHLTNYADETISVAVDVTNVYIMGYLAGDVSYFFNEASATEAAKF VFKDAKKKVTLPYSGNYERLQTAAGKIRENTPLGLPALDSAITTLY YYTASSAASALLVLIQSTAESARYKFIEQQIGKRVDKTFLPSLATI SLENNWSALSKQIQIASTNNGQFESPVVLIDGNNQRVSITNASARV VTSNIALLLNRNNIA | Bryodin |
| 74 | IEVMYPPPYLDNEKSNGTIIHVKGKHLCPSPLFPGPSKP | CD28 ectodomain spacer (aa) |
| 75 | VTSITLDLVNPTAGQYSSFVDKIRNNVKDPNLKYGGTDIAVIPPSK EKFLRINFQSSRGTVSLGLKRDNLYVVAYLAMDNTNVNRAYYFRSE ITSAESTALFPEATTANQKALEYTEDYQSIEKNAQITQGDQSRKEL GLGIDLLSTSMEAVNKKARVVKDEARFLLTATQMTAEAARFRYIQN LVIKNFPNKFNSENKVIQFEVNWKKISTAIYGDAKNGVENKDYDEG FGKVRQVKDLQMGLLMYLGKPKSSNEANSTVRHYGPLKPTLLIT | Saporin-6 |
| 76 | RSKRSRLLHSDYMNMTPRRPGPIRKHYQPYAPPRDFAAYRS | CD28 endodomain (aa) |
| 77 | APTLETIASLDLNNPTTYLSFITNIRTKVADKTEQCTIQKISKTFT QRYSYIDLIVSSTQKITLAIDMADLYVLGYSDIANNKGRAFFFKDV TEAVANNFFPGATGTNRIKLTFTGSYGDLEKNGGLRKDNPLGIFRL ENSIVNIYGKAGDVKKQAKFFLLAIQMVSEAARFKYISDKIPSEKY EEVTVDEYMTALENNWAKLSTAVYNSKPSTTTATKCQLATSPVTIS PWIFKTVEEIKLVMGLLKSS | Anti-Viral Protein MAP |
| 78 | IEVMYPPPYLDNEKSNGTIIHVKGKHLCPSPLFPGPSKPFWVLVVV GGVLACYSLLVTVAFIIFWV | Human CD28 (amino acids 114-179 of Accession No. P10747) |
| 79 | KEFTLDFSTAKTYVDSLNVIRSAIGTPLQTISSGGTSLLMIDSGTG DNLFAVDVRGIDPEEGRFNNLRLIVERNNLYVTGEVNRTNNVEYRF ADFSHVTFPGTTAVTLSGDSSYTTLQRVAGISRTGMQINRHSLTTS YLDLMSHSGTSLTQSVARAMLRFVTVTAEALRFRQIQRGFRTTLDD LSGRSYVMTAEDVDLTLNWGRLSSVLPDYHGQDSVRVGRISFGSIN AILGSVALILNCHHHASRVARMASDEFPSMCPADGRVRGITHNKIL WDSSTLGAILMRRTISS | Shiga Toxin A-Chain |
| 80 | MKCILEKWVLCLLLGESSVSYSREFTIDFSTQQSYVSSLNSIRTEI STPLEHISQGTTSVSVINHTPPGSYFAVDIRGLDVYQARFDHLRLI | Shiga-Like Toxin Subunit A |

-continued

| Sequences | | |
|---|---|---|
| # | SEQUENCE | ANNOTATION |
| | IEQNNLYVAGFVNTATNTFYRFSDFTHISVPGVTTVSMTTDSSYTT<br>LQRVAALERSGMQISRHSLVSSYLALMEFSGNTMTRDASRAVLRFV<br>TVTAEALRFRQIQREFRQALSETAPVYTMTPGDVDLTLNWGRISNV<br>LPEYRGEDGVRVGRISFNNISAILGTVAVILNCHHQGARSVRAVNE<br>ESQPECQITGDRPVIKINNTLWESNTAAAFLNRKSQFLYTTGK | (Verotoxin 2) |
| 81 | ESKYGPPCPPCPGQPREPQVYTLPPSQEEMTKNQVSLTCLVKGFYP<br>SDIAVEWESNGQPENNYKTTPPVLDSDGSFFLYSRLTVDKSRWQEG<br>NVFSCSVMHEALHNHYTQKSLSLSLGK | Human IgG4 hinge-CH3 spacer (aa) |
| 82 | ggatctgcgatcgctccggtgcccgtcagtgggcagagcgcacatc<br>gcccacagtccccgagaagttggggggaggggtcggcaattgaacc<br>ggtgcctagagaaggtggcgcggggtaaactgggaaagtgatgtcg<br>tgtactggctccgcctttttcccgagggtgggggagaaccgtatat<br>aagtgcagtagtcgccgtgaacgttctttttcgcaacgggtttgcc<br>gccagaacacagctgaagcttcgaggggctcgcatctctccttcac<br>gcgcccgccgccctacctgaggccgccatccacgccggttgagtcg<br>cgttctgccgcctcccgcctgtggtgcctcctgaactgcgtccgcc<br>gtctaggtaagtttaaagctcaggtcgagaccgggcctttgtccgg<br>cgctcccttggagcctacctagactcagccggctctccacgctttg<br>cctgaccctgcttgctcaactctacgtctttgtttcgttttctgtt<br>ctgcgccgttacagatccaagctgtgaccggcgcctacggctagcg<br>cc | EF1a promoter (modified EF1a promoter) |
| 83 | MASVGTLAFDEYGRPFLIIKDQDRKSRLMGLEALKSHIMAAKAVAN<br>TMRTSLGPNGLDKMMVDKDGDVTITNDGATILSMMDVDHQIAKLMV<br>ELSKSQDDEIGDGTTGVVVLAGALLEEAEQLLDRGIHPIRIADGYE<br>QAARIAIQHLDKISDKVLVDINNPEPLIQTAKTTLGSKVINSCHRQ<br>MAEIAVNAVLTVADMERRDVDFELIKVEGKVGGRLEDTKLIKGVIV<br>DKDFSHPQMPKKVVDAKIAILTCPFEPPKPKTKHKLDVMSVEDYKA<br>LQKYEKEKFEEMIKQIKETGANLAICQWGFDDEANHLLLQNGLPAV<br>RWVGGPEIELIAIATGGRIVPRFSELTSEKLGFAGVVQEISFGTTK<br>DKMLVIEKCKNSRAVTIFIRGGNKMIIEEAKRSLHDALCVIRNLIR<br>DNRVVYGGGAAEISCALAVSQEADKCPTLEQYAMRAFADALEVIPM<br>ALSENSGMNPIQTMTEVRARQVKESNPALGIDCLHKGSNDMQYQHV<br>IETLIGKKQQISLATQMVRMILKIDDIRKPGESEE | Mouse CCT5 (aa) (UniProt P80316) |
| 84 | ASVGTLAFDEYGRPFLIIKDQDRKSRLMGLEALKSHIMAAKAVANT<br>MRTSLGPNGLDKMMVDKDGDVTITNDGATILSMMDVDHQIAKLMVE<br>LSKSQDDEIGDGTTGVVVLAGALLEEAEQLLDRGIHPIRIADGYEQ<br>AARIAIQHLDKISDKVLVDINNPEPLIQTAKTTLGSKVINSCHRQM<br>AEIAVNAVLTVADMERRDVDFELIKVEGKVGGRLEDTKLIKGVIVD<br>KDFSHPQMPKKVVDAKIAILTCPFEPPKPKTKHKLDVMSVEDYKAL<br>QKYEKEKFEEMIKQIKETGANLAICQWGFDDEANHLLLQNGLPAVR<br>WVGGPEIELIAIATGGRIVPRFSELTSEKLGFAGVVQEISFGTTKD<br>KMLVIEKCKNSRAVTIFIRGGNKMIIEEAKRSLHDALCVIRNLIRD<br>NRVVYGGGAAEISCALAVSQEADKCPTLEQYAMRAFADALEVIPMA<br>LSENSGMNPIQTMTEVRARQVKESNPALGIDCLHKGSNDMQYQHVI<br>ETLIGKKQQISLATQMVRMILKIDDIRKPGESEE | Mouse CCT5 (aa) (UniProt P80316) |
| 85 | $(XDEL)_n$ | exemplary sorting signal, where X is Lys or Arg and n = 1 to 6 |
| 86 | DVSFRLSGATSSSYGVFISNLRKALPNERKLYDIPLLRSSLPGSQR<br>YALIHLTNYADETISVAIDVTNVYIMGYRAGDTSYFFNEASATEAA<br>KYVFKDAMRKVTLPYSGNYERLQTAAGKIRENIPLGLPALDSAITT<br>LFYYNANSAASALMVLIQSTSEAARYKFIEQQIGKRVDKTFLPSLA<br>IISLENSWSALSKQIQIASTNNGQFESPVVLINAQNQRVTITNVDA<br>GVVTSNIALLLNRNNMA | Trichosanthin |

The invention claimed is:

1. An antibody or antigen-binding fragment thereof, wherein the antibody or antigen-binding fragment binds to a peptide sequence comprising the sequence TSVEDYKA (SEQ ID NO:70), SSVEAFKR (SEQ ID NO:71) or DSVEAIKA (SEQ ID NO:72), and wherein the antibody or antigen-binding fragment comprises a heavy chain variable ($V_H$) region comprising the amino acid sequence set forth in SEQ ID NO:1; and a light chain variable ($V_L$) region comprising the amino acid sequence set forth in SEQ ID NO:2.

2. The antibody or antigen-binding fragment thereof of claim 1, wherein the antigen-binding fragment comprises an scFv.

3. An antibody or antigen-binding fragment thereof that specifically binds to a chaperonin containing TCP1 subunit 5 (CCT5) protein comprising:

a heavy chain variable ($V_H$) region comprising a heavy chain complementarity determining region 1 (CDR-H1), a CDR-H2, and a CDR-H3, respectively, comprising the amino acid sequences of CDR-H1, CDR-H2, and CDR-H3 sequences contained within the $V_H$ region amino acid sequence set forth in SEQ ID NO: 1; and a light chain variable ($V_L$) region comprising a light chain complementarity determining region 1 (CDR-L1), a CDR-L2, and a CDR-L3, respectively, comprising the amino acid sequences of CDR-L1, CDR-L2, and CDR-L3 sequences contained within the light chain variable ($V_L$) region amino acid sequence set forth in SEQ ID NO: 2.

4. The antibody or antigen-binding fragment thereof of claim 3, wherein:

the $V_H$ region comprises a CDR-H1 comprising the amino acid sequence set forth in SEQ ID NO:11; a CDR-H2 comprising the amino acid sequence set forth in SEQ ID NO: 12; and a CDR-H3 comprising the amino acid sequence set forth in SEQ ID NO: 13; and the $V_L$ region comprises a CDR-L1 comprising the amino acid sequence set forth in SEQ ID NO:21; a CDR-L2 comprising the amino acid sequence set forth in SEQ ID NO: 22; and a CDR-L3 comprising the amino acid sequence set forth in SEQ ID NO: 23.

5. A chimeric antigen receptor (CAR) comprising an extracellular portion comprising the antibody or antigen-binding fragment thereof of claim 3, a transmembrane domain, and an intracellular signaling region.

6. The antibody or antigen-binding fragment thereof of claim 3, wherein the antigen-binding fragment comprises an scFv.

7. The antibody or antigen-binding fragment thereof of claim 3, wherein the antibody is a bispecific antibody that further specifically binds to a second antigen.

8. An antibody or antigen-binding fragment thereof that specifically binds to a chaperonin containing TCP1 subunit 5 (CCT5) protein, wherein the antibody or antigen-binding fragment comprises:

a heavy chain variable ($V_H$) region comprising a CDR-H1 comprising the amino acid sequence set forth in SEQ ID NO:11; a CDR-H2 comprising the amino acid sequence set forth in SEQ ID NO: 12; and a CDR-H3 comprising the amino acid sequence set forth in SEQ ID NO:13; and a light chain variable ($V_L$) region comprising a CDR-L1 comprising the amino acid sequence set forth in SEQ ID NO:21; a CDR-L2 comprising the amino acid sequence set forthin SEQ ID NO: 22; and a CDR-L3 comprising the amino acid sequence set forth in SEQ ID NO: 23.

9. The antibody or antigen-binding fragment thereof of claim 8, wherein the antibody or antigen-binding fragment comprises a heavy chain variable ($V_H$) region having at least 95% sequence identity to the $V_H$ region amino acid sequence set forth in SEQ ID NO:1; and a light chain variable ($V_L$) region having at least 95% sequence identity to the $V_L$ region amino acid sequence set forth in SEQ ID NO:2.

10. The antibody or antigen-binding fragment of claim 8, wherein the $V_H$ and $V_L$ regions of the antibody or antigen-binding fragment thereof comprise the amino acid sequences of SEQ ID NOs: 1 and 2, respectively.

11. The antibody or antigen-binding fragment of claim 8, wherein the antigen-binding fragment comprises an scFv.

12. The antibody or antigen-binding fragment of claim 11, wherein the scFv comprises the amino acid sequence set forth in SEQ ID NO:52.

13. The antibody or antigen-binding fragment of claim 8, wherein the antibody is a bispecific antibody that further specifically binds to a second antigen.

14. The antibody or antigen-binding fragment of claim 13, wherein the second antigen is expressed on a tumor cell or a T cell.

15. A single chain cell-surface protein, comprising the antibody or antigen-binding fragment thereof of claim 8.

16. The single chain cell-surface protein of claim 15, wherein the antibody or antigen-binding fragment thereof is an scFv, and wherein the scFv comprises the amino acid sequence set forth in SEQ ID NO: 52.

17. A conjugate comprising the antibody or antigen-binding fragment thereof of claim 8 and a heterologous molecule or moiety.

18. The conjugate of claim 17, wherein the heterologous molecule or moiety is a protein, peptide, nucleic acid, or small molecule.

19. A chimeric antigen receptor (CAR) comprising an extracellular portion comprising the antibody or antigen-binding fragment thereof of claim 8, a transmembrane domain, and an intracellular signaling region.

20. The chimeric antigen receptor of claim 19, wherein the extracellular portion comprises an antigen-binding fragment and the antigen-binding fragment is an scFv.

21. The chimeric antigen receptor of claim 20, wherein the scFv comprises the amino acid sequence set forth in SEQ ID NO: 52.

22. The chimeric antigen receptor of claim 19, wherein the intracellular signaling region is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM).

23. The chimeric antigen receptor of claim 19, wherein the intracellular signaling region is or comprises a CD3-zeta (CD3) chain.

24. The chimeric antigen receptor of claim 19, wherein the transmembrane domain comprises a transmembrane portion of CD28.

25. The chimeric antigen receptor of claim 19, wherein the intracellular signaling region further comprises a costimulatory signaling domain.

26. The chimeric antigen receptor of claim 25, wherein the costimulatory signaling domain comprises an intracellular signaling domain of a CD28, a 4-1BB or an ICOS or a signaling portion thereof.

27. An engineered cell expressing a receptor comprising the antibody or antigen-binding fragment thereof of claim 8.

28. A composition comprising the antibody or antigen-binding fragment thereof of claim 8 and a pharmaceutically acceptable carrier.

* * * * *

UNITED STATES PATENT AND TRADEMARK OFFICE
CERTIFICATE OF CORRECTION

PATENT NO. : 12,006,356 B2
APPLICATION NO. : 16/771954
DATED : June 11, 2024
INVENTOR(S) : Susan Byrne Page 1 of 1

It is certified that error appears in the above-identified patent and that said Letters Patent is hereby corrected as shown below:

In the Claims

At Column 219, Claim number 1, Line number 53: please replace "the sequence" with -- the amino acid sequence --;

At Column 220, Claim number 3, Line numbers 54-55: please replace "the $V_H$ region" with -- the heavy chain variable ($V_H$) region --; and At Column 221, Claim number 8, Line number 32: please replace "forthin" with -- forth in --.

Signed and Sealed this
Twenty-eighth Day of January, 2025

Coke Morgan Stewart
*Acting Director of the United States Patent and Trademark Office*

SEQUENCE LISTING

<160> NUMBER OF SEQ ID NOS: 86

<210> SEQ ID NO 1
<211> LENGTH: 133
<212> TYPE: PRT
<213> ORGANISM: Artificial Sequence
<220> FEATURE:
<223> OTHER INFORMATION: Synthetic construct
<220> FEATURE:
<223> OTHER INFORMATION: Antibody variable heavy (VH) chain (aa)

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Phe Lys Gly Asp Cys Ser Ser Thr Ser Cys Tyr Arg Gly
            100                 105                 110

Gly Tyr Tyr Tyr Tyr Gly Met Asp Val Trp Gly Gln Gly Thr Thr
        115                 120                 125

Val Thr Val Ser Ser
    130
```

<210> SEQ ID NO 2
<211> LENGTH: 106
<212> TYPE: PRT
<213> ORGANISM: Artificial Sequence
<220> FEATURE:
<223> OTHER INFORMATION: Synthetic construct
<220> FEATURE:
<223> OTHER INFORMATION: Antibody variable light (VL) chain (aa)

<400> SEQUENCE: 2

```
Ser Tyr Glu Leu Thr Gln Pro Pro Ser Val Ser Val Ser Pro Gly Gln
1               5                   10                  15

Thr Ala Ser Ile Thr Cys Phe Gly Asp Gln Leu Gly Asp Lys Tyr Val
            20                  25                  30

Ser Trp Tyr Gln Lys Lys Pro Gly Gln Ser Pro Val Leu Val Ile Tyr
        35                  40                  45

Gln Asp Ala Asn Arg Pro Ser Gly Ile Pro Glu Arg Phe Ser Gly Ser
    50                  55                  60

Asn Ser Gly Asn Thr Ala Thr Leu Thr Ile Arg Gly Thr Gln Asn Leu
65                  70                  75                  80

Asp Glu Ala Asp Tyr Tyr Cys Gln Thr Trp Gly Thr Thr Thr Ala Leu
                85                  90                  95

Phe Gly Gly Gly Thr Lys Leu Thr Val Leu
            100                 105
```

<210> SEQ ID NO 3
<211> LENGTH: 399
<212> TYPE: DNA
<213> ORGANISM: Artificial Sequence
<220> FEATURE:
<223> OTHER INFORMATION: Synthetic construct
<220> FEATURE:
<223> OTHER INFORMATION: Antibody variable heavy (VH) chain (nt)

<400> SEQUENCE: 3

```
gaggtgcagc ttgtggagtc aggcggaggg cttgtacagc ccggcggcag tcttagactc    60
```

```
agttgtgccg cctctggctt actttctca tcttactcca tgaactgggt gagacaggcc    120
cctggaaaag gacttgagtg ggttagttat atttcatctt caagcagcac aatatattat    180
gcagactcag tgaagggcag attcaccatt agtcgggaca atgcaaaaaa cagtctgtac    240
ttgcagatga attccctcag ggatgaagat acagcagtgt actattgtgc cagagacttc    300
aaaggcgatt gctcctctac gtcctgctat cgcggtggat actactatta ttatggaatg    360
gacgtttggg gccagggtac cacagtgacc gtgtcttcc                           399
```

```
<210> SEQ ID NO 4
<211> LENGTH: 318
<212> TYPE: DNA
<213> ORGANISM: Artificial Sequence
<220> FEATURE:
<223> OTHER INFORMATION: Synthetic construct
<220> FEATURE:
<223> OTHER INFORMATION: Antibody variable light (VL) chain (nt)

<400> SEQUENCE: 4
```

```
agctatgagc tgacccagcc cccctccgtt agcgtcagtc cggtcaaac cgccagcatc      60 acctgtttcg gggaccagct gggagataag tatgtgagct ggtatcagaa aaaaccaggt    120
cagtctcccg tgcttgtcat ttatcaggat gccaacagac aagcgggat ccctgaacga    180 ttctcaggga gcaacagcgg gaatactgcc acgcttacta tcaggggac ccagaatctg    240 gacgaggccg attactactg ccaaacctgg gggacaacaa ctgcgctgtt cggcggggc    300 acaaagctga ccgttctg                                                  318
```

```
<210> SEQ ID NO 5
<211> LENGTH: 228
<212> TYPE: PRT
<213> ORGANISM: Artificial Sequence
<220> FEATURE:
<223> OTHER INFORMATION: Synthetic construct
<220> FEATURE:
<223> OTHER INFORMATION: IgG4/IgG2 hinge- IgG2/IgG4 CH2- IgG4 CH3
    extracellular spacer

<400> SEQUENCE: 5
```

Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Gln Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

```
Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys
225

<210> SEQ ID NO 6
<211> LENGTH: 12
<212> TYPE: PRT
<213> ORGANISM: Homo sapiens
<220> FEATURE:
<223> OTHER INFORMATION: IgG4 hinge extracellular spacer

<400> SEQUENCE: 6

Glu Ser Lys Tyr Gly Pro Pro Cys Pro Pro Cys Pro
1               5                   10

<210> SEQ ID NO 7
<211> LENGTH: 27
<212> TYPE: PRT
<213> ORGANISM: Homo sapiens
<220> FEATURE:
<223> OTHER INFORMATION: CD28 transmembrane domain

<400> SEQUENCE: 7

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 8
<211> LENGTH: 42
<212> TYPE: PRT
<213> ORGANISM: Homo sapiens
<220> FEATURE:
<223> OTHER INFORMATION: 4-1BB-derived intracellular co-signaling
      sequence

<400> SEQUENCE: 8

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 9
<211> LENGTH: 112
<212> TYPE: PRT
<213> ORGANISM: Homo sapiens
<220> FEATURE:
<223> OTHER INFORMATION: CD3-zeta derived intracellular signaling domain
      (aa)

<400> SEQUENCE: 9

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
```

```
                    20                  25                  30
Asp Val Leu Asp Lys Arg Arg Gly Arg Asp Pro Glu Met Gly Gly Lys
                35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 10
<211> LENGTH: 20
<212> TYPE: PRT
<213> ORGANISM: Artificial Sequence
<220> FEATURE:
<223> OTHER INFORMATION: Synthetic construct
<220> FEATURE:
<223> OTHER INFORMATION: (Gly4Ser)4 linker

<400> SEQUENCE: 10

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 11
<211> LENGTH: 5
<212> TYPE: PRT
<213> ORGANISM: Artificial Sequence
<220> FEATURE:
<223> OTHER INFORMATION: Synthetic construct
<220> FEATURE:
<223> OTHER INFORMATION: CDR-H1

<400> SEQUENCE: 11

```
Ser Tyr Ser Met Asn
1               5
```

<210> SEQ ID NO 12
<211> LENGTH: 17
<212> TYPE: PRT
<213> ORGANISM: Artificial Sequence
<220> FEATURE:
<223> OTHER INFORMATION: Synthetic construct
<220> FEATURE:
<223> OTHER INFORMATION: CDR-H2

<400> SEQUENCE: 12

```
Tyr Ile Ser Ser Ser Ser Ser Thr Ile Tyr Tyr Ala Asp Ser Val Lys
1               5                   10                  15

Gly
```

<210> SEQ ID NO 13
<211> LENGTH: 24
<212> TYPE: PRT
<213> ORGANISM: Artificial Sequence
<220> FEATURE:
<223> OTHER INFORMATION: Synthetic construct
<220> FEATURE:
<223> OTHER INFORMATION: CDR-H3

<400> SEQUENCE: 13

```
Asp Phe Lys Gly Asp Cys Ser Ser Thr Ser Cys Tyr Arg Gly Gly Tyr
1               5                   10                  15

Tyr Tyr Tyr Tyr Gly Met Asp Val
            20
```

<210> SEQ ID NO 14
<211> LENGTH: 7
<212> TYPE: PRT
<213> ORGANISM: Artificial Sequence
<220> FEATURE:
<223> OTHER INFORMATION: Synthetic construct
<220> FEATURE:
<223> OTHER INFORMATION: CDR-H1

<400> SEQUENCE: 14

```
Gly Phe Thr Phe Ser Ser Tyr
1               5
```

<210> SEQ ID NO 15
<211> LENGTH: 6
<212> TYPE: PRT
<213> ORGANISM: Artificial Sequence
<220> FEATURE:
<223> OTHER INFORMATION: Synthetic construct
<220> FEATURE:
<223> OTHER INFORMATION: CDR-H2

<400> SEQUENCE: 15

```
Ser Ser Ser Ser Ser Thr
1               5
```

<210> SEQ ID NO 16
<211> LENGTH: 10
<212> TYPE: PRT
<213> ORGANISM: Artificial Sequence
<220> FEATURE:
<223> OTHER INFORMATION: Synthetic construct
<220> FEATURE:
<223> OTHER INFORMATION: CDR-H1

<400> SEQUENCE: 16

```
Gly Phe Thr Phe Ser Ser Tyr Ser Met Asn
1               5                   10
```

<210> SEQ ID NO 17
<211> LENGTH: 14
<212> TYPE: PRT
<213> ORGANISM: Artificial Sequence
<220> FEATURE:
<223> OTHER INFORMATION: Synthetic construct
<220> FEATURE:
<223> OTHER INFORMATION: CDR-H2

<400> SEQUENCE: 17

```
Trp Val Arg Gln Ala Pro Gly Lys Gly Leu Glu Trp Val Ser
1               5                   10
```

<210> SEQ ID NO 18
<211> LENGTH: 6
<212> TYPE: PRT
<213> ORGANISM: Artificial Sequence
<220> FEATURE:
<223> OTHER INFORMATION: Synthetic construct
<220> FEATURE:
<223> OTHER INFORMATION: CDR-H1

<400> SEQUENCE: 18

```
Ser Ser Tyr Ser Met Asn
```

<210> SEQ ID NO 19
<211> LENGTH: 13
<212> TYPE: PRT
<213> ORGANISM: Artificial Sequence
<220> FEATURE:
<223> OTHER INFORMATION: Synthetic construct
<220> FEATURE:
<223> OTHER INFORMATION: CDR-H2

<400> SEQUENCE: 19

Trp Val Ser Tyr Ile Ser Ser Ser Ser Thr Ile Tyr
1               5                   10

<210> SEQ ID NO 20
<211> LENGTH: 25
<212> TYPE: PRT
<213> ORGANISM: Artificial Sequence
<220> FEATURE:
<223> OTHER INFORMATION: Synthetic construct
<220> FEATURE:
<223> OTHER INFORMATION: CDR-H3

<400> SEQUENCE: 20

Ala Arg Asp Phe Lys Gly Asp Cys Ser Ser Thr Ser Cys Tyr Arg Gly
1               5                   10                  15

Gly Tyr Tyr Tyr Tyr Tyr Gly Met Asp
            20                  25

<210> SEQ ID NO 21
<211> LENGTH: 11
<212> TYPE: PRT
<213> ORGANISM: Artificial Sequence
<220> FEATURE:
<223> OTHER INFORMATION: Synthetic construct
<220> FEATURE:
<223> OTHER INFORMATION: CDR-L1

<400> SEQUENCE: 21

Phe Gly Asp Gln Leu Gly Asp Lys Tyr Val Ser
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Synthetic construct
<220> FEATURE:
<223> OTHER INFORMATION: CDR-L2

<400> SEQUENCE: 22

Gln Asp Ala Asn Arg Pro Ser
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic construct
<220> FEATURE:
<223> OTHER INFORMATION: CDR-L3

<400> SEQUENCE: 23

Gln Thr Trp Gly Thr Thr Thr Ala Leu
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic construct
<220> FEATURE:
<223> OTHER INFORMATION: CDR-L1

<400> SEQUENCE: 24

Asp Lys Tyr Val Ser Trp Tyr
1               5

<210> SEQ ID NO 25
<211> LENGTH: 10
<212> TYPE: PRT
<213> ORGANISM: Artificial Sequence
<220> FEATURE:
<223> OTHER INFORMATION: Synthetic construct
<220> FEATURE:
<223> OTHER INFORMATION: CDR-L2

<400> SEQUENCE: 25

Leu Val Ile Tyr Gln Asp Ala Asn Arg Pro
1               5                   10

<210> SEQ ID NO 26
<211> LENGTH: 8
<212> TYPE: PRT
<213> ORGANISM: Artificial Sequence
<220> FEATURE:
<223> OTHER INFORMATION: Synthetic construct
<220> FEATURE:
<223> OTHER INFORMATION: CDR-L3

<400> SEQUENCE: 26

Gln Thr Trp Gly Thr Thr Thr Ala
1               5

<210> SEQ ID NO 27
<211> LENGTH: 399
<212> TYPE: DNA
<213> ORGANISM: Artificial Sequence
<220> FEATURE:
<223> OTHER INFORMATION: Synthetic construct
<220> FEATURE:
<223> OTHER INFORMATION: MND promoter

<400> SEQUENCE: 27
tttatttagt ctccagaaaa agggggggaat gaaagacccc acctgtaggt ttggcaagct     60
aggatcaagg ttaggaacag agagacagca gaatatgggc caaacaggat atctgtggta    120
agcagttcct gccccggctc agggccaaga acagttggaa cagcagaata tgggccaaac    180
aggatatctg tggtaagcag ttcctgcccc ggctcagggc caagaacaga tggtccccag    240
atgcggtccc gccctcagca gtttctagag aaccatcaga tgtttccagg gtgccccaag    300
gacctgaaat gaccctgtgc cttatttgaa ctaaccaatc agttcgcttc tcgcttctgt    360
tcgcgcgctt ctgctccccg agctcaataa aagagccca                           399

<210> SEQ ID NO 28
<211> LENGTH: 20
<212> TYPE: RNA
<213> ORGANISM: Homo sapiens
<220> FEATURE:
<223> OTHER INFORMATION: Human Nur77 gRNA 1 targeting domain

<400> SEQUENCE: 28
caugaagauc uugucaauga                                             20

<210> SEQ ID NO 29
<211> LENGTH: 19
<212> TYPE: RNA
<213> ORGANISM: Homo sapiens
<220> FEATURE:
<223> OTHER INFORMATION: Human Nur77 gRNA 2 targeting domain

<400> SEQUENCE: 29
ugcacacgug uucccaggc                                              19

<210> SEQ ID NO 30
<211> LENGTH: 3341
<212> TYPE: DNA
<213> ORGANISM: Artificial Sequence
<220> FEATURE:
<223> OTHER INFORMATION: Synthetic construct
<220> FEATURE:
<223> OTHER INFORMATION: Nur77 knock-in construct sequence

<400> SEQUENCE: 30
cagcctccta aagtgctggg attacaggtg tgagccacca cgcctagccc ttcactgtga    60
cttctgacag tgcagatcag attggttgtg cctgttttgg actttatgta aatgtagttc   120
tgcaggatgg aatctggtgt tgaatgcaga ggttttcaga tttctctgtt ttttaaagga   180
aagaatccac cctcgttcat tttttcactt aaattgcaca ggggacccaa cgatatagaa   240
cacaatcaga ggtactctgg gctgagggag tgctgagttc tgaggctggg tttctcagaa   300
cagtctagat tttaaaaacc caatgatcta gccagaaaac gtaggttagg attttatttc   360
ccgtttgtga ccctgggcaa gtcattagcc tcctgggcct cgggttctca cttggagtat   420
gaggataatg agggttactg cttctcagac ttgtgacgat gcttactaat ggccaacatg   480
tgaatgcgct tttgtgaagt gccagcagag catgaggggt ggtcagggc agcagtttta    540 ggggcctggg ggaggctggg gctttggggg cctggttctc agatgtacag ctaatcctgt   600
acccttcccg cagaccggca tgggctgcag gagccgcggc gggtggagga gctgcagaac   660
cgcatcgcca gctgcctgaa ggagcacgtg gcagctgtgg cgggcgagcc ccagccagcc   720
agctgcctgt cacgtctgtt gggcaaactg cccgagctgc ggaccctgtg cacccagggc   780
ctgcagcgta tcttctacct caagctggag gacttggtgc cccctccacc tatcatcgac   840
aagatcttca tggacacgct gccccttcgga tccggagaag gcagaggctc tctcctcaca   900 tgtgggatg ttgaagaaaa tccaggtccc ggtgtgagca agggcgagga ggtgatcaag    960
gagtttatga gattcaaagt ccggatggag ggcagcatga acggacatga gttcgaaatt  1020
gagggagaag gcgagggacg accttacgag ggaacacaga ccgccaaact gaaagtgaca  1080
aaaggcggac ctctgccatt tgcttgggac atcctgagtc cacagttcat gtatggctct  1140
aaggcttacg tgaaacaccc tgccgatatt cccgactaca aaaaactgag tttccctgaa  1200
ggcttcaaat gggaacgagt gatgaacttt gaggacggag cctggtgac agtgacacag    1260 gactctagtc tccaggacgg cacactcatc tacaaagtga aatgaggggg caccaatttc  1320
cctcccgatg gacctgtcat gcagaaaaaa acaatgggat gggaggcttc taccgaacga  1380
ctgtacccac gggatggagt gctgaaaggc gagatccatc aggcactgaa actgaaggat  1440
ggcggccatt acctggtcga gttcaaaacc atctatatgg ccaaaaaacc cgtccagctg  1500

```
cctggctact attacgtgga taccaaactg gacattacct ctcacaatga agactacaca    1560
atcgtcgagc agtacgagag gagtgagggc cgacaccacc tcttcctcgg gcatggcacc    1620
ggcagcaccg gcagcggcag ctccggcacc gctagttccg aggacaacaa catggccgtc    1680
atcaaagagt tcatgcgctt caaggtgcgc atggagggct ccatgaacgg ccacgagttc    1740
gagatcgagg gcgagggcga gggccgcccc tacgagggca cccagaccgc caagctgaag    1800
gtgaccaagg gcggccccct gcccttcgcc tgggacatcc tgtcccccca gttcatgtac    1860
ggctccaagg cgtacgtgaa gcaccccgcc gacatccccg attacaagaa gctgtccttc    1920
cccgagggct tcaagtggga gcgcgtgatg aacttcgagg acggcggtct ggtgaccgtg    1980
acccaggact cctccctgca ggacggcacg ctgatctaca aggtgaagat gcgcggcacc    2040
aacttccccc ccgacggccc cgtaatgcag aagaagacca tgggctggga ggcctccacc    2100
gagcgcctgt accccgcga cggcgtgctg aagggcgaga tccaccaggc cctgaagctg    2160
aaggacggcg gccactacct ggtggagttc aagaccatct acatggccaa gaagcccgtg    2220
caactgcccg gctactacta cgtggacacc aagctggaca tcacctccca caacgaggac    2280
tacaccatcg tggaacagta cgagcgctcc gagggccgcc accacctgtt cctgtacggc    2340
atggacgagc tgtacaaatg actcgagcct gggaacacgt gtgcacatgc gcactctcat    2400
atgccacccc atgtgccttt agtccacgga ccccagagc accccaagc ctgggcttga    2460 gctgcagaat gactccacct tctcacctgc tccaggaggt ttgcagggag ctcaagccct    2520
tggggagggg gatgccttca tgggggtgac ccacgatttt gtcttatccc ccccagcctg    2580
gccccggcct ttatgttttt tgtaagataa accgttttta acacatagcg ccgtgctgta    2640
aataagccca gtgctgctgt aaatacagga agaaagagct tgaggtggga gcggggctgg    2700
gaggaaggga tgggccccgc cttcctgggc agcctttcca gcctcctgct ggctctctct    2760 tcctacccte cttccacatg tacataaact gtcactctag aagaagaca aatgacagat    2820 tctgacattt atatttgtgt atttttcctgg atttatagta tgtgactttt ctgattaata    2880
tatttaatat attgaataaa aaatagacat gtagttggaa ctgagattca gtctgtctct    2940
gatgccccct ccccactccc ccaccagaca caccccatca ttacataaga gatgggctgc    3000
tcaagatgaa acttggatgt taccagcctg agctgtcagg cctcagtgta ctcatttgta    3060
aaaggcggat aataatgaca cctgcttcac gaggttgtta tgcaaagcac ttagactaat    3120
ttctaacacg tgggaagcct gcattagctg tgcctggcta gctgtgcctg gctcattgct    3180
ggggtctgca gtggctgact agcccagggg tcactgcagg gccctagcaa tagacttagc    3240
cgcagatctc agggttgtca tgtttcctaa actggacata tattctctga ttcttgattt    3300
ccacatccat aaaacaagaa tagacccagc ctcacagagc t                        3341
```

<210> SEQ ID NO 31
<211> LENGTH: 54
<212> TYPE: DNA
<213> ORGANISM: Artificial Sequence
<220> FEATURE:
<223> OTHER INFORMATION: Synthetic construct
<220> FEATURE:
<223> OTHER INFORMATION: T2A DNA

<400> SEQUENCE: 31

```
gaaggcagag gctctctcct cacatgtggg gatgttgaag aaaatccagg tccc          54
```

<210> SEQ ID NO 32
<211> LENGTH: 18

```
<212> TYPE: PRT
<213> ORGANISM: Artificial Sequence
<220> FEATURE:
<223> OTHER INFORMATION: Synthetic construct
<220> FEATURE:
<223> OTHER INFORMATION: T2A peptide (aa)

<400> SEQUENCE: 32

Glu Gly Arg Gly Ser Leu Leu Thr Cys Gly Asp Val Glu Glu Asn Pro
1               5                   10                  15

Gly Pro

<210> SEQ ID NO 33
<211> LENGTH: 21
<212> TYPE: PRT
<213> ORGANISM: Artificial Sequence
<220> FEATURE:
<223> OTHER INFORMATION: Synthetic construct
<220> FEATURE:
<223> OTHER INFORMATION: T2A peptide (aa)

<400> SEQUENCE: 33

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 34
<211> LENGTH: 24
<212> TYPE: PRT
<213> ORGANISM: Artificial Sequence
<220> FEATURE:
<223> OTHER INFORMATION: Synthetic construct
<220> FEATURE:
<223> OTHER INFORMATION: T2A peptide (aa)

<400> SEQUENCE: 34

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 35
<211> LENGTH: 19
<212> TYPE: PRT
<213> ORGANISM: Artificial Sequence
<220> FEATURE:
<223> OTHER INFORMATION: Synthetic construct
<220> FEATURE:
<223> OTHER INFORMATION: P2A peptide (aa)

<400> SEQUENCE: 35

Ala Thr Asn Phe Ser Leu Leu Lys Gln Ala Gly Asp Val Glu Glu Asn
1               5                   10                  15

Pro Gly Pro

<210> SEQ ID NO 36
<211> LENGTH: 22
<212> TYPE: PRT
<213> ORGANISM: Artificial Sequence
<220> FEATURE:
<223> OTHER INFORMATION: Synthetic construct
<220> FEATURE:
<223> OTHER INFORMATION: P2A peptide (aa)

<400> SEQUENCE: 36
```

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 37
<211> LENGTH: 20
<212> TYPE: PRT
<213> ORGANISM: Artificial Sequence
<220> FEATURE:
<223> OTHER INFORMATION: Synthetic construct
<220> FEATURE:
<223> OTHER INFORMATION: E2A peptide (aa)

<400> SEQUENCE: 37

Gln Cys Thr Asn Tyr Ala Leu Leu Lys Leu Ala Gly Asp Val Glu Ser
1               5                   10                  15

Asn Pro Gly Pro
            20

<210> SEQ ID NO 38
<211> LENGTH: 23
<212> TYPE: PRT
<213> ORGANISM: Artificial Sequence
<220> FEATURE:
<223> OTHER INFORMATION: Synthetic construct
<220> FEATURE:
<223> OTHER INFORMATION: E2A peptide (aa)

<400> SEQUENCE: 38

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 39
<211> LENGTH: 22
<212> TYPE: PRT
<213> ORGANISM: Artificial Sequence
<220> FEATURE:
<223> OTHER INFORMATION: Synthetic construct
<220> FEATURE:
<223> OTHER INFORMATION: F2A peptide (aa)

<400> SEQUENCE: 39

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 40
<211> LENGTH: 25
<212> TYPE: PRT
<213> ORGANISM: Artificial Sequence
<220> FEATURE:
<223> OTHER INFORMATION: Synthetic construct
<220> FEATURE:
<223> OTHER INFORMATION: F2A peptide (aa)

<400> SEQUENCE: 40

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

```
<210> SEQ ID NO 41
<211> LENGTH: 1422
<212> TYPE: DNA
<213> ORGANISM: Artificial Sequence
<220> FEATURE:
<223> OTHER INFORMATION: Synthetic construct
<220> FEATURE:
<223> OTHER INFORMATION: tdTomato DNA

<400> SEQUENCE: 41
gtgagcaagg gcgaggaggt gatcaaggag tttatgagat tcaaagtccg gatggagggc    60
agcatgaacg gacatgagtt cgaaattgag ggagaaggcg agggacgacc ttacgaggga   120
acacagaccg ccaaactgaa agtgacaaaa ggcggacctc tgccatttgc ttgggacatc   180
ctgagtccac agttcatgta tggctctaag gcttacgtga acaccctgc cgatattccc   240
gactacaaaa aactgagttt ccctgaaggc ttcaaatggg aacgagtgat gaactttgag   300
gacggaggcc tggtgacagt gacacaggac tctagtctcc aggacggcac actcatctac   360
aaagtgaaaa tgaggggcac caatttccct cccgatggac tgtcatgca gaaaaaaaca   420
atgggatggg aggcttctac cgaacgactg tacccacggg atggagtgct gaaaggcgag   480
atccatcagg cactgaaact gaaggatggc ggccattacc tggtcgagtt caaaaccatc   540
tatatggcca aaaaacccgt ccagctgcct ggctactatt acgtggatac caaactggac   600
attacctctc acaatgaaga ctacacaatc gtcgagcagt acgagaggag tgagggccga   660
caccacctct cctcgggca tggcaccggc agcaccggca gcggcagctc cggcaccgct   720
agttccgagg acaacaacat ggccgtcatc aaagagttca tgcgcttcaa ggtgcgcatg   780
gagggctcca tgaacggcca cgagttcgag atcgagggcg agggcgaggg ccgcccctac   840
gagggcaccc agaccgccaa gctgaaggtg accaagggcg gccccctgcc cttcgcctgg   900
gacatcctgt ccccccagtt catgtacggc tccaaggcgt acgtgaagca ccccgccgac   960
atccccgatt acaagaagct gtccttcccc gagggcttca gtggggagcg cgtgatgaac  1020
ttcgaggacg gcggtctggt gaccgtgacc caggactcct ccctgcagga cggcacgctg  1080
atctacaagg tgaagatgcg cggcaccaac ttccccccg acggcccgt aatgcagaag  1140
aagaccatgg gctgggaggc ctccaccgag cgcctgtacc ccgcgacgg cgtgctgaag  1200
ggcgagatcc accaggccct gaagctgaag gacggcggcc actacctggt ggagttcaag  1260
accatctaca tggccaagaa gcccgtgcaa ctgcccggct actacgt ggacaccaag  1320
ctggacatca cctcccacaa cgaggactac accatcgtgg aacagtacga gcgctccgag  1380
ggccgccacc acctgttcct gtacggcatg gacgagctgt ac                    1422

<210> SEQ ID NO 42
<211> LENGTH: 474
<212> TYPE: PRT
<213> ORGANISM: Artificial Sequence
<220> FEATURE:
<223> OTHER INFORMATION: Synthetic construct
<220> FEATURE:
<223> OTHER INFORMATION: tdTomato protein

<400> SEQUENCE: 42

Val Ser Lys Gly Glu Glu Val Ile Lys Glu Phe Met Arg Phe Lys Val
1               5                   10                  15

Arg Met Glu Gly Ser Met Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45
```

```
Thr Lys Gly Gly Pro Leu Pro Phe Ala Trp Asp Ile Leu Ser Pro Gln
    50                  55                  60

Phe Met Tyr Gly Ser Lys Ala Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Leu Val Thr Val Thr Gln Asp Ser Ser
                100                 105                 110

Leu Gln Asp Gly Thr Leu Ile Tyr Lys Val Lys Met Arg Gly Thr Asn
                115                 120                 125

Phe Pro Pro Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Ile His Gln Ala Leu Lys Leu Lys Asp Gly Gly His Tyr Leu Val Glu
                165                 170                 175

Phe Lys Thr Ile Tyr Met Ala Lys Lys Pro Val Gln Leu Pro Gly Tyr
                180                 185                 190

Tyr Tyr Val Asp Thr Lys Leu Asp Ile Thr Ser His Asn Glu Asp Tyr
                195                 200                 205

Thr Ile Val Glu Gln Tyr Glu Arg Ser Glu Gly Arg His His Leu Phe
    210                 215                 220

Leu Gly His Gly Thr Gly Ser Thr Gly Ser Gly Ser Ser Gly Thr Ala
225                 230                 235                 240

Ser Ser Glu Asp Asn Asn Met Ala Val Ile Lys Glu Phe Met Arg Phe
                245                 250                 255

Lys Val Arg Met Glu Gly Ser Met Asn Gly His Glu Phe Glu Ile Glu
                260                 265                 270

Gly Glu Gly Glu Gly Arg Pro Tyr Glu Gly Thr Gln Thr Ala Lys Leu
                275                 280                 285

Lys Val Thr Lys Gly Gly Pro Leu Pro Phe Ala Trp Asp Ile Leu Ser
    290                 295                 300

Pro Gln Phe Met Tyr Gly Ser Lys Ala Tyr Val Lys His Pro Ala Asp
305                 310                 315                 320

Ile Pro Asp Tyr Lys Lys Leu Ser Phe Pro Glu Gly Phe Lys Trp Glu
                325                 330                 335

Arg Val Met Asn Phe Glu Asp Gly Gly Leu Val Thr Val Thr Gln Asp
                340                 345                 350

Ser Ser Leu Gln Asp Gly Thr Leu Ile Tyr Lys Val Lys Met Arg Gly
                355                 360                 365

Thr Asn Phe Pro Pro Asp Gly Pro Val Met Gln Lys Lys Thr Met Gly
    370                 375                 380

Trp Glu Ala Ser Thr Glu Arg Leu Tyr Pro Arg Asp Gly Val Leu Lys
385                 390                 395                 400

Gly Glu Ile His Gln Ala Leu Lys Leu Lys Asp Gly Gly His Tyr Leu
                405                 410                 415

Val Glu Phe Lys Thr Ile Tyr Met Ala Lys Lys Pro Val Gln Leu Pro
                420                 425                 430

Gly Tyr Tyr Tyr Val Asp Thr Lys Leu Asp Ile Thr Ser His Asn Glu
                435                 440                 445

Asp Tyr Thr Ile Val Glu Gln Tyr Glu Arg Ser Glu Gly Arg His His
    450                 455                 460
```

Leu Phe Leu Tyr Gly Met Asp Glu Leu Tyr
465                 470

<210> SEQ ID NO 43
<211> LENGTH: 927
<212> TYPE: DNA
<213> ORGANISM: Artificial Sequence
<220> FEATURE:
<223> OTHER INFORMATION: Synthetic construct
<220> FEATURE:
<223> OTHER INFORMATION: Nur77 left homology arm
      (chr12:52,058,015-52,058,941 hg38 assembly), with
      silent mutations

<400> SEQUENCE: 43

```
aatctcacta tgttgcccga gctggtctcg aactcctggg ctcaaatgat cctcctgtct    60
cagcctccta aagtgctggg attacaggtg tgagccacca cgcctagccc ttcactgtga   120
cttctgacag tgcagatcag attggttgtg cctgttttgg actttatgta aatgtagttc   180
tgcaggatgg aatctggtgt tgaatgcaga ggttttcaga tttctctgtt ttttaaagga   240
aagaatccac cctcgttcat ttttcactt aaattgcaca ggggacccaa cgatatagaa    300
cacaatcaga ggtactctgg gctgagggag tgctgagttc tgaggctggg tttctcagaa   360
cagtctagat tttaaaaacc caatgatcta ccagaaaac gtaggttagg attttatttc    420
ccgtttgtga ccctgggcaa gtcattagcc tcctgggcct cgggttctca cttggagtat   480
gaggataatg agggttactg cttctcagac ttgtgacgat gcttactaat ggccaacatg   540
tgaatgcgct tttgtgaagt gccagcagag catgaggggt ggtcagggc agcagtttta    600
ggggcctggg ggaggctggg gctttggggg cctggttctc agatgtacag ctaatcctgt   660
acccttcccg cagaccggca tgggctgcag gagccgcggc gggtggagga gctgcagaac   720
cgcatcgcca gctgcctgaa ggagcacgtg gcagctgtgg cgggcgagcc ccagccagcc   780
agctgcctgt cacgtctgtt gggcaaactg cccgagctgc ggaccctgtg cacccagggc   840
ctgcagcgta tcttctacct caagctggag gacttggtgc cccctccacc tatcatcgac   900
aagatcttca tggacacgct gcccttc                                       927
```

<210> SEQ ID NO 44
<211> LENGTH: 975
<212> TYPE: DNA
<213> ORGANISM: Artificial Sequence
<220> FEATURE:
<223> OTHER INFORMATION: Synthetic construct
<220> FEATURE:
<223> OTHER INFORMATION: Nur77 right homology arm
      (chr12:52,058,950-52,059,924 hg38 assembly)

<400> SEQUENCE: 44

```
gcctgggaac acgtgtgcac atgcgcactc tcatatgcca ccccatgtgc ctttagtcca    60
cggaccccca gagcaccccc aagcctgggc ttgagctgca gaatgactcc accttctcac   120
ctgctccagg aggtttgcag ggagctcaag cccttgggga gggggatgcc ttcatggggg   180
tgaccccacg atttgtctta tccccccag cctggccccg gcctttatgt tttttgtaag    240
ataaaccgtt tttaacacat agcgccgtgc tgtaaataag cccagtgctg ctgtaaatac   300
aggaagaaag agcttgaggt gggagcgggg ctggaggaa gggatgggcc ccgccttcct    360
gggcagcctt tccagcctcc tgctggctct ctcttcctac cctccttcca catgtacata   420
aactgtcact ctaggaagaa gacaaatgac agattctgac atttatattt gtgtattttc   480
ctggatttat agtatgtgac ttttctgatt aatatattta atatattgaa taaaaaatag   540
```

```
acatgtagtt ggaactgaga ttcagtctgt ctctgatgcc ccctcccac tcccccacca      600 gacacacccc atcattacat aagagatggg ctgctcaaga tgaaacttgg atgttaccag      660
cctgagctgt caggcctcag tgtactcatt tgtaaaaggc ggataataat gacacctgct      720
tcacgaggtt gttatgcaaa gcacttagac taatttctaa cacgtgggaa gcctgcatta      780
gctgtgcctg gctagctgtg cctggctcat tgctggggtc tgcagtggct gactagccca      840
ggggtcactg cagggcccta gcaatagact tagccgcaga tctcagggtt gtcatgtttc      900
ctaaactgga catatattct ctgattcttg atttccacat ccataaaaca agaatagacc      960
cagcctcaca gagct                                                      975

<210> SEQ ID NO 45
<211> LENGTH: 541
<212> TYPE: PRT
<213> ORGANISM: Homo sapiens
<220> FEATURE:
<223> OTHER INFORMATION: human CCT5
      (Uniprot P48643)

<400> SEQUENCE: 45

Met Ala Ser Met Gly Thr Leu Ala Phe Asp Glu Tyr Gly Arg Pro Phe
1               5                   10                  15

Leu Ile Ile Lys Asp Gln Asp Arg Lys Ser Arg Leu Met Gly Leu Glu
            20                  25                  30

Ala Leu Lys Ser His Ile Met Ala Ala Lys Ala Val Ala Asn Thr Met
        35                  40                  45

Arg Thr Ser Leu Gly Pro Asn Gly Leu Asp Lys Met Met Val Asp Lys
    50                  55                  60

Asp Gly Asp Val Thr Val Thr Asn Asp Gly Ala Thr Ile Leu Ser Met
65                  70                  75                  80

Met Asp Val Asp His Gln Ile Ala Lys Leu Met Val Glu Leu Ser Lys
                85                  90                  95

Ser Gln Asp Asp Glu Ile Gly Asp Gly Thr Thr Gly Val Val Val Leu
            100                 105                 110

Ala Gly Ala Leu Leu Glu Glu Ala Glu Gln Leu Leu Asp Arg Gly Ile
        115                 120                 125

His Pro Ile Arg Ile Ala Asp Gly Tyr Glu Gln Ala Ala Arg Val Ala
    130                 135                 140

Ile Glu His Leu Asp Lys Ile Ser Asp Ser Val Leu Val Asp Ile Lys
145                 150                 155                 160

Asp Thr Glu Pro Leu Ile Gln Thr Ala Lys Thr Thr Leu Gly Ser Lys
                165                 170                 175

Val Val Asn Ser Cys His Arg Gln Met Ala Glu Ile Ala Val Asn Ala
            180                 185                 190

Val Leu Thr Val Ala Asp Met Glu Arg Arg Asp Val Asp Phe Glu Leu
        195                 200                 205

Ile Lys Val Glu Gly Lys Val Gly Gly Arg Leu Glu Asp Thr Lys Leu
    210                 215                 220

Ile Lys Gly Val Ile Val Asp Lys Asp Phe Ser His Pro Gln Met Pro
225                 230                 235                 240

Lys Lys Val Glu Asp Ala Lys Ile Ala Ile Leu Thr Cys Pro Phe Glu
                245                 250                 255

Pro Pro Lys Pro Lys Thr Lys His Lys Leu Asp Val Thr Ser Val Glu
            260                 265                 270
```

Asp Tyr Lys Ala Leu Gln Lys Tyr Glu Lys Glu Lys Phe Glu Glu Met
              275                 280                 285

Ile Gln Gln Ile Lys Glu Thr Gly Ala Asn Leu Ala Ile Cys Gln Trp
    290                 295                 300

Gly Phe Asp Asp Glu Ala Asn His Leu Leu Gln Asn Asn Leu Pro
305                 310                 315                 320

Ala Val Arg Trp Val Gly Pro Glu Ile Glu Leu Ile Ala Ile Ala
                325                 330                 335

Thr Gly Gly Arg Ile Val Pro Arg Phe Ser Glu Leu Thr Ala Glu Lys
                340                 345                 350

Leu Gly Phe Ala Gly Leu Val Gln Glu Ile Ser Phe Gly Thr Thr Lys
                355                 360                 365

Asp Lys Met Leu Val Ile Glu Gln Cys Lys Asn Ser Arg Ala Val Thr
    370                 375                 380

Ile Phe Ile Arg Gly Gly Asn Lys Met Ile Ile Glu Glu Ala Lys Arg
385                 390                 395                 400

Ser Leu His Asp Ala Leu Cys Val Ile Arg Asn Leu Ile Arg Asp Asn
                405                 410                 415

Arg Val Val Tyr Gly Gly Gly Ala Ala Glu Ile Ser Cys Ala Leu Ala
                420                 425                 430

Val Ser Gln Glu Ala Asp Lys Cys Pro Thr Leu Glu Gln Tyr Ala Met
    435                 440                 445

Arg Ala Phe Ala Asp Ala Leu Glu Val Ile Pro Met Ala Leu Ser Glu
    450                 455                 460

Asn Ser Gly Met Asn Pro Ile Gln Thr Met Thr Glu Val Arg Ala Arg
465                 470                 475                 480

Gln Val Lys Glu Met Asn Pro Ala Leu Gly Ile Asp Cys Leu His Lys
                485                 490                 495

Gly Thr Asn Asp Met Lys Gln Gln His Val Ile Glu Thr Leu Ile Gly
                500                 505                 510

Lys Lys Gln Gln Ile Ser Leu Ala Thr Gln Met Val Arg Met Ile Leu
                515                 520                 525

Lys Ile Asp Asp Ile Arg Lys Pro Gly Glu Ser Glu Glu
                530                 535                 540

<210> SEQ ID NO 46
<211> LENGTH: 540
<212> TYPE: PRT
<213> ORGANISM: Homo sapiens
<220> FEATURE:
<223> OTHER INFORMATION: human CCT5
      (Uniprot P48643)

<400> SEQUENCE: 46

Ala Ser Met Gly Thr Leu Ala Phe Asp Glu Tyr Gly Arg Pro Phe Leu
1               5                   10                  15

Ile Ile Lys Asp Gln Asp Arg Lys Ser Arg Leu Met Gly Leu Glu Ala
                20                  25                  30

Leu Lys Ser His Ile Met Ala Ala Lys Ala Val Ala Asn Thr Met Arg
            35                  40                  45

Thr Ser Leu Gly Pro Asn Gly Leu Asp Lys Met Met Val Asp Lys Asp
        50                  55                  60

Gly Asp Val Thr Val Thr Asn Asp Gly Ala Thr Ile Leu Ser Met Met
65                  70                  75                  80

Asp Val Asp His Gln Ile Ala Lys Leu Met Val Glu Leu Ser Lys Ser
                85                  90                  95

```
Gln Asp Asp Glu Ile Gly Asp Gly Thr Thr Gly Val Val Leu Ala
            100                 105                 110

Gly Ala Leu Leu Glu Glu Ala Glu Gln Leu Leu Asp Arg Gly Ile His
            115                 120                 125

Pro Ile Arg Ile Ala Asp Gly Tyr Glu Gln Ala Ala Arg Val Ala Ile
130                 135                 140

Glu His Leu Asp Lys Ile Ser Asp Ser Val Leu Val Asp Ile Lys Asp
145                 150                 155                 160

Thr Glu Pro Leu Ile Gln Thr Ala Lys Thr Thr Leu Gly Ser Lys Val
                165                 170                 175

Val Asn Ser Cys His Arg Gln Met Ala Glu Ile Ala Val Asn Ala Val
            180                 185                 190

Leu Thr Val Ala Asp Met Glu Arg Arg Asp Val Asp Phe Glu Leu Ile
            195                 200                 205

Lys Val Glu Gly Lys Val Gly Gly Arg Leu Glu Asp Thr Lys Leu Ile
            210                 215                 220

Lys Gly Val Ile Val Asp Lys Asp Phe Ser His Pro Gln Met Pro Lys
225                 230                 235                 240

Lys Val Glu Asp Ala Lys Ile Ala Ile Leu Thr Cys Pro Phe Glu Pro
                245                 250                 255

Pro Lys Pro Lys Thr Lys His Lys Leu Asp Val Thr Ser Val Glu Asp
            260                 265                 270

Tyr Lys Ala Leu Gln Lys Tyr Glu Lys Glu Lys Phe Glu Glu Met Ile
            275                 280                 285

Gln Gln Ile Lys Glu Thr Gly Ala Asn Leu Ala Ile Cys Gln Trp Gly
            290                 295                 300

Phe Asp Asp Glu Ala Asn His Leu Leu Leu Gln Asn Asn Leu Pro Ala
305                 310                 315                 320

Val Arg Trp Val Gly Gly Pro Glu Ile Glu Leu Ile Ala Ile Ala Thr
                325                 330                 335

Gly Gly Arg Ile Val Pro Arg Phe Ser Glu Leu Thr Ala Glu Lys Leu
            340                 345                 350

Gly Phe Ala Gly Leu Val Gln Glu Ile Ser Phe Gly Thr Thr Lys Asp
            355                 360                 365

Lys Met Leu Val Ile Glu Gln Cys Lys Asn Ser Arg Ala Val Thr Ile
            370                 375                 380

Phe Ile Arg Gly Gly Asn Lys Met Ile Ile Glu Glu Ala Lys Arg Ser
385                 390                 395                 400

Leu His Asp Ala Leu Cys Val Ile Arg Asn Leu Ile Arg Asp Asn Arg
                405                 410                 415

Val Val Tyr Gly Gly Gly Ala Ala Glu Ile Ser Cys Ala Leu Ala Val
            420                 425                 430

Ser Gln Glu Ala Asp Lys Cys Pro Thr Leu Glu Gln Tyr Ala Met Arg
            435                 440                 445

Ala Phe Ala Asp Ala Leu Glu Val Ile Pro Met Ala Leu Ser Glu Asn
            450                 455                 460

Ser Gly Met Asn Pro Ile Gln Thr Met Thr Glu Val Arg Ala Arg Gln
465                 470                 475                 480

Val Lys Glu Met Asn Pro Ala Leu Gly Ile Asp Cys Leu His Lys Gly
                485                 490                 495

Thr Asn Asp Met Lys Gln Gln His Val Ile Glu Thr Leu Ile Gly Lys
            500                 505                 510
```

Lys Gln Gln Ile Ser Leu Ala Thr Gln Met Val Arg Met Ile Leu Lys
            515                 520                 525

Ile Asp Asp Ile Arg Lys Pro Gly Glu Ser Glu Glu
        530                 535                 540

<210> SEQ ID NO 47
<211> LENGTH: 5
<212> TYPE: PRT
<213> ORGANISM: Artificial Sequence
<220> FEATURE:
<223> OTHER INFORMATION: Synthetic construct
<220> FEATURE:
<223> OTHER INFORMATION: 4GS linker (aa)

<400> SEQUENCE: 47

Gly Gly Gly Gly Ser
1               5

<210> SEQ ID NO 48
<211> LENGTH: 4
<212> TYPE: PRT
<213> ORGANISM: Artificial Sequence
<220> FEATURE:
<223> OTHER INFORMATION: Synthetic construct
<220> FEATURE:
<223> OTHER INFORMATION: 3GS linker (aa)

<400> SEQUENCE: 48

Gly Gly Gly Ser
1

<210> SEQ ID NO 49
<211> LENGTH: 15
<212> TYPE: PRT
<213> ORGANISM: Artificial Sequence
<220> FEATURE:
<223> OTHER INFORMATION: Synthetic construct
<220> FEATURE:
<223> OTHER INFORMATION: (4GS)3 linker (aa)

<400> SEQUENCE: 49

Gly Gly Gly Gly Ser Gly Gly Gly Gly Ser Gly Gly Gly Gly Ser
1               5                   10                  15

<210> SEQ ID NO 50
<211> LENGTH: 18
<212> TYPE: PRT
<213> ORGANISM: Artificial Sequence
<220> FEATURE:
<223> OTHER INFORMATION: Synthetic construct
<220> FEATURE:
<223> OTHER INFORMATION: Linker (aa)

<400> SEQUENCE: 50

Gly Ser Thr Ser Gly Ser Gly Lys Pro Gly Ser Gly Glu Gly Ser Thr
1               5                   10                  15

Lys Gly

<210> SEQ ID NO 51
<211> LENGTH: 60
<212> TYPE: DNA
<213> ORGANISM: Artificial Sequence
<220> FEATURE:
<223> OTHER INFORMATION: Synthetic construct
<220> FEATURE:
<223> OTHER INFORMATION: (4GS)3 linker (nt)

<400> SEQUENCE: 51

```
ggaggcggag gatctggtgg cggaggaagt ggcggaggcg gtagtggtgg tggtggatct    60
```

<210> SEQ ID NO 52
<211> LENGTH: 259
<212> TYPE: PRT
<213> ORGANISM: Artificial Sequence
<220> FEATURE:
<223> OTHER INFORMATION: Synthetic construct
<220> FEATURE:
<223> OTHER INFORMATION: CCT5 scFv (aa)

<400> SEQUENCE: 52

```
Ser Tyr Glu Leu Thr Gln Pro Pro Ser Val Ser Val Ser Pro Gly Gln
1               5                   10                  15

Thr Ala Ser Ile Thr Cys Phe Gly Asp Gln Leu Gly Asp Lys Tyr Val
            20                  25                  30

Ser Trp Tyr Gln Lys Lys Pro Gly Gln Ser Pro Val Leu Val Ile Tyr
        35                  40                  45

Gln Asp Ala Asn Arg Pro Ser Gly Ile Pro Glu Arg Phe Ser Gly Ser
    50                  55                  60

Asn Ser Gly Asn Thr Ala Thr Leu Thr Ile Arg Gly Thr Gln Asn Leu
65                  70                  75                  80

Asp Glu Ala Asp Tyr Tyr Cys Gln Thr Trp Gly Thr Thr Thr Ala Leu
                85                  90                  95

Phe Gly Gly Gly Thr Lys Leu Thr Val Leu Gly Gly Gly Ser Gly
            100                 105                 110

Gly Gly Gly Ser Gly Gly Gly Ser Gly Gly Gly Ser Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Phe Ser Ser Tyr Ser Met
145                 150                 155                 160

Asn Trp Val Arg Gln Ala Pro Gly Lys Gly Leu Glu Trp Val Ser Tyr
                165                 170                 175

Ile Ser Ser Ser Ser Thr Ile Tyr Tyr Ala Asp Ser Val Lys Gly
            180                 185                 190

Arg Phe Thr Ile Ser Arg Asp Asn Ala Lys Asn Ser Leu Tyr Leu Gln
        195                 200                 205

Met Asn Ser Leu Arg Asp Glu Asp Thr Ala Val Tyr Tyr Cys Ala Arg
    210                 215                 220

Asp Phe Lys Gly Asp Cys Ser Ser Thr Ser Cys Tyr Arg Gly Tyr
225                 230                 235                 240

Tyr Tyr Tyr Tyr Gly Met Asp Val Trp Gly Gln Gly Thr Thr Val Thr
                245                 250                 255

Val Ser Ser
```

<210> SEQ ID NO 53
<211> LENGTH: 777
<212> TYPE: DNA
<213> ORGANISM: Artificial Sequence
<220> FEATURE:
<223> OTHER INFORMATION: Synthetic construct
<220> FEATURE:
<223> OTHER INFORMATION: CCT5 scFv (nt)

<400> SEQUENCE: 53

```
agctatgagc tgacccagcc cccctccgtt agcgtcagtc ccggtcaaac cgccagcatc    60
```

```
acctgtttcg gggaccaact gggagataaa tatgtgagct ggtatcagaa aaaaccaggc    120
cagtctcccg tgcttgtcat ttatcaagac gccaacagac caagcgggat ccctgaacga    180
ttctcaggga gcaacagcgg gaatactgcc acgcttacta tccgggggac ccagaatctg    240
gacgaggccg attactactg ccaaacctgg gggacaacaa ctgcgctgtt cggcggggc    300 acaaagctga ccgttctggg aggcggagga tctggtggcg aggaagtgg cggaggcggt    360 agtggtggtg gtggatctga ggtgcagctt gtggagtcag gcggagggct tgtacagccc    420
ggcggcagtc ttagactcag ttgtgccgcc tctggcttta ctttctcatc ttactccatg    480
aactgggtca gacaggcccc tggaaaagga cttgagtggg ttagttatat ttcatcttca    540
agcagcacaa tatattatgc agactcagtg aagggcagat tcaccattag tcgggacaat    600
gcaaaaaaca gcctgtactt gcaaatgaat tccctccggg atgaagatac agcagtgtac    660
tattgtgcca gagacttcaa aggcgattgc tcctctacgt cctgctatcg cggtggatac    720
tactattatt atggaatgga cgtttggggc agggtacca cagtgaccgt gtcttcc        777
```

<210> SEQ ID NO 54
<211> LENGTH: 685
<212> TYPE: PRT
<213> ORGANISM: Artificial Sequence
<220> FEATURE:
<223> OTHER INFORMATION: Synthetic construct
<220> FEATURE:
<223> OTHER INFORMATION: CCT5 CAR

<400> SEQUENCE: 54

```
Met Pro Leu Leu Leu Leu Pro Leu Leu Trp Ala Gly Ala Leu Ala
1               5                   10                  15

Ser Tyr Glu Leu Thr Gln Pro Pro Ser Val Ser Val Ser Pro Gly Gln
            20                  25                  30

Thr Ala Ser Ile Thr Cys Phe Gly Asp Gln Leu Gly Asp Lys Tyr Val
        35                  40                  45

Ser Trp Tyr Gln Lys Lys Pro Gly Gln Ser Pro Val Leu Val Ile Tyr
    50                  55                  60

Gln Asp Ala Asn Arg Pro Ser Gly Ile Pro Glu Arg Phe Ser Gly Ser
65                  70                  75                  80

Asn Ser Gly Asn Thr Ala Thr Leu Thr Ile Arg Gly Thr Gln Asn Leu
                85                  90                  95

Asp Glu Ala Asp Tyr Tyr Cys Gln Thr Trp Gly Thr Thr Thr Ala Leu
            100                 105                 110

Phe Gly Gly Gly Thr Lys Leu Thr Val Leu Gly Gly Gly Gly Ser Gly
        115                 120                 125

Gly Gly Gly Ser Gly Gly Gly Ser Gly Gly Gly Gly Ser Glu Val
    130                 135                 140

Gln Leu Val Glu Ser Gly Gly Gly Leu Val Gln Pro Gly Gly Ser Leu
145                 150                 155                 160

Arg Leu Ser Cys Ala Ala Ser Gly Phe Thr Phe Ser Ser Tyr Ser Met
                165                 170                 175

Asn Trp Val Arg Gln Ala Pro Gly Lys Gly Leu Glu Trp Val Ser Tyr
            180                 185                 190

Ile Ser Ser Ser Ser Thr Ile Tyr Tyr Ala Asp Ser Val Lys Gly
        195                 200                 205

Arg Phe Thr Ile Ser Arg Asp Asn Ala Lys Asn Ser Leu Tyr Leu Gln
    210                 215                 220

Met Asn Ser Leu Arg Asp Glu Asp Thr Ala Val Tyr Tyr Cys Ala Arg
```

-continued

```
             225                 230                 235                 240

Asp Phe Lys Gly Asp Cys Ser Thr Ser Cys Tyr Arg Gly Gly Tyr
                245                 250                 255

Tyr Tyr Tyr Tyr Gly Met Asp Val Trp Gly Gln Gly Thr Thr Val Thr
                260                 265                 270

Val Ser Ser Glu Ser Lys Tyr Gly Pro Pro Cys Pro Pro Cys Pro Ala
                275                 280                 285

Pro Pro Val Ala Gly Pro Ser Val Phe Leu Phe Pro Pro Lys Pro Lys
290                 295                 300

Asp Thr Leu Met Ile Ser Arg Thr Pro Glu Val Thr Cys Val Val
305                 310                 315                 320

Asp Val Ser Gln Glu Asp Pro Glu Val Gln Phe Asn Trp Tyr Val Asp
                325                 330                 335

Gly Val Glu Val His Asn Ala Lys Thr Lys Pro Arg Glu Glu Gln Phe
                340                 345                 350

Gln Ser Thr Tyr Arg Val Val Ser Val Leu Thr Val Leu His Gln Asp
                355                 360                 365

Trp Leu Asn Gly Lys Glu Tyr Lys Cys Lys Val Ser Asn Lys Gly Leu
                370                 375                 380

Pro Ser Ser Ile Glu Lys Thr Ile Ser Lys Ala Lys Gly Gln Pro Arg
385                 390                 395                 400

Glu Pro Gln Val Tyr Thr Leu Pro Pro Ser Gln Glu Glu Met Thr Lys
                405                 410                 415

Asn Gln Val Ser Leu Thr Cys Leu Val Lys Gly Phe Tyr Pro Ser Asp
                420                 425                 430

Ile Ala Val Glu Trp Glu Ser Asn Gly Gln Pro Glu Asn Asn Tyr Lys
                435                 440                 445

Thr Thr Pro Pro Val Leu Asp Ser Asp Gly Ser Phe Phe Leu Tyr Ser
                450                 455                 460

Arg Leu Thr Val Asp Lys Ser Arg Trp Gln Glu Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Leu Gly Lys Met Phe Trp Val Leu Val Val Val Gly
                500                 505                 510

Gly Val Leu Ala Cys Tyr Ser Leu Leu Val Thr Val Ala Phe Ile Ile
                515                 520                 525

Phe Trp Val Lys Arg Gly Arg Lys Lys Leu Leu Tyr Ile Phe Lys Gln
                530                 535                 540

Pro Phe Met Arg Pro Val Gln Thr Thr Gln Glu Glu Asp Gly Cys Ser
545                 550                 555                 560

Cys Arg Phe Pro Glu Glu Glu Glu Gly Gly Cys Glu Leu Arg Val Lys
                565                 570                 575

Phe Ser Arg Ser Ala Asp Ala Pro Ala Tyr Gln Gln Gly Gln Asn Gln
                580                 585                 590

Leu Tyr Asn Glu Leu Asn Leu Gly Arg Arg Glu Glu Tyr Asp Val Leu
                595                 600                 605

Asp Lys Arg Arg Gly Arg Asp Pro Glu Met Gly Gly Lys Pro Arg Arg
                610                 615                 620

Lys Asn Pro Gln Glu Gly Leu Tyr Asn Glu Leu Gln Lys Asp Lys Met
625                 630                 635                 640

Ala Glu Ala Tyr Ser Glu Ile Gly Met Lys Gly Glu Arg Arg Arg Gly
                645                 650                 655
```

```
Lys Gly His Asp Gly Leu Tyr Gln Gly Leu Ser Thr Ala Thr Lys Asp
            660                 665                 670

Thr Tyr Asp Ala Leu His Met Gln Ala Leu Pro Pro Arg
        675                 680             685

<210> SEQ ID NO 55
<211> LENGTH: 2055
<212> TYPE: DNA
<213> ORGANISM: Artificial Sequence
<220> FEATURE:
<223> OTHER INFORMATION: Synthetic construct
<220> FEATURE:
<223> OTHER INFORMATION: CCT5 CAR (nt)

<400> SEQUENCE: 55
atgccgctgc tgctactgct gcccctgctg tgggcagggg ctctagccag ctatgagctg      60
acccagcccc cctccgttag cgtcagtccc ggtcaaaccg ccagcatcac ctgtttcggg     120
gaccaactgg gagataaata tgtgagctgg tatcagaaaa aaccaggcca gtctcccgtg     180
cttgtcattt atcaagacgc caacagacca agcgggatcc ctgaacgatt ctcaggagc     240
aacagcggga atactgccac gcttactatc cggggaccc agaatctgga cgaggccgat      300
tactactgcc aaacctgggg acaacaact gcgctgttcg gcggggcac aaagctgacc       360
gttctgggag gcgaggatc tggtggcgga ggaagtggcg gaggcggtag tggtggtggt      420
ggatctgagg tgcagcttgt ggagtcaggc ggagggcttg tacagcccgg cggcagtctt     480
agactcagtt gtgccgcctc tggctttact ttctcatctt actccatgaa ctgggtcaga     540
caggcccctg gaaaggact tgagtggtt agttatattt catcttcaag cagcacaata       600
tattatgcag actcagtgaa gggcagattc accattagtc gggacaatgc aaaaaacagc    660
ctgtacttgc aaatgaattc cctccgggat gaagatacag cagtgtacta ttgtgccaga    720
gacttcaaag gcgattgctc ctctacgtcc tgctatcgcg gtggatacta ctattattat    780
ggaatggacg tttggggcca gggtaccaca gtgaccgtgt cttccgaatc taaatacgga    840
ccgcctgtc ctccatgtcc tgctcctcca gttgccggac cttccgtgtt cctgtttcct     900
ccaaagccta aggacaccct gatgatcagc agaaccctg aagtgacctg cgtggtggtg     960
gacgtgtccc aagaggatcc tgaggtgcag ttcaactggt atgtggacgg cgtggaagtg    1020
cacaacgcca gaccaagcc tagagaggaa cagttccaga gcacctacag agtggtgtcc    1080
gtgctgacag tgctgcacca ggattggctg aacggcaaag agtacaagtg caaggtgtcc    1140
aacaagggcc tgcctagcag catcgagaaa accatcagca aggccaaggg ccagcccaga    1200
gaacccagg tgtacacact gcctccaagc caagaggaaa tgaccaagaa ccaggtgtcc     1260
ctgacctgcc tggtcaaggg cttctaccct tccgatatcg ccgtggaatg ggagagcaat    1320
ggccagcctg agaacaacta caagaccaca cctcctgtgc tggacagcga cggctcattc    1380
ttcctgtaca gccggctgac cgtggacaag agcagatggc aagagggcaa cgtgttcagc    1440
tgcagcgtga tgcacgaggc cctgcacaac cactacaccc agaagtctct gagcctgagc    1500
ctgggcaaga tgttctgggt gctcgttgtt gttggcggcg tgctggcctg ttactccctg    1560
ctggttaccg tggccttcat catcttttgg gtcaagcggg gcagaaagaa gctgctctac    1620
atcttcaagc agcccttcat gcggcccgtg cagaccacac aagaggaaga tggctgctcc    1680
tgcagattcc ccgaggaaga agaaggcggc tgcgagctga gagtgaagtt cagcagatcc    1740
gccgacgctc cagcctatca gcagggacag aaccagctgt acaacgagct gaacctgggg    1800
```

```
agaagagaag agtacgacgt gctggataag cggagaggca gagatcctga gatgggcggc    1860
aagcccagac ggaagaatcc tcaagagggc ctgtataatg agctgcagaa agacaagatg    1920
gccgaggcct acagcgagat cggaatgaag ggcgagcgca gaagaggcaa gggacacgat    1980
ggactgtacc agggactgag caccgccacc aaggatacct atgacgcact gcacatgcag    2040
gccctgccac ctaga                                                    2055
```

```
<210> SEQ ID NO 56
<211> LENGTH: 20
<212> TYPE: PRT
<213> ORGANISM: Homo sapiens
<220> FEATURE:
<223> OTHER INFORMATION: human IgG -kappa signaling sequence (aa)

<400> SEQUENCE: 56
```

Met Val Leu Gln Thr Gln Val Phe Ile Ser Leu Leu Leu Trp Ile Ser
1               5                   10                  15

Gly Ala Tyr Gly
            20

```
<210> SEQ ID NO 57
<211> LENGTH: 60
<212> TYPE: DNA
<213> ORGANISM: Homo sapiens
<220> FEATURE:
<223> OTHER INFORMATION: human IgG -kappa signaling sequence (nt)

<400> SEQUENCE: 57
```
atggtgctgc agacccaggt gttcatcagc ctgctgctgt ggatctccgg agcatacgga    60

```
<210> SEQ ID NO 58
<211> LENGTH: 541
<212> TYPE: PRT
<213> ORGANISM: Rattus rattus
<220> FEATURE:
<223> OTHER INFORMATION: Rat CCT5 (aa) (UniProt Q68FQ0)

<400> SEQUENCE: 58
```

Met Ala Ser Val Gly Thr Leu Ala Phe Asp Glu Tyr Gly Arg Pro Phe
1               5                   10                  15

Leu Ile Ile Lys Asp Gln Asp Arg Lys Ser Arg Leu Met Gly Leu Glu
            20                  25                  30

Ala Leu Lys Ser His Ile Met Ala Ala Lys Ala Val Ala Asn Thr Met
        35                  40                  45

Arg Thr Ser Leu Gly Pro Asn Gly Leu Asp Lys Met Met Val Asp Lys
    50                  55                  60

Asp Gly Asp Val Thr Val Thr Asn Asp Gly Ala Thr Ile Leu Ser Met
65                  70                  75                  80

Met Asp Val Asp His Gln Ile Ala Lys Leu Met Val Glu Leu Ser Lys
                85                  90                  95

Ser Gln Asp Asp Glu Ile Gly Asp Gly Thr Thr Gly Val Val Val Leu
            100                 105                 110

Ala Gly Ala Leu Leu Glu Glu Ala Glu Gln Leu Leu Asp Arg Gly Ile
        115                 120                 125

His Pro Ile Arg Ile Ala Asp Gly Tyr Glu Gln Ala Ala Arg Ile Ala
    130                 135                 140

Ile Gln His Leu Asp Lys Ile Ser Asp Asn Val Leu Val Asp Ile Asn
145                 150                 155                 160

Asn Pro Glu Pro Leu Ile Gln Thr Ala Lys Thr Thr Leu Gly Ser Lys 165                 170                 175
Val Val Asn Ser Cys His Arg Gln Met Ala Glu Ile Ala Val Asn Ala
            180                 185                 190

Val Leu Thr Val Ala Asp Met Glu Arg Arg Asp Val Asp Phe Glu Leu
            195                 200                 205

Ile Lys Val Glu Gly Lys Val Gly Gly Arg Leu Glu Asp Thr Lys Leu
            210                 215                 220

Ile Lys Gly Val Ile Val Asp Lys Asp Phe Ser His Pro Gln Met Pro
225                 230                 235                 240

Lys Glu Val Leu Asn Ala Lys Ile Ala Ile Leu Thr Cys Pro Phe Glu
            245                 250                 255

Pro Pro Lys Pro Lys Thr Lys His Lys Leu Asp Val Thr Ser Val Glu
            260                 265                 270

Asp Tyr Lys Ala Leu Gln Lys Tyr Glu Lys Glu Lys Phe Glu Glu Met
            275                 280                 285

Ile Ala Gln Ile Lys Glu Thr Gly Ala Asn Leu Ala Ile Cys Gln Trp
            290                 295                 300

Gly Phe Asp Asp Glu Ala Asn His Leu Leu Leu Gln Asn Gly Leu Pro
305                 310                 315                 320

Ala Val Arg Trp Val Gly Gly Pro Glu Ile Glu Leu Ile Ala Ile Ala
            325                 330                 335

Thr Gly Gly Arg Ile Val Pro Arg Phe Ser Glu Leu Thr Ser Glu Lys
            340                 345                 350

Leu Gly Phe Ala Gly Val Val Arg Glu Ile Ser Phe Gly Thr Thr Lys
            355                 360                 365

Asp Lys Met Leu Val Ile Glu Gln Cys Lys Asn Ser Arg Ala Val Thr
            370                 375                 380

Ile Phe Ile Arg Gly Gly Asn Lys Met Ile Ile Glu Glu Ala Lys Arg
385                 390                 395                 400

Ser Leu His Asp Ala Leu Cys Val Ile Arg Asn Leu Ile Arg Asp Asn
            405                 410                 415

Arg Val Val Tyr Gly Gly Gly Ala Ala Glu Ile Ser Cys Ala Leu Ala
            420                 425                 430

Val Ser Gln Glu Ala Asp Lys Cys Pro Thr Leu Glu Gln Tyr Ala Met
            435                 440                 445

Arg Ala Phe Ala Asp Ala Leu Glu Val Ile Pro Met Ala Leu Ser Glu
            450                 455                 460

Asn Ser Gly Met Asn Pro Ile Gln Thr Met Thr Glu Val Arg Ala Arg
465                 470                 475                 480

Gln Val Lys Glu Ser Asn Pro Ala Leu Gly Ile Asp Cys Leu His Lys
            485                 490                 495

Gly Ser Asn Asp Met Gln Tyr Gln His Val Ile Glu Thr Leu Ile Gly
            500                 505                 510

Lys Lys Gln Gln Ile Ser Leu Ala Thr Gln Met Val Arg Met Ile Leu
            515                 520                 525

Lys Ile Asp Asp Ile Arg Lys Pro Gly Glu Ser Glu Glu
            530                 535                 540

<210> SEQ ID NO 59
<211> LENGTH: 540
<212> TYPE: PRT
<213> ORGANISM: Rattus rattus
<220> FEATURE:
<223> OTHER INFORMATION: Rat CCT5 (aa) (UniProt Q68FQ0)

```
<400> SEQUENCE: 59

Ala Ser Val Gly Thr Leu Ala Phe Asp Glu Tyr Gly Arg Pro Phe Leu
1               5                   10                  15

Ile Ile Lys Asp Gln Asp Arg Lys Ser Arg Leu Met Gly Leu Glu Ala
            20                  25                  30

Leu Lys Ser His Ile Met Ala Ala Lys Ala Val Ala Asn Thr Met Arg
        35                  40                  45

Thr Ser Leu Gly Pro Asn Gly Leu Asp Lys Met Met Val Asp Lys Asp
    50                  55                  60

Gly Asp Val Thr Val Thr Asn Asp Gly Ala Thr Ile Leu Ser Met Met
65                  70                  75                  80

Asp Val Asp His Gln Ile Ala Lys Leu Met Val Glu Leu Ser Lys Ser
                85                  90                  95

Gln Asp Asp Glu Ile Gly Asp Gly Thr Thr Gly Val Val Val Leu Ala
            100                 105                 110

Gly Ala Leu Leu Glu Glu Ala Glu Gln Leu Leu Asp Arg Gly Ile His
        115                 120                 125

Pro Ile Arg Ile Ala Asp Gly Tyr Glu Gln Ala Ala Arg Ile Ala Ile
    130                 135                 140

Gln His Leu Asp Lys Ile Ser Asp Asn Val Leu Val Asp Ile Asn Asn
145                 150                 155                 160

Pro Glu Pro Leu Ile Gln Thr Ala Lys Thr Thr Leu Gly Ser Lys Val
                165                 170                 175

Val Asn Ser Cys His Arg Gln Met Ala Glu Ile Ala Val Asn Ala Val
            180                 185                 190

Leu Thr Val Ala Asp Met Glu Arg Arg Asp Val Asp Phe Glu Leu Ile
        195                 200                 205

Lys Val Glu Gly Lys Val Gly Gly Arg Leu Glu Asp Thr Lys Leu Ile
    210                 215                 220

Lys Gly Val Ile Val Asp Lys Asp Phe Ser His Pro Gln Met Pro Lys
225                 230                 235                 240

Glu Val Leu Asn Ala Lys Ile Ala Ile Leu Thr Cys Pro Phe Glu Pro
                245                 250                 255

Pro Lys Pro Lys Thr Lys His Lys Leu Asp Val Thr Ser Val Glu Asp
            260                 265                 270

Tyr Lys Ala Leu Gln Lys Tyr Glu Lys Glu Lys Phe Glu Glu Met Ile
        275                 280                 285

Ala Gln Ile Lys Glu Thr Gly Ala Asn Leu Ala Ile Cys Gln Trp Gly
    290                 295                 300

Phe Asp Asp Glu Ala Asn His Leu Leu Leu Gln Asn Gly Leu Pro Ala
305                 310                 315                 320

Val Arg Trp Val Gly Gly Pro Glu Ile Glu Leu Ile Ala Ile Ala Thr
                325                 330                 335

Gly Gly Arg Ile Val Pro Arg Phe Ser Glu Leu Thr Ser Glu Lys Leu
            340                 345                 350

Gly Phe Ala Gly Val Val Arg Glu Ile Ser Phe Gly Thr Thr Lys Asp
        355                 360                 365

Lys Met Leu Val Ile Glu Gln Cys Lys Asn Ser Arg Ala Val Thr Ile
    370                 375                 380

Phe Ile Arg Gly Gly Asn Lys Met Ile Ile Glu Glu Ala Lys Arg Ser
385                 390                 395                 400

Leu His Asp Ala Leu Cys Val Ile Arg Asn Leu Ile Arg Asp Asn Arg
                405                 410                 415
```

```
Val Val Tyr Gly Gly Ala Ala Glu Ile Ser Cys Ala Leu Ala Val
            420             425                 430

Ser Gln Glu Ala Asp Lys Cys Pro Thr Leu Glu Gln Tyr Ala Met Arg
        435                 440                 445

Ala Phe Ala Asp Ala Leu Glu Val Ile Pro Met Ala Leu Ser Glu Asn
    450                 455                 460

Ser Gly Met Asn Pro Ile Gln Thr Met Thr Glu Val Arg Ala Arg Gln
465                 470                 475                 480

Val Lys Glu Ser Asn Pro Ala Leu Gly Ile Asp Cys Leu His Lys Gly
                485                 490                 495

Ser Asn Asp Met Gln Tyr Gln His Val Ile Glu Thr Leu Ile Gly Lys
                500                 505                 510

Lys Gln Gln Ile Ser Leu Ala Thr Gln Met Val Arg Met Ile Leu Lys
            515                 520                 525

Ile Asp Asp Ile Arg Lys Pro Gly Glu Ser Glu Glu
            530                 535                 540
```

<210> SEQ ID NO 60
<211> LENGTH: 112
<212> TYPE: PRT
<213> ORGANISM: Homo sapiens
<220> FEATURE:
<223> OTHER INFORMATION: CD3-zeta derived intracellular signaling domain
      (aa)

<400> SEQUENCE: 60

```
Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 61
<211> LENGTH: 41
<212> TYPE: PRT
<213> ORGANISM: Homo sapiens
<220> FEATURE:
<223> OTHER INFORMATION: CD28 (amino acids 180-220 of P10747) Homo
      sapiens

<400> SEQUENCE: 61

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 62

<211> LENGTH: 16
<212> TYPE: PRT
<213> ORGANISM: Artificial Sequence
<220> FEATURE:
<223> OTHER INFORMATION: Synthetic construct
<220> FEATURE:
<223> OTHER INFORMATION: CD3-zeta derived intracellular signaling domain
      (aa)

<400> SEQUENCE: 62

Met Pro Leu Leu Leu Leu Leu Pro Leu Leu Trp Ala Gly Ala Leu Ala
1               5                   10                  15

<210> SEQ ID NO 63
<211> LENGTH: 41
<212> TYPE: PRT
<213> ORGANISM: Homo sapiens
<220> FEATURE:
<223> OTHER INFORMATION: CD28 (LL to GG) Homo sapiens

<400> SEQUENCE: 63

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 64
<211> LENGTH: 4
<212> TYPE: PRT
<213> ORGANISM: Artificial Sequence
<220> FEATURE:
<223> OTHER INFORMATION: Synthetic construct
<220> FEATURE:
<223> OTHER INFORMATION: peptide linker

<400> SEQUENCE: 64

Ala Leu Ala Ala
1

<210> SEQ ID NO 65
<211> LENGTH: 357
<212> TYPE: PRT
<213> ORGANISM: Artificial Sequence
<220> FEATURE:
<223> OTHER INFORMATION: Synthetic construct
<220> FEATURE:
<223> OTHER INFORMATION: EGFRt

<400> SEQUENCE: 65

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu

```
              100                 105                 110
Glu Ile Ile Arg Gly Arg Thr Lys Gln His Gly Gln Phe Ser Leu Ala
            115                 120                 125

Val Val Ser Leu Asn Ile Thr Ser Leu Gly Leu Arg Ser Leu Lys Glu
130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Leu Val Val Ala Leu Gly
            340                 345                 350

Ile Gly Leu Phe Met
        355

<210> SEQ ID NO 66
<211> LENGTH: 335
<212> TYPE: PRT
<213> ORGANISM: Artificial Sequence
<220> FEATURE:
<223> OTHER INFORMATION: Synthetic construct
<220> FEATURE:
<223> OTHER INFORMATION: EGFRt

<400> SEQUENCE: 66

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95
```

-continued

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335

<210> SEQ ID NO 67
<211> LENGTH: 112
<212> TYPE: PRT
<213> ORGANISM: Artificial Sequence
<220> FEATURE:
<223> OTHER INFORMATION: Synthetic construct
<220> FEATURE:
<223> OTHER INFORMATION: CD3-zeta derived intracellular signaling domain
      (aa)

<400> SEQUENCE: 67

Arg Val Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

```
<210> SEQ ID NO 68
<211> LENGTH: 8
<212> TYPE: PRT
<213> ORGANISM: Artificial Sequence
<220> FEATURE:
<223> OTHER INFORMATION: Synthetic construct
<220> FEATURE:
<223> OTHER INFORMATION: epitope
<220> FEATURE:
<221> NAME/KEY: VARIANT
<222> LOCATION: 1, 5, 6, 8
<223> OTHER INFORMATION: Xaa = any amino acid

<400> SEQUENCE: 68

Xaa Ser Val Glu Xaa Xaa Lys Xaa
1               5

<210> SEQ ID NO 69
<211> LENGTH: 8
<212> TYPE: PRT
<213> ORGANISM: Artificial Sequence
<220> FEATURE:
<223> OTHER INFORMATION: Synthetic construct
<220> FEATURE:
<223> OTHER INFORMATION: epitope
<220> FEATURE:
<221> NAME/KEY: VARIANT
<222> LOCATION: 1
<223> OTHER INFORMATION: Xaa = Thr, Ser or Asp
<220> FEATURE:
<221> NAME/KEY: VARIANT
<222> LOCATION: 5
<223> OTHER INFORMATION: Xaa = Asp or Ala
<220> FEATURE:
<221> NAME/KEY: VARIANT
<222> LOCATION: 6
<223> OTHER INFORMATION: Xaa = Tyr, Phe or Ile
<220> FEATURE:
<221> NAME/KEY: VARIANT
<222> LOCATION: 8
<223> OTHER INFORMATION: Xaa = Ala or Arg

<400> SEQUENCE: 69

Xaa Ser Val Glu Xaa Xaa Lys Xaa
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic construct
<220> FEATURE:
<223> OTHER INFORMATION: epitope

<400> SEQUENCE: 70

Thr Ser Val Glu Asp Tyr Lys Ala
1               5

<210> SEQ ID NO 71
<211> LENGTH: 8
<212> TYPE: PRT
<213> ORGANISM: Artificial Sequence
<220> FEATURE:
<223> OTHER INFORMATION: Synthetic construct
<220> FEATURE:
<223> OTHER INFORMATION: epitope

<400> SEQUENCE: 71

Ser Ser Val Glu Ala Phe Lys Arg
```

<210> SEQ ID NO 72
<211> LENGTH: 8
<212> TYPE: PRT
<213> ORGANISM: Artificial Sequence
<220> FEATURE:
<223> OTHER INFORMATION: Synthetic construct
<220> FEATURE:
<223> OTHER INFORMATION: epitope

<400> SEQUENCE: 72

Asp Ser Val Glu Ala Ile Lys Ala
1               5

<210> SEQ ID NO 73
<211> LENGTH: 245
<212> TYPE: PRT
<213> ORGANISM: Artificial Sequence
<220> FEATURE:
<223> OTHER INFORMATION: Bryodin

<400> SEQUENCE: 73

Asp Val Ser Phe Arg Leu Ser Gly Ala Thr Thr Thr Ser Tyr Gly Val
1               5                   10                  15

Phe Ile Lys Asn Leu Arg Glu Ala Leu Pro Tyr Glu Arg Lys Val Tyr
                20                  25                  30

Asn Ile Pro Leu Leu Arg Ser Ser Ile Ser Gly Arg Tyr Thr Leu Leu
            35                  40                  45

His Leu Thr Asn Tyr Ala Asp Glu Thr Ile Ser Val Ala Val Asp Val
50                  55                  60

Thr Asn Val Tyr Ile Met Gly Tyr Leu Ala Gly Asp Val Ser Tyr Phe
65                  70                  75                  80

Phe Asn Glu Ala Ser Ala Thr Glu Ala Ala Lys Phe Val Phe Lys Asp
                85                  90                  95

Ala Lys Lys Lys Val Thr Leu Pro Tyr Ser Gly Asn Tyr Glu Arg Leu
            100                 105                 110

Gln Thr Ala Ala Gly Lys Ile Arg Glu Asn Ile Pro Leu Gly Leu Pro
        115                 120                 125

Ala Leu Asp Ser Ala Ile Thr Thr Leu Tyr Tyr Tyr Thr Ala Ser Ser
130                 135                 140

Ala Ala Ser Ala Leu Leu Val Leu Ile Gln Ser Thr Ala Glu Ser Ala
145                 150                 155                 160

Arg Tyr Lys Phe Ile Glu Gln Gln Ile Gly Lys Arg Val Asp Lys Thr
                165                 170                 175

Phe Leu Pro Ser Leu Ala Thr Ile Ser Leu Glu Asn Asn Trp Ser Ala
            180                 185                 190

Leu Ser Lys Gln Ile Gln Ile Ala Ser Thr Asn Asn Gly Gln Phe Glu
        195                 200                 205

Ser Pro Val Val Leu Ile Asp Gly Asn Asn Gln Arg Val Ser Ile Thr
210                 215                 220

Asn Ala Ser Ala Arg Val Val Thr Ser Asn Ile Ala Leu Leu Leu Asn
225                 230                 235                 240

Arg Asn Asn Ile Ala
            245

<210> SEQ ID NO 74
<211> LENGTH: 39
<212> TYPE: PRT

<213> ORGANISM: Artificial Sequence
<220> FEATURE:
<223> OTHER INFORMATION: CD28 ectodomain spacer (aa)

<400> SEQUENCE: 74

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 75
<211> LENGTH: 274
<212> TYPE: PRT
<213> ORGANISM: Artificial Sequence
<220> FEATURE:
<223> OTHER INFORMATION: Saporin-6

<400> SEQUENCE: 75

Val Thr Ser Ile Thr Leu Asp Leu Val Asn Pro Thr Ala Gly Gln Tyr
1               5                   10                  15

Ser Ser Phe Val Asp Lys Ile Arg Asn Asn Val Lys Asp Pro Asn Leu
            20                  25                  30

Lys Tyr Gly Gly Thr Asp Ile Ala Val Ile Pro Pro Ser Lys Glu Lys
        35                  40                  45

Phe Leu Arg Ile Asn Phe Gln Ser Ser Arg Gly Thr Val Ser Leu Gly
    50                  55                  60

Leu Lys Arg Asp Asn Leu Tyr Val Val Ala Tyr Leu Ala Met Asp Asn
65                  70                  75                  80

Thr Asn Val Asn Arg Ala Tyr Tyr Phe Arg Ser Glu Ile Thr Ser Ala
                85                  90                  95

Glu Ser Thr Ala Leu Phe Pro Glu Ala Thr Thr Ala Asn Gln Lys Ala
            100                 105                 110

Leu Glu Tyr Thr Glu Asp Tyr Gln Ser Ile Glu Lys Asn Ala Gln Ile
        115                 120                 125

Thr Gln Gly Asp Gln Ser Arg Lys Glu Leu Gly Leu Gly Ile Asp Leu
    130                 135                 140

Leu Ser Thr Ser Met Glu Ala Val Asn Lys Lys Ala Arg Val Val Lys
145                 150                 155                 160

Asp Glu Ala Arg Phe Leu Leu Ile Ala Ile Gln Met Thr Ala Glu Ala
                165                 170                 175

Ala Arg Phe Arg Tyr Ile Gln Asn Leu Val Ile Lys Asn Phe Pro Asn
            180                 185                 190

Lys Phe Asn Ser Glu Asn Lys Val Ile Gln Phe Glu Val Asn Trp Lys
        195                 200                 205

Lys Ile Ser Thr Ala Ile Tyr Gly Asp Ala Lys Asn Gly Val Phe Asn
    210                 215                 220

Lys Asp Tyr Asp Phe Gly Phe Gly Lys Val Arg Gln Val Lys Asp Leu
225                 230                 235                 240

Gln Met Gly Leu Leu Met Tyr Leu Gly Lys Pro Lys Ser Ser Asn Glu
                245                 250                 255

Ala Asn Ser Thr Val Arg His Tyr Gly Pro Leu Lys Pro Thr Leu Leu
            260                 265                 270

Ile Thr

```
<210> SEQ ID NO 76
<211> LENGTH: 41
<212> TYPE: PRT
<213> ORGANISM: Artificial Sequence
<220> FEATURE:
<223> OTHER INFORMATION: CD28 endodomain (aa)

<400> SEQUENCE: 76

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 77
<211> LENGTH: 250
<212> TYPE: PRT
<213> ORGANISM: Artificial Sequence
<220> FEATURE:
<223> OTHER INFORMATION: Anti-Viral Protein MAP

<400> SEQUENCE: 77

Ala Pro Thr Leu Glu Thr Ile Ala Ser Leu Asp Leu Asn Asn Pro Thr
1               5                   10                  15

Thr Tyr Leu Ser Phe Ile Thr Asn Ile Arg Thr Lys Val Ala Asp Lys
            20                  25                  30

Thr Glu Gln Cys Thr Ile Gln Lys Ile Ser Lys Thr Phe Thr Gln Arg
        35                  40                  45

Tyr Ser Tyr Ile Asp Leu Ile Val Ser Ser Thr Gln Lys Ile Thr Leu
50                  55                  60

Ala Ile Asp Met Ala Asp Leu Tyr Val Leu Gly Tyr Ser Asp Ile Ala
65                  70                  75                  80

Asn Asn Lys Gly Arg Ala Phe Phe Lys Asp Val Thr Glu Ala Val
                85                  90                  95

Ala Asn Asn Phe Phe Pro Gly Ala Thr Gly Thr Asn Arg Ile Lys Leu
            100                 105                 110

Thr Phe Thr Gly Ser Tyr Gly Asp Leu Glu Lys Asn Gly Gly Leu Arg
        115                 120                 125

Lys Asp Asn Pro Leu Gly Ile Phe Arg Leu Glu Asn Ser Ile Val Asn
130                 135                 140

Ile Tyr Gly Lys Ala Gly Asp Val Lys Lys Gln Ala Lys Phe Phe Leu
145                 150                 155                 160

Leu Ala Ile Gln Met Val Ser Glu Ala Ala Arg Phe Lys Tyr Ile Ser
                165                 170                 175

Asp Lys Ile Pro Ser Glu Lys Tyr Glu Glu Val Thr Val Asp Glu Tyr
            180                 185                 190

Met Thr Ala Leu Glu Asn Asn Trp Ala Lys Leu Ser Thr Ala Val Tyr
        195                 200                 205

Asn Ser Lys Pro Ser Thr Thr Thr Ala Thr Lys Cys Gln Leu Ala Thr
210                 215                 220

Ser Pro Val Thr Ile Ser Pro Trp Ile Phe Lys Thr Val Glu Glu Ile
225                 230                 235                 240

Lys Leu Val Met Gly Leu Leu Lys Ser Ser
                245                 250

<210> SEQ ID NO 78
<211> LENGTH: 66
```

<212> TYPE: PRT
<213> ORGANISM: Homo sapiens
<220> FEATURE:
<223> OTHER INFORMATION: CD28 (amino acids 114-179 of Accession No. P10747)

<400> SEQUENCE: 78

```
Ile Glu Val Met Tyr Pro Pro Pro Tyr Leu Asp Asn Glu Lys Ser Asn
1               5                   10                  15
Gly Thr Ile Ile His Val Lys Gly Lys His Leu Cys Pro Ser Pro Leu
            20                  25                  30
Phe Pro Gly Pro Ser Lys Pro Phe Trp Val Leu Val Val Val Gly Gly
        35                  40                  45
Val Leu Ala Cys Tyr Ser Leu Leu Val Thr Val Ala Phe Ile Ile Phe
    50                  55                  60
Trp Val
65
```

<210> SEQ ID NO 79
<211> LENGTH: 293
<212> TYPE: PRT
<213> ORGANISM: Artificial Sequence
<220> FEATURE:
<223> OTHER INFORMATION: Shiga Toxin A-Chain

<400> SEQUENCE: 79

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Thr Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg Met Ala Ser Asp Glu
```

```
                      245                 250                 255
Phe Pro Ser Met Cys Pro Ala Asp Gly Arg Val Arg Gly Ile Thr His
            260                 265                 270

Asn Lys Ile Leu Trp Asp Ser Ser Thr Leu Gly Ala Ile Leu Met Arg
        275                 280                 285

Arg Thr Ile Ser Ser
        290

<210> SEQ ID NO 80
<211> LENGTH: 319
<212> TYPE: PRT
<213> ORGANISM: Artificial Sequence
<220> FEATURE:
<223> OTHER INFORMATION: Shiga-Like Toxin Subunit A (Verotoxin 2)

<400> SEQUENCE: 80

Met Lys Cys Ile Leu Phe Lys Trp Val Leu Cys Leu Leu Leu Gly Phe
1               5                   10                  15

Ser Ser Val Ser Tyr Ser Arg Glu Phe Thr Ile Asp Phe Ser Thr Gln
            20                  25                  30

Gln Ser Tyr Val Ser Ser Leu Asn Ser Ile Arg Thr Glu Ile Ser Thr
        35                  40                  45

Pro Leu Glu His Ile Ser Gln Gly Thr Thr Ser Val Ser Val Ile Asn
    50                  55                  60

His Thr Pro Pro Gly Ser Tyr Phe Ala Val Asp Ile Arg Gly Leu Asp
65                  70                  75                  80

Val Tyr Gln Ala Arg Phe Asp His Leu Arg Leu Ile Ile Glu Gln Asn
                85                  90                  95

Asn Leu Tyr Val Ala Gly Phe Val Asn Thr Ala Thr Asn Thr Phe Tyr
            100                 105                 110

Arg Phe Ser Asp Phe Thr His Ile Ser Val Pro Gly Val Thr Thr Val
        115                 120                 125

Ser Met Thr Thr Asp Ser Ser Tyr Thr Thr Leu Gln Arg Val Ala Ala
    130                 135                 140

Leu Glu Arg Ser Gly Met Gln Ile Ser Arg His Ser Leu Val Ser Ser
145                 150                 155                 160

Tyr Leu Ala Leu Met Glu Phe Ser Gly Asn Thr Met Thr Arg Asp Ala
                165                 170                 175

Ser Arg Ala Val Leu Arg Phe Val Thr Val Thr Ala Glu Ala Leu Arg
            180                 185                 190

Phe Arg Gln Ile Gln Arg Glu Phe Arg Gln Ala Leu Ser Glu Thr Ala
        195                 200                 205

Pro Val Tyr Thr Met Thr Pro Gly Asp Val Asp Leu Thr Leu Asn Trp
    210                 215                 220

Gly Arg Ile Ser Asn Val Leu Pro Glu Tyr Arg Gly Glu Asp Gly Val
225                 230                 235                 240

Arg Val Gly Arg Ile Ser Phe Asn Asn Ile Ser Ala Ile Leu Gly Thr
                245                 250                 255

Val Ala Val Ile Leu Asn Cys His His Gln Gly Ala Arg Ser Val Arg
            260                 265                 270

Ala Val Asn Glu Glu Ser Gln Pro Glu Cys Gln Ile Thr Gly Asp Arg
        275                 280                 285

Pro Val Ile Lys Ile Asn Asn Thr Leu Trp Glu Ser Asn Thr Ala Ala
    290                 295                 300

Ala Phe Leu Asn Arg Lys Ser Gln Phe Leu Tyr Thr Thr Gly Lys
```

<210> SEQ ID NO 81
<211> LENGTH: 119
<212> TYPE: PRT
<213> ORGANISM: Homo sapiens
<220> FEATURE:
<223> OTHER INFORMATION: IgG4 hinge-CH3 spacer (aa)

<400> SEQUENCE: 81

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115

<210> SEQ ID NO 82
<211> LENGTH: 554
<212> TYPE: DNA
<213> ORGANISM: Artificial Sequence
<220> FEATURE:
<223> OTHER INFORMATION: Synthetic construct
<220> FEATURE:
<223> OTHER INFORMATION: EF1a promoter (modified EF1a promoter)

<400> SEQUENCE: 82
ggatctgcga tcgctccggt gcccgtcagt gggcagagcg cacatcgccc acagtccccg      60
agaagttggg gggaggggtc ggcaattgaa ccggtgccta gagaaggtgg cgcggggtaa     120
actgggaaag tgatgtcgtg tactggctcc gcctttttcc cgagggtggg ggagaaccgt     180
atataagtgc agtagtcgcc gtgaacgttc tttttcgcaa cgggtttgcc gccagaacac     240
agctgaagct cgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacggctag cgcc                                                       554

<210> SEQ ID NO 83
<211> LENGTH: 541
<212> TYPE: PRT
<213> ORGANISM: Mus musculus
<220> FEATURE:
<223> OTHER INFORMATION: Mouse CCT5 (aa) (UniProt P80316)

<400> SEQUENCE: 83

Met Ala Ser Val Gly Thr Leu Ala Phe Asp Glu Tyr Gly Arg Pro Phe

```
1               5                   10                  15
Leu Ile Ile Lys Asp Gln Asp Arg Lys Ser Arg Leu Met Gly Leu Glu
                20                  25                  30

Ala Leu Lys Ser His Ile Met Ala Ala Lys Ala Val Ala Asn Thr Met
                35                  40                  45

Arg Thr Ser Leu Gly Pro Asn Gly Leu Asp Lys Met Met Val Asp Lys
            50                  55                  60

Asp Gly Asp Val Thr Ile Thr Asn Asp Gly Ala Thr Ile Leu Ser Met
65                  70                  75                  80

Met Asp Val Asp His Gln Ile Ala Lys Leu Met Val Glu Leu Ser Lys
                85                  90                  95

Ser Gln Asp Asp Glu Ile Gly Asp Gly Thr Thr Gly Val Val Val Leu
                100                 105                 110

Ala Gly Ala Leu Leu Glu Glu Ala Glu Gln Leu Leu Asp Arg Gly Ile
                115                 120                 125

His Pro Ile Arg Ile Ala Asp Gly Tyr Glu Gln Ala Ala Arg Ile Ala
            130                 135                 140

Ile Gln His Leu Asp Lys Ile Ser Asp Lys Val Leu Val Asp Ile Asn
145                 150                 155                 160

Asn Pro Glu Pro Leu Ile Gln Thr Ala Lys Thr Thr Leu Gly Ser Lys
                165                 170                 175

Val Ile Asn Ser Cys His Arg Gln Met Ala Glu Ile Ala Val Asn Ala
                180                 185                 190

Val Leu Thr Val Ala Asp Met Glu Arg Arg Asp Val Asp Phe Glu Leu
            195                 200                 205

Ile Lys Val Glu Gly Lys Val Gly Gly Arg Leu Glu Asp Thr Lys Leu
210                 215                 220

Ile Lys Gly Val Ile Val Asp Lys Asp Phe Ser His Pro Gln Met Pro
225                 230                 235                 240

Lys Lys Val Val Asp Ala Lys Ile Ala Ile Leu Thr Cys Pro Phe Glu
                245                 250                 255

Pro Pro Lys Pro Lys Thr Lys His Lys Leu Asp Val Met Ser Val Glu
                260                 265                 270

Asp Tyr Lys Ala Leu Gln Lys Tyr Glu Lys Glu Lys Phe Glu Glu Met
            275                 280                 285

Ile Lys Gln Ile Lys Glu Thr Gly Ala Asn Leu Ala Ile Cys Gln Trp
            290                 295                 300

Gly Phe Asp Asp Glu Ala Asn His Leu Leu Leu Gln Asn Gly Leu Pro
305                 310                 315                 320

Ala Val Arg Trp Val Gly Gly Pro Glu Ile Glu Leu Ile Ala Ile Ala
                325                 330                 335

Thr Gly Gly Arg Ile Val Pro Arg Phe Ser Glu Leu Thr Ser Glu Lys
            340                 345                 350

Leu Gly Phe Ala Gly Val Val Gln Glu Ile Ser Phe Gly Thr Thr Lys
            355                 360                 365

Asp Lys Met Leu Val Ile Glu Lys Cys Lys Asn Ser Arg Ala Val Thr
            370                 375                 380

Ile Phe Ile Arg Gly Gly Asn Lys Met Ile Ile Glu Glu Ala Lys Arg
385                 390                 395                 400

Ser Leu His Asp Ala Leu Cys Val Ile Arg Asn Leu Ile Arg Asp Asn
                405                 410                 415

Arg Val Val Tyr Gly Gly Gly Ala Ala Glu Ile Ser Cys Ala Leu Ala
                420                 425                 430
```

```
Val Ser Gln Glu Ala Asp Lys Cys Pro Thr Leu Glu Gln Tyr Ala Met
        435                 440                 445

Arg Ala Phe Ala Asp Ala Leu Glu Val Ile Pro Met Ala Leu Ser Glu
450                 455                 460

Asn Ser Gly Met Asn Pro Ile Gln Thr Met Thr Glu Val Arg Ala Arg
465                 470                 475                 480

Gln Val Lys Glu Ser Asn Pro Ala Leu Gly Ile Asp Cys Leu His Lys
            485                 490                 495

Gly Ser Asn Asp Met Gln Tyr Gln His Val Ile Glu Thr Leu Ile Gly
        500                 505                 510

Lys Lys Gln Gln Ile Ser Leu Ala Thr Gln Met Val Arg Met Ile Leu
    515                 520                 525

Lys Ile Asp Asp Ile Arg Lys Pro Gly Glu Ser Glu Glu
530                 535                 540
```

<210> SEQ ID NO 84
<211> LENGTH: 540
<212> TYPE: PRT
<213> ORGANISM: Mus musculus
<220> FEATURE:
<223> OTHER INFORMATION: Mouse CCT5 (aa) (UniProt P80316)

<400> SEQUENCE: 84

```
Ala Ser Val Gly Thr Leu Ala Phe Asp Glu Tyr Gly Arg Pro Phe Leu
1               5                   10                  15

Ile Ile Lys Asp Gln Asp Arg Lys Ser Arg Leu Met Gly Leu Glu Ala
            20                  25                  30

Leu Lys Ser His Ile Met Ala Ala Lys Ala Val Ala Asn Thr Met Arg
        35                  40                  45

Thr Ser Leu Gly Pro Asn Gly Leu Asp Lys Met Met Val Asp Lys Asp
50                  55                  60

Gly Asp Val Thr Ile Thr Asn Asp Gly Ala Thr Ile Leu Ser Met Met
65                  70                  75                  80

Asp Val Asp His Gln Ile Ala Lys Leu Met Val Glu Leu Ser Lys Ser
                85                  90                  95

Gln Asp Asp Glu Ile Gly Asp Gly Thr Thr Gly Val Val Leu Ala
            100                 105                 110

Gly Ala Leu Leu Glu Glu Ala Glu Gln Leu Leu Asp Arg Gly Ile His
        115                 120                 125

Pro Ile Arg Ile Ala Asp Gly Tyr Glu Gln Ala Ala Arg Ile Ala Ile
130                 135                 140

Gln His Leu Asp Lys Ile Ser Asp Lys Val Leu Val Asp Ile Asn Asn
145                 150                 155                 160

Pro Glu Pro Leu Ile Gln Thr Ala Lys Thr Thr Leu Gly Ser Lys Val
                165                 170                 175

Ile Asn Ser Cys His Arg Gln Met Ala Glu Ile Ala Val Asn Ala Val
            180                 185                 190

Leu Thr Val Ala Asp Met Glu Arg Arg Asp Val Asp Phe Glu Leu Ile
        195                 200                 205

Lys Val Glu Gly Lys Val Gly Gly Arg Leu Glu Asp Thr Lys Leu Ile
210                 215                 220

Lys Gly Val Ile Val Asp Lys Asp Phe Ser His Pro Gln Met Pro Lys
225                 230                 235                 240

Lys Val Val Asp Ala Lys Ile Ala Ile Leu Thr Cys Pro Phe Glu Pro
                245                 250                 255
```

Pro Lys Pro Lys Thr Lys His Lys Leu Asp Val Met Ser Val Glu Asp
            260                 265                 270

Tyr Lys Ala Leu Gln Lys Tyr Glu Lys Glu Lys Phe Glu Glu Met Ile
            275                 280                 285

Lys Gln Ile Lys Glu Thr Gly Ala Asn Leu Ala Ile Cys Gln Trp Gly
            290                 295                 300

Phe Asp Asp Glu Ala Asn His Leu Leu Gln Asn Gly Leu Pro Ala
305                 310                 315                 320

Val Arg Trp Val Gly Gly Pro Glu Ile Glu Leu Ile Ala Ile Ala Thr
                    325                 330                 335

Gly Gly Arg Ile Val Pro Arg Phe Ser Glu Leu Thr Ser Glu Lys Leu
                    340                 345                 350

Gly Phe Ala Gly Val Val Gln Glu Ile Ser Phe Gly Thr Thr Lys Asp
                    355                 360                 365

Lys Met Leu Val Ile Glu Lys Cys Lys Asn Ser Arg Ala Val Thr Ile
                    370                 375                 380

Phe Ile Arg Gly Gly Asn Lys Met Ile Ile Glu Ala Lys Arg Ser
385                 390                 395                 400

Leu His Asp Ala Leu Cys Val Ile Arg Asn Leu Ile Arg Asp Asn Arg
                    405                 410                 415

Val Val Tyr Gly Gly Gly Ala Ala Glu Ile Ser Cys Ala Leu Ala Val
                    420                 425                 430

Ser Gln Glu Ala Asp Lys Cys Pro Thr Leu Glu Gln Tyr Ala Met Arg
                    435                 440                 445

Ala Phe Ala Asp Ala Leu Glu Val Ile Pro Met Ala Leu Ser Glu Asn
450                 455                 460

Ser Gly Met Asn Pro Ile Gln Thr Met Thr Glu Val Arg Ala Arg Gln
465                 470                 475                 480

Val Lys Glu Ser Asn Pro Ala Leu Gly Ile Asp Cys Leu His Lys Gly
                    485                 490                 495

Ser Asn Asp Met Gln Tyr Gln His Val Ile Glu Thr Leu Ile Gly Lys
                    500                 505                 510

Lys Gln Gln Ile Ser Leu Ala Thr Gln Met Val Arg Met Ile Leu Lys
                    515                 520                 525

Ile Asp Asp Ile Arg Lys Pro Gly Glu Ser Glu Glu
                    530                 535                 540

<210> SEQ ID NO 85
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 1
<223> OTHER INFORMATION: Xaa = Lys or Arg
<220> FEATURE:
<221> NAME/KEY: REPEAT
<222> LOCATION: (1)...(4)
<223> OTHER INFORMATION: XDEL is repeated 1 to 6 times
<220> FEATURE:
<223> OTHER INFORMATION: exemplary sorting signal

<400> SEQUENCE: 85

Xaa Asp Glu Leu
1

```
<210> SEQ ID NO 86
<211> LENGTH: 247
<212> TYPE: PRT
<213> ORGANISM: Artificial Sequence
<220> FEATURE:
<223> OTHER INFORMATION: Trichosanthin

<400> SEQUENCE: 86

Asp Val Ser Phe Arg Leu Ser Gly Ala Thr Ser Ser Ser Tyr Gly Val
1               5                   10                  15

Phe Ile Ser Asn Leu Arg Lys Ala Leu Pro Asn Glu Arg Lys Leu Tyr
            20                  25                  30

Asp Ile Pro Leu Leu Arg Ser Ser Leu Pro Gly Ser Gln Arg Tyr Ala
        35                  40                  45

Leu Ile His Leu Thr Asn Tyr Ala Asp Glu Thr Ile Ser Val Ala Ile
    50                  55                  60

Asp Val Thr Asn Val Tyr Ile Met Gly Tyr Arg Ala Gly Asp Thr Ser
65                  70                  75                  80

Tyr Phe Phe Asn Glu Ala Ser Ala Thr Glu Ala Ala Lys Tyr Val Phe
                85                  90                  95

Lys Asp Ala Met Arg Lys Val Thr Leu Pro Tyr Ser Gly Asn Tyr Glu
            100                 105                 110

Arg Leu Gln Thr Ala Ala Gly Lys Ile Arg Glu Asn Ile Pro Leu Gly
        115                 120                 125

Leu Pro Ala Leu Asp Ser Ala Ile Thr Thr Leu Phe Tyr Tyr Asn Ala
    130                 135                 140

Asn Ser Ala Ala Ser Ala Leu Met Val Leu Ile Gln Ser Thr Ser Glu
145                 150                 155                 160

Ala Ala Arg Tyr Lys Phe Ile Glu Gln Gln Ile Gly Lys Arg Val Asp
                165                 170                 175

Lys Thr Phe Leu Pro Ser Leu Ala Ile Ile Ser Leu Glu Asn Ser Trp
            180                 185                 190

Ser Ala Leu Ser Lys Gln Ile Gln Ile Ala Ser Thr Asn Asn Gly Gln
        195                 200                 205

Phe Glu Ser Pro Val Val Leu Ile Asn Ala Gln Asn Gln Arg Val Thr
    210                 215                 220

Ile Thr Asn Val Asp Ala Gly Val Val Thr Ser Asn Ile Ala Leu Leu
225                 230                 235                 240

Leu Asn Arg Asn Asn Met Ala
                245
```